US009809583B2

(12) United States Patent
Choi et al.

(10) Patent No.: US 9,809,583 B2
(45) Date of Patent: Nov. 7, 2017

(54) OXAZOLIDINE-BASED COMPOUND AND SELECTIVE ANDROGEN RECEPTOR AGONIST COMPRISING SAME

(71) Applicant: DONG-A ST CO., LTD., Seoul (KR)

(72) Inventors: Sung Pil Choi, Gyeonggi-do (KR); Seul Min Choi, Gyeonggi-do (KR); Byoung Hwa Son, Gyeonggi-do (KR); Hyun Jung Kim, Gyeonggi-do (KR); Ju Mi Kim, Gyeonggi-do (KR); Byung Jun Jang, Seoul (KR); Ji Hyun Sung, Seoul (KR); Ji Hye Lee, Gyeonggi-do (KR); Eunjin Kim, Gyeonggi-do (KR); Kyung Koo Kang, Gyeonggi-do (KR); Soon-Hoe Kim, Gyeonggi-do (KR)

(73) Assignee: DONG-A ST CO., LTD. (KR)

( * ) Notice: Subject to any disclaimer, the term of this patent is extended or adjusted under 35 U.S.C. 154(b) by 0 days.

(21) Appl. No.: 15/305,929

(22) PCT Filed: Apr. 7, 2015

(86) PCT No.: PCT/KR2015/003477
§ 371 (c)(1),
(2) Date: Oct. 21, 2016

(87) PCT Pub. No.: WO2015/163604
PCT Pub. Date: Oct. 29, 2015

(65) Prior Publication Data
US 2017/0050955 A1 Feb. 23, 2017

(30) Foreign Application Priority Data

Apr. 24, 2014 (KR) .......................... 10-2014-0049277

(51) Int. Cl.
C07D 413/12 (2006.01)
C07D 413/06 (2006.01)
C07D 263/04 (2006.01)
C07D 263/06 (2006.01)
A61K 31/421 (2006.01)

(52) U.S. Cl.
CPC .......... *C07D 413/12* (2013.01); *A61K 31/421* (2013.01); *C07D 263/04* (2013.01); *C07D 263/06* (2013.01); *C07D 413/06* (2013.01)

(58) Field of Classification Search
None
See application file for complete search history.

(56) References Cited

FOREIGN PATENT DOCUMENTS

| KR | 20090035707 A | 4/2009 |
| KR | 20100049644 A | 5/2010 |
| WO | 97006791 A1 | 2/1997 |
| WO | 2008011072 A2 | 1/2008 |
| WO | 2012047617 A1 | 4/2012 |

OTHER PUBLICATIONS

Anumula et al. Heterocyclic Communications (2008), 14(3), 187-194 ("Anumula I").*
Anumula et al. Heterocyclic Communications (2007), 13(5), 315-322 ("Anumula II").*
Hayashi et al. Chemical and Pharmaceutical Bulletin (1971), 19(11), 2404-2409.*
A.K. Roy et al., "Regulation of Androgen Action,", Vitamiins and Hormones, Vol. 55, pp. 309-352, 1999.
George, Fredrick W. and Wilson, Jean D, "Hormonal Control of Sexual Development," Vitamins and Hormones, vol. 43, pp. 145-196, 1986.
Mooradian, A.D., et al., "Biological Actions of Androgens," Endocrine Reviews, vol. 8, No. 1, pp. 1-28, Feb. 1987.
Takeda, H., et al., "Immunohistochemical localization of androgen receptors with mono- and polyclonal antibodies to androgen receptor," Journal of Endocrinology, 126, pp. 17-25, 1990.
Davis, Susan R. and Burger, Henry G., "Androgens and the Postmenopausal Woman," Journal of Clinical Endocrinology and Metabolism, vol. 81, No. 8, pp. 2759-2763, 1996.
Davis, Susan, "Androgen Replacement in Women: A Commentary," The Journal of Clinical Endocrinology & Metabolism, vol. 84, No. 6, pp. 1886-1891, 1999.
S.R. Davis, "The therapeutic use of androgens in women," The Jean Hailes Foundation, 267 Clayton Road, Clayton, Victoria 3168, Australia, Journal of Steroid Biochemistry and Molecular Biology, 69, pp. 177-184, 1999.
Yin, Donghua et al., "Pharmacodynamics of Selective Androgen Receptor Modulators," The Journal of Pharmacology and Experimental Therapeutics, vol. 304, No. 3, pp. 1334-1340, 2003.
Davis, Susan R. et al., "Efficacy and safety of a testosterone patch for the treatment of hypoactive sexual desire disorder in surgically menopausal women: a randomized, placebo-controlled trial," Menopause: The Journal of the North American Menopause Society, vol. 13, No. 3, pp. 387-396, 2006.
Wang, Christina et al., "Transdermal Testosterone Gel lmrproves Sexual Function, Mood, Muscle Strength, and Body Composition Parameters in Hypogonadal Men," The Journal of Clinical Endocrinology & Metabolism, vol. 85 No. 8, pp. 2839-2853, 2000.
Snyder, Peter J. et al., "Effects of Testosterone Replacement in Hypogonadal Men," The Journal of Clinical Endocrinology & Metabolism, vol. 85, No. 8, pp. 2670-2677, 2000.

(Continued)

*Primary Examiner* — Nyeemah A Grazier
(74) *Attorney, Agent, or Firm* — Lerner, David, Littenberg, Krumholz & Mentlik, LLP

(57) ABSTRACT

Provided are novel selective androgen receptor agonists, a preparation method thereof, and a pharmaceutical composition including the same at a pharmaceutically effective amount. The selective androgen receptor agonists according to the present invention act on androgen receptors to increase androgen activity, thereby being usefully applied as a therapeutic and prophylactic agent for diseases or conditions, of which symptoms may be improved or may respond to treatment by increased activities of androgen receptors, namely, a variety of hormone-related diseases in male and female, muscle wasting disorders, osteoporosis, etc.

14 Claims, No Drawings

(56) References Cited

OTHER PUBLICATIONS

Rhoden, Ernani L. et al., "Risks of Testosterone-Replacement Therapy and Recommendations for Monitoring," The New England Journal of Medicine, vol. 350, No. 5, pp. 482-492, www.nejm.org, Jan. 29, 2004.

Negro-Vilar, Andrés, "Selective Androgen Receptor Modulators (SARMs): A Novel Approach to Androgen Therapy for the New Millennium," The Journal of Clinical Endocrinology & Metabolism, vol. 84, No. 10, pp. 3459-3462, 1999.

Anumula, R.R. et al., "Synthesis of New Oxazolidinonyl-lOxazolidinyl Carbazole erivatives for beta-Blocking Activity", Hetercyclic Communications, De Gruyter, DE, Jan. 1, 2007, vol. 13, No. 5, pp. 315-322. XP009147491.

Extended European Search Report for Application No. EP15782235.4 dated Aug. 3, 2017.

\* cited by examiner

OXAZOLIDINE-BASED COMPOUND AND SELECTIVE ANDROGEN RECEPTOR AGONIST COMPRISING SAME

CROSS-REFERENCE TO RELATED APPLICATION

This application is a national phase entry under 35 U.S.C. §371 of International Application No. PCT/KR2015/003477, filed Apr. 7, 2015, which claims priority to Korean Patent Application No. 10-2014-0049277, filed Apr. 24, 2014, the disclosures of which are incorporated herein by reference.

TECHNICAL FIELD

The present disclosure relates to a compound effective as a selective androgen receptor agonist, a preparation method thereof, and a pharmaceutical composition including the same at a pharmaceutically effective amount.

BACKGROUND ART

Androgen receptor (AR) is an intracellular receptor having androgen such as testosterone or dihydrotestosterone as a ligand, and a DNA transcriptional regulatory protein that is activated by binding of the ligand to translocate into the nucleus (Vitam Horm, 55:309-352, 1999).

Androgen plays a key role in the establishment and maintenance of male phenotype (Vitam Horm, 43:145-196, 1986: Endocr Rev 8:1-28, 1987). That is, androgen plays an essential role in differentiation and growth of the male sexual organs, initiation and regulation of spermatogenesis, and regulation of male sexual behavior. Further, androgen also plays an important role in the development associated with virilization in the tissues other than sexual organs, such as muscle, bone, hair, larynx, skin, adipose tissue, or kidney (J Endocrinol, 126:17-25, 1990). Physiological roles of androgen in females have not been clearly revealed, but it is known that the blood level of androgen decreases with aging to cause symptoms such as lessened sexual desire and sexuality, lack of vitality, decreased sense of happiness, reduced bone mineral density in postmenopausal women, etc. (J Clin Endocrinol Metab, 81:2759-2763, 1996; J Clin Endocrinol Metab 84:1886-1892, 1999; J Steroid Biochem Mol Biol, 69:177-184, 1999). Therefore, the reduction in androgen may cause many diseases in men and women, for example, delayed puberty in boys, anaemia, osteoporosis, hereditary angioneurotic edema, endometriosis, estrogen receptor-positive breast cancer, muscle-related diseases, a decline in male reproductive ability, etc. (J Pharmacol Exp Ther, 304:1334-1340, 2003).

Current androgen replacement therapy which is a widely used therapy has effects of increasing bone density, actual weight, and sexual desire in men and women (Menopause, 13:387-396, 2006: J Clin Endocrinol Metab, 85:2839-2853, 2000: J Clin Endocrinol Metab, 85:2670-2677, 2000). However, this therapy has limitations in broad clinical trials, because of potential safety problems of androgen (N Engl J Med 350:482-492, 2004). The therapy may cause hepatotoxicity as well as severe adverse effects of prostate stimulation in men and virilism of woman Selective androgen receptor agonists (SARM agonists) are androgen receptor ligands having tissue-selective effects, and shows positive therapeutic effects of androgen without stimulation of prostate and skin, and their oral administration is possible (J Clin Endocrinol Metab, 84:3459-3462, 1999). In other words, SARM agonists show therapeutic effects without common androgenic side effects such as prostatic hypertrophy, hirsutism, or virilism. These compounds act on androgen receptors tissue-selectively to increase their activities, thereby showing the androgenic effects while eliminating or reducing negative or unwanted androgenic properties. Accordingly, these compounds are effective in the treatment and prevention of diseases or conditions, of which symptoms may be improved or may respond to treatment by increased activities of androgen receptors, namely, disorders including those listed below:

a) symptoms associated with androgen decline in male such as sexual dysfunction, decreased sexual libido, male erectile dysfunction, hypogonadism, sarcopenia, osteopenia, osteoporosis, alterations in cognition and mood, depression, anemia, hair loss, obesity, b) symptoms associated with androgen decline in female such as sexual dysfunction, decreased sexual libido, sarcopenia, osteopenia, osteoporosis, alterations in cognition and mood, depression, anemia, hair loss, obesity, endometriosis, breast cancer, uterine cancer and ovarian cancer, c) muscle wasting disorder caused by aging, bone fracture, serious burns, end-stage renal disease, cancer, AIDS, chronic obstructive pulmonary disease, stroke, etc., and d) osteopenia and osteoporosis, muscle dystrophy caused by reduction in the number or mass of muscle cells, muscular dystrophy, post-operative muscle loss, neuromuscular disease caused by neurotransmitter system disorder, rheumatic disease, sarcopenic obesity, etc.

DISCLOSURE

Technical Problem

In this regard, the present inventors prepared novel selective androgen receptor agonists and pharmaceutically acceptable salts thereof, and they found that these compounds bind to androgen receptors to activate their activities, and therefore, the compounds may be effectively used for the treatment of a variety of diseases or conditions, of which symptoms may be improved or may respond to treatment by increased activity of androgen.

Technical Solution

An aspect of the present invention relates to an oxazolidine-based compound effective as a selective androgen receptor agonist, a preparation method thereof, and a pharmaceutical composition including the same at a pharmaceutically effective amount.

Another aspect of the present invention relates to a pharmaceutical composition including the androgen receptor agonists and pharmaceutically acceptable salts thereof for the treatment and prevention of diseases or conditions, of which symptoms may be improved or may respond to treatment by increased activity of androgen.

Still another aspect of the present invention relates to a health functional food composition including the oxazolidine-based compound for the prevention and/or improvement of diseases or conditions which may be improved or may respond to treatment by increased activity of androgen.

Still another aspect of the present invention relates to a method of treating and preventing diseases or conditions, of which symptoms may be improved or may respond to treatment by increased activity of androgen, by using the androgen receptor agonists and the pharmaceutically acceptable salts thereof.

BEST MODE FOR CARRYING OUT THE INVENTION

An aspect of the present invention relates to a compound represented by the following Chemical Formula 1, an isomer thereof, or a pharmaceutically acceptable salt thereof:

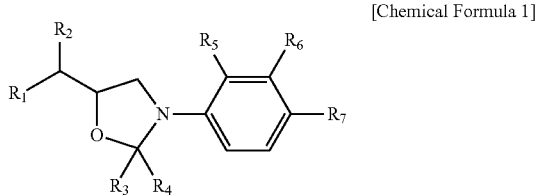

[Chemical Formula 1]

in Chemical Formula 1, $R_1$ is a substituent of the following Chemical Formula 2 or Chemical Formula 3, $R_2$ is hydrogen, oxo, or $C_1$-$C_6$ alkyl, $R_3$ and $R_4$ each independently include one or more substituents selected from the group consisting of hydrogen and $C_1$-$C_6$ alkyl, $R_5$ and $R_6$ each independently include one or more substituents selected from the group consisting of hydrogen, halogen, and $C_1$-$C_6$ alkyl, $R_7$ is halogen, cyano or nitro, the $C_1$-$C_6$ alkyl includes one or more substituents selected from the group consisting of hydrogen, hydroxy, and halogen;

$$—X(CH_2)nR_8 \quad \text{[Chemical Formula 2]}$$

in Chemical Formula 2, X is O, N, S or $S(O)_2$, $R_8$ is hydrogen, $C_3$-$C_7$ heterocycle including a nitrogen atom, aryl, or heteroaryl having a nitrogen atom, the heterocycle, aryl or heteroaryl each independently includes one or more substituents selected from the group consisting of hydrogen, hydroxy, halogen, $C_1$-$C_6$ alkyl, $C_1$-$C_6$ alkoxy, a cyano group, a nitro group, a hydroxyimino group, a $C_1$-$C_6$ alkoxyimino group, $(CH_2)_pNR_{10}R_{11}$, $(CH_2)_pNC(O)R_{10}$, $(CH_2)_pNC(O)OR_{10}$, $(CH_2)_pNC(O)NR_{10}R_{11}$, $(CH_2)_pC(O)NR_{10}R_{11}$, $(CH_2)_pNS(O)_2R_{10}$, $(CH_2)_pS(O)_2R_{10}$ $(CH_2)_pC(O)OR_{10}$,

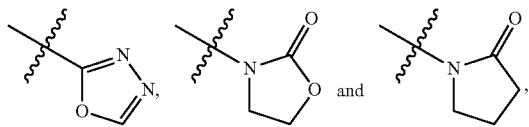 [SMILES: *c1nnco1 ; *N1CCOC1=O ; "and" ; *N1CCCC1=O]

p is an integer of 0 or 1, $R_{10}$ and $R_{11}$ each independently include one or more substituents selected from the group consisting of hydrogen, $C_1$-$C_6$ alkyl, pyrrolidinyl, and phenyl, the $C_1$-$C_6$ alkyl includes one or more substituents selected from the group consisting of hydrogen, hydroxy, amino, cyano and halogen, n is 0 or 1;

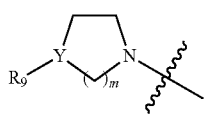

[Chemical Formula 3]

in Chemical Formula 3, Y is C or N, m is an integer of 0, 1 or 2, $R_9$ is a substituent selected from the group consisting of hydrogen, oxo, hydroxy, $C_1$-$C_6$ alkyl, cyano, $C(O)R_{12}$, $C(O)OR_{12}$, $C(O)NR_{12}R_{13}$, $S(O)_2R_{12}$, $NC(O)R_{13}$, $NR_{12}R_{13}$, and $NC(O)OR_{12}$, $R_{12}$ and $R_{13}$ each independently include one or more substituents selected from the group consisting of hydrogen, hydroxy and $C_1$-$C_6$ alkyl, and the $C_1$-$C_6$ alkyl includes one or more substituents selected from the group consisting of hydrogen, hydroxy, halogen and cyano.

In an embodiment of the present invention, in Chemical Formula 1, $R_2$ is hydrogen, oxo, or $C_1$-$C_6$ alkyl, $R_3$ and $R_4$ each independently include one or more substituents selected from the group consisting of hydrogen and $C_1$-$C_6$ alkyl.

$R_5$ and $R_6$ each independently include one or more substituents selected from the group consisting of hydrogen, halogen and $C_1$-$C_6$ alkyl, $R_7$ is halogen, cyano, or nitro, and the $C_1$-$C_6$ alkyl includes one or more substituents selected from the group consisting of hydrogen, hydroxy, and halogen.

In a preferred embodiment of the present invention, $R_3$ and $R_4$ of Chemical Formula 1 may each independently include one or more substituents selected from the group consisting of hydrogen and $C_1$-$C_6$ alkyl, the $C_1$-$C_6$ alkyl may include one or more substituents selected from the group consisting of hydrogen and halogen, and $R_7$ may be halogen, cyano, or nitro.

In an embodiment of the present invention, R1 of Chemical Formula 1 may be a substituent having Chemical Formula 2 or Chemical Formula 3.

If R1 of Chemical Formula 1 is a compound having the substituent of Chemical Formula 2, the Chemical Formula 2 may be defined as follows:

$$—X(CH_2)nR_8 \quad \text{[Chemical Formula 2]}$$

in Chemical Formula 2, X is O, N, S or $S(O)_2$, $R_8$ is hydrogen, $C_3$-$C_7$ heterocycle including a nitrogen atom, aryl, or heteroaryl including a nitrogen atom, the heterocycle, aryl or heteroaryl each independently includes one or more substituents selected from the group consisting of hydrogen, hydroxy, halogen, $C_1$-$C_6$ alkyl, $C_1$-$C_6$ alkoxy, a cyano group, a nitro group, a hydroxyimino group, a $C_1$-$C_6$ alkoxyimino group, $(CH_2)_pNR_{10}R_{11}$, $(CH_2)_pNC(O)R_{10}$, $(CH_2)_pNC(O)OR_{10}$, $(CH_2)_pNC(O)NR_{10}R_{11}$, $(CH_2)_pC(O)NR_{10}R_{11}$, $(CH_2)_pNS(O)_2R_{10}$, $(CH_2)_pS(O)_2R_{10}$ $(CH_2)_pC(O)OR_{10}$,

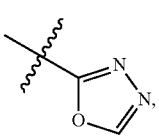 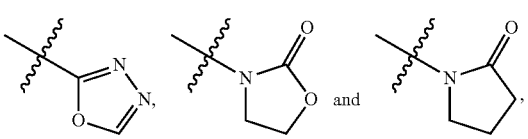 [SMILES: *c1nnco1 ; *N1CCOC1=O ; "and" ; *N1CCCC1=O]

p is an integer of 0 or 1, $R_{10}$ and $R_{11}$ each independently include one or more substituents selected from the group consisting of hydrogen, $C_1$-$C_6$ alkyl, pyrrolidinyl, and phenyl, the $C_1$-$C_6$ alkyl includes one or more substituents selected from the group consisting of hydrogen, hydroxy, amino, cyano and halogen, and n is 0 or 1.

In a preferred embodiment of the present invention, in $R_8$ of Chemical Formula 2, the heterocycle may be piperidine, the aryl may be phenyl, and the heteroaryl may be pyridine.

Further, if R1 of Chemical Formula 1 is a compound having the substituent of Chemical Formula 3, the Chemical Formula 3 may be defined as follows:

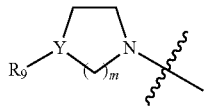

[Chemical Formula 3]

in Chemical Formula 3, Y is C or N, m is an integer of 0, 1 or 2, $R_9$ is a substituent selected from the group consisting of hydrogen, oxo, hydroxy, $C_1$-$C_6$ alkyl, cyano, $C(O)R_{12}$, $C(O)OR_{12}$, $C(O)NR_{12}R_{13}$, $S(O)_2R_{12}$, $NC(O)R_{13}$, $NR_{12}R_{13}$, and $NC(O)OR_{12}$, $R_{12}$ and $R_{13}$ each independently include one or more substituents selected from the group consisting of hydrogen, hydroxy and $C_1$-$C_6$ alkyl, and the $C_1$-$C_6$ alkyl includes one or more substituents selected from the group consisting of hydrogen, hydroxy, halogen and cyano.

Hereinbelow, unless otherwise specified, the compound of Chemical Formula 1 as an active ingredient of the therapeutic agent includes all pharmaceutically acceptable salts and isomers thereof, and these compounds should be construed as being included in the scope of the present invention. However, for the convenience of explanation, all these compounds are simply expressed as 'the compound of Chemical Formula 1' herein. The isomer may be in the form of a racemic mixture, an enantiomer, a diastereomer, a mixture of enantiomers, or a mixture of diastereomers.

The terminology used herein will be described briefly.

As used herein, the term 'pharmaceutically acceptable salt' refers to a salt of a compound that does not cause significant irritation to an organism to which it is administered and does not abrogate the biological activity and properties of the compound. The pharmaceutical salts include acid addition salts formed by acids that form non-toxic acid addition salts containing a pharmaceutically acceptable anion, for example, inorganic acids such as hydrochloric acid, sulfuric acid, nitric acid, phosphoric acid, hydrobromic acid, hydroiodic acid or the like, organocarbonic acid such as tartaric acid, formic acid, citric acid, acetic acid, trichloroacetic acid, trifluoroacetic acid, gluconic acid, benzoic acid, lactic acid, fumaric acid, maleic acid, salicylic acid or the like, and sulfonic acid such as methanesulfonic acid, ethanesulfonic acid, benzenesulfonic acid, p-toluenesulfonic acid or the like. Further, the pharmaceutically acceptable salts include an alkaline metal salt or alkaline earth metal salt formed by lithium, sodium, potassium, calcium, magnesium or the like; salts of amino acids such as lysine, arginine, guanidine or the like; and organic salts such as dicyclohexylamine, N-methyl-D-glucamine, tris(hydroxymethyl)methylamine, diethanolamine, choline, triethylamine or the like.

As used herein, the term 'isomer' refers to a compound of the present invention or a salt thereof that has the same chemical formula or molecular formula but is optically or sterically different therefrom. The isomer and salt thereof and a mixture of isomers (racemic mixture) are also included in the scope of the present invention.

As used herein, the term 'aryl' refers to a carbocyclic (e.g. phenyl) group which has a conjugated pi electron system and at least one ring. This term includes a monocyclic or fused-ring polycyclic (i.e., rings which share adjacent pairs of carbon atoms) groups.

As used herein, the term 'heteroaryl' refers to a heterocyclic aryl group which has a conjugated pi electron system and at least one ring, and is exemplified by furan, thiophene, pyrrole, imidazole, oxazole, isoxazole, oxadiazole, tetrazole, thiazole, imidazole, pyrazole, isothiazole, triazole, thiadiazole, pyridine, pyridazine, pyrimidine, pyrazine, triazine, etc., but is not limited thereto.

As used herein, the term 'alkyl' refers to an aliphatic hydrocarbon group. An alkyl moiety may be a 'saturated alkyl' group containing no alkene or alkyne moiety or an 'unsaturated alkyl' group containing at least one alkene or alkyne moiety. The 'alkene' moiety refers to a group composed of at least one carbon-carbon double bond, and the 'alkyne' moiety refers to a group composed of at least one carbon-carbon triple bond. The alkyl moiety, regardless of whether it is saturated or unsaturated, may be branched, linear or cyclic.

As used herein, the term 'heterocycle' refers to a group in which a cyclic carbon is replaced by oxygen, nitrogen, sulfur, etc., and the group may contain any double bond. The heterocycle may be exemplified by pyrroline, pyrrolidine, tetrahydrofuran, imidazoline, imidazolidin, pyrazoline, pyrazolidine, pyran, piperidine, piperazine, morpholine, thiomorpholine, etc., but is not limited thereto.

Terminology other than those described above may be construed as meaning commonly understood by those skilled in the art to which the present invention pertains.

According to an embodiment of the present invention, $R_1$ of Chemical Formula 1 may be a substituent represented by the following Chemical Formula 2, and may be a compound selected from the group consisting of the following compounds, an isomer thereof, or a pharmaceutically acceptable salt thereof:

4-(5-(hydroxymethyl)-2-(trifluoromethyl)oxazolidin-3-yl)-2-(trifluoromethyl)benzonitrile, 4-(5-(((4-cyanobenzyl)oxy)methyl)-2-(trifluoromethyl) oxazolidin-3-yl)-2-(trifluoromethyl)benzonitrile, 4-(5-(hydroxymethyl)-2-(trifluoromethyl)oxazolidin-3-yl)-2-(trifluoromethyl)benzonitrile, 4-(5-(((4-cyanobenzyl)oxy)methyl)-2-(trifluoromethyl) oxazolidin-3-yl)-2-(trifluoromethyl)benzonitrile, 4-(5-((4-cyanophenoxy)methyl)-2-(trifluoromethyl)oxazolidin-3-yl)-2-(trifluoromethyl)benzonitrile, 4-(5-((4-cyanophenoxy)methyl)-2-(trifluoromethyl)oxazolidin-3-yl)-2-(trifluoromethyl)benzonitrile, methyl 4-((3-(4-cyano-3-(trifluoromethyl)phenyl)-2-(trifluoromethyl)oxazolidin-5-yl)methoxy)benzoate, 4-(5-((4-nitrophenoxy)methyl)-2-(trifluoromethyl)oxazolidin-3-yl)-2-(trifluoromethyl)benzonitrile, 4-(3-(4-cyano-3-(trifluoromethyl)phenyl)-2-(trifluoromethyl)oxazolidin-5-yl)methoxy)benzoic acid, 4-(5-((3,4-difluorophenoxy)methyl)-2-(trifluoromethyl) oxazolidin-3-yl)-2-(trifluoromethyl)benzonitrile, 4-(5-((4-cyano-2-fluorophenoxy)methyl)-2-(trifluoromethyl)oxazolidin-3-yl)-2-(trifluoromethyl)benzonitrile, 4-(5-((2-chloro-4-nitrophenoxy)methyl)-2-(trifluoromethyl)oxazolidin-3-yl)-2-(trifluoromethyl)benzonitrile, 2-(trifluoromethyl)-4-(2-(trifluoromethyl)-5-((2,4,5-trifluorophenoxy)methyl)oxazolidin-3-yl)benzonitrile, 4-(5-((4-aminophenoxy)methyl)-2-(trifluoromethyl)oxazolidin-3-yl)-2-(trifluoromethyl)benzonitrile, 1-(4-((3-(4-cyano-3-(trifluoromethyl)phenyl)-2-(trifluoromethyl)oxazolidin-5-yl)methoxy)phenyl)urea, 1-(4-((3-(4-cyano-3-(trifluoromethyl)phenyl)-2-(trifluoromethyl)oxazolidin-5-yl)methoxy)phenyl)-3-methylurea, 4-(5-((4-(2-oxopyrrolidin-1-yl)phenoxy)methyl)-2-(trifluoromethyl)oxazolidin-3-yl)-2-(trifluoromethyl)benzonitrile, 4-(5-((4-(1,3,4-oxadiazol-2-yl)phenoxy)methyl)-2-(trifluoromethyl)oxazolidin-3-yl)-2-(trifluoromethyl)benzonitrile, 4-(5-((4-cyanophenoxy)methyl)-2-(trifluoromethyl)oxazolidin-3-yl)-2-(trifluoromethyl)benzonitrile, 4-(5-((4-cyanophenoxy)methyl)-2-(trifluoromethyl)oxazolidin-3-yl)-2-(trifluoromethyl)benzonitrile, 4-(5-(2,2,2-trifluoro-1-hydroxyethyl)-2-(trifluoromethyl)oxazolidin-3-yl)-2-(trifluoromethyl)benzonitrile, 4-(5-(2,2,2-trifluoro-1-hydroxyethyl)-2-(trifluoromethyl)oxazolidin-3-yl)-2-(trifluoromethyl)benzonitrile, 4-(5-(2,2,2-trifluoro-1-hydroxyethyl)-2-(trifluoromethyl)oxazolidin-3-yl)-2-(trifluoromethyl)benzonitrile, 4-(5-(2,2,2-trifluoro-1-hydroxyethyl)-2-(trifluoromethyl)oxazolidin-3-yl)-2-(trifluoromethyl)benzonitrile, N-(4-((3-(4-cyano-3-(trifluoromethyl)phenyl)-2-(trifluoromethyl)oxazolidin-5-yl)methoxy)phenyl)acetamide, 4-(5-(((4-chlorophenyl)thio)methyl)-2-(trifluoromethyl)oxazolidin-3-yl)-2-(trifluoromethyl)benzonitrile, 4-(5-((4-methoxyphenoxy)methyl)-2-(trifluoromethyl)oxazolidin-3-yl)-2-(trifluoromethyl)benzonitrile, 4-(5-((3-methoxyphenoxy)methyl)-2-(trifluoromethyl)oxazolidin-3-yl)-2-(trifluoromethyl)benzonitrile, 4-(5-(((4-cyanophenyl)thio)methyl)-2-(trifluoromethyl)oxazolidin-3-yl)-2-(trifluoromethyl)benzonitrile, N-(4-((3-(4-cyano-3-(trifluoromethyl)phenyl)-2-(trifluoromethyl)oxazolidin-5-yl)methoxy)phenyl)acetamide, 4-(5-((3-fluoro-4-nitrophenoxy)methyl)-2-(trifluoromethyl)oxazolidin-3-yl)-2-(trifluoromethyl)benzonitrile, 4-(3-(4-cyano-3-(trifluoromethyl)phenyl)-2-(trifluoromethyl)oxazolidin-5-yl)methoxy)-N-methylbenzamide, 4-(5-((2-fluoro-4-nitrophenoxy)methyl)-2-(trifluoromethyl)oxazolidin-3-yl)-2-(trifluoromethyl)benzonitrile, 4-(3-(4-cyano-3-(trifluoromethyl)phenyl)-2-(trifluoromethyl)oxazolidin-5-yl)methoxy)-N,N-dimethylbenzamide, 4-(5-((4-nitrophenoxy)methyl)-2-(trifluoromethyl)oxazolidin-3-yl)-2-(trifluoromethyl)benzonitrile, methyl (4-((3-(4-cyano-3-(trifluoromethyl)phenyl)-2-(trifluoromethyl)oxazolidin-5-yl)methoxy)phenyl)carbamate, 2-(trifluoromethyl)-4-(2-(trifluoromethyl)-5-((4-(trifluoromethyl)phenoxy)methyl)oxazolidin-3-yl)benzonitrile, 4-(5-((4-(2-oxooxazolidin-3-yl)phenoxy)methyl)-2-(trifluoromethyl)oxazolidin-3-yl)-2-(trifluoromethyl)benzonitrile, N-(4-((3-(4-cyano-3-(trifluoromethyl)phenyl)-2-(trifluoromethyl)oxazolidin-5-yl)methoxy)phenyl)methanesulfonamide, 3-(4-((3-(4-cyano-3-(trifluoromethyl)phenyl)-2-(trifluoromethyl)oxazolidin-5-yl)methoxy)phenyl)-1,1-dimethylurea, ethyl (4-((3-(4-cyano-3-(trifluoromethyl)phenyl)-2-(trifluoromethyl)oxazolidin-5-yl)methoxy)phenyl)carbamate, isopropyl (4-((3-(4-cyano-3-(trifluoromethyl)phenyl)-2-(trifluoromethyl)oxazolidin-5-yl)methoxy)phenyl)carbamate, phenyl(4-((3-(4-cyano-3-(trifluoromethyl)phenyl)-2-(trifluoromethyl)oxazolidin-5-yl)methoxy)phenyl)carbamate, 5-((3-(4-cyano-3-(trifluoromethyl)phenyl)-2-(trifluoromethyl)oxazolidin-5-yl)methoxy)picolinonitrile, 5-((3-(4-cyano-3-(trifluoromethyl)phenyl)-2-(trifluoromethyl)oxazolidin-5-yl)methoxy)picolinonitrile, 4-(5-((3-cyanophenoxy)methyl)-2-(trifluoromethyl)oxazolidin-3-yl)-2-(trifluoromethyl)benzonitrile, 4-(5-((4-cyanophenoxy)methyl)-2-(hydroxymethyl)oxazolidin-3-yl)-2-(trifluoromethyl)benzonitrile, 4-(5-((4-cyanophenoxy)methyl)-2-((R)-2,2,2-trifluoro-1-hydroxyethyl)oxazolidin-3-yl)-2-(trifluoromethyl)benzonitrile, 4-(5-((4-cyanophenoxy)methyl)-2-((S)-2,2,2-trifluoro-1-hydroxyethyl)oxazolidin-3-yl)-2-(trifluoromethyl)benzonitrile, 2-amino-N-(4-((3-(4-cyano-3-(trifluoromethyl)phenyl)-2-(trifluoromethyl)oxazolidin-5-yl)methoxy)phenyl)acetamide, N-(4-((3-(4-cyano-3-(trifluoromethyl)phenyl)-2-(trifluoromethyl)oxazolidin-5-yl)methoxy)phenyl)pyrrolidine-2-carboxamide, 2-(4-((3-(4-cyano-3-(trifluoromethyl)phenyl)-2-(trifluoromethyl)oxazolidin-5-yl)methoxy)phenyl)acetic acid, 4-((3-(3-methyl-4-nitrophenyl)-2-(trifluoromethyl)oxazolidin-5-yl)methoxy)benzonitrile, N-(4-((3-(3-methyl-4-nitrophenyl)-2-(trifluoromethyl)oxazolidin-5-yl)methoxy)phenyl)acetamide, 5-((3-(3-methyl-4-nitrophenyl)-2-(trifluoromethyl)oxazolidin-5-yl)methoxy)picolinonitrile, 4-(5-((4-chlorophenoxy)methyl)-2-(trifluoromethyl)oxazolidin-3-yl)-2-(trifluoromethyl)benzonitrile, 4-(5-((4-((E)-(hydroxyimino)methyl)phenoxy)methyl)-2-(trifluoromethyl)oxazolidin-3-yl)-2-(trifluoromethyl)benzonitrile, 4-(5-(phenoxymethyl)-2-(trifluoromethyl)oxazolidin-3-yl)-2-(trifluoromethyl)benzonitrile, 4-(5-((pyridin-4-yloxy)methyl)-2-(trifluoromethyl)oxazolidin-3-yl)-2-(trifluoromethyl)benzonitrile, 4-(5-((pyridin-3-yloxy)methyl)-2-(trifluoromethyl)oxazolidin-3-yl)-2-(trifluoromethyl)benzonitrile, 4-(5-((4-cyanophenoxy)methyl)-2,2-dimethyloxazolidin-3-yl)-2-(trifluoromethyl)benzonitrile, 4-(5-((4-(methylsulfonyl)phenoxy)methyl)-2-(trifluoromethyl)oxazolidin-3-yl)-2-(trifluoromethyl)benzonitrile, 4-((3-(3,4-dichlorophenyl)-2-(trifluoromethyl)oxazolidin-5-yl)methoxy)benzonitrile, 4-((3-(4-nitro-3-(trifluoromethyl)phenyl)-2-(trifluoromethyl)oxazolidin-5-yl)methoxy)benzonitrile, 5-((3-(4-nitro-3-(trifluoromethyl)phenyl)-2-(trifluoromethyl)oxazolidin-5-yl)methoxy)picolinonitrile, 3-(4-nitro-3-(trifluoromethyl)phenyl)-5-((pyridin-4-yloxy)methyl)-2-(trifluoromethyl)oxazolidine, 4-(5-((4-(hydroxymethyl)phenoxy)methyl)-2-(trifluoromethyl)oxazolidin-3-yl)-2-(trifluoromethyl)benzonitrile, 4-(5-(((2-chloropyridin-4-yl)oxy)methyl)-2-(trifluoromethyl)oxazolidin-3-yl)-2-(trifluoromethyl)benzonitrile, 3-(3-methyl-4-nitrophenyl)-5-((pyridin-4-yloxy)methyl)-2-(trifluoromethyl)oxazolidine, (E)-4-((3-(3-methyl-4-nitrophenyl)-2-(trifluoromethyl)oxazolidin-5-yl)methoxy)benzaldehyde oxime, 2-chloro-4-(5-((4-cyanophenoxy)methyl)-2-(trifluoromethyl)oxazolidin-3-yl)benzonitrile, 2-chloro-4-(5-((pyridin-4-yloxy)methyl)-2-(trifluoromethyl)oxazolidin-3-yl)benzonitrile, 5-((3-(3-chloro-4-cyanophenyl)-2-(trifluoromethyl)oxazolidin-5-yl)methoxy)picolinonitrile, 2-chloro-4-(5-((4-((E)-(hydroxyimino)methyl)phenoxy)methyl)-2-(trifluoromethyl)oxazolidin-3-yl)benzonitrile, 2-chloro-4-(5-((4-cyanophenoxy)methyl)-2-(trifluoromethyl)oxazolidin-3-yl)-3-methylbenzonitrile, 2-chloro-3-methyl-4-(5-((pyridin-4-yloxy)methyl)-2-(trifluoromethyl)oxazolidin-3-yl)benzonitrile, 5-((3-(3-chloro-4-cyano-2-methylphenyl)-2-(trifluoromethyl)oxazolidin-5-yl)methoxy)picolinonitrile, 2-chloro-4-(5-((4-((E)-(hydroxyimino)methyl)phenoxy)methyl)-2-(trifluoromethyl)oxazolidin-3-yl)-3-methylbenzonitrile, 5-(((6-bromopyridin-3-yl)oxy)methyl)-3-(3-methyl-4-nitrophenyl)-2-(trifluoromethyl)oxazolidine, 4-(((pyridin-4-yloxy)methyl)-2-(trifluoromethyl)oxazolidin-3-yl)-2-(trifluoromethyl)benzonitrile, 4-((3-(4-nitro-3-(trifluoromethyl)phenyl)-2-(trifluoromethyl)oxazolidin-5-yl)methoxy)benzonitrile, 4-((3-(3-methyl-4-nitrophenyl)-2-(trifluoromethyl)oxazolidin-5-yl)methoxy)benzonitrile, 2-chloro-4-(5-((4-cyanophenoxy)methyl)-2-(trifluoromethyl)oxazolidin-3-yl)benzonitrile, 2-chloro-4-(5-((4-cyanophenoxy)methyl)-2-(trifluoromethyl)oxazolidin-3-yl)-3-methylbenzonitrile, 4-(5-((4-((E)-(methoxyimino)methyl)phenoxy)methyl)-2-(trifluoromethyl)oxazolidin-3-yl)-2-(trifluoromethyl)benzonitrile, 4-(5-((4-((E)-(hydroxyimino)methyl)phenoxy)methyl)-2-(trifluoromethyl)oxazolidin-3-yl)-2-(trifluoromethyl)benzonitrile, (E)-4-((3-(4-nitro-3-(trifluoromethyl)phenyl)-2-(trifluoromethyl)oxazolidin-5-yl)methoxy)benzaldehyde oxime, (t-butyl (4-((3-(4-cyano-3-(trifluoromethyl)phenyl)-2-(trifluoromethyl)oxazolidin-5-yl)methoxy)benzyl)carbamate, 4-(5-((4-(aminomethyl)phenoxy)methyl)-2-(trifluoromethyl)oxazolidin-3-yl)-2-(trifluoromethyl)benzonitrile, N-(4-((3-(4-cyano-3-(trifluoromethyl)phenyl)-2-(trifluoromethyl)oxazolidin-5-yl)methoxy)benzyl)acetamide, 1-(4-((3-(4-cyano-3-(trifluoromethyl)phenyl)-2-(trifluoromethyl)oxazolidin-5-yl)methoxy)benzyl)urea, 1-(4-((3-(4-cyano-3-(trifluoromethyl)phenyl)-2-(trifluoromethyl)oxazolidin-5-yl)methoxy)benzyl)-3-methylurea, methyl (4-((3-(4-cyano-3-(trifluoromethyl)phenyl)-2-(trifluoromethyl)oxazolidin-5-yl)methoxy)benzyl)carbamate, N-(4-((3-(4-cyano-3-(trifluoromethyl)phenyl)-2-(trifluoromethyl)oxazolidin-5-yl)methoxy)phenyl)-2-hydroxyacetamide, 2-cyano-N-(4-((3-(4-cyano-3-(trifluoromethyl)phenyl)-2-(trifluoromethyl)oxazolidin-5-yl)methoxy)phenyl)acetamide, 2-(4-((3-(4-cyano-3-(trifluoromethyl)phenyl)-2-(trifluoromethyl)oxazolidin-5-yl)methoxy)phenyl)acetamide, 4-(3-(4-cyano-3-(trifluoromethyl)phenyl)-2-(trifluoromethyl)oxazolidin-5-yl)methoxy)benzamide, 4-(5-((4-((E)-(hydroxyimino)methyl)-2-nitrophenoxy)methyl)-2-(trifluoromethyl)oxazolidin-3-yl)-2-(trifluoromethyl)benzonitrile, 4-(5-((4-cyano-2-nitrophenoxy)methyl)-2-(trifluoromethyl)oxazolidin-3-yl)-2-(trifluoromethyl)benzonitrile, 4-(5-((2-amino-4-cyanophenoxy)methyl)-2-(trifluoromethyl)oxazolidin-3-yl)-2-(trifluoromethyl)benzonitrile, methyl (5-cyano-2-((3-(4-cyano-3-(trifluoromethyl)phenyl)-2-(trifluoromethyl)oxazolidin-5-yl)methoxy)phenyl)carbamate, 4-(5-(((4-cyanophenyl)amino)methyl)-2-(trifluoromethyl)oxazolidin-3-yl)-2-(trifluoromethyl)benzonitrile, 4-(5-(((4-cyanophenyl)amino)methyl)-2-(trifluoromethyl)oxazolidin-3-yl)-2-(trifluoromethyl)benzonitrile, N-(4-amino-2-fluorophenyl)-3-(4-cyano-3-(trifluoromethyl)phenyl)-2-(trifluoromethyl)oxazolidine-5-carboxamide, N-(4-acetamido-2-fluorophenyl)-3-(4-cyano-3-(trifluoromethyl)phenyl)-2-(trifluoromethyl)oxazolidine-5-carboxamide, 3-(4-cyano-3-(trifluoromethyl)phenyl)-N-(pyridin-4-yl)-2-(trifluoromethyl)oxazolidine-5-carboxamide, 3-(4-cyano-3-(trifluoromethyl)phenyl)-N-(6-cyanopyridin-3-yl)-2-(trifluoromethyl)oxazolidine-5-carboxamide, N-(4-acetamidophenyl)-3-(4-cyano-3-(trifluoromethyl)phenyl)-2-(trifluoromethyl)oxazolidine-5-carboxamide, 3-(4-cyano-3-(trifluoromethyl)phenyl)-N-(pyridin-3-yl)-2-(trifluoromethyl)oxazolidine-5-carboxamide, N-(4-cyanophenyl)-3-(3-methyl-4-nitrophenyl)-2-(trifluoromethyl)oxazolidine-5-carboxamide, N-(4-acetamidophenyl)-3-(3-methyl-4-nitrophenyl)-2-(trifluoromethyl)oxazolidine-5-carboxamide, N-(4-cyano-2-fluorophenyl)-3-(3-methyl-4-nitrophenyl)-2-(trifluoromethyl)oxazolidine-5-carboxamide, N-(2-chloro-4-cyanophenyl)-3-(4-cyano-3-(trifluoromethyl)phenyl)-2-(trifluoromethyl)oxazolidine-5-carboxamide, 3-(4-cyano-3-(trifluoromethyl)phenyl)-N-(2,4-difluorophenyl)-2-(trifluoromethyl)oxazolidine-5-carboxamide, N-(6-cyanopyridin-3-yl)-3-(3-methyl-4-nitrophenyl)-2-(trifluoromethyl)oxazolidine-5-carboxamide, 3-(3-chloro-4-cyanophenyl)-N-(4-cyanophenyl)-2-(trifluoromethyl)oxazolidine-5-carboxamide, N-(4-acetamidophenyl)-3-(3-chloro-4-cyanophenyl)-2-(trifluoromethyl)oxazolidine-5-carboxamide, 3-(3-chloro-4-cyanophenyl)-N-(4-cyano-2-fluorophenyl)-2-(trifluoromethyl)oxazolidine-5-carboxamide, 3-(3-chloro-4-cyanophenyl)-N-(6-cyanopyridin-3-yl)-2-(trifluoromethyl)oxazolidine-5-carboxamide, 3-(3-chloro-4-cyanophenyl)-N-(pyridin-4-yl)-2-(trifluoromethyl)oxazolidine-5-carboxamide, 3-(3-chloro-4-nitrophenyl)-N-(4-cyanophenyl)-2-(trifluoromethyl)oxazolidine-5-carboxamide, N-(4-acetamidophenyl)-3-(3-chloro-4-nitrophenyl)-2-(trifluoromethyl)oxazolidine-5-carboxamide, 3-(3-chloro-4-nitrophenyl)-N-(4-cyano-2-fluorophenyl)-2-(trifluoromethyl)oxazolidine-5-carboxamide, 3-(3-chloro-4-nitrophenyl)-N-(6-cyanopyridin-3-yl)-2-(trifluoromethyl)oxazolidine-5-carboxamide, 3-(3-chloro-4-nitrophenyl)-N-(pyridin-4-yl)-2-(trifluoromethyl)oxazolidine-5-carboxamide, 3-(4-cyano-3-(trifluoromethyl)phenyl)-N-(4-cyano-3-methoxyphenyl)-2-(trifluoromethyl)oxazolidine-5-carboxamide, N-(4-cyano-2-(trifluoromethyl)phenyl)-3-(4-cyano-3-(trifluoromethyl)phenyl)-2-(trifluoromethyl)oxazolidine-5-carboxamide, N-(4-cyano-2,6-difluorophenyl)-3-(4-cyano-3-(trifluoromethyl)phenyl)-2-(trifluoromethyl)oxazolidine-5-carboxamide, N-(3-chloro-4-cyano-2-fluorophenyl)-3-(4-cyano-3-(trifluoromethyl)phenyl)-2-(trifluoromethyl)oxazolidine-5-carboxamide, N-(4-cyano-2,5-difluorophenyl)-3-(4-cyano-3-(trifluoromethyl)phenyl)-2-(trifluoromethyl)oxazolidine-5-carboxamide, 3-(4-cyano-3-(trifluoromethyl)phenyl)-N-(3,4-dicyanophenyl)-2-(trifluoromethyl)oxazolidine-5-carboxamide, N-(4-cyano-2-methylphenyl)-3-(4-cyano-3-(trifluoromethyl)phenyl)-2-(trifluoromethyl)oxazolidine-5-carboxamide, N-(3-chloro-4-cyanophenyl)-3-(4-cyano-3-(trifluoromethyl)phenyl)-2-(trifluoromethyl)oxazolidine-5-carboxamide, N-(6-acetamidopyridin-3-yl)-3-(4-cyano-3-(trifluoromethyl)phenyl)-2-(trifluoromethyl)oxazolidine-5-carboxamide, 3-(3-chloro-4-cyanophenyl)-N-(2-chloropyridin-4-yl)-2-(trifluoromethyl)oxazolidine-5-carboxamide, N-(2-chloropyridin-4-yl)-3-(3-methyl-4-nitrophenyl)-2-(trifluoromethyl)oxazolidine-5-carboxamide, 3-(4-cyano-3-(trifluoromethyl)phenyl)-N-(4-cyanophenyl)-2-(trifluoromethyl)oxazolidine-5-carboxamide, N-(4-cyano-2-fluorophenyl)-3-(4-cyano-3-(trifluoromethyl)phenyl)-2-(trifluoromethyl)oxazolidine-5-carboxamide, 3-(4-cyano-3-(trifluoromethyl)phenyl)-N-(3,4-difluorophenyl)-2-(trifluoromethyl)oxazolidine-5-carboxamide, 3-(4-cyano-3-(trifluoromethyl)phenyl)-N-(3-cyanophenyl)-2-(trifluoromethyl)oxazolidine-5-carboxamide, N-(2-chloropyridin-4-yl)-3-(4-cyano-3-(trifluoromethyl)phenyl)-2-(trifluoromethyl)oxazolidine-5-carboxamide, N-(4-cyano-2,3,5,6-tetrafluorophenyl)-3-(4-cyano-3-(trifluoromethyl)phenyl)-2-(trifluoromethyl)oxazolidine-5-carboxamide, N,3-bis(4-cyano-3-(trifluoromethyl)phenyl)-2-(trifluoromethyl)oxazolidine-5-carboxamide, N-(4-cyano-2-ethylphenyl)-3-(4-cyano-3-(trifluoromethyl)phenyl)-2-(trifluoromethyl)oxazolidine-5-carboxamide, N-(2-chloro-4-cyano-6-methylphenyl)-3-(4-cyano-3-(trifluoromethyl)phenyl)-2-(trifluoromethyl)oxazolidine-5-carboxamide, 3-(4-cyano-3-(trifluoromethyl)phenyl)-N-(4-cyano-3-fluorophenyl)-2-(trifluoromethyl)oxazolidine-5-carboxamide, 3-(4-cyano-3-(trifluoromethyl)phenyl)-N-(4-hydroxyphenyl)-2-(trifluoromethyl)oxazolidine-5-carboxamide, 3-(3-chloro-4-nitrophenyl)-N-(6-chloropyridin-3-yl)-2-(trifluoromethyl)oxazolidine-5-carboxamide, N-(4-acetamidophenyl)-3-(4-nitro-3-(trifluoromethyl)phenyl)-2-(trifluoromethyl)oxazolidine-5-carboxamide, N-(2-chloro-4-nitrophenyl)-3-(4-cyano-3-(trifluoromethyl)phenyl)-2-(trifluoromethyl)oxazolidine-5-carboxamide, N-(4-amino-2-chlorophenyl)-3-(4-cyano-3-(trifluoromethyl)phenyl)-2-(trifluoromethyl)oxazolidine-5-carboxamide, N-(4-acetamido-2-chlorophenyl)-3-(4-cyano-3-(trifluoromethyl)phenyl)-2-(trifluoromethyl)oxazolidine-5-carboxamide, methyl(3-chloro-4-(3-(4-cyano-3-(trifluoromethyl)phenyl)-2-(trifluoromethyl)oxazolidine-5-carboxamido)phenyl)carbamate, 3-(4-cyano-3-(trifluoromethyl)phenyl)-N-(4-nitrophenyl)-2-(trifluoromethyl)oxazolidine-5-carboxamide, N-(4-aminophenyl)-3-(4-cyano-3-(trifluoromethyl)phenyl)-2-(trifluoromethyl)oxazolidine-5-carboxamide, methyl (4-(3-(4-cyano-3-(trifluoromethyl)phenyl)-2-(trifluoromethyl)oxazolidine-5-carboxamido)phenyl)carbamate, 3-(4-cyano-3-(trifluoromethyl)phenyl)-N-(4-propionamidophenyl)-2-(trifluoromethyl)oxazolidine-5-carboxamide, 3-(4-cyano-3-(trifluoromethyl)phenyl)-N-(4-isobutylamidophenyl)-2-(trifluoromethyl)oxazolidine-5-carboxamide, 3-(4-cyano-3-(trifluoromethyl)phenyl)-N-(4-(2-hydroxyacetamido)phenyl)-2-(trifluoromethyl)oxazolidine-5-carboxamide, 3-(4-cyano-3-(trifluoromethyl)phenyl)-2-(trifluoromethyl)-N-(4-ureidophenyl)oxazolidine-5-carboxamide, 3-(4-cyano-3-(trifluoromethyl)phenyl)-N-(4-(2-cyanoacetamido)phenyl)-2-(trifluoromethyl)oxazolidine-5-carboxamide, N-(4-(2-aminoacetamido)phenyl)-3-(4-cyano-3-(trifluoromethyl)phenyl)-2-(trifluoromethyl)oxazolidine-5-carboxamide, 3-(4-cyano-3-(trifluoromethyl)phenyl)-N-(4-cyanophenyl)-2-(trifluoromethyl)oxazolidine-5-carboxamide, 4-(5-(((4-cyanophenyl)sulfonyl)methyl)-2-(trifluoromethyl)oxazolidin-3-yl)-2-(trifluoromethyl)benzonitrile, t-butyl 4-(3-(4-cyano-3-(trifluoromethyl)phenyl)-2-(trifluoromethyl)oxazolidine-5-carboxamido)piperidine-1-carboxylate, 3-(4-cyano-3-(trifluoromethyl)phenyl)-N-(piperidin-4-yl)-2-(trifluoromethyl)oxazolidine-5-carboxamide, and N-(1-acetylpiperidin-4-yl)-3-(4-cyano-3-(trifluoromethyl)phenyl)-2-(trifluoromethyl)oxazolidine-5-carboxamide According to an embodiment of the present invention, $R_1$ of Chemical Formula 1 may be a substituent represented by the following Chemical Formula 3, and may be a compound selected from the group consisting of the following compounds, an isomer thereof, or a pharmaceutically acceptable salt thereof:

4-(5-(4-isocyanopiperidine-1-carbonyl)-2-(trifluoromethyl)oxazolidin-3-yl)-2-(trifluoromethyl)benzonitrile, 4-(5-(piperazine-1-carbonyl)-2-(trifluoromethyl)oxazolidin-3-yl)-2-(trifluoromethyl)benzonitrile, 4-(5-(4-acetylpiperazine-1-carbonyl)-2-(trifluoromethyl)oxazolidin-3-yl)-2-(trifluoromethyl)benzonitrile, methyl 4-(3-(4-cyano-3-(trifluoromethyl)phenyl)-2-(trifluoromethyl)oxazolidine-5-carbonyl)piperazine-1-carboxylate, 4-(3-(4-cyano-3-(trifluoromethyl)phenyl)-2-(trifluoromethyl)oxazolidine-5-carbonyl)piperazine-1-carbonitrile, 4-(5-(4-aminopiperidine-1-carbonyl)-2-(trifluoromethyl)oxazolidin-3-yl)-2-(trifluoromethyl)benzonitrile, 4-(5-(4-acetylpiperazine-1-carbonyl)-2-(trifluoromethyl)oxazolidin-3-yl)-2-(trifluoromethyl)benzonitrile, t-butyl 4-(3-(4-cyano-3-(trifluoromethyl)phenyl)-2-(trifluoromethyl)oxazolidine-5-carboxamido)piperidine-1-carboxylate, methyl 4-(3-(3-chloro-4-cyanophenyl)-2-(trifluoromethyl)oxazolidine-5-carbonyl)piperazine-1-carboxylate methyl 4-(3-(3-methyl-4-nitrophenyl)-2-(trifluoromethyl)oxazolidine-5-carbonyl)piperazine-1-carboxylate, methyl (2-(3-(4-cyano-3-(trifluoromethyl)phenyl)-2-(trifluoromethyl)oxazolidine-5-carboxamido)ethyl)carbamate, 4-(5-(4-(methylsulfonyl)piperazine-1-carbonyl)-2-(trifluoromethyl)oxazolidin-3-yl)-2-(trifluoromethyl)benzonitrile, 4-(5-(4-isopropylpiperazine-1-carbonyl)-2-(trifluoromethyl)oxazolidin-3-yl)-2-(trifluoromethyl)benzonitrile, 4-(5-(4-(2-cyanoethyl)piperazine-1-carbonyl)-2-(trifluoromethyl)oxazolidin-3-yl)-2-(trifluoromethyl)benzonitrile, 4-(5-(4-(2-hydroxyethyl)piperazine-1-carbonyl)-2-(trifluoromethyl)oxazolidin-3-yl)-2-trifluoromethyl)benzonitrile, 1-((3-(4-cyano-3-(trifluoromethyl)phenyl)-2-(trifluoromethyl)oxazolidin-5-yl)methyl)piperidine-4-carbonitrile, 1-(3-(4-cyano-3-(trifluoromethyl)phenyl)-2-(trifluoromethyl)oxazolidine-5-carbonyl)piperidine-4-carboxamide, ethyl 4-(3-(4-cyano-3-(trifluoromethyl)phenyl)-2-(trifluoromethyl)oxazolidine-5-carbonyl)piperazine-1-carboxylate, 4-(3-(4-cyano-3-(trifluoromethyl)phenyl)-2-(trifluoromethyl)oxazolidine-5-carbonyl)piperazine-1-carboxamide, methyl 4-(3-(3-chloro-4-nitrophenyl)-2-(trifluoromethyl)oxazolidine-5-carbonyl)piperazine-1-carboxylate, methyl 4-(3-(4-nitro-3-(trifluoromethyl)phenyl)-2-(trifluoromethyl)oxazolidine-5-carbonyl)piperazine-1-carboxylate, methyl 4-(3-(4-cyano-3-(trifluoromethyl)phenyl)-2-(trifluoromethyl)oxazolidine-5-carbonyl)-1,4-diazepane-1-carboxylate, and methyl ((R)-1-(3-(4-cyano-3-(trifluoromethyl)phenyl)-2-(trifluoromethyl)oxazolidine-5-carbonyl)pyrrolidin-3-yl)carbamate.

According to an embodiment of the present invention, $R_1$ of Chemical Formula 1 may be a substituent represented by the following Chemical Formula 2, and may be an isomer of a compound selected from the group consisting of the following compounds, or a pharmaceutically acceptable salt thereof:

4-((2R,5S)-5-(hydroxymethyl)-2-(trifluoromethyl)oxazolidin-3-yl)-2-(trifluoromethyl)benzonitrile, 4-((2R,5S)-5-(((4-cyanobenzyl)oxy)methyl)-2-(trifluoromethyl)oxazolidin-3-yl)-2-(trifluoromethyl)benzonitrile, 4-((2S,5R)-5-(hydroxymethyl)-2-(trifluoromethyl)oxazolidin-3-yl)-2-(trifluoromethyl)benzonitrile, 4-((2S,5R)-5-(((4-cyanobenzyl)oxy)methyl)-2-(trifluoromethyl)oxazolidin-3-yl)-2-(trifluoromethyl)benzonitrile, 4-((2R,5R)-5-((4-cyanophenoxy)methyl)-2-(trifluoromethyl)oxazolidin-3-yl)-2-(trifluoromethyl)benzonitrile, 4-((2S,5S)-5-((4-cyanophenoxy)methyl)-2-(trifluoromethyl)oxazolidin-3-yl)-2-(trifluoromethyl)benzonitrile, methyl 4-(((2R,5S)-3-(4-cyano-3-(trifluoromethyl)phenyl)-2-(trifluoromethyl)oxazolidin-5-yl)methoxy)benzoate, 4-((2R,5S)-5-((4-nitrophenoxy)methyl)-2-(trifluoromethyl)oxazolidin-3-yl)-2-(trifluoromethyl)benzonitrile, 4-(((2R,5S)-3-(4-cyano-3-(trifluoromethyl)phenyl)-2-(trifluoromethyl)oxazolidin-5-yl)methoxy)benzoic acid, 4-((2R,5S)-5-((3,4-difluorophenoxy)methyl)-2-(trifluoromethyl)oxazolidin-3-yl)-2-(trifluoromethyl)benzonitrile, 4-((2R,5S)-5-((4-cyano-2-fluorophenoxy)methyl)-2-(trifluoromethyl)oxazolidin-3-yl)-2-(trifluoromethyl)benzonitrile, 4-((2R,5S)-5-((2-chloro-4-nitrophenoxy)methyl)-2-(trifluoromethyl)oxazolidin-3-yl)-2-(trifluoromethyl)benzonitrile, 2-(trifluoromethyl)-4-((2R,5S)-2-(trifluoromethyl)-5-((2,4,5-trifluorophenoxy)methyl)oxazolidin-3-yl)benzonitrile, 4-((2R,5S)-5-((4-aminophenoxy)methyl)-2-(trifluoromethyl)oxazolidin-3-yl)-2-(trifluoromethyl)benzonitrile, 1-(4-(((2R,5S)-3-(4-cyano-3-(trifluoromethyl)phenyl)-2-(trifluoromethyl)oxazolidin-5-yl)methoxy)phenyl)urea, 1-(4-(((2R,5S)-3-(4-cyano-3-(trifluoromethyl)phenyl)-2-(trifluoromethyl)oxazolidin-5-yl)methoxy)phenyl)-3-methylurea, 4-((2R,5S)-5-((4-(2-oxopyrrolidin-1-yl)phenoxy)methyl)-2-(trifluoromethyl)oxazolidin-3-yl)-2-(trifluoromethyl)benzonitrile, 4-((2R,5S)-5-((4-(1,3,4-oxadiazol-2-yl)phenoxy)methyl)-2-(trifluoromethyl)oxazolidin-3-yl)-2-(trifluoromethyl)benzonitrile, 4-((2R,5S)-5-((4-cyanophenoxy)methyl)-2-(trifluoromethyl)oxazolidin-3-yl)-2-(trifluoromethyl)benzonitrile, 4-((2S,5R)-5-((4-cyanophenoxy)methyl)-2-(trifluoromethyl)oxazolidin-3-yl)-2-(trifluoromethyl)benzonitrile, 4-((2S,5R)-5-((R)-2,2,2-trifluoro-1-hydroxyethyl)-2-(trifluoromethyl)oxazolidin-3-yl)-2-(trifluoromethyl)benzonitrile, 4-((2S,5R)-5-((S)-2,2,2-trifluoro-1-hydroxyethyl)-2-(trifluoromethyl)oxazolidin-3-yl)-2-(trifluoromethyl)benzonitrile, 4-((2R,5S)-5-((R)-2,2,2-trifluoro-1-hydroxyethyl)-2-(trifluoromethyl)oxazolidin-3-yl)-2-(trifluoromethyl)benzonitrile, 4-((2R,5S)-5-((S)-2,2,2-trifluoro-1-hydroxyethyl)-2-(trifluoromethyl)oxazolidin-3-yl)-2-(trifluoromethyl)benzonitrile, N-(4-(((2R,5S)-3-(4-cyano-3-(trifluoromethyl)phenyl)-2-(trifluoromethyl)oxazolidin-5-yl)methoxy)phenyl)acetamide, 4-((2R,5S)-5-(((4-chlorophenyl)thio)methyl)-2-(trifluoromethyl)oxazolidin-3-yl)-2-(trifluoromethyl)benzonitrile, 4-((2R,5S)-5-((4-methoxyphenoxy)methyl)-2-(trifluoromethyl)oxazolidin-3-yl)-2-(trifluoromethyl)benzonitrile, 4-((2R,5S)-5-((3-methoxyphenoxy)methyl)-2-(trifluoromethyl)oxazolidin-3-yl)-2-(trifluoromethyl)benzonitrile, 4-((2R,5S)-5-(((4-cyanophenyl)thio)methyl)-2-(trifluoromethyl)oxazolidin-3-yl)-2-(trifluoromethyl)benzonitrile, N-(4-(((2S,5S)-3-(4-cyano-3-(trifluoromethyl)phenyl)-2-(trifluoromethyl)oxazolidin-5-yl)methoxy)phenyl)acetamide, 4-(2R,5S)-5-((3-fluoro-4-nitrophenoxy)methyl)-2-(trifluoromethyl)oxazolidin-3-yl)-2-(trifluoromethyl)benzonitrile, 4-(((2R,5S)-3-(4-cyano-3-(trifluoromethyl)phenyl)-2-(trifluoromethyl)oxazolidin-5-yl)methoxy)-N-methylbenzamide, 4-((2R,5S)-5-((2-fluoro-4-nitrophenoxy)methyl)-2-(trifluoromethyl)oxazolidin-3-yl)-2-(trifluoromethyl)benzonitrile, 4-(((2R,5S)-3-(4-cyano-3-(trifluoromethyl)phenyl)-2-(trifluoromethyl)oxazolidin-5-yl)methoxy)-N,N-dimethylbenzamide, 4-((2S,5S)-5-((4-nitrophenoxy)methyl)-2-(trifluoromethyl)oxazolidin-3-yl)-2-(trifluoromethyl)benzonitrile, methyl (4-(((2R,5S)-3-(4-cyano-3-(trifluoromethyl)phenyl)-2-(trifluoromethyl)oxazolidin-5-yl)methoxy)phenyl)carbamate, 2-(trifluoromethyl)-4-((2R,5S)-2-(trifluoromethyl)-5-((4-(trifluoromethyl)phenoxy)methyl)oxazolidin-3-yl)benzonitrile, 4-((2R,5S)-5-((4-(2-oxooxazolidin-3-yl)phenoxy)methyl)-2-(trifluoromethyl)oxazolidin-3-yl)-2-(trifluoromethyl)benzonitrile, N-(4-(((2R,5S)-3-(4-cyano-3-(trifluoromethyl)phenyl)-2-(trifluoromethyl)oxazolidin-5-yl)methoxy)phenyl)methanesulfonamide, 3-(4-(((2R,5S)-3-(4-cyano-3-(trifluoromethyl)phenyl)-2-(trifluoromethyl)oxazolidin-5-yl)methoxy)phenyl)-1,1-dimethylurea, ethyl (4-(((2R,5S)-3-(4-cyano-3-(trifluoromethyl)phenyl)-2-(trifluoromethyl)oxazolidin-5-yl)methoxy)phenyl)carbamate, isopropyl (4-(((2R,5S)-3-(4-cyano-3-(trifluoromethyl)phenyl)-2-(trifluoromethyl)oxazolidin-5-yl)methoxy)phenyl)carbamate, phenyl(4-(((2R,5S)-3-(4-cyano-3-(trifluoromethyl)phenyl)-2-(trifluoromethyl)oxazolidin-5-yl)methoxy)phenyl)carbamate, 5-(((2R,5S)-3-(4-cyano-3-(trifluoromethyl)phenyl)-2-(trifluoromethyl)oxazolidin-5-yl)methoxy)picolinonitrile, 5-(((2S,5S)-3-(4-cyano-3-(trifluoromethyl)phenyl)-2-(trifluoromethyl)oxazolidin-5-yl)methoxy)picolinonitrile, 4-((2R,5S)-5-((3-cyanophenoxy)methyl)-2-(trifluoromethyl)oxazolidin-3-34)-2-(trifluoromethyl)benzonitrile, 4-((2R,5S)-5-((4-cyanophenoxy)methyl)-2-(hydroxymethyl)oxazolidin-3-yl)-2-(trifluoromethyl)benzonitrile, 4-((2R,5S)-5-((4-cyanophenoxy)methyl)-2-((R)-2,2,2-trifluoro-1-hydroxyethyl)oxazolidin-3-yl)-2-(trifluoromethyl)benzonitrile, 4-((2R,5S)-5-((4-cyanophenoxy)methyl)-2-((S)-2,2,2-trifluoro-1-hydroxyethyl)oxazolidin-3-yl)-2-(trifluoromethyl)benzonitrile, 2-amino-N-(4-(((2R,5S)-3-(4-cyano-3-(trifluoromethyl)phenyl)-2-(trifluoromethyl)oxazolidin-5-yl)methoxy)phenyl)acetamide, (S)-N-(4-(((2R,5S)-3-(4-cyano-3-(trifluoromethyl)phenyl)-2-(trifluoromethyl)oxazolidin-5-yl)methoxy)phenyl)pyrrolidine-2-carboxamide, 2-(4-(((2R,5S)-3-(4-cyano-3-(trifluoromethyl)phenyl)-2-(trifluoromethyl)oxazolidin-5-yl)methoxy)phenyl)acetic acid, 4-(((2R,5S)-3-(3-methyl-4-nitrophenyl)-2-(trifluoromethyl)oxazolidin-5-yl)methoxy)benzonitrile, N-(4-(((2R,5S)-3-(3-methyl-4-nitrophenyl)-2-(trifluoromethyl)oxazolidin-5-yl)methoxy)phenyl)acetamide, 5-(((2R,5S)-3-(3-methyl-4-nitrophenyl)-2-(trifluoromethyl)oxazolidin-5-yl)methoxy)picolinonitrile, 4-((2R,5S)-5-((4-chlorophenoxy)methyl)-2-(trifluoromethyl)oxazolidin-3-34)-2-(trifluoromethyl)benzonitrile, 4-((2R,5S)-5-((4-((E)-(hydroxyimino)methyl)phenoxy)methyl)-2-(trifluoromethyl)oxazolidin-3-yl)-2-(trifluoromethyl)benzonitrile, 4-((2R,5S)-5-(phenoxymethyl)-2-(trifluoromethyl)oxazolidin-3-yl)-2-(trifluoromethyl)benzonitrile, 4-((2R,5S)-5-((pyridin-4-yloxy)methyl)-2-(trifluoromethyl)oxazolidin-3-yl)-2-(trifluoromethyl)benzonitrile, 4-((2R,5S)-5-((pyridin-3-yloxy)methyl)-2-(trifluoromethyl)oxazolidin-3-yl)-2-(trifluoromethyl)benzonitrile, (S)-4-(5-((4-cyanophenoxy)methyl)-2,2-dimethyloxazolidin-3-yl)-2-(trifluoromethyl)benzonitrile, 4-((2R,5S)-5-((4-(methylsulfonyl)phenoxy)methyl)-2-(trifluoromethyl)oxazolidin-3-yl)-2-(trifluoromethyl)benzonitrile, 4-(((2R,5S)-3-(3,4-dichlorophenyl)-2-(trifluoromethyl)oxazolidin-5-yl)methoxy)benzonitrile, 4-(((2R,5S)-3-(4-nitro-3-(trifluoromethyl)phenyl)-2-(trifluoromethyl)oxazolidin-5-yl)methoxy)benzonitrile, 5-(((2R,5S)-3-(4-nitro-3-(trifluoromethyl)phenyl)-2-(trifluoromethyl)oxazolidin-5-yl)methoxy)picolinonitrile, (2R,5S)-3-(4-nitro-3-(trifluoromethyl)phenyl)-5-((pyridin-4-yloxy)methyl)-2-(trifluoromethyl)oxazolidine, 4-((2R,5S)-5-((4-(hydroxymethyl)phenoxy)methyl)-2-(trifluoromethyl)oxazolidin-3-yl)-2-(trifluoromethyl)benzonitrile, 4-((2R,5S)-5-(((2-chloropyridin-4-yl)oxy)methyl)-2-(trifluoromethyl)oxazolidin-3-yl)-2-(trifluoromethyl)benzonitrile, (2R,5S)-3-(3-methyl-4-nitrophenyl)-5-((pyridin-4-yloxy)methyl)-2-(trifluoromethyl)oxazolidine, (E)-4-(((2R,5S)-3-(3-methyl-4-nitrophenyl)-2-(trifluoromethyl)oxazolidin-5-yl)methoxy)benzaldehyde oxime, 2-chloro-4-((2R,5S)-5-((4-cyanophenoxy)methyl)-2-(trifluoromethyl)oxazolidin-3-yl)benzonitrile, 2-chloro-4-((2R,5S)-5-((pyridin-4-yloxy)methyl)-2-(trifluoromethyl)oxazolidin-3-yl)benzonitrile, 5-(((2R,5S)-3-(3-chloro-4-cyanophenyl)-2-(trifluoromethyl)oxazolidin-5-yl)methoxy)picolinonitrile, 2-chloro-4-((2R,5S)-5-((4-((E)-(hydroxyimino)methyl)phenoxy)methyl)-2-(trifluoromethyl)oxazolidin-3-yl)benzonitrile, 2-chloro-4-((2R,5S)-5-((4-cyanophenoxy)methyl)-2-(trifluoromethyl)oxazolidin-3-yl)-3-methylbenzonitrile, 2-chloro-3-methyl-4-((2R,5S)-5-((pyridin-4-yloxy)methyl)-2-(trifluoromethyl)oxazolidin-3-yl)benzonitrile, 5-(((2R,5S)-3-(3-chloro-4-cyano-2-methylphenyl)-2-(trifluoromethyl)oxazolidin-5-yl)methoxy)picolinonitrile, 2-chloro-4-((2R,5S)-5-((4-((E)-(hydroxyimino)methyl)phenoxy)methyl)-2-(trifluoromethyl)oxazolidin-3-yl)-3-methylbenzonitrile, (2R,5S)-5-(((6-bromopyridin-3-yl)oxy)methyl)-3-(3-methyl-4-nitronyl)-2-(trifluoromethyl)oxazolidine, 4-((2S,5S)-5-((pyridin-4-yloxy)methyl)-2-(trifluoromethyl)oxazolidin-3-yl)-2-(trifluoromethyl)benzonitrile, 4-(((2S,5S)-3-(4-nitro-3-(trifluoromethyl)phenyl)-2-(trifluoromethyl)oxazolidin-5-yl)methoxy)benzonitrile, 4-(((2S,5S)-3-(3-methyl-4-nitrophenyl)-2-(trifluoromethyl)oxazolidin-5-yl)methoxy)benzonitrile, 2-chloro-4-((2S,5S)-5-((4-cyanophenoxy)methyl)-2-(trifluoromethyl)oxazolidin-3-yl)benzonitrile, 2-chloro-4-((2S,5S)-5-((4-cyanophenoxy)methyl)-2-(trifluoromethyl)oxazolidin-3-yl)-3-methylbenzonitrile, 4-((2R,5S)-5-((4-((E)-(methoxyimino)methyl)phenoxy)methyl)-2-(trifluoromethyl)oxazolidin-3-yl)-2-(trifluoromethyl)benzonitrile, 4-((2R,5S)-5-((4-((E)-(hydroxyimino)methyl)phenoxy)methyl)-2-(trifluoromethyl)oxazolidin-3-yl)-2-(trifluoromethyl)benzonitrile, (E)-4-(((2R,5S)-3-(4-nitro-3-(trifluoromethyl)phenyl)-2-(trifluoromethyl)oxazolidin-5-yl)methoxy)benzaldehyde oxime, (t-butyl (4-(((2R,5S)-3-(4-cyano-3-(trifluoromethyl)phenyl)-2-(trifluoromethyl)oxazolidin-5-yl)methoxy)benzyl)carbamate, 4-((2R,5S)-5-((4-(aminomethyl)phenoxy)methyl)-2-(trifluoromethyl)oxazolidin-3-yl)-2-(trifluoromethyl)benzonitrile, N-(4-(((2R,5S)-3-(4-cyano-3-(trifluoromethyl)phenyl)-2-(trifluoromethyl)oxazolidin-5-yl)methoxy)benzyl)acetamide, 1-(4-(((2R,5S)-3-(4-cyano-3-(trifluoromethyl)phenyl)-2-(trifluoromethyl)oxazolidin-5-yl)methoxy)benzyl)urea, 1-(4-(((2R,5S)-3-(4-cyano-3-(trifluoromethyl)phenyl)-2-(trifluoromethyl)oxazolidin-5-yl)methoxy)benzyl)-3-methylurea, methyl (4-(((2R,5S)-3-(4-cyano-3-(trifluoromethyl)phenyl)-2-(trifluoromethyl)oxazolidin-5-yl)methoxy)benzyl)carbamate, N-(4-(((2R,5S)-3-(4-cyano-3-(trifluoromethyl)phenyl)-2-(trifluoromethyl)oxazolidin-5-yl)methoxy)phenyl)-2-hydroxyacetamide, 2-cyano-N-(4-(((2R,5S)-3-(4-cyano-3-(trifluoromethyl)phenyl)-2-(trifluoromethyl)oxazolidin-5-yl)methoxy)phenyl)acetamide, 2-(4-(((2R,5S)-3-(4-cyano-3-(trifluoromethyl)phenyl)-2-(trifluoromethyl)oxazolidin-5-yl)methoxy)phenyl)acetamide, 4-(((2R,5S)-3-(4-cyano-3-(trifluoromethyl)phenyl)-2-(trifluoromethyl)oxazolidin-5-yl)methoxy)benzamide, 4-((2R,5S)-5-((4-((E)-(hydroxyimino)methyl)-2-nitrophenoxy)methyl)-2-(trifluoromethyl)oxazolidin-3-yl)-2-(trifluoromethyl)benzonitrile, 4-((2R,5S)-5-((4-cyano-2-nitrophenoxy)methyl)-2-(trifluoromethyl)oxazolidin-3-yl)-2-(trifluoromethyl)benzonitrile, 4-((2R,5S)-5-((2-amino-4-cyanophenoxy)methyl)-2-(trifluoromethyl)oxazolidin-3-yl)-2-(trifluoromethyl)benzonitrile, methyl (5-cyano-2-(((2R,5S)-3-(4-cyano-3-(trifluoromethyl)phenyl)-2-(trifluoromethyl)oxazolidin-5-yl)methoxy)phenyl)carbamate, 4-((2R,5R)-5-(((4-cyanophenyl)amino)methyl)-2-(trifluoromethyl)oxazolidin-3-yl)-2-(trifluoromethyl)benzonitrile, 4-((2R,5R)-5-(((4-cyanophenyl)amino)methyl)-2-(trifluoromethyl)oxazolidin-3-yl)-2-(trifluoromethyl)benzonitrile, (2R,5S)-N-(4-amino-2-fluorophenyl)-3-(4-cyano-3-(trifluoromethyl)phenyl)-2-(trifluoromethyl)oxazolidine-5-carboxamide, (2R,5S)-N-(4-acetamido-2-fluorophenyl)-3-(4-cyano-3-(trifluoromethyl)phenyl)-2-(trifluoromethyl)oxazolidine-5-carboxamide, (2R,5S)-3-(4-cyano-3-(trifluoromethyl)phenyl)-N-(pyridin-4-yl)-2-(trifluoromethyl)oxazolidine-5-carboxamide, (2R,5S)-3-(4-cyano-3-(trifluoromethyl)phenyl)-N-(6-cyanopyridin-3-yl)-2-(trifluoromethyl)oxazolidine-5-carboxamide, (2R,5S)-N-(4-acetamidophenyl)-3-(4-cyano-3-(trifluoromethyl)phenyl)-2-(trifluoromethyl)oxazolidine-5-carboxamide, (2R,5S)-3-(4-cyano-3-(trifluoromethyl)phenyl)-N-(pyridin-3-yl)-2-(trifluoromethyl)oxazolidine-5-carboxamide, (2R,5S)-N-(4-cyanophenyl)-3-(3-methyl-4-nitrophenyl)-2-(trifluoromethyl)oxazolidine-5-carboxamide, (2R,5S)-N-(4-acetamidophenyl)-3-(3-methyl-4-nitrophenyl)-2-(trifluoromethyl)oxazolidine-5-carboxamide, (2R,5S)-N-(4-cyano-2-fluorophenyl)-3-(3-methyl-4-nitrophenyl)-2-(trifluoromethyl)oxazolidine-5-carboxamide, (2R,5S)-N-(2-chloro-4-cyanophenyl)-3-(4-cyano-3-(trifluoromethyl)phenyl)-2-(trifluoromethyl)oxazolidine-5-carboxamide, (2R,5S)-3-(4-cyano-3-(trifluoromethyl)phenyl)-N-(2,4-difluorophenyl)-2-(trifluoromethyl)oxazolidine-5-carboxamide, (2R,5S)-N-(6-cyanopyridin-3-yl)-3-(3-methyl-4-nitrophenyl)-2-(trifluoromethyl)oxazolidine-5-carboxamide, (2R,5S)-3-(3-chloro-4-cyanophenyl)-N-(4-cyanophenyl)-2-(trifluoromethyl)oxazolidine-5-carboxamide, (2R,5S)-N-(4-acetamidophenyl)-3-(3-chloro-4-cyanophenyl)-2-(trifluoromethyl)oxazolidine-5-carboxamide, (2R,5S)-3-(3-chloro-4-cyanophenyl)-N-(4-cyano-2-fluorophenyl)-2-(trifluoromethyl)oxazolidine-5-carboxamide, (2R,5S)-3-(3-chloro-4-cyanophenyl)-N-(6-cyanopyridin-3-yl)-2-(trifluoromethyl)oxazolidine-5-carboxamide, (2R,5S)-3-(3-chloro-4-cyanophenyl)-N-(pyridin-4-yl)-2-(trifluoromethyl)oxazolidine-5-carboxamide, (2R,5S)-3-(3-chloro-4-nitrophenyl)-N-(4-cyanophenyl)-2-(trifluoromethyl)oxazolidine-5-carboxamide, (2R,5S)-N-(4-acetamidophenyl)-3-(3-chloro-4-nitrophenyl)-2-(trifluoromethyl)oxazolidine-5-carboxamide, (2R,5S)-3-(3-chloro-4-nitrophenyl)-N-(4-cyano-2-fluorophenyl)-2-(trifluoromethyl)oxazolidine-5-carboxamide, (2R,5S)-3-(3-chloro-4-nitrophenyl)-N-(6-cyanopyridin-3-yl)-2-(trifluoromethyl)oxazolidine-5-carboxamide, (2R,5S)-3-(3-chloro-4-nitrophenyl)-N-(pyridin-4-yl)-2-(trifluoromethyl)oxazolidine-5-carboxamide, (2R,5S)-3-(4-cyano-3-(trifluoromethyl)phenyl)-N-(4-cyano-3-methoxyphenyl)-2-(trifluoromethyl)oxazolidine-5-carboxamide, (2R,5S)-N-(4-cyano-2-(trifluoromethyl)phenyl)-3-(4-cyano-3-(trifluoromethyl)phenyl)-2-(trifluoromethyl)oxazolidine-5-carboxamide, (2R,5S)-N-(4-cyano-2,6-difluorophenyl)-3-(4-cyano-3-(trifluoromethyl)phenyl)-2-(trifluoromethyl)oxazolidine-5-carboxamide, (2R,5S)-N-(3-chloro-4-cyano-2-fluorophenyl)-3-(4-cyano-3-(trifluoromethyl)phenyl)-2-(trifluoromethyl)oxazolidine-5-carboxamide, (2R,5S)-N-(4-cyano-2,5-difluorophenyl)-3-(4-cyano-3-(trifluoromethyl)phenyl)-2-(trifluoromethyl)oxazolidine-5-carboxamide, (2R,5S)-3-(4-cyano-3-(trifluoromethyl)phenyl)-N-(3,4-dicyanophenyl)-2-(trifluoromethyl)oxazolidine-5-carboxamide, (2R,5S)-N-(4-cyano-2-methylphenyl)-3-(4-cyano-3-(trifluoromethyl)phenyl)-2-(trifluoromethyl)oxazolidine-5-carboxamide, (2R,5S)-N-(3-chloro-4-cyanophenyl)-3-(4-cyano-3-(trifluoromethyl)phenyl)-2-(trifluoromethyl)oxazolidine-5-carboxamide, (2R,5S)-N-(6-acetamidopyridin-3-yl)-3-(4-cyano-3-(trifluoromethyl)phenyl)-2-(trifluoromethyl)oxazolidine-5-carboxamide, (2R,5S)-3-(3-chloro-4-cyanophenyl)-N-(2-chloropyridin-4-yl)-2-(trifluoromethyl)oxazolidine-5-carboxamide, (2R,5S)-N-(2-chloropyridin-4-yl)-3-(3-methyl-4-nitrophenyl)-2-(trifluoromethyl)oxazolidine-5-carboxamide, (2R,5S)-3-(4-cyano-3-(trifluoromethyl)phenyl)-N-(4-cyanophenyl)-2-(trifluoromethyl)oxazolidine-5-carboxamide, (2R,5S)-N-(4-cyano-2-fluorophenyl)-3-(4-cyano-3-(trifluoromethyl)phenyl)-2-(trifluoromethyl)oxazolidine-5-carboxamide, (2R,5S)-3-(4-cyano-3-(trifluoromethyl)phenyl)-N-(3,4-difluorophenyl)-2-(trifluoromethyl)oxazolidine-5-carboxamide, (2R,5S)-3-(4-cyano-3-(trifluoromethyl)phenyl)-N-(3-cyanophenyl)-2-(trifluoromethyl)oxazolidine-5-carboxamide, (2R,5S)-N-(2-chloropyridin-4-yl)-3-(4-cyano-3-(trifluoromethyl)phenyl)-2-(trifluoromethyl)oxazolidine-5-carboxamide, (2R,5S)-N-(4-cyano-2,3,5,6-tetrafluorophenyl)-3-(4-cyano-3-(trifluoromethyl)phenyl)-2-(trifluoromethyl)oxazolidine-5-carboxamide, (2R,5S)-N,3-bis(4-cyano-3-(trifluoromethyl)phenyl)-2-(trifluoromethyl)oxazolidine-5-carboxamide, (2R,5S)-N-(4-cyano-2-ethylphenyl)-3-(4-cyano-3-(trifluoromethyl)phenyl)-2-(trifluoromethyl)oxazolidine-5-carboxamide, (2R,5S)-N-(2-chloro-4-cyano-6-methylphenyl)-3-(4-cyano-3-(trifluoromethyl)phenyl)-2-(trifluoromethyl)oxazolidine-5-carboxamide, (2R,5S)-3-(4-cyano-3-(trifluoromethyl)phenyl)-N-(4-cyano-3-fluorophenyl)-2-(trifluoromethyl)oxazolidine-5-carboxamide, (2R,5S)-3-(4-cyano-3-(trifluoromethyl)phenyl)-N-(4-hydroxyphenyl)-2-(trifluoromethyl)oxazolidine-5-carboxamide, (2R,5S)-3-(3-chloro-4-nitrophenyl)-N-(6-chloropyridin-3-yl)-2-(trifluoromethyl)oxazolidine-5-carboxamide, (2R,5S)-N-(4-acetamidophenyl)-3-(4-nitro-3-(trifluoromethyl)phenyl)-2-(trifluoromethyl)oxazolidine-5-carboxamide, (2R,5S)-N-(2-chloro-4-nitrophenyl)-3-(4-cyano-3-(trifluoromethyl)phenyl)-2-(trifluoromethyl)oxazolidine-5-carboxamide, (2R,5S)-N-(4-amino-2-chlorophenyl)-3-(4-cyano-3-(trifluoromethyl)phenyl)-2-(trifluoromethyl)oxazolidine-5-carboxamide, (2R,5S)-N-(4-acetamido-2-chlorophenyl)-3-(4-cyano-3-(trifluoromethyl)phenyl)-2-(trifluoromethyl)oxazolidine-5-carboxamide, methyl (3-chloro-4-((2R,5S)-3-(4-cyano-3-(trifluoromethyl)phenyl)-2-(trifluoromethyl)oxazolidine-5-carboxamido)phenyl)carbamate, (2R,5S)-3-(4-cyano-3-(trifluoromethyl)phenyl)-N-(4-nitrophenyl)-2-(trifluoromethyl)oxazolidine-5-carboxamide, (2R,5S)-N-(4-aminophenyl)-3-(4-cyano-3-(trifluoromethyl)phenyl)-2-(trifluoromethyl)oxazolidine-5-carboxamide, methyl (4-((2R,5S)-3-(4-cyano-3-(trifluoromethyl)phenyl)-2-(trifluoromethyl)oxazolidine-5-carboxamido)phenyl)carbamate, (2R,5S)-3-(4-cyano-3-(trifluoromethyl)phenyl)-N-(4-propionamidophenyl)-2-(trifluoromethyl)oxazolidine-5-carboxamide, (2R,5S)-3-(4-cyano-3-(trifluoromethyl)phenyl)-N-(4-isobutylamidophenyl)-2-(trifluoromethyl)oxazolidine-5-carboxamide, (2R,5S)-3-(4-cyano-3-(trifluoromethyl)phenyl)-N-(4-(2-hydroxyacetamido)phenyl)-2-(trifluoromethyl)oxazolidine-5-carboxamide, (2R,5S)-3-(4-cyano-3-(trifluoromethyl)phenyl)-2-(trifluoromethyl)-N-(4-ureidophenyl)oxazolidine-5-carboxamide, (2R,5S)-3-(4-cyano-3-(trifluoromethyl)phenyl)-N-(4-(2-cyanoacetamido)phenyl)-2-(trifluoromethyl)oxazolidine-5-carboxamide, (2R,5S)-N-(4-(2-aminoacetamido)phenyl)-3-(4-cyano-3-(trifluoromethyl)phenyl)-2-(trifluoromethyl)oxazolidine-5-carboxamide, (2S,5S)-3-(4-cyano-3-(trifluoromethyl)phenyl)-N-(4-cyanophenyl)-2-(trifluoromethyl)oxazolidine-5-carboxamide, 4-((2R,5S)-5-(((4-cyanophenyl)sulfonyl)methyl)-2-(trifluoromethyl)oxazolidin-3-yl)-2-(trifluoromethyl)benzonitrile, t-butyl 4-((2R,5S)-3-(4-cyano-3-(trifluoromethyl)phenyl)-2-(trifluoromethyl)oxazolidine-5-carboxamido)piperidine-1-carboxylate, (2R,5S)-3-(4-cyano-3-(trifluoromethyl)phenyl)-N-(piperidin-4-yl)-2-(trifluoromethyl)oxazolidine-5-carboxamide, and (2R,5S)-N-(1-acetylpiperidin-4-yl)-3-(4-cyano-3-(trifluoromethyl)phenyl)-2-(trifluoromethyl)oxazolidine-5-carboxamide According to an embodiment of the present invention, $R_1$ of Chemical Formula 1 may be a substituent represented by the following Chemical Formula 3, and may be an isomer of a compound selected from the group consisting of the following compounds, thereof, or a pharmaceutically acceptable salt thereof:

4-((2R,5S)-5-(4-isocyanopiperidine-1-carbonyl)-2-(trifluoromethyl)oxazolidin-3-yl)-2-(trifluoromethyl)benzonitrile, 4-((2R,5S)-5-(piperazine-1-carbonyl)-2-(trifluoromethyl)oxazolidin-3-yl)-2-(trifluoromethyl)benzonitrile, 4-((2R,5S)-5-(4-acetylpiperazine-1-carbonyl)-2-(trifluoromethyl)oxazolidin-3-yl)-2-(trifluoromethyl)benzonitrile, methyl 4-((2R,5S)-3-(4-cyano-3-(trifluoromethyl)phenyl)-2-(trifluoromethyl)oxazolidine-5-carbonyl)piperazine-1-carboxylate, 4-((2R,5S)-3-(4-cyano-3-(trifluoromethyl)phenyl)-2-(trifluoromethyl)oxazolidine-5-carbonyl)piperazine-1-carbonitrile, 4-((2R,5S)-5-(4-aminopiperidine-1-carbonyl)-2-(trifluoromethyl)oxazolidin-3-yl)-2-(trifluoromethyl)benzonitrile, 4-((2R,5S)-5-(4-acetylpiperazine-1-carbonyl)-2-(trifluoromethyl)oxazolidin-3-yl)-2-(trifluoromethyl)benzonitrile, t-butyl 4-((2R,5S)-3-(4-cyano-3-(trifluoromethyl)phenyl)-2-(trifluoromethyl)oxazolidine-5-carboxamido)piperidine-1-carboxylate, methyl 4-((2R,5S)-3-(3-chloro-4-cyanophenyl)-2-(trifluoromethyl)oxazolidine-5-carbonyl)piperazine-1-carboxylate methyl 4-((2R,5S)-3-(3-methyl-4-nitrophenyl)-2-(trifluoromethyl)oxazolidine-5-carbonyl)piperazine-1-carboxylate, methyl (2-((2R,5S)-3-(4-cyano-3-(trifluoromethyl)phenyl)-2-(trifluoromethyl)oxazolidine-5-carboxamido)ethyl)carbamate, 4-((2R,5S)-5-(4-(methylsulfonyl)piperazine-1-carbonyl)-2-(trifluoromethyl)oxazolidin-3-yl)-2-(trifluoromethyl)benzonitrile, 4-((2R,5S)-5-(4-isopropylpiperazine-1-carbonyl)-2-(trifluoromethyl)oxazolidin-3-yl)-2-(trifluoromethyl)benzonitrile, 4-((2R,5S)-5-(4-(2-cyanoethyl)piperazine-1-carbonyl)-2-(trifluoromethyl)oxazolidin-3-yl)-2-(trifluoromethyl)benzonitrile, 4-((2R,5S)-5-(4-(2-hydroxyethyl)piperazine-1-carbonyl)-2-(trifluoromethyl)oxazolidin-3-yl)-2-trifluoromethyl)benzonitrile, 1-(((2R,5R)-3-(4-cyano-3-(trifluoromethyl)phenyl)-2-(trifluoromethyl)oxazolidin-5-yl)methyl)piperidine-4-carbonitrile, 1-((2R,5S)-3-(4-cyano-3-(trifluoromethyl)phenyl)-2-(trifluoromethyl)oxazolidine-5-carbonyl)piperidine-4-carboxamide, ethyl 4-((2R,5S)-3-(4-cyano-3-(trifluoromethyl)phenyl)-2-(trifluoromethyl)oxazolidine-5-carbonyl)piperazine-1-carboxylate, 4-((2R,5S)-3-(4-cyano-3-(trifluoromethyl)phenyl)-2-(trifluoromethyl)oxazolidine-5-carbonyl)piperazine-1-carboxamide, methyl 4-((2R,5S)-3-(3-chloro-4-nitrophenyl)-2-(trifluoromethyl)oxazolidine-5-carbonyl)piperazine-1-carboxylate, methyl 4-((2R,5S)-3-(4-nitro-3-(trifluoromethyl)phenyl)-2-(trifluoromethyl)oxazolidine-5-carbonyl)piperazine-1-carboxylate, methyl 4-((2R,5S)-3-(4-cyano-3-(trifluoromethyl)phenyl)-2-(trifluoromethyl)oxazolidine-5-carbonyl)-1,4-diazepane-1-carboxylate, and methyl ((R)-1-((2R,5S)-3-(4-cyano-3-(trifluoromethyl)phenyl)-2-(trifluoromethyl)oxazolidine-5-carbonyl)pyrrolidin-3-yl)carbamate.

Further, the present invention provides a method of preparing the compound of Chemical Formula 1. Those skilled in the art of the present invention will prepare the compound by various methods, based on the structure of Chemical Formula 1, and all these methods should be construed as being included in the scope of the present invention. That is, the compound of Chemical Formula 1 may be prepared within the scope of the present invention by arbitrary combinations of various synthetic methods described herein or disclosed in the prior art. Therefore, the preparation method according to the present invention is not limited to those described below.

The method of preparing the compound of Chemical Formula 1 according to an embodiment of the present invention may include the steps according to the following Reaction Scheme 1, specifically; the method of preparing a compound of Chemical Formula 1a may include the steps of:

preparing a compound of Chemical Formula 5 from a fluorobenzene compound of Chemical Formula 4 by substitution reaction, and preparing the compound of Chemical Formula 1a from the compound of Chemical Formula 5 by cyclodehydration reaction with aldehyde, ketone, or a precursor thereof:

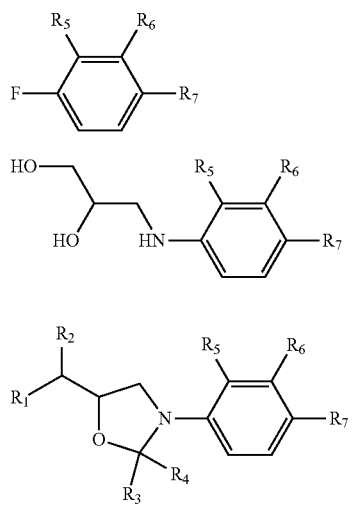

[Chemical Formula 4]

[Chemical Formula 5]

[Chemical Formula 1a]

in Chemical Formula 1a, $R_1$ is a substituent of the following Chemical Formula 2, $R_2$ is hydrogen,

[Chemical Formula 2]

in Chemical Formula 2, X is O, n is 0, $R_8$ is hydrogen, $R_3$ and $R_4$ each independently include one or more substituents selected from the group consisting of hydrogen and $C_1$-$C_6$ alkyl, $R_5$ and $R_6$ each independently include one or more substituents selected from the group consisting of hydrogen, halogen and $C_1$-$C_6$ alkyl, $R_7$ is halogen, cyano, or nitro, and $C_1$-$C_6$ alkyl includes one or more substituents selected from the group consisting of hydrogen, hydroxy, and halogen.

[Reaction Scheme 1]

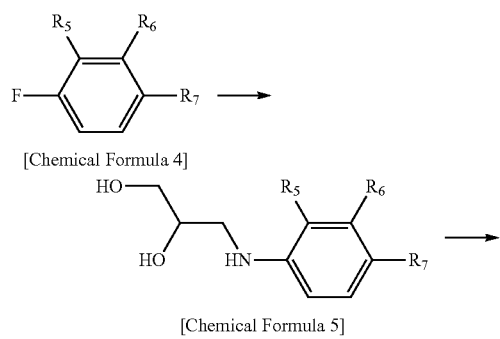

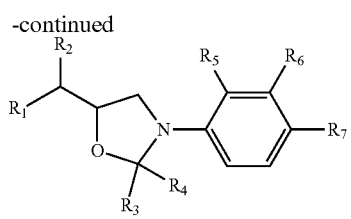

[Chemical Formula 1a]

(Substituents not specifically defined in the above Chemical Formulae are the same as those defined in Chemical Formula 1)

The method of preparing the compound of Chemical Formula 1 according to an embodiment of the present invention may include the steps according to the following Reaction Scheme 2, and specifically, the method may further include the step of preparing the compound of Chemical Formula 1b from the compound of Chemical Formula 1a prepared in Reaction Scheme 1 via mesylate with phenol or thiophenol.

Specifically, the method of preparing the compound of Chemical Formula 1 may include the steps according to the following Reaction Scheme 2, and the method includes the steps of:

preparing the compound of Chemical Formula 5 from the fluorobenzene compound of Chemical Formula 4 by substitution reaction, preparing the compound of Chemical Formula 1a from the compound of Chemical Formula 5 by cyclodehydration reaction with aldehyde, ketone, or a precursor thereof, and preparing the compound of Chemical Formula 1b from the compound of Chemical Formula 1a via mesylate with phenol or thiophenol.

[Chemical Formula 4]

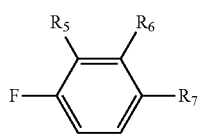

[Chemical Formula 5]

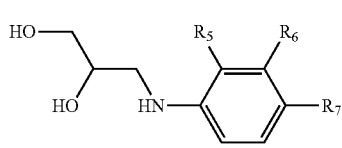

[Chemical Formula 1a]

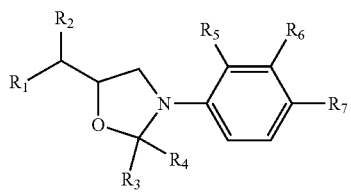

in Chemical Formula 1a, $R_1$ is a substituent of the following Chemical Formula 2, $R_2$ is hydrogen,

[Chemical Formula 2]

in Chemical Formula 2, X is O, n is 0, $R_8$ is hydrogen, $R_3$ and $R_4$ each independently include one or more substituents selected from the group consisting of hydrogen and $C_1$-$C_6$ alkyl, $R_5$ and $R_6$ each independently include one or more substituents selected from the group consisting of hydrogen, halogen, and $C_1$-$C_6$ alkyl, $R_7$ is halogen, cyano, or nitro, the $C_1$-$C_6$ alkyl includes one or more substituents selected from the group consisting of hydrogen, hydroxy, and halogen,

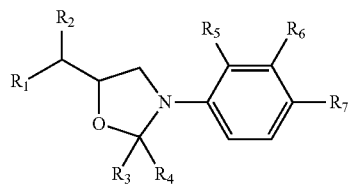

[Chemical Formula 1b]

in Chemical Formula 1b, $R_1$ is a substituent of the following Chemical Formula 2, $R_2$ is hydrogen, $R_3$ and $R_4$ each independently include one or more substituents selected from the group consisting of hydrogen and $C_1$-$C_6$ alkyl, $R_5$ and $R_6$ each independently include one or more substituents selected from the group consisting of hydrogen, halogen, and $C_1$-$C_6$ alkyl, $R_7$ is halogen, cyano, or nitro, the $C_1$-$C_6$ alkyl includes one or more substituents selected from the group consisting of hydrogen, hydroxy, and halogen;

 [Chemical Formula 2]

in Chemical Formula 2, X is O or S, n is an integer of 0 or 1, $R_8$ is hydrogen, $C_3$-$C_7$ heterocycle including a nitrogen atom, aryl, or heteroaryl including a nitrogen atom, the heterocycle, aryl or heteroaryl each independently includes one or more substituents selected from the group consisting of hydrogen, hydroxy, halogen, $C_1$-$C_6$ alkyl, $C_1$-$C_6$ alkoxy, a cyano group, a nitro group, a hydroxyimino group, a $C_1$-$C_6$ alkoxyimino group, $(CH_2)_pNR_{10}R_{11}$, $(CH_2)_pNC(O)R_{10}$, $(CH_2)_pNC(O)OR_{10}$, $(CH_2)_pNC(O)NR_{10}R_{11}$, $(CH_2)_pC(O)NR_{10}R_{11}$, $(CH_2)_pNS(O)_2R_{10}$, $(CH_2)_pS(O)_2R_{10}$, $(CH_2)_pC(O)OR_{10}$,

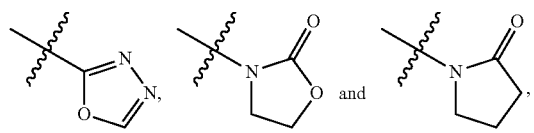 [SMILES: *c1nnco1 ; *N1CCOC1=O ; "and" ; *N1CCCC1=O]

p is an integer of 0 or 1, $R_{10}$ and $R_{11}$ each independently include one or more substituents selected from the group consisting of hydrogen, $C_1$-$C_6$ alkyl, pyrrolidinyl, and phenyl, the $C_1$-$C_6$ alkyl includes one or more substituents selected from the group consisting of hydrogen, hydroxy, amino, cyano and halogen, and n is 0 or 1.

[Reaction Scheme 2]

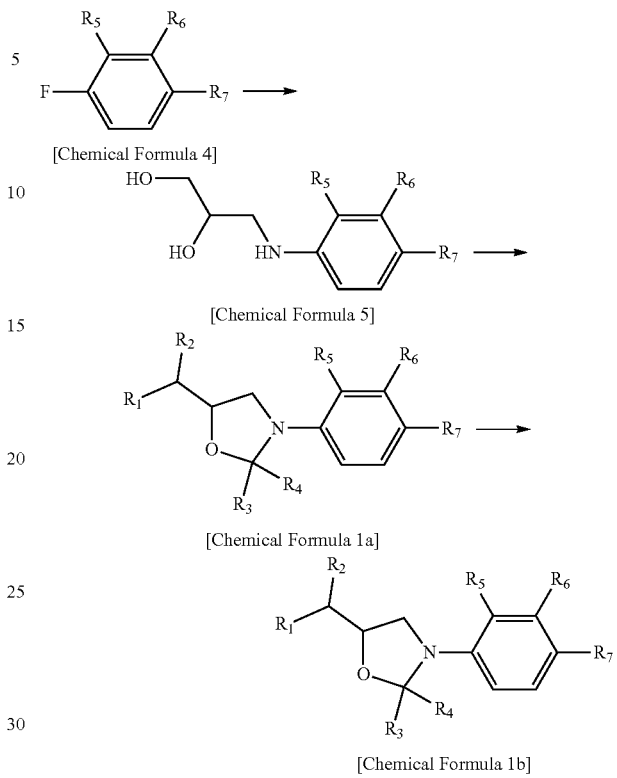

(Substituents not specifically defined in the above Chemical Formulae are the same as those defined in Chemical Formula 1)

The method of preparing the compound of Chemical Formula 1 according to an embodiment of the present invention may include the step according to the following Reaction Scheme 3, and specifically, the method includes the steps of: preparing a compound of Chemical Formula 6 from the compound of Chemical Formula 1a prepared in Reaction Scheme 1, and preparing a compound of Chemical Formula 1c by reacting the compound of Chemical Formula 6 with a silane compound, followed by acid treatment.

Specifically, the preparation method includes the steps of:

preparing the compound of Chemical Formula 5 from the fluorobenzene compound of Chemical Formula 4 by substitution reaction, preparing the compound of Chemical Formula 1a from the compound of Chemical Formula 5 by cyclodehydration reaction with aldehyde, ketone, or a precursor thereof, preparing the compound of Chemical Formula 6 from the compound of Chemical Formula 1a by oxidation reaction, and preparing the compound of Chemical Formula 1c by reacting the compound of Chemical Formula 6 with a silane compound, followed by acid treatment.

[Chemical Formula 4]

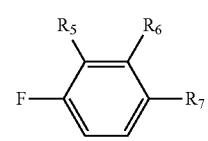

-continued

[Chemical Formula 5]

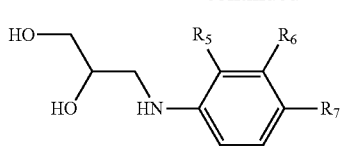

[Chemical Formula 1a]

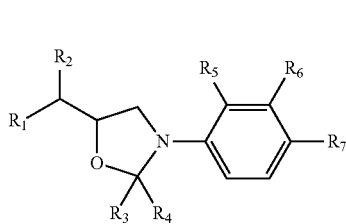

in Chemical Formula 1a, $R_1$ is a substituent of the following Chemical Formula 2, $R_2$ is hydrogen, —X(CH$_2$)nR$_8$  [Chemical Formula 2]

in Chemical Formula 2, X is O, n is 0, $R_8$ is hydrogen, $R_3$ and $R_4$ each independently include one or more substituents selected from the group consisting of hydrogen and $C_1$-$C_6$ alkyl, $R_5$ and $R_6$ each independently include one or more substituents selected from the group consisting of hydrogen, halogen and $C_1$-$C_6$ alkyl, $R_7$ is halogen, cyano or nitro, the $C_1$-$C_6$ alkyl includes one or more substituents selected from the group consisting of hydrogen, hydroxy, and halogen,

[Chemical Formula 6]

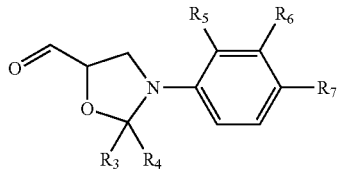

[Chemical Formula 1c]

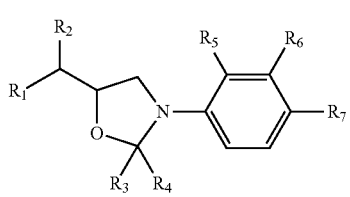

in Chemical Formula 1c, $R_1$ is a substituent of the following Chemical Formula 2, $R_2$ is $C_1$-$C_6$ alkyl, and the $C_1$-$C_6$ alkyl includes one or more substituents selected from the group consisting of hydrogen, hydroxy and halogen, —X(CH$_2$)nR$_8$  [Chemical Formula 2]

in Chemical Formula 2, X is O, n is 0, $R_8$ is hydrogen, $R_3$ and $R_4$ each independently include one or more substituents selected from the group consisting of hydrogen and $C_1$-$C_6$ alkyl, $R_5$ and $R_6$ each independently include one or more substituents selected from the group consisting of hydrogen, halogen and $C_1$-$C_6$ alkyl, $R_7$ is halogen, cyano, or nitro, and the $C_1$-$C_6$ alkyl includes one or more substituents selected from the group consisting of hydrogen, hydroxy and halogen.

[Reaction Scheme 3]

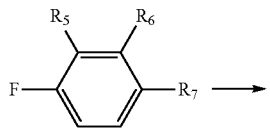

[Chemical Formula 4]

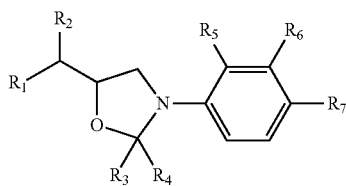

[Chemical Formula 5]

[Chemical Formula 1a]

[Chemical Formula 6]

[Chemical Formula 1c]

(Substituents not specifically defined in the above Chemical Formulae are the same as those defined in Chemical Formula 1)

In another specific embodiment of the present invention, the method of preparing the compound of Chemical Formula 1 may include the steps according to the following Reaction Scheme 4, and specifically, the method includes the steps of:

preparing a compound of Chemical Formula 7 from the fluorobenzene compound of Chemical Formula 4 by substitution reaction, preparing a compound of Chemical Formula 8 from the compound of Chemical Formula 7 by cyclodehydration reaction with aldehyde, ketone, or a precursor thereof, and preparing a compound of Chemical Formula 1d from the compound of Chemical Formula 8 by amide formation reaction with amine.

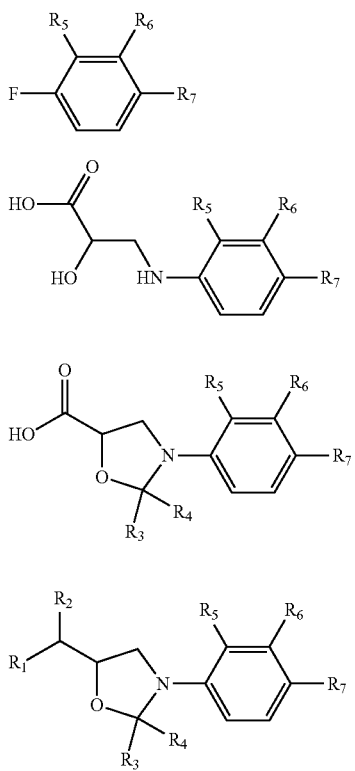

[Chemical Formula 4]

[Chemical Formula 7]

[Chemical Formula 8]

[Chemical Formula 1d]

in Chemical Formula 1d, $R_1$ is a substituent of the following Chemical Formula 2 or Chemical Formula 3, $R_2$ is an oxo group, $R_3$ and $R_4$ each independently include one or more substituents selected from the group consisting of hydrogen and $C_1$-$C_6$ alkyl, $R_5$ and $R_6$ each independently include one or more substituents selected from the group consisting of hydrogen, halogen, and $C_1$-$C_6$ alkyl, $R_7$ is halogen, cyano, or nitro, and the $C_1$-$C_6$ alkyl includes one or more substituents selected from the group consisting of hydrogen, hydroxy, and halogen;

 —X(CH$_2$)nR$_8$       [Chemical Formula 2]

in Chemical Formula 2, X is N, n is an integer of 0 or 1, $R_8$ is hydrogen, $C_3$-$C_7$ heterocycle including a nitrogen atom, aryl, or heteroaryl including a nitrogen atom, the heterocycle, aryl, or heteroaryl each independently includes one or more substituents selected from the group consisting of hydrogen, hydroxy, halogen, $C_1$-$C_6$ alkyl, $C_1$-$C_6$ alkoxy, a cyano group, a nitro group, a hydroxyimino group, a $C_1$-$C_6$ alkoxyimino group, (CH$_2$)$_p$NR$_{10}$R$_{11}$, (CH$_2$)$_p$NC(O)R$_{10}$, (CH$_2$)$_p$NC(O)OR$_{10}$, (CH$_2$)$_p$NC(O)NR$_{10}$R$_{11}$, (CH$_2$)$_p$C(O)NR$_{10}$R$_{11}$, (CH$_2$)$_p$NS(O)$_2$R$_{10}$, (CH$_2$)$_p$S(O)$_2$R$_{10}$ (CH$_2$)$_p$C(O)OR$_{10}$,

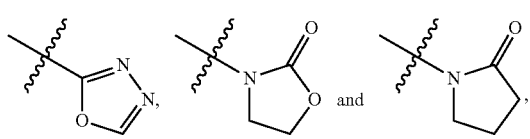 [SMILES: *c1nnco1 ; *N1CCOC1=O ; "and" ; *N1CCCC1=O]

p is an integer of 0 or 1, $R_{10}$ and $R_{11}$ each independently include one or more substituents selected from the group consisting of hydrogen, $C_1$-$C_6$ alkyl, pyrrolidinyl, and phenyl, and the $C_1$-$C_6$ alkyl includes one or more substituents selected from the group consisting of hydrogen, hydroxy, amino, cyano and halogen,

[Chemical Formula 3]

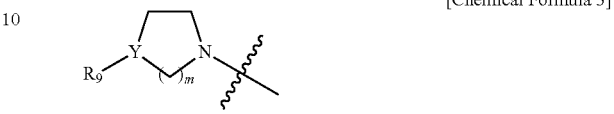

in Chemical Formula 3, Y is C or N, m is an integer of 0, 1 or 2, $R_9$ is a substituent selected from the group consisting of hydrogen, oxo, hydroxy, $C_1$-$C_6$ alkyl, cyano, C(O)R$_{12}$, C(O)OR$_{12}$, C(O)NR$_{12}$R$_{13}$, S(O)$_2$R$_{12}$, NC(O)R$_{13}$, NR$_{12}$R$_{13}$, and NC(O)OR$_{12}$, $R_{12}$ and $R_{13}$ each independently include one or more substituents selected from the group consisting of hydrogen, hydroxy, and $C_1$-$C_6$ alkyl, and the $C_1$-$C_6$ alkyl includes one or more substituents selected from the group consisting of hydrogen, hydroxy, halogen and cyano.

[Reaction Scheme 4]

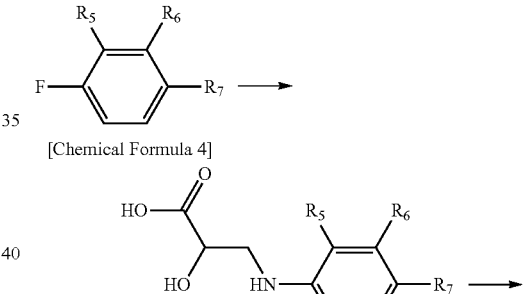

[Chemical Formula 4]

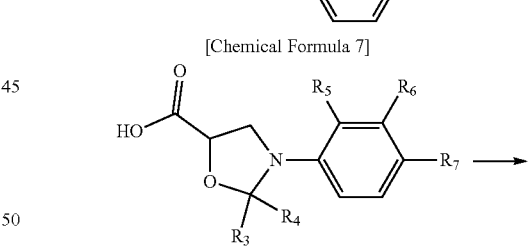

[Chemical Formula 7]

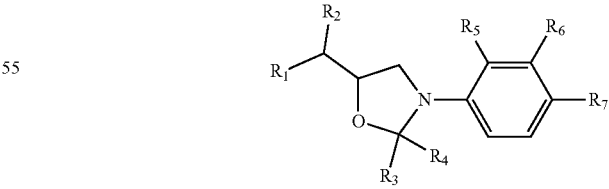

[Chemical Formula 8]

[Chemical Formula 1d]

(Substituents not specifically defined in the above Chemical Formulae are the same as those defined in Chemical Formula 1)

The compound of Chemical Formula 1 according to the present invention has a structure different from those of the known androgen receptor agonists, and as shown in the following Experimental Examples, the compound has excellent agonistic effects on androgen receptors, and therefore, it may be used for the treatment and prevention of diseases or conditions, of which symptoms may be improved or may respond to treatment by increased activity of androgen receptor, namely, a variety of hormone-related diseases, muscle-wasting diseases, and osteoporosis in men and women.

Meanwhile, according to still another embodiment of the present invention, provided is a pharmaceutical composition including the above described compound represented by Chemical Formula 1, an isomer thereof, or a pharmaceutically acceptable salt thereof as an active ingredient for the treatment and prevention of diseases or conditions, of which symptoms may be improved or may respond to treatment by increased activity of androgen receptor, namely, disorders including those listed below.

The diseases, of which symptoms may be improved or may respond to treatment by increased activity of androgen receptor, may be selected from the group consisting of sexual dysfunction, decreased sexual libido, male erectile dysfunction, hypogonadism, sarcopenia, muscle dystrophy caused by reduction in the number or mass of muscle cells, cachexia, muscular dystrophy, post-operative muscle loss, neuromuscular disease caused by neurotransmitter system disorder, rheumatic disease, sarcopenic obesity, alterations in cognition and mood, depression, anemia, hair loss, obesity, endometriosis, breast cancer, uterine cancer, ovarian cancer, muscle wasting disorder, osteopenia, and osteoporosis.

The diseases or conditions, of which symptoms may be improved or may respond to treatment by increased activity of androgen, may be selected from the group consisting of a variety of hormone-related diseases in men and women, sexual dysfunction, decreased sexual libido, male erectile dysfunction, hypogonadism, sarcopenia, muscle dystrophy caused by reduction in the number or mass of muscle cells, cachexia, alterations in cognition and mood, depression, anemia, hair loss, obesity, endometriosis, breast cancer, uterine cancer, ovarian cancer, muscle wasting disorder, osteopenia, and osteoporosis, for example, one or more of those listed below:

a) diseases or symptoms associated with androgen decline in male such as sexual dysfunction, decreased sexual libido, male erectile dysfunction, hypogonadism, sarcopenia, age-related sarcopenia, osteopenia, osteoporosis, alterations in cognition and mood, depression, anemia, hair loss, and obesity, b) diseases or symptoms associated with androgen decline in female such as sexual dysfunction, decreased sexual libido, sarcopenia, age-related sarcopenia, osteopenia, osteoporosis, alterations in cognition and mood, depression, anemia, hair loss, obesity, endometriosis, breast cancer, uterine cancer and ovarian cancer, c) muscle wasting disorder (caused by aging, bone fracture, serious burns, end-stage renal disease, cancer, AIDS, chronic obstructive pulmonary disease, stroke, etc.), and d) osteopenia and osteoporosis (e.g., osteopenia or osteoporosis caused by factors other than androgen decline in male or female, for example, female hormone decline), muscle dystrophy caused by reduction in the number or mass of muscle cells, cancer or chronic disease-related cachexia, muscular dystrophy, post-operative muscle loss (muscle loss caused by muscle resection and myotomy), neuromuscular disease caused by neurotransmitter system disorder, rheumatic disease, sarcopenic obesity, etc.

The pharmaceutical composition including the compound represented by Chemical Formula 1, the isomer thereof, or the pharmaceutically acceptable salt thereof as an active ingredient may be used in the form of a general drug formulation. The drug formulation may be administered in the form of various formulations such as oral and parenteral formulations upon administration, and the formulation may be determined by a method of use.

The composition may be prepared into various oral and parenteral formulations using general diluents or excipients such as a filler, a bulking agent, a binder, a wetting agent, a disintegrant, a surfactant, etc.

The solid formulations for oral administration may include tablets, pills, powders, granules, capsules, etc. The solid formulations may be prepared by mixing the active ingredient with at least one excipient, for example, one or more selected from the group consisting of starch, calcium carbonate, sucrose, lactose, gelatin, etc. In addition to such simple excipients, lubricants such as magnesium stearate or talc may also be used. The liquid formulations for oral administration may include suspensions, solutions for internal use, emulsions, syrups, etc. In addition to simple diluents commonly used, such as water and/or liquid paraffin, different excipients, for example, one or more selected from the group consisting of wetting agents, flavors, fragrances, preserves, etc. may be further included to prepare the liquid formulations.

The parenteral administration may be performed via an intravenous route, an intramuscular route, a subcutaneous route, an intraperitoneal route, an intranasal route, or a percutaneous route. The formulation for parenteral administration may include sterile aqueous solutions, non-aqueous solutions, suspensions, emulsions, lyophilized preparations, suppositories, etc. A non-aqueous solvent for the preparation of the non-aqueous solutions and a suspension solvent for the preparation of the suspensions may include propylene glycol, polyethylene glycol, vegetable oil such as olive oil, injectable ester such as ethyloleate, etc. The base for suppositories may include witepsol, macrogol, tween 61, cacao butter, laurin butter, glycerogelatin, etc.

The content of one or more active ingredients selected from the group consisting of the compound represented by Chemical Formula 1, the isomer thereof, and the pharmaceutically acceptable salt thereof in the pharmaceutical composition may be, for example, 0.001 to 99.9% by weight, 0.01 to 90% by weight, or 0.1 to 50% by weight, but is not limited thereto. It is possible to control the content appropriately, depending on the type of formulation, the administration method, the purpose of administration, etc.

Further, the pharmaceutical composition including the compound represented by Chemical Formula 1 of the present invention, the isomer thereof, or the pharmaceutically acceptable salt thereof as an active ingredient may exhibit an effective amount within an administration range from about 0.1 mg to about 1,000 mg. The administration amount or dosage may be administered once or several times per day, depending on a patient's body weight, age, gender, health condition, diet, administration time, administration method, excretion rate and severity of the disease, and it is possible to administer the composition with various doses and methods of administration.

The patient may be mammals, for example, primates including humans, rodents including mice, rats, etc., and specifically humans. For example, the patient may be a mammal, for example, a human in need of increasing androgen activity or in need of preventing and/or treating the diseases or conditions which may be improved or may respond to treatment by increased activity of androgen.

Still another aspect provides a health functional food composition including one or more selected from the group consisting of the compound of Chemical Formula 1, the isomer thereof, and the pharmaceutically acceptable salt thereof for increasing androgen activity or for preventing and/or improving diseases or conditions which may be improved or may respond to treatment by increased activity of androgen. The diseases or conditions which may be improved or may respond to treatment by increased activity of androgen are the same as described above.

EFFECT OF THE INVENTION

The present disclosure provides novel androgen receptor agonists and pharmaceutically acceptable salts thereof, and the androgen receptor agonists may be usefully applied as a therapeutic and prophylactic agent for androgen receptor-mediated diseases or conditions, namely, various hormone-related diseases in male and female, muscle wasting diseases, osteoporosis, etc.

DETAILED DESCRIPTION OF THE EMBODIMENTS

Hereinafter, preferred Examples and Experimental Examples are provided for better understanding of the present invention. However, these Examples and Experimental Examples are for better understanding of the present invention, and the present invention is not intended to be limited by these Examples.

Descriptions for the abbreviations of compounds used in the following Preparation Examples and Examples are as follows.

t-Boc: t-butoxycarbonyl
CsF: cesium fluoride
HATU: O-(7-azabenzotriazol-1-yl)-N,N,N,N-tetramethyluronium hexafluorophosphate
EDC-HCl: N-ethyl-N'-(3-dimethylaminopropyl)carbodiimide hydrochloride
HOBt: hydroxybenzotriazole
K$_2$CO$_3$: potassium carbonate
LiOH: lithium hydroxide
MgSO4: magnesium sulfate
NaBH$_4$: sodium borohydride
NaCl: sodium chloride
NaH: sodium hydride
NaOH: sodium hydroxide
NH$_4$Cl: ammonium chloride
Pd/C: palladium/charcoal
Pd(OH)$_2$/C: palladium hydroxide/charcoal

PREPARATION EXAMPLE 1

Preparation of (S)-4-((2,3-dihydroxypropyl)amino)-2-(trifluoromethyl)benzonitrile

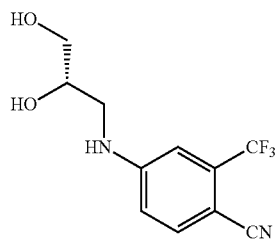 [SMILES: N#Cc1ccc(NC[C@H](O)CO)cc1C(F)(F)F]

To a 2-L flask, 180 g (952 mmol) of 4-fluoro-2-(trifluoromethyl)benzonitrile was added, and 1 L of dimethyl sulfoxide was added thereto, followed by stirring. 86.72 g (952 mmol, 1 eq) of (S)-3-aminopropane-1,2-diol was added and 267.6 ml (1.90 mol, 2 eq) of triethylamine was added, and followed by stirring at 120° C. about 16 hours. After completion of the reaction, the reaction solution was diluted with ethyl acetate (1 L), and then washed with water (1 L) three times. After separation of layers, an aqueous layer was removed and an organic layer was washed with a saturated NaCl aqueous solution, and dehydrated and dried over MgSO$_4$, and concentrated under reduced pressure to obtain 223 g (90%) of a title compound.

$^1$H NMR (Acetone-d6, 400 MHz) δ 7.66(d, 1H), 7.17(d, 1H), 6.99(dd, 1H), 6.44(s, 1H), 3.87(t, 1H), 3.59(t, 2H), 3.51~3.45(m, 1H), 3.30~3.23(m, 1H)

Mass[M+H]: 261.22

PREPARATION EXAMPLE 2

Preparation of 4-((2S,5S)-5-(hydroxymethyl)-2-(trifluoromethyl)oxazolidin-3-yl)-2-(trifluoromethyl)benzonitrile

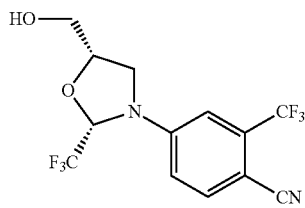 [SMILES: N#Cc1ccc(N2C[C@@H](CO)O[C@H]2C(F)(F)F)cc1C(F)(F)F]

To a 50-mL flask, 20 g (77 mmol) of (S)-4-((2,3-dihydroxypropyl)amino)-2-(trifluoromethyl)benzonitrile obtained from Preparation Example 1 was added, and 600 ml of trifluoroacetic acid was added thereto, followed by stirring. 45 ml (384 mmol, 5 eq) of trifluoroacetaldehyde ethylhemiacetal was added thereto, followed by stirring at 100° C. about 5 hours. After completion of the reaction, the reaction solution was concentrated under reduced pressure, and layers were separated using water (1 L) and ethyl acetate (1 L), and then an aqueous layer was removed, followed by washing with a 2 N NaOH aqueous solution (1 L). An organic layer was washed with water and a saturated NaCl aqueous solution, and dehydrated and dried over MgSO$_4$, and concentrated under reduced pressure. A concentrate was subjected to column chromatography to separate (2S,5S)-isomers, thereby obtaining 8 g (25%) of a title compound.

$^1$H NMR (CDCl$_3$, 400 MHz) δ 7.66(d, 1H), 7.02(d, 1H), 6.89(dd, 1H), 5.67(q, 1H), 4.44~4.38(m, 1H), 3.95~3.90(m, 2H), 3.84~3.77(m, 1H), 3.63(t, 1H)

Mass[M+H]: 341.06

PREPARATION EXAMPLE 3

Preparation of ((2S,5S)-3-(4-cyano-3-(trifluoromethyl)phenyl)-2-(trifluoromethyl)oxazolidin-5-yl)methyl methanesulfonate

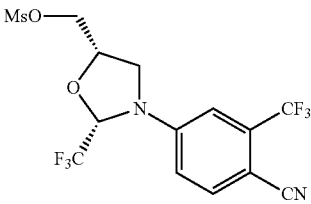 [SMILES: CS(=O)(=O)OC[C@@H]1CN(c2ccc(C#N)c(C(F)(F)F)c2)[C@H](C(F)(F)F)O1]

To a 50-mL flask, 1 g (2.94 mmol) of the compound 4-((2S,5S)-5-(hydroxymethyl)-2-(trifluoromethyl)oxazolidin-3-yl)-2-(trifluoromethyl)benzonitrile obtained from Preparation Example 2 was added. 8 ml of dichloromethane was added thereto, followed by stirring. To a reaction solution, 500 ul (6.47 mmol, 2.2 eq) of methanesulfonyl chloride and 990 ul (7.06 mmol, 2.4 eq) of triethylamine were added, followed by stirring at room temperature for about 4 hours. After completion of the reaction, the reaction solution was concentrated under reduced pressure, and layers were separated using ethyl acetate (20 ml) and water (20 mL), and then an organic layer was separated and washed with a NaCl aqueous solution. The organic layer was dehydrated and dried over MgSO$_4$, and concentrated under reduced pressure. A concentrate was subjected to column chromatography to obtain 1.15 g (90%) of a title compound.

$^1$H NMR (CDCl$_3$, 400 MHz) δ 7.70(d, 1H), 7.03(d, 1H), 6.91(dd, 1H), 5.70(q, 1H), 4.62~4.57(m, 1H), 4.44(d, 1H), 4.05(t, 1H), 3.62(t, 1H), 3.09(s, 3H)

Mass[M+H]: 419.04

PREPARATION EXAMPLE 4

Preparation of (S)-3-((3-methyl-4-nitrophenyl)amino)propane-1,2-diol

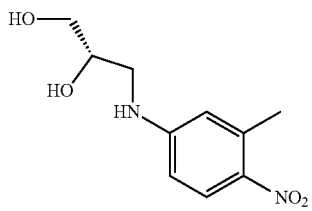

In a 100-ml flask, 1 ml (8.2 mmol) of 4-fluoro-2-methyl-1-nitrobenzene and 822 mg (9.02 mmol, 1.1 eq) of (S)-3-aminopropane-1,2-diol were used to obtain 1.4 g (75%) of a title compound in the same manner as in Preparation Example 1.

$^1$H NMR (CDCl$_3$, 600 MHz) δ 8.04(d, 1H), 6.44(dd, 1H), 6.39(d, 1H), 4.71(br, 1H), 4.00~3.97(m, 1H), 3.81~3.78(m, 1H), 3.67~3.64(m, 1H), 3.39~3.35(m, 1H), 3.27~3.23(m, 1H), 2.59(s, 3H), 2.34(d, 1H)

Mass[M+H]: 227.10

PREPARATION EXAMPLE 5

Preparation of ((2R,5S)-3-(3-methyl-4-nitrophenyl)-2-(trifluoromethyl)oxazolidin-5-yl)methanol

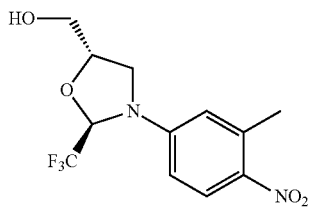 [SMILES: Cc1cc(N2C[C@@H](CO)O[C@@H]2C(F)(F)F)ccc1[N+](=O)[O-]]

The compound (S)-3-((3-methyl-4-nitrophenyl)amino)propane-1,2-diol obtained in Preparation Example 4 was used to obtain a reaction product in the same manner as in Preparation Example 2, and this reaction product was applied to a silica gel column to separate (2R,5S)-isomers, thereby obtaining 400 mg (21%) of a title compound.

$^1$H NMR (CDCl$_3$, 400 MHz) δ 8.09(d, 1H), 6.57(dd, 1H), 6.52(d, 1H), 5.56(q, 1H), 4.77~4.74(m, 1H), 3.95(dd, 1H), 3.76(t, 1H), 3.71(dd, 1H), 3.58(t, 1H), 2.64(s, 3H)

Mass[M+H]: 307.08

PREPARATION EXAMPLE 6

Preparation of ((2R,5S)-3-(3-methyl-4-nitrophenyl)-2-(trifluoromethyl)oxazolidin-5-yl)methyl methanesulfonate

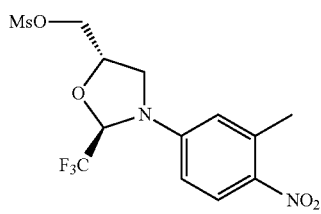 [SMILES: Cc1cc(N2C[C@@H](COS(C)(=O)=O)O[C@@H]2C(F)(F)F)ccc1[N+](=O)[O-]]

The compound ((2R,5S)-3-(3-methyl-4-nitrophenyl)-2-(trifluoromethyl)oxazolidin-5-yl)methanol obtained in Preparation Example 5 was used to obtain 302 mg (60%) of a title compound in the same manner as in Preparation Example 3.

$^1$H NMR (CDCl$_3$, 600 MHz) δ 8.09(d, 1H), 6.59(dd, 1H), 6.53(d, 1H), 5.61(q, 1H), 4.90~4.88(m, 1H), 4.42(dd, 1H), 4.33(dd, 1H), 3.87(t, 1H), 3.57(t, 1H), 3.00(s, 3H), 2.64(s, 3H)

Mass[M+H]: 385.06

PREPARATION EXAMPLE 7

Preparation of (S)-3-((4-nitro-3-(trifluoromethyl)phenyl)amino)propane-1,2-diol

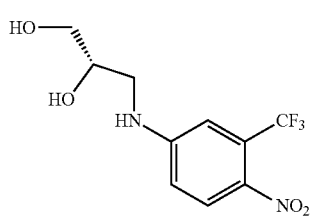 [SMILES: O=[N+]([O-])c1ccc(NC[C@H](O)CO)cc1C(F)(F)F]

In a 100-ml flask, 5 g (23.9 mmol) of 4-fluoro-2-trifluoromethyl-1-nitrobenzene and 2.18 g (23.9 mmol, 1.0 eq) of (S)-3-aminopropane-1,2-diol were used to obtain 5.8 g (87%) of a title compound in the same manner as in Preparation Example 1.

Mass[M+H]: 281.07

PREPARATION EXAMPLE 8

Preparation of ((2R,5S)-3-(3-trifluoromethyl-4-nitrophenyl)-2-(trifluoromethyl)oxazolidin-5-yl)methanol

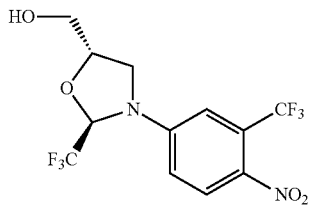

The compound (S)-3-trifluoromethyl-4-nitrophenyl)amino)propane-1,2-diol obtained in Preparation Example 7 was used to obtain 5.3 g (71%) of a title compound in the same manner as in Preparation Example 5.
Mass[M+H]: 361.05

PREPARATION EXAMPLE 9

Preparation of ((2R,5S)-3-(3-trifluoromethyl-4-nitrophenyl)-2-(trifluoromethyl)oxazolidin-5-yl)methyl methanesulfonate

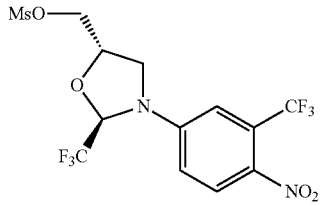

The compound ((2R,5S)-3-(3-trifluoromethyl-4-nitrophenyl)-2-(trifluoromethyl)oxazolidin-5-yl)methanol obtained in Preparation Example 8 was used to obtain 302 mg (60%) of a title compound in the same manner as in Preparation Example 3.
Mass[M+H]: 439.03

PREPARATION EXAMPLE 10

Preparation of t-butyl(4-hydroxybenzyl)carbamate

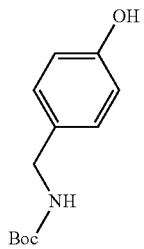

To a 100-mL flask, 500 mg (4.06 mmol) of 4-hydroxy benzylamine was added, and 9.4 ml of tetrahydrofuran and 4 ml of water were added thereto, followed by stirring. Then, 570 ul (4.06 mmol, 1.0 eq) of triethylamine was added thereto, followed by stirring. To the reaction solution, 886 mg (4.06 mmol, 1.0 eq) of di-t-butyl dicarbonate was added, followed by stirring at room temperature for 16 hours. After completion of the reaction, the reaction solution was concentrated under reduced pressure, and diluted with ethyl acetate (10 ml) and washed with water (20 mL). After separation of layers, the layer was washed with a NaCl aqueous solution, and dehydrated and dried over $MgSO_4$, and concentrated under reduced pressure to obtain 550 mg (70%) of a title compound.
Mass[M+H]: 224.12

PREPARATION EXAMPLE 11

Preparation of 4-((2R,5S)-5-(azidomethyl)-2-(trifluoromethyl)oxazolidin-3-yl)-2-(trifluoromethyl)benzonitrile

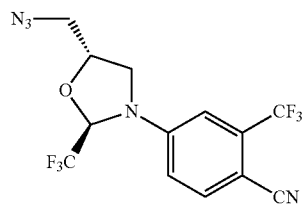 [SMILES: N#Cc1ccc(N2C[C@@H](CN=[N+]=[N-])O[C@@H]2C(F)(F)F)cc1C(F)(F)F]

To a 50-ml flask, 185 mg (0.442 mmol) of the ((2R,5S)-3-(4-cyano-3-(trifluoromethyl)phenyl)-2-(trifluoromethyl)oxazolidin-5-yl)methylmethanesulfonate obtained in step 1 of Example 7 and 5 ml of N,N-dimethylformamide were added, followed by stirring. To this reaction solution, 40 mg (0.601 mmol, 1.36 eq) of sodium azide was added, and refluxed at 80° C. for 16 hours. After completion of the reaction, the reaction solution was concentrated under reduced pressure, and diluted with ethyl acetate (10 ml) and washed with water (20 mL). After separation of layers, an organic layer was washed with a saturated $NH_4Cl$ aqueous solution, and then washed with water. The organic layer was separated, and then washed with a NaCl aqueous solution, dehydrated and dried over $MgSO_4$, and concentrated under reduced pressure to obtain 150 mg (85%) of a title compound.
Mass[M+H]: 366.07

PREPARATION EXAMPLE 12

Preparation of 4-((2R,5R)-5-(aminomethyl)-2-(trifluoromethyl)oxazolidin-3-yl)-2-(trifluoromethyl)benzonitrile

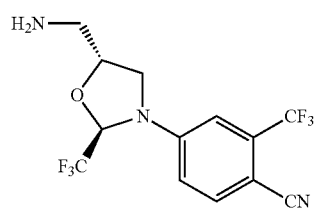 [SMILES: N#Cc1ccc(N2C[C@@H](CN)O[C@@H]2C(F)(F)F)cc1C(F)(F)F]

To a 25-ml flask, 150 mg (0.41 mmol) of the compound 4-((2R,5S)-5-(azidomethyl)-2-(trifluoromethyl)oxazolidin-3-yl)-2-(trifluoromethyl)benzonitrile obtained in Preparation Example 11 was added and 8 ml of methanol was added thereto, followed by stirring. 30 mg (20% wt) of Pd/C was added, and the atmosphere was replaced with hydrogen gas, followed by stirring at room temperature for 1 hour. After completion of the reaction, filtration was performed using Celite and a filtrate was concentrated to obtain 100 mg (72%) of a title compound.

Mass[M+H]: 340.08

PREPARATION EXAMPLE 13

Preparation of (S)-3-((4-cyano-3-(trifluoromethyl)phenyl)amino)-2-hydroxypropanoic acid

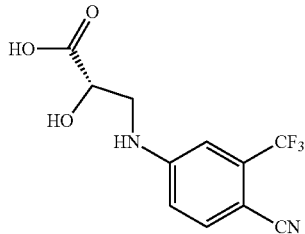 [SMILES: N#Cc1ccc(NC[C@H](O)C(=O)O)cc1C(F)(F)F]

To a 250-ml flask, 20 g (105.7 mmol) of 4-fluoro-2-(trifluoromethyl)benzonitrile was added and 106 ml of dimethylsulfoxide and 46 ml of water were added thereto, followed by stirring. To this reaction solution, 13.34 g (126.9 mmol, 1.2 eq) of (S)-isoserine and 44.6 ml (317.1 mmol, 3.0 eq) of triethylamine were added, followed by stirring at 120° C. for 16 hours. After completion of the reaction, the reaction product was diluted with 150 ml of ethyl acetate and washed with 200 ml of water three times. After separation of layers, the layer was washed with a NaCl aqueous solution, dehydrated and dried over MgSO$_4$, and concentrated under reduced pressure to obtain 28 g (95%) of a title compound.

$^1$H NMR (Acetone-d6, 400 MHz) δ 7.66(d, 1H), 7.22(d, 1H), 7.04(dd, 1H), 6.49(s, 1H), 4.43(q, 1H), 3.72~3.575(m, 2H)

Mass[M+H]: 275.06

PREPARATION EXAMPLE 14

Preparation of ethyl(S)-3-((4-cyano-3-(trifluoromethyl)phenyl)amino)-2-hydroxypropanoate

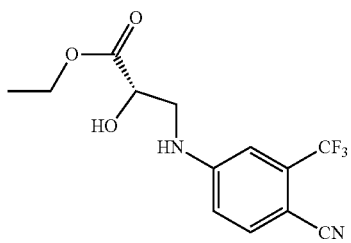 [SMILES: CCOC(=O)[C@@H](O)CNc1ccc(C#N)c(C(F)(F)F)c1]

To a 250-ml flask, 28 g (102.1 mmol) of the compound (S)-3-((4-cyano-3-(trifluoromethyl)phenyl)amino)-2-hydroxypropanoic acid obtained in Preparation Example 13 was added and 196 ml of ethanol was added, followed by stirring. The reaction solution was cooled to 0° C., and then 22.3 ml (306.3 mmol, 3.0 eq) of SOCl$_2$ was added dropwise, and refluxed at 100° C. for 4 hours. After completion of the reaction, the reaction product was concentrated under reduced pressure, and diluted with 250 ml of ethyl acetate and washed with 200 ml of water. After separation of layers, the layer was washed with a saturated sodium hydrogen carbonate aqueous solution. An organic layer was washed with a NaCl aqueous solution, and then dehydrated and dried over MgSO$_4$, and then concentrated under reduced pressure to obtain 28.7 g (93%) of a title compound.

$^1$H NMR (CDCl$_3$, 400 MHz) δ 7.54(d, 1H), 6.91(d, 1H), 6.75(dd, 1H), 4.87(t, 1H), 4.40(q, 1H), 4.30~4.19(m, 2H), 3.63~3.50(m, 2H), 3.19(d, 1H), 1.29(t, 3H)

Mass[M+H]: 303.09

PREPARATION EXAMPLE 15

Preparation of ethyl(2R,5S)-3-(4-cyano-3-(trifluoromethyl)phenyl)-2-(trifluoromethyl)oxazolidine-5-carboxylate

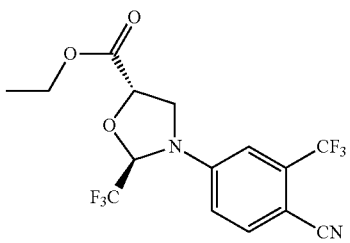 [SMILES: CCOC(=O)[C@@H]1CN(c2ccc(C#N)c(C(F)(F)F)c2)[C@@H](C(F)(F)F)O1]

To a 250-ml flask, 28.7 g (94.9 mmol) of the compound ethyl (S)-3-((4-cyano-3-(trifluoromethyl)phenyl)amino)-2-hydroxypropanoate obtained in Preparation Example 14 was added and 150 ml of toluene was added, followed by stirring. To this reaction solution, 22 ml (190 mmol, 2.0 eq) of trifluoroacetaldehyde ethylhemiacetal and 3.6 ml (28.5 mmol, 0.3 eq) of BF$_3$.Et$_2$O was added, followed by stirring at 110° C. for 16 hours. After completion of the reaction, the reaction product was concentrated under reduced pressure, and diluted with 250 ml of ethyl acetate and washed with 200 ml of water. After separation of layers, an organic layer was washed with a NaCl aqueous solution, and then dehydrated and dried over MgSO$_4$, and then concentrated under reduced pressure. (2R,5S)-isomers were separated using a silica gel column to obtain 16 g (45%) of a title compound.

$^1$H NMR (CDCl$_3$, 600 MHz) δ 7.70(d, 1H), 7.00(d, 1H), 6.90(dd, 1H), 5.75(q, 1H), 5.02(q, 1H), 4.25~4.19(m, 2H), 4.02(q, 1H), 3.85(q, 1H), 1.25(t, 3H)

Mass[M+H]: 383.08

PREPARATION EXAMPLE 16

Preparation of ethyl(2R,5S)-3-(4-cyano-3-(trifluoromethyl)phenyl)-2-(trifluoromethyl)oxazolidine-5-carboxylate

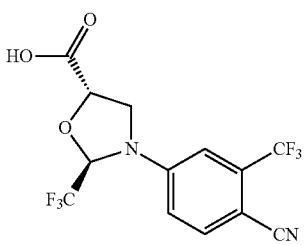 [SMILES: N#Cc1ccc(N2C[C@@H](C(=O)O)O[C@@H]2C(F)(F)F)cc1C(F)(F)F]

To a 250-ml flask, 16 g (42.7 mmol) of the compound ethyl (2R,5S)-3-(4-cyano-3-(trifluoromethyl)phenyl)-2-(trifluoromethyl)oxazolidine-5-carboxylate obtained in Preparation Example 15 was added, and 300 ml of tetrahydrofuran was added, followed by stirring. To this reaction solution, 3 g (128.1 mmol, 3.0 eq) of LiOH and 30 ml of water were added, followed by stirring at room temperature for 1 hour. After completion of the reaction, the reaction product was concentrated under reduced pressure, and diluted with 200 ml of water, and acidified with a 2 N hydrochloric acid aqueous solution, and then extracted with 100 ml of ethyl acetate twice. An organic layer was washed with 200 ml of water, and then washed with a NaCl aqueous solution, dehydrated and dried over MgSO$_4$, and concentrated under reduced pressure to obtain 14 g (90%) of a title compound.

$^1$H NMR (CDCl$_3$, 600 MHz) δ 7.71(d, 1H), 7.01(d, 1H), 6.91(dd, 1H), 5.77(q, 1H), 5.07(q, 1H), 4.09~4.05(m, 1H), 3.92 (q, 1H)

Mass[M+H]: 355.04

PREPARATION EXAMPLE 17

Preparation of (S)-3-((3-chloro-4-cyanophenyl)amino)-2-hydroxypropanoic acid

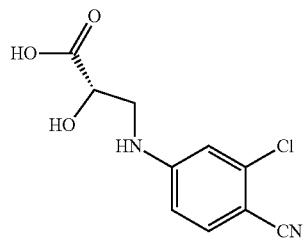 [SMILES: N#Cc1ccc(NC[C@H](O)C(=O)O)cc1Cl]

2-chloro-4-fluorobenzonitrile and (S)-isoserine were used to obtain a title compound in the same manner as in Preparation Example 13.

Mass[M+H]: 241.03

PREPARATION EXAMPLE 18

Preparation of ethyl(S)-3-((3-chloro-4-cyanophenyl)amino)-2-hydroxypropanoate

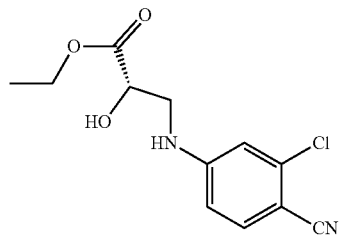 [SMILES: CCOC(=O)[C@@H](O)CNc1ccc(C#N)c(Cl)c1]

The compound (S)-3-((3-chloro-4-cyanophenyl)amino)-2-hydroxypropanoic acid obtained in Preparation Example 17 was used to obtain a title compound in the same manner as in Preparation Example 14.

Mass[M+H]: 269.06

PREPARATION EXAMPLE 19

Preparation of ethyl(2R,5S)-3-(3-chloro-4-cyanophenyl)-2-(trifluoromethyl)oxazolidine-5-carboxylate

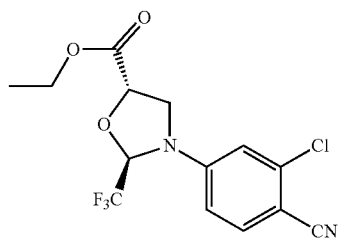 [SMILES: CCOC(=O)[C@@H]1CN(c2ccc(C#N)c(Cl)c2)[C@@H](C(F)(F)F)O1]

The compound ethyl (S)-3-((3-chloro-4-cyanophenyl)amino)-2-hydroxypropanoate obtained in Preparation Example 18 was used to obtain a title compound in the same manner as in Preparation Example 15.

Mass[M+H]: 349.05

PREPARATION EXAMPLE 20

Preparation of (2R,5S)-3-(3-chloro-4-cyanophenyl)-2-(trifluoromethyl)oxazolidine-5-carboxylic acid

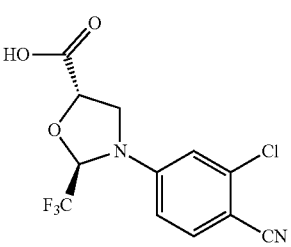 [SMILES: N#Cc1ccc(N2C[C@@H](C(=O)O)O[C@@H]2C(F)(F)F)cc1Cl]

The compound ethyl (2R,5S)-3-(3-chloro-4-cyanophenyl)-2-(trifluoromethyl)oxazolidine-5-carboxylate obtained in Preparation Example 19 was used to obtain a title compound in the same manner as in Preparation Example 16.

Mass[M+H]: 321.02

PREPARATION EXAMPLE 21

Preparation of (S)-2-hydroxy-3-((3-methyl-4-nitrophenyl)amino)propanoic acid

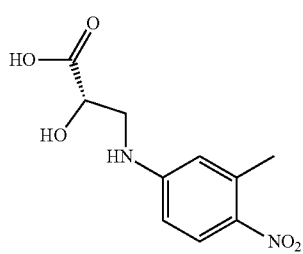 [SMILES: Cc1cc(NC[C@H](O)C(=O)O)ccc1[N+](=O)[O-]]

4-Fluoro-2-methyl-1-nitrobenzene and (S)-isoserine were used to obtain a title compound in the same manner as in Preparation Example 13.
Mass[M+H]: 241.07

PREPARATION EXAMPLE 22

Preparation of ethyl(S)-2-hydroxy-3-((3-methyl-4-nitrophenyl)amino)propanoate

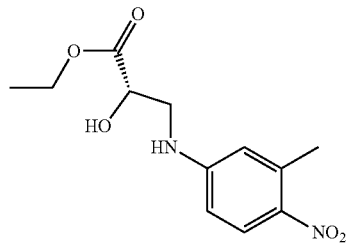 [SMILES: CCOC(=O)[C@@H](O)CNc1ccc([N+](=O)[O-])c(C)c1]

The compound (S)-2-hydroxy-3((3-methyl-4-nitrophenyl)amino)propanoic acid obtained in Preparation Example 21 was used to obtain a title compound in the same manner as in Preparation Example 14.
Mass[M+H]: 269.11

PREPARATION EXAMPLE 23

Preparation of ethyl(2R,5S)-3-(3-methyl-4-nitrophenyl)-2-(trifluoromethyl)oxazolidine-5-carboxylate

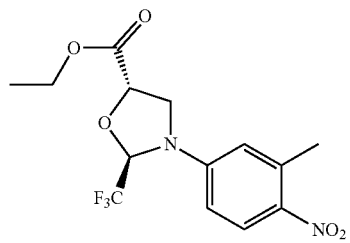

The compound ethyl (S)-2-hydroxy-3-((3-methyl-4-nitrophenyl)amino)propanoate obtained in Preparation Example 22 was used to obtain a title compound in the same manner as in Preparation Example 15.
Mass[M+H]: 349.09

PREPARATION EXAMPLE 24

Preparation of (2R,5S)-3-(3-methyl-4-nitrophenyl)-2-(trifluoromethyl)oxazolidine-5-carboxylic acid

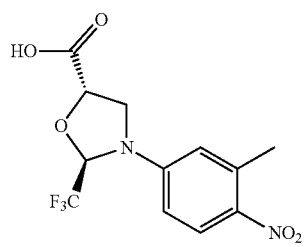 [SMILES: Cc1cc(N2C[C@@H](C(=O)O)O[C@@H]2C(F)(F)F)ccc1[N+](=O)[O-]]

The compound ethyl (2R,5S)-3-(3-methyl-4-nitrophenyl)-2-(trifluoromethyl)oxazolidine-5-carboxylate obtained in Preparation Example 23 was used to obtain a title compound in the same manner as in Preparation Example 16.
Mass[M+H]: 321.06

PREPARATION EXAMPLE 25

Preparation of (S)-3-((3-chloro-4-nitrophenyl)amino)-2-hydroxypropanoic acid

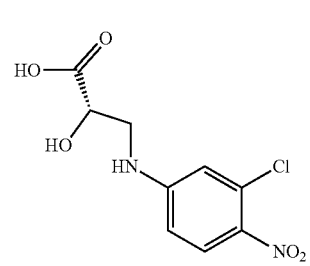 [SMILES: O=C(O)[C@@H](O)CNc1ccc([N+](=O)[O-])c(Cl)c1]

2-Chloro-4-fluoro-1-nitrobenzene and (S)-isoserine were used to obtain a title compound in the same manner as in Preparation Example 13.
Mass[M+H]: 261.02

PREPARATION EXAMPLE 26

Preparation of ethyl(S)-3-((3-chloro-4-nitrophenyl)amino)-2-hydroxypropanoate

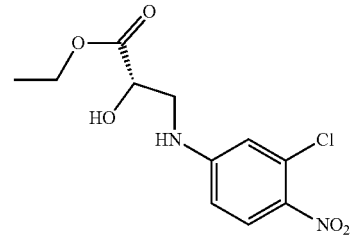 [SMILES: CCOC(=O)[C@@H](O)CNc1ccc([N+](=O)[O-])c(Cl)c1]

The compound (S)-3-((3-chloro-4-nitrophenyl)amino)-2-hydroxypropanoic acid obtained in Preparation Example 25 was used to obtain a title compound as in Preparation Example 14.
Mass[M+H]: 289.05

PREPARATION EXAMPLE 27

Preparation of ethyl(2R,5S)-3-(3-chloro-4-nitrophenyl)-2-(trifluoromethyl)oxazolidine-5-carboxylate

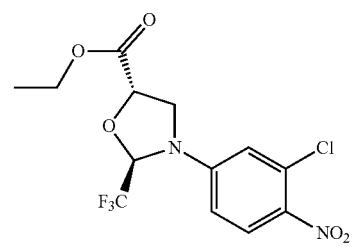 [SMILES: CCOC(=O)[C@@H]1CN(c2ccc([N+](=O)[O-])c(Cl)c2)[C@@H](C(F)(F)F)O1]

The compound ethyl (S)-3-((3-chloro-4-nitrophenyl)amino)-2-hydroxypropanoate obtained in Preparation Example 26 was used to obtain a title compound in the same manner as in Preparation Example 15.
Mass[M+H]: 369.04

PREPARATION EXAMPLE 28

Preparation of (2R,5S)-3-(3-chloro-4-nitrophenyl)-2-(trifluoromethyl)oxazolidine-5-carboxylic acid

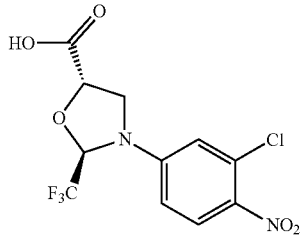

The compound ethyl (2R,5S)-3-(3-chloro-4-nitrophenyl)-2-(trifluoromethyl)oxazolidine-5-carboxylate obtained in Preparation Example 27 was used to obtain a title compound in the same manner as in Preparation Example 16.
Mass[M+H]: 341.01

PREPARATION EXAMPLE 29

Preparation of (S)-2-hydroxy-3-((4-nitro-3-(trifluoromethyl)phenyl)amino)propanoic acid

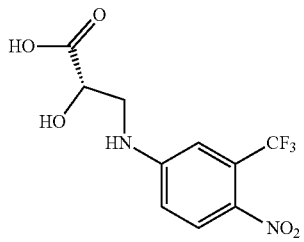

4-Fluoro-1-nitro-2-(trifluoromethyl)benzene and (S)-isoserine were used to obtain a title compound in the same manner as in Preparation Example 13.
Mass[M+H]: 295.05

PREPARATION EXAMPLE 30

Preparation of ethyl(S)-2-hydroxy-3-((4-nitro-3-(trifluoromethyl)phenyl)amino)propanoate

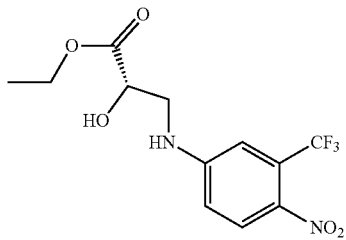 [SMILES: CCOC(=O)[C@@H](O)CNc1ccc([N+](=O)[O-])c(C(F)(F)F)c1]

The compound (S)-2-hydroxy-3-((4-nitro-3-(trifluoromethyl)phenyl)amino)propanoic acid obtained in Preparation Example 29 was used to obtain a title compound in the same manner as in Preparation Example 14.
Mass[M+H]: 323.08

PREPARATION EXAMPLE 31

Preparation of ethyl(2R,5S)-3-(4-nitro-3-(trifluoromethyl)phenyl)-2-(trifluoromethyl)oxazolidine-5-carboxylate

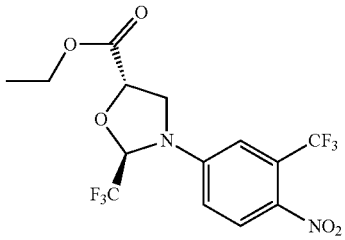 [SMILES: CCOC(=O)[C@@H]1CN(c2ccc([N+](=O)[O-])c(C(F)(F)F)c2)[C@@H](C(F)(F)F)O1]

The compound ethyl (S)-2-hydroxy-3-((4-nitro-3-(trifluoromethyl)phenyl)amino)propanoate obtained in Preparation Example 30 was used to obtain a title compound in the same manner as in Preparation Example 15.
Mass[M+H]: 403.07

PREPARATION EXAMPLE 32

Preparation of (2R,5S)-3-(4-nitro-3-(trifluoromethyl)phenyl)-2-(trifluoromethyl)oxazolidine-5-carboxylic acid

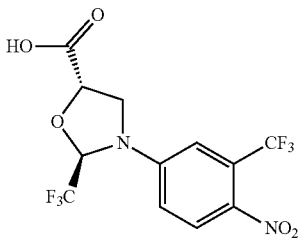 [SMILES: O=C(O)[C@@H]1CN(c2ccc([N+](=O)[O-])c(C(F)(F)F)c2)[C@@H](C(F)(F)F)O1]

The compound ethyl (2R,5S)-3-(4-nitro-3-(trifluoromethyl)phenyl)-2-(trifluoromethyl)oxazolidine-5-carboxylate obtained in Preparation Example 31 was used to obtain a title compound in the same manner as in Preparation Example 16.
Mass[M+H]: 375.03

PREPARATION EXAMPLE 33

Preparation of ((2S,5S)-3-(3-methyl-4-nitrophenyl)-2-(trifluoromethyl)oxazolidin-5-yl)methanol

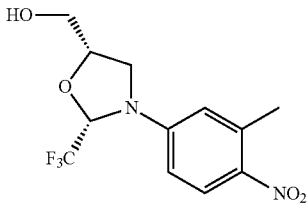 [SMILES: Cc1cc(N2C[C@@H](CO)O[C@H]2C(F)(F)F)ccc1[N+](=O)[O-]]

The compound (S)-3-((3-methyl-4-nitrophenyl)amino)propane-1,2-diol obtained in Preparation Example 4 was used to obtain a title compound in the same manner as in Preparation Example 2.
Mass[M+H]: 306.08

PREPARATION EXAMPLE 34

Preparation of ((2S,5S)-3-(3-methyl-4-nitrophenyl)-2-(trifluoromethyl)oxazolidin-5-yl)methyl methanesulfonate

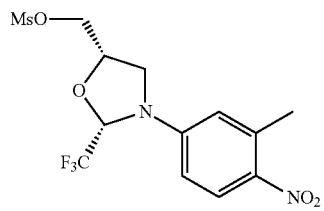 [SMILES: Cc1cc(N2C[C@@H](COS(C)(=O)=O)O[C@H]2C(F)(F)F)ccc1[N+](=O)[O-]]

The compound ((2S,5S)-3-(3-methyl-4-nitrophenyl)-2-(trifluoromethyl)oxazolidin-5-yl)methanol obtained in Preparation Example 33 was used to obtain a title compound in the same manner as in Preparation Example 3.
Mass[M+H]: 385.06

PREPARATION EXAMPLE 35

Preparation of (S)-2-chloro-4-((2,3-dihydroxypropyl)amino)benzonitrile

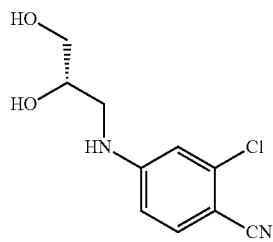 [SMILES: N#Cc1ccc(NC[C@H](O)CO)cc1Cl]

2-Chloro-4-fluorobenzonitrile was used to obtain a title compound in the same manner as in Preparation Example 1.
Mass[M+H]: 227.05

PREPARATION EXAMPLE 36

Preparation of 2-chloro-4-((2S,5S)-5-(hydroxymethyl)-2-(trifluoromethyl)oxazolidin-3-yl)benzonitrile

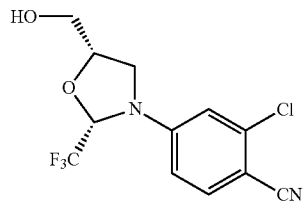 [SMILES: N#Cc1ccc(N2C[C@@H](CO)O[C@H]2C(F)(F)F)cc1Cl]

The compound (S)-2-chloro-4-((2,3-dihydroxypropyl)amino)benzonitrile obtained in Preparation Example 35 was used to obtain a title compound in the same manner as in Preparation Example 2.
Mass[M+H]: 307.04

PREPARATION EXAMPLE 37

Preparation of ((2S,5S)-3-(3-chloro-4-cyanophenyl)-2-(trifluoromethyl)oxazolidin-5-yl)methyl methanesulfonate

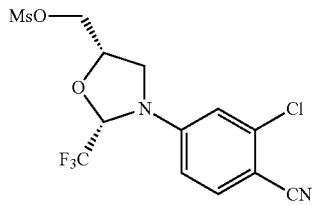 [SMILES: CS(=O)(=O)OC[C@@H]1CN(c2ccc(C#N)c(Cl)c2)[C@H](C(F)(F)F)O1]

The compound 2-chloro-4-((2S,5S)-5-(hydroxymethyl)-2-(trifluoromethyl)oxazolidin-3-yl)benzonitrile obtained in Preparation Example 36 was used to obtain a title compound in the same manner as in Preparation Example 3.
Mass[M+H]: 385.02

PREPARATION EXAMPLE 38

Preparation of 2-chloro-4-((2R,5S)-5-(hydroxymethyl)-2-(trifluoromethyl)oxazolidin-3-yl)benzonitrile

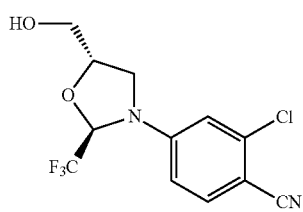 [SMILES: N#Cc1ccc(N2C[C@@H](CO)O[C@@H]2C(F)(F)F)cc1Cl]

The compound (S)-2-chloro-4-((2,3-dihydroxypropyl)amino)benzonitrile obtained in Preparation Example 35 was used to obtain a title compound in the same manner as in Preparation Example 5.
Mass[M+H]: 307.04

PREPARATION EXAMPLE 39

Preparation of ((2R,5S)-3-(3-chloro-4-cyanophenyl)-2-(trifluoromethyl)oxazolidin-5-yl)methyl methanesulfonate

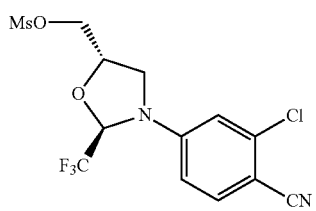 [SMILES: CS(=O)(=O)OC[C@@H]1CN(c2ccc(C#N)c(Cl)c2)[C@@H](C(F)(F)F)O1]

The compound 2-chloro-4-((2R,5S)-5-(hydroxymethyl)-2-(trifluoromethyl)oxazolidin-3-yl)benzonitrile obtained in Preparation Example 38 was used to obtain a title compound in the same manner as in Preparation Example 3.
Mass[M+H]: 385.02

PREPARATION EXAMPLE 40

Preparation of (S)-2-chloro-4-((2,3-dihydroxypropyl)amino)-3-methylbenzonitrile

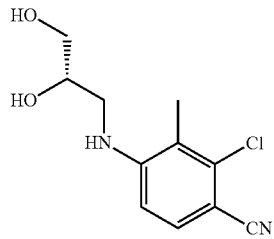 [SMILES: Cc1c(NC[C@H](O)CO)ccc(C#N)c1Cl]

2-Chloro-4-fluoro-3-methylbenzonitrile was used to obtain a title compound in the same manner as in Preparation Example 1.
Mass[M+H]: 241.07

PREPARATION EXAMPLE 41

Preparation of 2-chloro-4-((2S,5S)-5-(hydroxymethyl)-2-(trifluoromethyl)oxazolidin-3-yl)-3-methylbenzonitrile

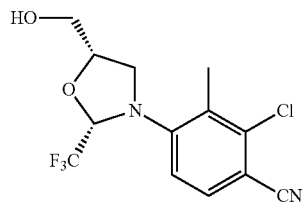 [SMILES: Cc1c(N2C[C@@H](CO)O[C@H]2C(F)(F)F)ccc(C#N)c1Cl]

The compound (S)-2-chloro-4-((2,3-dihydroxypropyl)amino)-3-methylbenzonitrile obtained in Preparation Example 40 was used to obtain a title compound in the same manner as in Preparation Example 2.
Mass[M+H]: 321.05

PREPARATION EXAMPLE 42

Preparation of ((2S,5S)-3-(3-chloro-4-cyano-2-methylphenyl)-2-(trifluoromethyl)oxazolidin-5-yl)methyl methanesulfonate

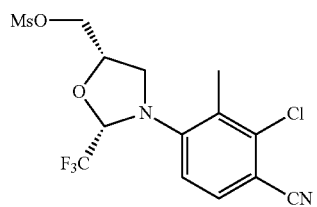 [SMILES: Cc1c(N2C[C@@H](COS(C)(=O)=O)O[C@H]2C(F)(F)F)ccc(C#N)c1Cl]

The compound 2-chloro-4-((2S,5S)-5-(hydroxymethyl)-2-(trifluoromethyl)oxazolidin-3-yl)-3-methylbenzonitrile obtained in Preparation Example 41 was used to obtain a title compound in the same manner as in Preparation Example 3.
Mass[M+H]: 399.03

PREPARATION EXAMPLE 43

Preparation of 2-chloro-4-((2R,5S)-5-(hydroxymethyl)-2-(trifluoromethyl)oxazolidin-3-yl)-3-methylbenzonitrile

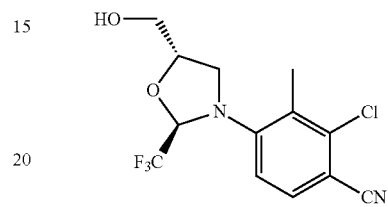

The compound (S)-2-chloro-4-((2,3-dihydroxypropyl)amino)-3-methylbenzonitrile obtained in Preparation Example 40 was used to obtain a title compound in the same manner as in Preparation Example 5.
Mass[M+H]: 321.05

PREPARATION EXAMPLE 44

Preparation of ((2R,5S)-3-(3-chloro-4-cyano-2-methylphenyl)-2-(trifluoromethyl)oxazolidin-5-yl)methyl methanesulfonate

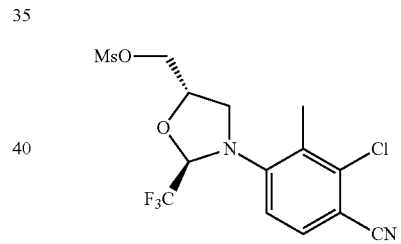

The compound 2-chloro-4-((2R,5S)-5-(hydroxymethyl)-2-(trifluoromethyl)oxazolidin-3-yl)-3-methylbenzonitrile obtained in Preparation Example 43 was used to obtain a title compound in the same manner as in Preparation Example 3.
Mass[M+H]: 399.03

PREPARATION EXAMPLE 45

Preparation of ((2S,5S)-3-(3-trifluoromethyl-4-nitrophenyl)-2-(trifluoromethyl)oxazolidin-5-yl)methanol

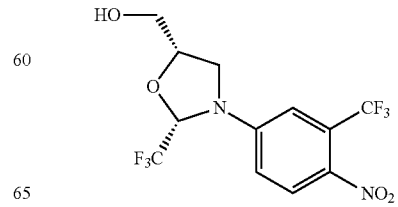

The compound (S)-3-((3-trifluoromethyl-4-nitrophenyl)amino)propane-1,2-diol obtained in Preparation Example 7 was used to obtain 2 g (35%) of a title compound in the same manner as in Preparation Example 2.

Mass[M+H]: 361.05

PREPARATION EXAMPLE 46

Preparation of ((2S,5S)-3-(3-trifluoromethyl-4-nitrophenyl)-2-(trifluoromethyl)oxazolidin-5-yl)methyl methanesulfonate

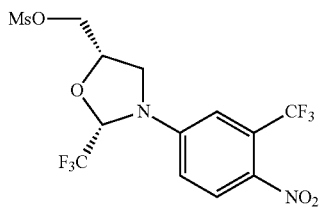 [SMILES: CS(=O)(=O)OC[C@@H]1CN(c2ccc([N+](=O)[O-])c(C(F)(F)F)c2)[C@H](C(F)(F)F)O1]

The compound ((2S,5S)-3-(3-trifluoromethyl-4-nitrophenyl)-2-(trifluoromethyl)oxazolidin-5-yl)methanol obtained in Preparation Example 45 was used to obtain 100 mg (24%) of a title compound in the same manner as in Preparation Example 3.

Mass[M+H]: 439.03

PREPARATION EXAMPLE 47

Preparation of ethyl(2S,5S)-3-(4-cyano-3-(trifluoromethyl)phenyl)-2-(trifluoromethyl)oxazolidine-5-carboxylate

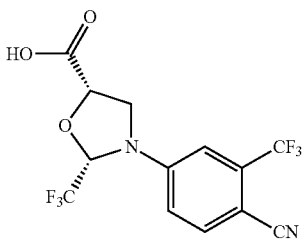 [SMILES: N#Cc1ccc(N2C[C@@H](C(=O)O)O[C@H]2C(F)(F)F)cc1C(F)(F)F]

In a 25-ml flask, 100 mg (0.33 mmol) of the compound ethyl (S)-3-((4-cyano-3-(trifluoromethyl)phenyl)amino)-2-hydroxypropanoate obtained in Preparation Example 14 was used to obtain a reaction product in the same manner as in Preparation Example 15, and the product was applied to a silica gel column to separate (2S,5S)-isomers, thereby obtaining 27 mg (21%) of a title compound.

$^1$H NMR (CDCl$_3$, 600 MHz) δ 7.70(d, 1H), 7.30(d, 1H), 6.91(dd, 1H), 5.70(q, 1H), 4.88(dd, 1H), 4.36~4.25(m, 2H), 4.12~4.08(m, 1H), 4.02~3.99(m, 1H), 1.33(t, 3H)

Mass[M+H]: 383.08

PREPARATION EXAMPLE 48

Preparation of (2S,5S)-3-(4-cyano-3-(trifluoromethyl)phenyl)-2-(trifluoromethyl)oxazolidine-5-carboxylic acid

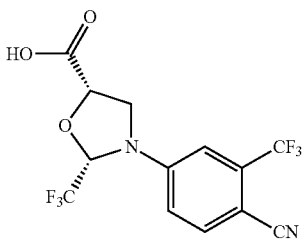 [SMILES: N#Cc1ccc(N2C[C@@H](C(=O)O)O[C@H]2C(F)(F)F)cc1C(F)(F)F]

In a 25-ml flask, 27 mg (0.07 mmol) of the compound ethyl (2S,5S)-3-(4-cyano-3-(trifluoromethyl)phenyl)-2-(trifluoromethyl)oxazolidine-5-carboxylate obtained in Preparation Example 47 was used to obtain 11 mg (44%) of a title compound in the same manner as in Preparation Example 16.

$^1$H NMR (CDCl$_3$, 400 MHz) δ 7.71(d, 1H), 7.04(d, 1H), 6.92(dd, 1H), 5.74(q, 1H), 4.93(t, 1H), 4.19(t, 1H), 3.98(dd, 1H)

Mass[M+H]: 355.04

EXAMPLE 1

Preparation of 4-((2R,5S)-5-(hydroxymethyl)-2-(trifluoromethyl)oxazolidin-3-yl)-2-(trifluoromethyl)benzonitrile

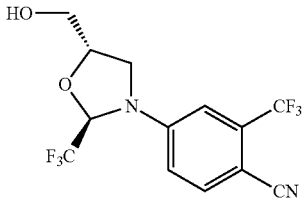 [SMILES: N#Cc1ccc(N2C[C@@H](CO)O[C@@H]2C(F)(F)F)cc1C(F)(F)F]

To a 50-ml flask, 30 g (115 mmol) of (S)-4-((2,3-dihydroxypropyl)amino)-2-(trifluoromethyl)benzonitrile obtained in Preparation Example 1 was added and 600 ml of trifluoroacetic acid was added, followed by stirring. 68 ml (575 mmol, 5 eq) of trifluoroacetaldehyde ethylhemiacetal was added thereto, followed by stirring at 100° C. for about 5 hours. After completion of the reaction, the reaction product was concentrated under reduced pressure, and separation of layers was performed with water (1 L) and ethyl acetate (1 L). Then, an aqueous layer was removed, followed by washing with 2N NaOH (1 L). An organic layer was washed with water and a saturated NaCl aqueous solution, dehydrated and dried over MgSO$_4$, and then concentrated under reduced pressure. A concentrate was subjected to column chromatography to separate (2R,5S)-isomers, thereby obtaining 15 g (38%) of a title compound.

$^1$H NMR (CDCl$_3$, 400 MHz) δ 7.67(d, 1H), 6.99(d, 1H), 6.87(dd, 1H), 5.57(q, 1H), 4.79~4.77(m, 1H), 3.98~3.96(m, 1H), 3.78(t, 1H), 3.74~3.70(m, 1H), 3.59(t, 1H), 1.87(t, 1H)

Mass[M+H]: 341.06

EXAMPLE 2

Preparation of 4-((2R,5S)-5-(((4-cyanobenzyl)oxy)methyl)-2-(trifluoromethyl)oxazolidin-3-yl)-2-(trifluoromethyl)benzonitrile

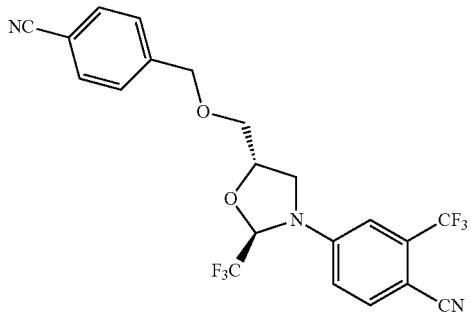 [SMILES: N#Cc1ccc(COC[C@@H]2CN(c3ccc(C#N)c(C(F)(F)F)c3)[C@@H](C(F)(F)F)O2)cc1]

To a 10-ml flask, 100 mg (0.294 mmol) of the compound 4-((2R,5S)-5-(hydroxymethyl)-2-(trifluoromethyl)oxazolidin-3-yl)-2-(trifluoromethyl)benzonitrile obtained in Example 1 was added and 3 ml of N,N-dimethylformamide was added, followed by stirring. 13 mg (0.323 mmol, 1.1 eq) of NaH was added thereto, followed by stirring for 30 minutes. Then, 4-bromomethyl-benzonitrile was added, followed by stirring at room temperature for about 12 hours.

After completion of the reaction, the reaction product was diluted with ethyl acetate (10 ml) and washed with water (10 ml). After separation of layers, an organic layer was washed with a saturated NH$_4$Cl aqueous solution, and then washed with water. The organic layer was separated and then washed with a NaCl aqueous solution, dehydrated and dried over MgSO$_4$, and then concentrated under reduced pressure. A concentrate was separated by a column to obtain 25 mg (19%) of a title compound.

$^1$H NMR (CDCl$_3$, 400 MHz) δ 7.70(d, 1H), 7.62(d, 2H), 7.37(d, 2H), 6.99(d, 1H), 6.87(dd, 1H), 5.57(q, 1H), 4.88~4.83(m, 1H), 4.62(s, 2H), 3.85(t, 1H), 3.72(qd, 2H), 3.54(t, 1H)

Mass[M+H]: 456.11

EXAMPLE 3

Preparation of 4-((2S,5R)-5-(hydroxymethyl)-2-(trifluoromethyl)oxazolidin-3-yl)-2-(trifluoromethyl)benzonitrile

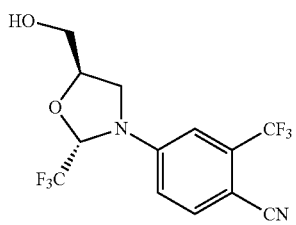 [SMILES: N#Cc1ccc(N2C[C@H](CO)O[C@H]2C(F)(F)F)cc1C(F)(F)F]

Step 1. Preparation of (R)-4-((2,3-dihydroxypropyl)amino)-2-(trifluoromethyl)benzonitrile

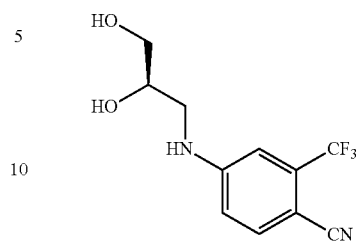

In a 100-ml flask, 1 g (5.29 mmol) of 4-fluoro-2-(trifluoromethyl)benzonitrile and 722 mg (1.5 eq) of (R)-3-aminopropane-1,2-diol were used to obtain 1.1 g (80%) of a title compound in the same manner as in Preparation Example 1.

$^1$H NMR (Acetone-d6, 400 MHz) δ 7.66(d, 1H), 7.17(d, 1H), 6.99(dd, 1H), 6.45(s, 1H), 3.88(br, 1H), 3.59(t, 2H), 3.51~3.46(m, 1H), 3.29~3.23(m, 1H)

Mass[M+H]: 261.22

Step 2. Preparation of 4-((2S,5R)-5-(hydroxymethyl)-2-(trifluoromethyl)oxazolidin-3-yl)-2-(trifluoromethyl)benzonitrile 3 g (11.5 mmol) of the compound (R)-4-((2,3-dihydroxypropyl)amino)-2-(trifluoromethyl)benzonitrile obtained in Step 1 of Example 3 was added, and 60 ml of trifluoroacetic acid was added, followed by stirring. 6.8 ml (57.5 mmol, 5 eq) of trifluoroacetaldehyde ethylhemiacetal was added, followed by stirring at 100° C. for about 5 hours. After completion of the reaction, the reaction product was concentrated under reduced pressure. After separation of layers with water (100 ml) and ethyl acetate (100 ml), an aqueous layer was removed, followed by washing with a 2 N NaOH aqueous solution (100 ml). An organic layer was washed with water and a saturated NaCl aqueous solution, dehydrated and dried over MgSO$_4$, and then concentrated under reduced pressure. A concentrate was subjected to column chromatography to separate (2S,5R)-isomers, thereby obtaining 1.5 g (38%) of a title compound.

760 mg (46%) of the title compound was obtained in the same manner as in Preparation Example 2.

$^1$H NMR (CDCl$_3$, 400 MHz) δ 7.70(d, 1H), 7.01(s, 1H), 6.89(d, 1H), 5.59(q, 1H), 4.81(t, 1H), 4.02~3.98(m, 1H), 3.81(t, 1H), 3.77~3.71(m, 1H), 3.61(t, 1H), 1.80(q, 1H)

Mass[M+H]: 341.06

EXAMPLE 4

Preparation of 4-((2S,5R)-5-(((4-cyanobenzyl)oxy)methyl)-2-(trifluoromethyl)oxazolidin-3-yl)-2-(trifluoromethyl)benzonitrile

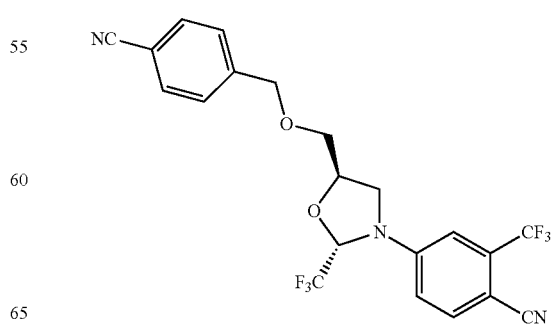

The compound 4-((2S,5R)-5-(hydroxymethyl)-2-(trifluoromethyl)oxazolidin-3-yl)-2-(trifluoromethyl)benzonitrile obtained in Step 2 of Example 3 and 4-bromomethylbenzonitrile were used to obtain 30 mg (20%) of a title compound in the same manner as in Example 2.

¹H NMR (CDCl₃, 400 MHz) δ 7.67(d, 1H), 7.59(d, 2H), 7.35(d, 2H), 6.97(d, 1H), 6.86(dd, 1H), 5.56(q, 1H), 4.86~4.81(m, 1H), 4.60(s, 2H), 3.83(t, 1H), 3.71(qd, 2H), 3.52(t, 1H)

Mass[M+H]: 456.11

EXAMPLE 5

Preparation of 4-((2R,5R)-5-((4-cyanophenoxy)methyl)-2-(trifluoromethyl)oxazolidin-3-yl)-2-(trifluoromethyl)benzonitrile

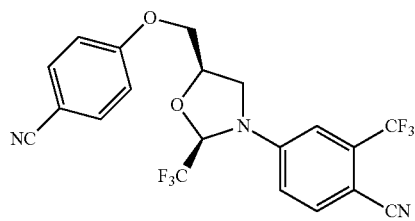 [SMILES: N#Cc1ccc(OC[C@H]2CN(c3ccc(C#N)c(C(F)(F)F)c3)[C@@H](C(F)(F)F)O2)cc1]

Step 1. Preparation of (R)-4-(3-(1,3-dioxoisoindolin-2-yl)-2-hydroxypropoxy)benzonitrile

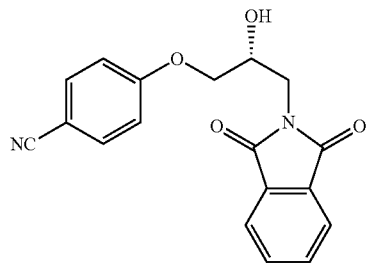 [SMILES: N#Cc1ccc(OC[C@H](O)CN2C(=O)c3ccccc3C2=O)cc1]

To a 500-ml flask, 5 g (24.6 mmol) of (R)-N-glycidylphthalimide was added and 150 ml of N,N-dimethylformamide was added, followed by stirring. 2.93 g (24.6 mmol, 1 eq) of 4-cyanophenol was added, and 10.2 g (73.8 mmol, 3 eq) of K₂CO₃ was added, followed by stirring at 120° C. for 16 hours. After completion of the reaction, the reaction product was diluted with ethyl acetate (200 ml), and washed with water (200 ml). After separation of layers, an organic layer was washed with a saturated NH₄Cl aqueous solution, and then washed with water. The organic layer was separated and then washed with a NaCl aqueous solution, dehydrated and dried over MgSO₄, and concentrated under reduced pressure. A concentrate was subjected to column chromatography to obtain 3.37 g (43%) of a title compound.

¹H NMR (CDCl₃, 400 MHz) δ 7.87~7.85(m, 2H), 7.75~7.73(m, 2H), 7.57(d, 2H), 6.94(d, 2H), 4.31(q, 1H), 4.29~3.96(m, 4H), 2.87(d, 1H)

Mass[M+H]: 323.10

Step 2. Preparation of (R)-4-(3-amino-2-hydroxypropoxy)benzonitrile

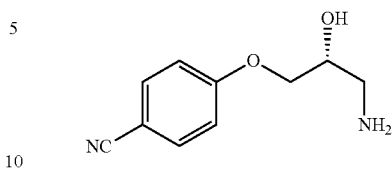

To a 500-ml flask, 3.37 g (10.5 mmol) of the compound (R)-4-(3-(1,3-dioxoisoindolin-2-yl)-2-hydroxypropoxy)benzonitrile obtained in Step 1 of Example 5 was added, and 250 ml of ethanol added, followed by stirring at room temperature. To the reaction solution, 19.6 ml (262 mmol, 25 eq) of hydrazine monohydrate was added dropwise, followed by stirring at room temperature for 2 hours. After completion of the reaction, the reaction product was concentrated under reduced pressure to obtain 2.02 g (95%) of a title compound.

Step 3. Preparation of (R)-4-((3-(4-cyanophenoxy)-2-hydroxypropyl)amino)-2-(trifluoromethyl)benzonitrile

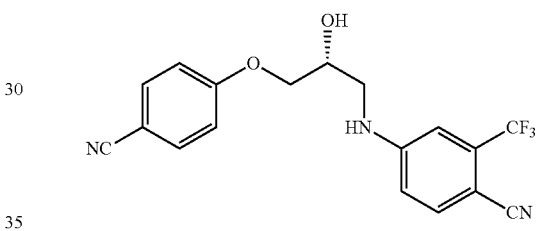

To a 250-ml flask, 2.02 g (10.5 mmol, 1.1 eq) of the compound (R)-4-(3-amino-2-hydroxypropoxy)benzonitrile obtained in Step 2 of Example 5 was added and 100 ml of dimethyl sulfoxide was added, followed by stirring. 1.81 g (9.55 mmol, 1 eq) of 4-fluoro-2-(trifluoromethyl)benzonitrile and 1.6 ml (11.5 mmol, 1.2 eq) of triethylamine were added thereto, followed by stirring at 60° C. for 16 hours. After completion of the reaction, the reaction solution was diluted with ethyl acetate (100 ml) and washed with water (200 ml) three times. After separation of layers, an aqueous layer was removed and an organic layer was washed with a saturated NaCl aqueous solution, dehydrated and dried over MgSO₄, and then concentrated under reduced pressure to obtain 2.6 g (70%) of a title compound.

¹H NMR (CDCl₃, 400 MHz) δ 7.60(d, 2H), 7.56(d, 1H), 7.72(s, 1H), 6.96(d, 2H), 6.91(d, 1H), 6.74(dd, 1H), 4.91(t, 1H), 4.31(br, 1H), 4.12~4.04(m, 2H), 3.50~3.47(m, 1H), 3.40~3.37(m, 1H)

Mass[M+H]: 362.10

Step 4. Preparation of 4-((2R,5R)-5-((4-cyanophenoxy)methyl)-2-(trifluoromethyl)oxazolidin-3-yl)-2-(trifluoromethyl)benzonitrile 70 mg (0.19 mmol) of the compound (R)-4-((3-(4-cyanophenoxy)-2-hydroxypropyl)amino)-2-(trifluoromethyl)benzonitrile obtained in Step 3 of Example 5 was added, and 20 ml of trifluoroacetic acid was added thereto, followed by stirring. To this reaction solution, 1 g (1 ea) of NaBH₄ was added, followed by stirring at 100° C. The reaction solution was concentrated under reduced pressure, and basified with a 2 N NaOH aqueous solution, and extracted with 10 ml of ethyl acetate three times. The extracted solution was concentrated under reduced pressure and subjected to column chromatography to separate (2R,5R)-isomers, thereby obtaining 17 mg (20%) of a title compound.

$^1$H NMR (CDCl$_3$, 400 MHz) δ 7.70(d, 1H), 7.61(d, 2H), 7.05(d, 1H), 6.98(d, 2H), 6.93(dd, 1H), 5.72(q, 1H), 4.73~4.66(m, 1H), 4.34~4.31(m, 1H), 4.23~4.18(m, 1H), 4.16~4.07(m, 1H), 3.72~3.66(m, 1H)

Mass[M+H]: 442.09

EXAMPLE 6

Preparation of 4-((2S,5S)-5-((4-cyanophenoxy)methyl)-2-(trifluoromethyl)oxazolidin-3-yl)-2-(trifluoromethyl)benzonitrile

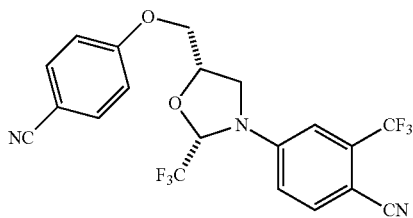

To a 50-ml flask, 200 mg (0.478 mmol) of the compound ((2S,5S)-3-(4-cyano-3-(trifluoromethyl)phenyl)-2-(trifluoromethyl)oxazolidin-5-yl)methyl methanesulfonate obtained in Preparation Example 3 was added, and 10 ml of N,N-dimethylformamide was added, followed by stirring. 57 mg (0.478 mmol, 1 eq) of 4-cyanophenol and 79 mg (0.574 mmol, 1.2 eq) of K$_2$CO$_3$ were added thereto, followed by stirring at 120° C. for about 4 hours. After completion of the reaction, the reaction product was diluted with ethyl acetate (20 ml) and washed with water (20 ml). After separation of layers, an organic layer was washed with a saturated NH$_4$Cl aqueous solution, and then washed with water. The organic layer was separated and washed with a NaCl aqueous solution, and then dehydrated and dried over MgSO$_4$, followed by concentration under reduced pressure. A concentrate was separated by column chromatography to obtain 50 mg (24%) of a title compound.

$^1$H NMR (CDCl$_3$, 400 MHz) δ 7.72(d, 1H), 7.62(d, 2H), 7.07(d, 1H), 7.00(d, 2H), 6.96(dd, 1H), 5.73(q, 1H), 4.75~4.68(m, 1H), 4.36~4.33(m, 1H), 4.25~4.21(m, 1H), 4.16~4.12(m, 1H), 3.74~3.69(m, 1H)

Mass[M+H]: 442.09

EXAMPLE 7

Preparation of methyl 4-(((2R,5S)-3-(4-cyano-3-(trifluoromethyl)phenyl)-2-(trifluoromethyl)oxazolidin-5-yl)methoxy)benzoate

Step 1. Preparation of ((2R,5S)-3-(4-cyano-3-(trifluoromethyl)phenyl)-2-(trifluoromethyl)oxazolidin-5-yl)methylmethanesulfonate

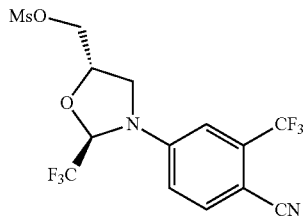

The compound 4-((2R,5S)-5-(hydroxymethyl)-2-(trifluoromethyl)oxazolidin-3-yl)-2-(trifluoromethyl)benzonitrile obtained in Example 1 was used to obtain 6.6 g (90%) of a title compound in the same manner as in Preparation Example 3.

$^1$H NMR (CDCl$_3$, 400 MHz) δ 7.71(d, 1H), 6.99(d, 1H), 6.88(dd, 1H), 5.62(q, 1H), 4.40(qd, 2H), 3.90(t, 1H), 3.56(t, 1H), 3.01(s, 3H)

Mass[M+H]: 419.04

Step 2. Preparation of methyl 4-(((2R,5S)-3-(4-cyano-3-(trifluoromethyl)phenyl)-2-(trifluoromethyl)oxazolidin-5-yl)methoxy)benzoate The compound ((2R,5S)-3-(4-cyano-3-(trifluoromethyl)phenyl)-2-(trifluoromethyl)oxazolidin-5-yl)methyl methanesulfonate obtained in Step 1 of Example 7 and methyl 4-hydroxybenzoate were used to obtain 250 mg (73%) of a title compound in the same manner as in Example 6.

$^1$H NMR (CDCl$_3$, 400 MHz) δ 7.96(d, 2H), 7.71(d, 1H), 7.01(s, 1H), 6.90(dd, 1H), 6.81(d, 2H), 5.62(q, 1H), 5.02~5.01(m, 1H), 4.22(qd, 2H), 3.95(t, 1H), 3.87(s, 3H), 3.71(t, 1H)

Mass[M+H]: 475.10

EXAMPLE 8

Preparation of 4-((2R,5S)-5-((4-nitrophenoxy)methyl)-2-(trifluoromethyl)oxazolidin-3-yl)-2-(trifluoromethyl)benzonitrile

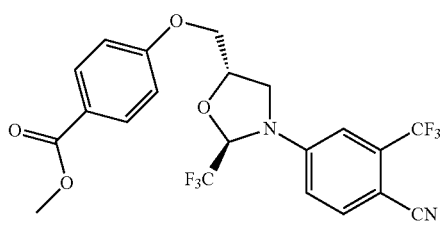 [SMILES: COC(=O)c1ccc(OC[C@@H]2CN(c3ccc(C#N)c(C(F)(F)F)c3)[C@@H](C(F)(F)F)O2)cc1]

The compound ((2R,5S)-3-(4-cyano-3-(trifluoromethyl)phenyl)-2-(trifluoromethyl)oxazolidin-5-yl)methyl methanesulfonate obtained in Step 1 of Example 7 and 4-nitrophenol were used to obtain 40 mg (36%) of a title compound in the same manner as in Example 6.

$^1$H NMR (CDCl$_3$, 400 MHz) δ 8.19(d, 2H), 7.73(d, 1H), 7.03(d, 1H), 6.92~6.88(m, 3H), 5.63(q, 1H), 5.05(m, 1H), 4.27(pd, 2H), 3.98(t, 1H), 3.69(t, 1H)

Mass[M+H]: 462.08

EXAMPLE 9

Preparation of 4-(((2R,5S)-3-(4-cyano-3-(trifluoromethyl)phenyl)-2-(trifluoromethyl)oxazolidin-5-yl)methoxy)benzoic acid

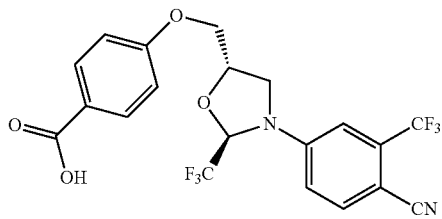 [SMILES: N#Cc1ccc(N2C[C@@H](COc3ccc(C(=O)O)cc3)O[C@@H]2C(F)(F)F)cc1C(F)(F)F]

To a 50-ml flask, 230 mg (0.485 mmol) of the compound methyl 4-(((2R,5S)-3-(4-cyano-3-(trifluoromethyl)phenyl)-2-(trifluoromethyl)oxazolidin-5-yl)methoxy)benzoate obtained in Step 2 of Example 7 was added and 5 ml of ethanol was added, followed by stirring. 47 mg (1.94 mmol, 4 eq) of LiOH was added thereto, followed by stirring at 60° C. for about 8 hours. The reaction product was concentrated under reduced pressure and diluted with 20 ml of water and acidified with a 2 N hydrochloric acid aqueous solution. This solution was extracted with ethyl acetate, and washed with water and a saturated NaCl aqueous solution, dehydrated and dried over MgSO$_4$, and then concentrated under reduced pressure. A concentrate was separated by column chromatography to obtain 100 mg (45%) of a title compound.

$^1$H NMR (CDCl$_3$, 400 MHz) δ 8.01(d, 2H), 7.72(d, 1H), 7.02(d, 1H), 6.91(dd, 1H), 6.84(d, 2H), 5.63(q, 1H), 5.03(m, 1H), 4.24(pd, 2H), 3.96(t, 1H), 3.71(t, 1H)

Mass[M+H]: 461.09

EXAMPLE 10

Preparation of 4-((2R,5S)-5-((3,4-difluorophenoxy)methyl)-2-(trifluoromethyl)oxazolidin-3-yl)-2-(trifluoromethyl)benzonitrile

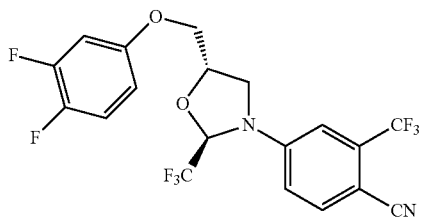 [SMILES: N#Cc1ccc(N2C[C@@H](COc3ccc(F)c(F)c3)O[C@@H]2C(F)(F)F)cc1C(F)(F)F]

The compound ((2R,5S)-3-(4-cyano-3-(trifluoromethyl)phenyl)-2-(trifluoromethyl)oxazolidin-5-yl)methyl methanesulfonate obtained in Step 1 of Example 7 and 3,4-difluorophenol were used to obtain 34 mg (33%) of a title compound in the same manner as in Example 6.

$^1$H NMR (CDCl$_3$, 400 MHz) δ 7.71(d, 1H), 7.08~7.01(m, 2H), 6.90(dd, 1H), 6.67~6.62(m, 1H), 6.52~6.49(m, 1H), 5.61(q, 1H), 4.99~4.97(m, 1H), 4.15~4.07(m, 2H), 3.93(t, 1H), 3.66(t, 1H)

Mass[M+H]: 453.08

EXAMPLE 11

Preparation of 4-((2R,5S)-5-((4-cyano-2-fluorophenoxy)methyl)-2-(trifluoromethyl)oxazolidin-3-yl)-2-(trifluoromethyl)benzonitrile

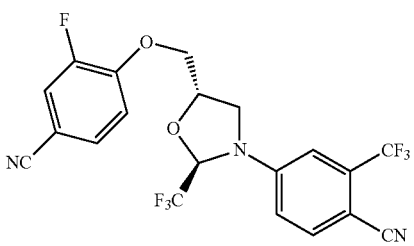 [SMILES: N#Cc1ccc(OC[C@@H]2CN(c3ccc(C#N)c(C(F)(F)F)c3)[C@@H](C(F)(F)F)O2)c(F)c1]

The compound ((2R,5S)-3-(4-cyano-3-(trifluoromethyl)phenyl)-2-(trifluoromethyl)oxazolidin-5-yl)methyl methanesulfonate obtained in Step 1 of Example 7 and 3-fluoro-4-hydroxybenzonitrile were used to obtain 50 mg (48%) of a title compound in the same manner as in Example 6.

$^1$H NMR (CDCl$_3$, 400 MHz) δ 7.69(d, 1H), 7.39(d, 1H), 7.32(d, 1H), 7.02~6.98(m, 2H), 6.90(dd, 1H), 5.64(q, 1H), 5.04~5.02(m, 1H), 4.29(qd, 2H), 3.98(t, 1H), 3.75(t, 1H)

Mass[M+H]: 460.08

EXAMPLE 12

Preparation of 4-((2R,5S)-5-((2-chloro-4-nitrophenoxy)methyl)-2-(trifluoromethyl)oxazolidin-3-yl)-2-(trifluoromethyl)benzonitrile

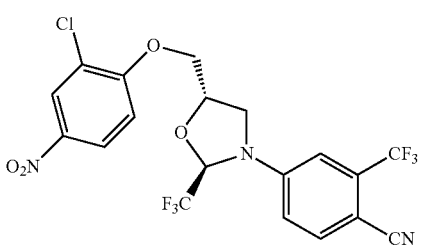

The compound ((2R,5S)-3-(4-cyano-3-(trifluoromethyl)phenyl)-2-(trifluoromethyl)oxazolidin-5-yl)methyl methanesulfonate obtained in Step 1 of Example 7 and 2-chloro-4-nitrophenol were used to obtain 45 mg (38%) of a title compound in the same manner as in Example 6.

$^1$H NMR (CDCl$_3$, 400 MHz) δ 8.23(dd, 1H), 8.12(dd, 1H), 7.69(d, 1H), 7.02~6.98(m, 2H), 6.91(dd, 1H), 5.69(q, 1H), 5.09~5.07(m, 1H), 4.35(qd, 2H), 4.01(t, 1H), 3.86(t, 1H)

Mass[M+H]: 496.04

EXAMPLE 13

Preparation of 2-(trifluoromethyl)-4-((2R,5S)-2-(trifluoromethyl)-5-((2,4,5-trifluorophenoxy)methyl)oxazolidin-3-yl)benzonitrile

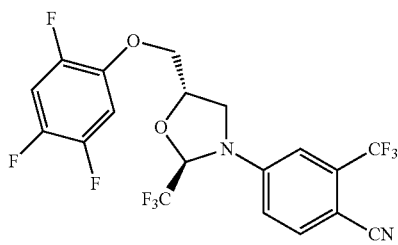 [SMILES: N#Cc1ccc(N2C[C@@H](COc3cc(F)c(F)cc3F)O[C@@H]2C(F)(F)F)cc1C(F)(F)F]

The compound ((2R,5S)-3-(4-cyano-3-(trifluoromethyl)phenyl)-2-(trifluoromethyl)oxazolidin-5-yl)methyl methanesulfonate obtained in Step 1 of Example 7 and 2,4,5-trifluorophenol were used to obtain 45 mg (40%) of a title compound in the same manner as in Example 6.

$^1$H NMR (CDCl$_3$, 400 MHz) δ 7.70(d, 1H), 7.01(s, 1H), 6.97~6.78(m, 3H), 5.63(q, 1H), 4.98~4.97(m, 1H), 4.22~4.14(m, 2H), 3.94(t, 1H), 3.74(t, 1H)

Mass[M+H]: 471.07

EXAMPLE 14

Preparation of 4-((2R,5S)-5-((4-aminophenoxy)methyl)-2-(trifluoromethyl)oxazolidin-3-yl)-2-(trifluoromethyl)benzonitrile

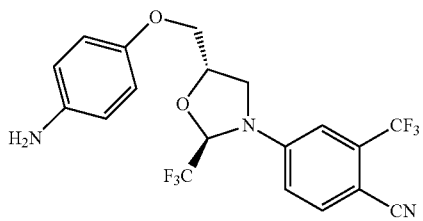

To a 25-ml flask, 45 mg (0.098 mmol) of 4-((2R,5S)-5-((4-nitrophenoxy)methyl)-2-(trifluoromethyl)oxazolidin-3-yl)-2-(trifluoromethyl)benzonitrile obtained in Example 8 was added and 5 ml of ethanol was added, followed by stirring. 9 mg (20% wt) of Pd/C was added thereto, and the atmosphere was replaced with hydrogen gas, followed by stirring at room temperature for 1 hour. After completion of the reaction, filtration was performed using Celite and a filtrate was concentrated to obtain 42 mg (99%) of a title compound.

$^1$H NMR (CDCl$_3$, 600 MHz) δ 7.70(d, 1H), 7.00(dd, 1H), 6.86(d, 1H), 6.63~6.58(m, 4H), 5.61(q, 1H), 4.99~4.93(m, 1H), 4.12~4.05(m, 2H), 3.91(dd, 1H), 3.70(t, 1H)

Mass[M+H]: 432.11

EXAMPLE 15

Preparation of 1-(4-(((2R,5S)-3-(4-cyano-3-(trifluoromethyl)phenyl)-2-(trifluoromethyl)oxazolidin-5-yl)methoxy)phenyl)urea

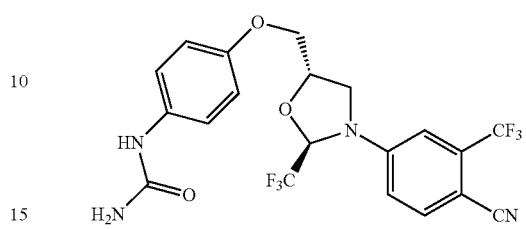

To a 10-ml flask, 60 mg (0.14 mmol) of the compound 4-((2R,5S)-5-((4-aminophenoxy)methyl)-2-(trifluoromethyl)oxazolidin-3-yl)-2-(trifluoromethyl)benzonitrile obtained in Example 14 was added, and 2 ml of toluene was added, followed by stirring. 22.6 mg (0.28 mmol, 2 eq) of potassium cyanate and 15 ul (0.196 mmol, 1.4 eq) of trifluoroacetic acid were added thereto, followed by stirring at 60° C. for about 4 hours. After completion of the reaction, the reaction product was concentrated under reduced pressure, and separated by a column to obtain 25 mg (37%) of a title compound.

$^1$H NMR (CDCl$_3$, 600 MHz) δ 7.70(d, 1H), 7.17(d, 2H), 7.01(s, 1H), 6.90(d, 1H), 6.74(d, 2H), 6.67(s, 1H), 5.62(q, 1H), 4.98~4.96(m, 1H), 4.78(s, 2H), 4.16~4.08(m, 2H), 3.93(t, 1H), 3.69(t, 1H)

Mass[M+H]: 475.11

EXAMPLE 16

Preparation of 1-(4-(((2R,5S)-3-(4-cyano-3-(trifluoromethyl)phenyl)-2-(trifluoromethyl)oxazolidin-5-yl)methoxy)phenyl)-3-methylurea

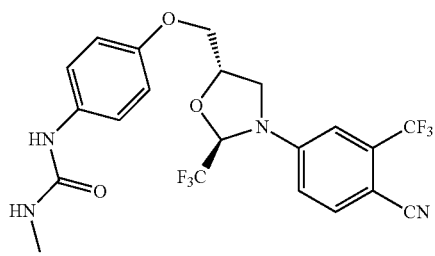 [SMILES: CNC(=O)Nc1ccc(OC[C@@H]2CN(c3ccc(C#N)c(C(F)(F)F)c3)[C@@H](C(F)(F)F)O2)cc1]

Step 1. Preparation of 4-((2R,5S)-5-((4-isocyanatophenoxy)methyl)-2-(trifluoromethyl)oxazolidin-3-yl)-2-(trifluoromethyl)benzonitrile

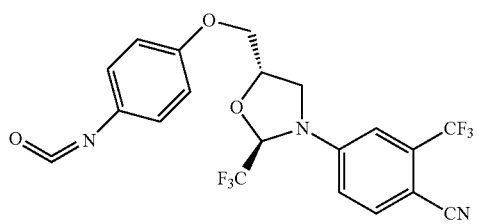 [SMILES: N#Cc1ccc(N2C[C@@H](COc3ccc(N=C=O)cc3)O[C@@H]2C(F)(F)F)cc1C(F)(F)F]

To a 10-ml flask, 100 mg (0.232 mmol) of the compound 4-((2R,5S)-5-((4-aminophenoxy)methyl)-2-(trifluoromethyl)oxazolidin-3-yl)-2-(trifluoromethyl)benzonitrile obtained in Example 14 was added, and 3 ml of dichloromethane was added, followed by stirring. This reaction solution was cooled to 0° C., and then 69 mg (0.232 mmol, 1 eq) of triphosgene and 36 ul (0.255 mmol, 1.1 eq) of triethylamine were added, followed by stirring at room temperature for about 24 hours. This reaction solution was concentrated to obtain 90 mg of a title compound.

Mass[M+H]: 458.09

Step 2. Preparation of 1-(4-(((2R,5S)-3-(4-cyano-3-(trifluoromethyl)phenyl)-2-(trifluoromethyl)oxazolidin-5-yl)methoxy)phenyl)-3-methylurea To a 10-ml flask, 90 mg (0.19 mmol) of the compound 4-((2R,5S)-5-((4-isocyanatophenoxy)methyl)-2-(trifluoromethyl)oxazolidin-3-yl)-2-(trifluoromethyl)benzonitrile obtained in Step 1 of Example 16 was added, and 5 ml of dichloromethane was added, followed by stirring. 28 ul (0.19 mmol, 1 eq) of triethylamine and 14 mg (0.19 mmol, 1 eq) of methylamine hydrochloride were added, followed by stirring at room temperature for about 14 hours. After completion of the reaction, the reaction product was concentrated, and layers were separated with ethyl acetate (10 ml) and water (10 ml). An organic layer was separated and washed with a saturated NaCl aqueous solution. The organic layer was dehydrated and dried over MgSO$_4$, concentrated under reduced pressure, and separated by a column to obtain 20 mg (21%) of a title compound.

$^1$H NMR (CDCl$_3$, 600 MHz) δ 7.68(d, 1H), 7.13(d, 2H), 7.00(s, 1H), 6.89(d, 1H), 6.75(br, 1H), 6.68(d, 2H), 5.62(d, 1H), 4.95(br, 1H), 4.13~4.05(m, 2H), 3.91(t, 1H), 3.68(t, 1H), 2.75(d, 3H)

Mass[M+H]: 489.13

EXAMPLE 17

Preparation of 4-((2R,5S)-5-((4-(2-oxopyrrolidin-1-yl)phenoxy)methyl)-2-(trifluoromethyl)oxazolidin-3-yl)-2-(trifluoromethyl)benzonitrile

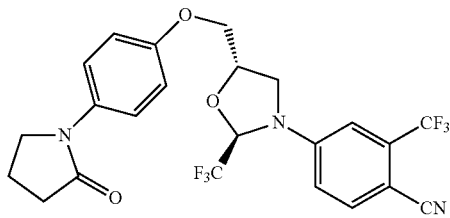 [SMILES: N#Cc1ccc(N2C[C@@H](COc3ccc(N4CCCC4=O)cc3)O[C@@H]2C(F)(F)F)cc1C(F)(F)F]

Step 1. Preparation of 4-bromo-N-(4-(((2R,5S)-3-(4-cyano-3-(trifluoromethyl)phenyl)-2-(trifluoromethyl)oxazolidin-5-yl)methoxy)phenyl)butanamide

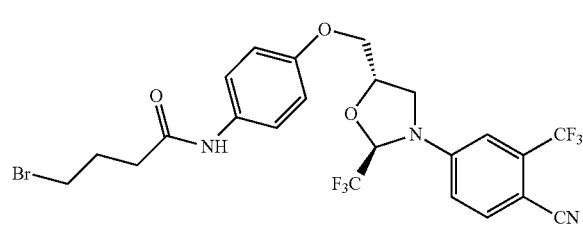 [SMILES: N#Cc1ccc(N2C[C@@H](COc3ccc(NC(=O)CCCBr)cc3)O[C@@H]2C(F)(F)F)cc1C(F)(F)F]

To a 10-ml flask, 60 mg (0.14 mmol) of the compound 4-((2R,5S)-5-((4-aminophenoxy)methyl)-2-(trifluoromethyl)oxazolidin-3-yl)-2-(trifluoromethyl)benzonitrile obtained in Example 14 was added, and 3 ml of dichloromethane was added, followed by stirring. 16.2 ul (0.14 mmol, 1 eq) of 4-bromobutyryl chloride and 14 ul (0.168 mmol, 1.2 eq) of pyridine were added, followed by stirring at room temperature for about 14 hours. After completion of the reaction, the reaction product was concentrated, and layers were separated with ethyl acetate (10 ml) and water (10 ml). Then, an organic layer was separated and washed with a saturated NaCl aqueous solution. The organic layer was dehydrated and dried over MgSO$_4$, concentrated under reduced pressure, and separated by a column to obtain 80 mg (96%) of a title compound.

Mass[M+H]: 580.06

Step 2. Preparation of 4-((2R,5S)-5-((4-(2-oxopyrrolidin-1-yl)phenoxy)methyl)-2-(trifluoromethyl)oxazolidin-3-yl)-2-(trifluoromethyl)benzonitrile To a 10-ml flask, 80 mg (0.14 mmol) of the compound 4-bromo-N-(4-(((2R,5S)-3-(4-cyano-3-(trifluoromethyl)phenyl)-2-(trifluoromethyl)oxazolidin-5-yl)methoxy)phenyl)butanamide obtained in Step 1 of Example 17 was added and 5 ml of N,N-dimethylformamide was added, followed by stirring. 7 mg (0.28 mmol, 2 eq) of NaH was added thereto, followed by stirring at room temperature for about 4 hours. After completion of the reaction, the reaction product was diluted with ethyl acetate (20 ml) and washed with water (20 ml). After separation of layers, an organic layer was washed with a saturated NH$_4$Cl aqueous solution and then washed with water. The organic layer was separated and then washed with a NaCl aqueous solution, and dehydrated and dried over MgSO$_4$, followed by concentration under reduced pressure. A concentrate was separated by a column to obtain 50 mg (70%) of a title compound.

$^1$H NMR (CDCl$_3$, 600 MHz) δ 7.69(d, 1H), 7.47(d, 2H), 7.01(d, 1H), 6.90(dd, 1H), 6.77(d, 2H), 5.62(q, 1H), 4.98~4.97(m, 1H), 4.14(qd, 2H), 3.92(t, 1H), 3.79(t, 2H), 3.70(t, 1H), 2.57(t, 2H), 2.13(t, 2H)

Mass[M+H]: 500.13

EXAMPLE 18

Preparation of 4-((2R,5S)-5-((4-(1,3,4-oxadiazol-2-yl)phenoxy)methyl)-2-(trifluoromethyl)oxazolidin-3-yl)-2-(trifluoromethyl)benzonitrile

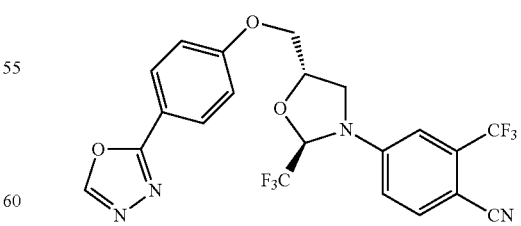

The compound ((2R,5S)-3-(4-cyano-3-(trifluoromethyl)phenyl)-2-(trifluoromethyl)oxazolidin-5-yl)methyl methanesulfonate obtained in Step 1 of Example 7 and 4-(1,3,4-oxadiazol-2-yl)phenol were used to obtain 45 mg (40%) of a title compound in the same manner as in Example 6.

¹H NMR (CDCl₃, 600 MHz) δ 8.40(s, 1H), 7.99(d, 2H), 7.11(d, 1H), 7.66~7.63(m, 1H), 7.44(td, 1H), 7.03(d, 1H), 6.92(d, 2H), 5.64(q, 1H), 5.05~5.02(m, 1H), 4.24(qd, 2H), 3.97(t, 1H), 3.72(t, 1H)
Mass[M+H]: 485.10

EXAMPLE 19

Preparation of 4-((2R,5S)-5-((4-cyanophenoxy)methyl)-2-(trifluoromethyl)oxazolidin-3-yl)-2-(trifluoromethyl)benzonitrile

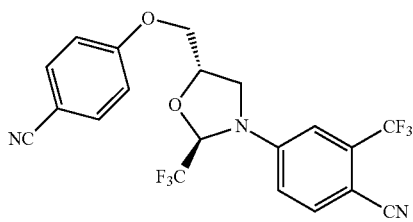 [SMILES: N#Cc1ccc(OC[C@@H]2CN(c3ccc(C#N)c(C(F)(F)F)c3)[C@@H](C(F)(F)F)O2)cc1]

The compound ((2R,5S)-3-(4-cyano-3-(trifluoromethyl)phenyl)-2-(trifluoromethyl)oxazolidin-5-yl)methyl methanesulfonate obtained in Step 1 of Example 7 and 4-cyanophenol were used to obtain 116 mg (70%) of a title compound in the same manner as in Example 6.

¹H NMR (CDCl₃, 600 MHz) δ 7.72(d, 1H), 7.57(d, 2H), 7.02(d, 1H), 6.90(dd, 1H), 6.87(d, 2H), 5.62(q, 1H), 5.04~5.02(m, 1H), 4.25~4.18(m, 2H), 3.96(dd, 1H), 3.68(t, 1H)
Mass[M+H]: 442.09

EXAMPLE 20

Preparation of 4-((2S,5R)-5-((4-cyanophenoxy)methyl)-2-(trifluoromethyl)oxazolidin-3-yl)-2-(trifluoromethyl)benzonitrile

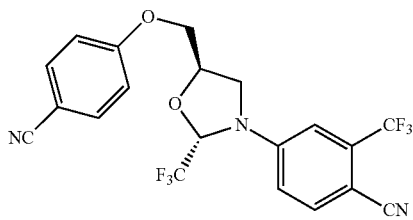 [SMILES: N#Cc1ccc(OC[C@H]2CN(c3ccc(C#N)c(C(F)(F)F)c3)[C@H](C(F)(F)F)O2)cc1]

Step 1. Preparation of ((2S,5R)-3-(4-cyano-3-(trifluoromethyl)phenyl)-2-(trifluoromethyl)oxazolidin-5-yl)methyl methanesulfonate

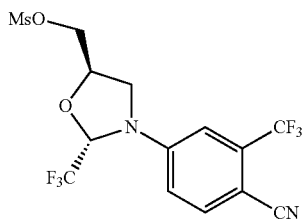 [SMILES: CS(=O)(=O)OC[C@H]1CN(c2ccc(C#N)c(C(F)(F)F)c2)[C@H](C(F)(F)F)O1]

In a 50-ml flask, the compound 4-((2S,5R)-5-(hydroxymethyl)-2-(trifluoromethyl)oxazolidin-3-yl)-2-(trifluoromethyl)benzonitrile obtained in Example 3 was used to obtain 123 mg (>99%) of a title compound in the same manner as in Preparation Example 3.

¹H NMR (CDCl₃, 400 MHz) 7.71(d, 1H), 6.99(d, 1H), 6.88(dd, 1H), 5.62(q, 1H), 4.94~4.91(m, 1H), 4.45(dd, 1H), 4.34(dd, 1H), 3.90(t, 1H), 3.58(t, 1H), 3.01(s, 3H)
Mass[M+H]: 419.04

Step 2. Preparation of 4-((2S,5R)-5-((4-cyanophenoxy)methyl)-2-(trifluoromethyl)oxazolidin-3-yl)-2-(trifluoromethyl)benzonitrile In a 50-ml flask, the compound ((2S,5R)-3-(4-cyano-3-(trifluoromethyl)phenyl)-2-(trifluoromethyl)oxazolidin-5-yl)methyl methanesulfonate obtained in Step 1 of Example 20 and 4-cyanophenol were used to obtain 98.5 mg (62%) of a title compound in the same manner as in Example 6.

¹H NMR (CDCl₃, 400 MHz) δ 7.72(d, 1H), 7.57(d, 2H), 7.02(d, 1H), 6.90(dd, 1H), 6.87(d, 2H), 5.62(q, 1H), 4.26~4.18(m, 2H), 3.98~3.94(m, 1H), 3.68(t, 1H)
Mass[M+H]: 442.09

EXAMPLE 21

Preparation of 4-((2S,5R)-5-((R)-2,2,2-trifluoro-1-hydroxyethyl)-2-(trifluoromethyl)oxazolidin-3-yl)-2-(trifluoromethyl)benzonitrile

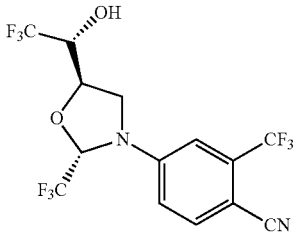 [SMILES: N#Cc1ccc(N2C[C@H]([C@@H](O)C(F)(F)F)O[C@H]2C(F)(F)F)cc1C(F)(F)F]

Step 1. Preparation of 4-((2S,5R)-5-formyl-2-(trifluoromethyl)oxazolidin-3-yl)-2-(trifluoromethyl)benzonitrile

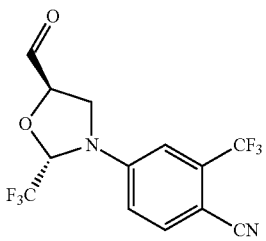 [SMILES: N#Cc1ccc(N2C[C@H](C=O)O[C@H]2C(F)(F)F)cc1C(F)(F)F]

To a 25-ml flask, 160 mg (0.470 mmol) of the compound 4-((2R,5S)-5-(hydroxymethyl)-2-(trifluoromethyl)oxazolidin-3-yl)-2-(trifluoromethyl)benzonitrile obtained in Example 1 was added and 4 ml of dichloromethane was added, followed by stirring. This reaction solution was cooled to 0° C., and then 481 mg (0.705 mmol, 1.5 eq) of Dess Martin periodinane was added, followed by stirring at room temperature for about 1 hour.

After completion of the reaction, the reaction product was diluted with ethyl acetate (30 ml) and washed with water (70 ml). After separation of layers, an organic layer was washed with a saturated NH₄Cl aqueous solution and washed with water. The organic layer was separated and then washed with a NaCl aqueous solution, and dehydrated and dried over MgSO$_4$, and concentrated under reduced pressure to obtain 106.5 mg (66%) of a title compound.

Mass[M+H]: 339.05

Step 2. Preparation of 4-((2S,5R)-5-((R)-2,2,2-trifluoro-1-hydroxyethyl)-2-(trifluoromethyl)oxazolidin-3-yl)-2-(trifluoromethyl)benzonitrile To a 25-ml flask, 106.5 mg (0.315 mmol) of 4-((2S,5R)-5-formyl-2-(trifluoromethyl)oxazolidin-3-yl)-2-(trifluoromethyl)benzonitrile obtained in Step 1 of Example 21 and 2 ml of tetrahydrofuran were added, the atmosphere was replaced with nitrogen under stirring, and 239 mg (1.57 mmol, 5.0 eq) of CsF was injected. This reaction solution was cooled to −78° C., and 70 ul (0.473 mmol, 1.5 eq) of (trifluoromethyl)trimethylsilane was added dropwise thereto. The temperature of the reaction solution was slowly raised to room temperature and stirred for 16 hours. 16 ml of ethanol was added to the reaction solution, followed by stirring for 1 hour. To this reaction solution, 30 ml of ethyl acetate and 30 ml of 1 N-hydrochloric acid aqueous solution were added, followed by stirring and separation of layers. An aqueous layer was removed and an organic layer was separated, and dehydrated and dried over MgSO$_4$, followed by concentration under reduced pressure. A concentrate was subjected to column chromatography to separate an (R)-isomer, thereby obtaining 13.4 mg (10%) of a title compound.

$^1$H NMR (CDCl$_3$, 400 MHz) δ 7.69(d, 1H), 7.00(s, 1H), 6.90(dd, 1H), 5.60(q, 1H), 4.90~4.86(m, 1H), 4.42~4.38(m, 1H), 3.88~3.75(m, 2H), 3.08(d, 1H)

Mass[M+H]: 409.05

EXAMPLE 22

Preparation of 4-((2S,5R)-5-((S)-2,2,2-trifluoro-1-hydroxyethyl)-2-(trifluoromethyl)oxazolidin-3-yl)-2-(trifluoromethyl)benzonitrile

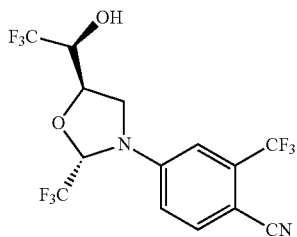 [SMILES: N#Cc1ccc(N2C[C@H]([C@H](O)C(F)(F)F)O[C@H]2C(F)(F)F)cc1C(F)(F)F]

To a 25-ml flask, 106.5 mg (0.315 mmol) of 4-((2S,5R)-5-formyl-2-(trifluoromethyl)oxazolidin-3-yl)-2-(trifluoromethyl)benzonitrile obtained in Step 1 of Example 21 and 2 ml of tetrahydrofuran were added, the atmosphere was replaced with nitrogen under stirring, and 239 mg (1.57 mmol, 5.0 eq) of CsF was injected. The reaction solution was cooled to −78° C., and 70 ul (0.473 mmol, 1.5 eq) of (trifluoromethyl)trimethylsilane was added dropwise to the reaction solution. The temperature of the reaction solution was slowly raised to room temperature and stirred for 16 hours. 16 ml of ethanol was added to the reaction solution, followed by stirring for 1 hour. To the reaction solution, 30 ml of ethyl acetate and 30 ml of 1 N-hydrochloric acid aqueous solution were injected, followed by stirring and separation of layers. An aqueous layer was removed and an organic layer was separated, and dehydrated and dried over MgSO$_4$, followed by concentration under reduced pressure. A concentrate was applied to a column to separate an (S)-isomer, thereby obtaining 14.8 mg (11%) of a title compound.

$^1$H NMR (CDCl$_3$, 400 MHz) δ 7.71(d, 1H), 6.99(s, 1H), 6.88(d, 1H), 5.64(s, 1H), 4.96(s,1H), 4.05(s, 1H), 3.93(t, 1H), 3.66(t, 1H)

Mass[M+H]: 409.05

EXAMPLE 23

Preparation of 4-((2R,5S)-5-((R)-2,2,2-trifluoro-1-hydroxyethyl)-2-(trifluoromethyl)oxazolidin-3-yl)-2-(trifluoromethyl)benzonitrile

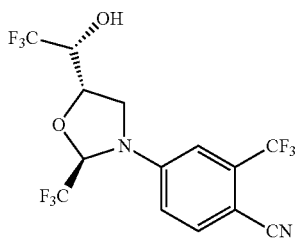 [SMILES: N#Cc1ccc(N2C[C@@H]([C@@H](O)C(F)(F)F)O[C@@H]2C(F)(F)F)cc1C(F)(F)F]

Step 1. Preparation of 4-((2R,5S)-5-formyl-2-(trifluoromethyl)oxazolidin-3-yl)-2-(trifluoromethyl)benzonitrile

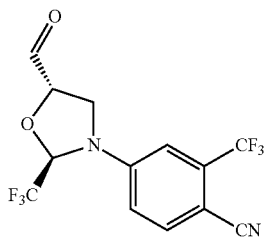 [SMILES: N#Cc1ccc(N2C[C@@H](C=O)O[C@@H]2C(F)(F)F)cc1C(F)(F)F]

In a 25-ml flask, the compound 4-((2R,5S)-5-(hydroxymethyl)-2-(trifluoromethyl)oxazolidin-3-yl)-2-(trifluoromethyl)benzonitrile obtained in Example 1 was used to obtain 254 mg (>99%) of a title compound in the same manner as in Step 1 of Example 21.

Mass[M+H]: 339.05

Step 2. Preparation of 4-((2R,5S)-5-((R)-2,2,2-trifluoro-1-hydroxyethyl)-2-(trifluoromethyl)oxazolidin-3-yl)-2-(trifluoromethyl)benzonitrile To a 25-ml flask, 254 mg (0.757 mmol) of the compound 4-((2R,5S)-5-formyl-2-(trifluoromethyl)oxazolidin-3-yl)-2-(trifluoromethyl)benzonitrile obtained in Step 1 of Example 23 and 2 ml of tetrahydrofuran were added, the atmosphere was replaced with nitrogen under stirring, and 576 mg (3.79 mmol, 5.0 eq) of CsF was injected. This reaction solution was cooled to −78° C., and 0.17 ml (1.34 mmol, 1.5 eq) of (trifluoromethyl)trimethylsilane was added dropwise thereto. The temperature of the reaction solution was slowly raised to room temperature and stirred for 16 hours. 16 ml of ethanol was added to the reaction solution, followed by stirring for 1 hour. To the reaction solution, 30 ml of ethyl acetate and 30 ml of 1 N-hydrochloric acid aqueous solution were added, followed by stirring and separation of layers. An aqueous layer was removed and an organic layer was separated, and dehydrated and dried over MgSO₄, followed by concentration under reduced pressure. A concentrate was subjected to column chromatography to separate an (R)-isomer, thereby obtaining 12.4 mg (4%) of a title compound.

¹H NMR (CDCl₃, 400 MHz) δ 7.69(d, 1H), 7.01(d, 1H), 6.90(dd, 1H), 5.60(q, 1H), 4.90~4.86(m, 1H), 4.41~4.40(m, 1H), 3.88~3.75(m, 2H), 2.94(s, 1H)

Mass[M+H]: 409.05

EXAMPLE 24

Preparation of 4-((2R,5S)-5-((S)-2,2,2-trifluoro-1-hydroxyethyl)-2-(trifluoromethyl)oxazolidin-3-yl)-2-(trifluoromethyl)benzonitrile

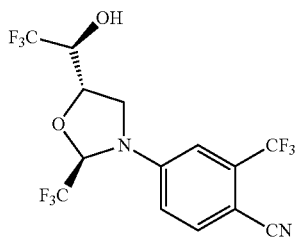 [SMILES: N#Cc1ccc(N2C[C@@H]([C@H](O)C(F)(F)F)O[C@@H]2C(F)(F)F)cc1C(F)(F)F]

To a 25-ml flask, 254 mg (0.757 mmol) of the compound 4-((2R,5S)-5-formyl-2-(trifluoromethyl)oxazolidin-3-yl)-2-(trifluoromethyl)benzonitrile obtained in Step 1 of Example 23 and 2 ml of tetrahydrofuran were added, and the atmosphere was replaced with nitrogen under stirring, and 576 mg (3.79 mmol, 5.0 eq) of CsF was injected. This reaction solution was cooled to −78° C., and 0.17 ml (1.34 mmol, 1.5 eq) of (trifluoromethyl)trimethylsilane was added dropwise thereto. The temperature of the reaction solution was slowly raised to room temperature and stirred for 16 hours. 16 ml of ethanol was added to the reaction solution, followed by stirring for 1 hour. To the reaction solution, 30 ml of ethyl acetate and 30 ml of 1 N-hydrochloric acid aqueous solution were added, followed by stirring and separation of layers. An aqueous layer was removed and an organic layer was separated, and dehydrated and dried over MgSO₄, followed by concentration under reduced pressure. A concentrate was subjected to column chromatography to separate an (S)-isomer, thereby obtaining 11.6 mg (4%) of a title compound.

¹H NMR (CDCl₃, 400 MHz) δ 7.71(d, 1H), 6.99(s, 1H), 6.89(d, 1H), 5.65(q, 1H), 4.95(t, 1H), 4.37(s, 1H), 4.07~4.04 (m, 1H), 3.93(t, 1H), 3.66(t, 1H)

Mass[M+H]: 409.05

EXAMPLE 25

Preparation of N-(4-(((2R,5S)-3-(4-cyano-3-(trifluoromethyl)phenyl)-2-(trifluoromethyl)oxazolidin-5-yl)methoxy)phenyl)acetamide

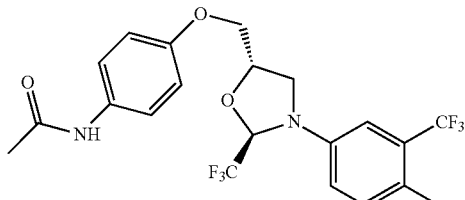

The compound ((2R,5S)-3-(4-cyano-3-(trifluoromethyl)phenyl)-2-(trifluoromethyl)oxazolidin-5-yl)methyl methanesulfonate obtained in Step 1 of Example 7 and 4-acetamidophenol were used to obtain 2.56 g (87%) of a title compound in the same manner as in Example 6.

¹H NMR (CDCl₃, 400 MHz) δ 7.70(d, 1H), 7.54(d, 2H), 7.01(d, 1H), 6.90(dd, 1H), 6.73(d, 2H), 5.62(q, 1H), 4.97(s, 1H), 4.17~4.07(m, 2H), 3.92(t, 1H), 3.68(t, 1H), 2.13(s, 3H)

Mass[M+H]: 474.12

EXAMPLE 26

Preparation of 4-((2R,5S)-5-(((4-chlorophenyl)thio)methyl)-2-(trifluoromethyl)oxazolidin-3-yl)-2-(trifluoromethyl)benzonitrile

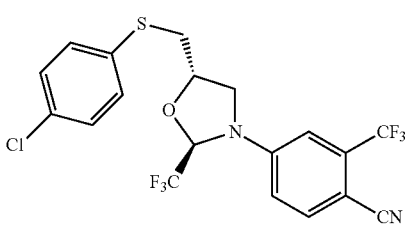 [SMILES: N#Cc1ccc(N2C[C@@H](CSc3ccc(Cl)cc3)O[C@@H]2C(F)(F)F)cc1C(F)(F)F]

The compound ((2R,5S)-3-(4-cyano-3-(trifluoromethyl)phenyl)-2-(trifluoromethyl)oxazolidin-5-yl)methyl methanesulfonate obtained in Step 1 of Example 7 and 4-chlorothiophenol were used to obtain 200 mg (60%) of a title compound in the same manner as in Example 6.

¹H NMR (CDCl₃, 400 MHz) δ 7.69(d, 1H), 7.32~7.25(m, 4H), 6.93(d, 1H), 6.82(dd, 1H), 5.50(q, 1H), 4.83~4.76(m, 1H), 3.87(dd, 1H), 3.40(t, 1H), 3.29~3.24(m, 1H), 3.10~3.05(m, 1H)

Mass[M+H]: 467.03

EXAMPLE 27

Preparation of 4-((2R,5S)-5-((4-methoxyphenoxy)methyl)-2-(trifluoromethyl)oxazolidin-3-yl)-2-(trifluoromethyl)benzonitrile

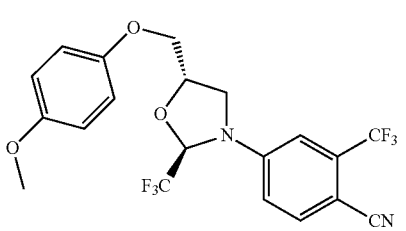 [SMILES: COc1ccc(OC[C@@H]2CN(c3ccc(C#N)c(C(F)(F)F)c3)[C@@H](C(F)(F)F)O2)cc1]

The compound ((2R,5S)-3-(4-cyano-3-(trifluoromethyl)phenyl)-2-(trifluoromethyl)oxazolidin-5-yl)methyl methanesulfonate obtained in Step 1 of Example 7 and 4-methoxyphenol were used to obtain 39.2 mg (37%) of a title compound in the same manner as in Example 6.

¹H NMR (CDCl₃, 400 MHz) δ 7.70(d, 1H), 7.01(d, 1H), 6.91(dd, 1H), 6.08~6.71(m, 4H), 5.61(q, 1H), 4.99~4.93(m, 1H), 4.12~4.07(m, 2H), 3.94~3.90(m, 1H), 3.74(s, 1H), 3.73~3.68(m, 1H)

Mass[M+H]: 447.11

EXAMPLE 28

Preparation of 4-((2R,5S)-5-((3-methoxyphenoxy)methyl)-2-(trifluoromethyl)oxazolidin-3-yl)-2-(trifluoromethyl)benzonitrile

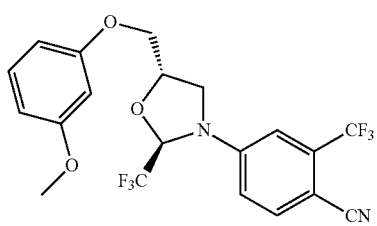 [SMILES: COc1cccc(OC[C@@H]2CN(c3ccc(C#N)c(C(F)(F)F)c3)[C@@H](C(F)(F)F)O2)c1]

The compound ((2R,5S)-3-(4-cyano-3-(trifluoromethyl)phenyl)-2-(trifluoromethyl)oxazolidin-5-yl)methyl methanesulfonate obtained in Step 1 of Example 7 and 3-methoxyphenol were used to obtain 30.3 mg (29%) of a title compound in the same manner as in Example 6.

$^1$H NMR (CDCl$_3$, 400 MHz) δ 7.70(d, 1H), 7.15(t, 1H), 7.02(d, 1H), 6.90(dd, 1H), 6.52(dd, 1H), 6.29(t, 1H), 5.63(q, 1H), 4.99~4.96(m, 1H), 4.18~4.10(m, 2H), 3.93(dd, 1H), 3.78~3.68(m, 1H), 3.73(s, 3H)

Mass[M+H]: 447.11

EXAMPLE 29

Preparation of 4-((2R,5S)-5-(((4-cyanophenyl)thio)methyl)-2-(trifluoromethyl)oxazolidin-3-yl)-2-(trifluoromethyl)benzonitrile

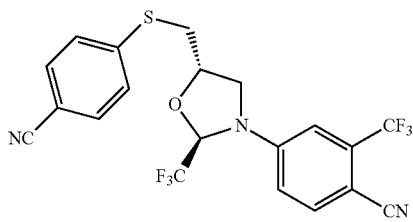

The compound ((2R,5S)-3-(4-cyano-3-(trifluoromethyl)phenyl)-2-(trifluoromethyl)oxazolidin-5-yl)methyl methanesulfonate obtained in Step 1 of Example 7 and 4-cyanothiophenol were used to obtain 88 mg (27%) of a title compound in the same manner as in Example 6.

$^1$H NMR (CDCl$_3$, 400 MHz) δ 7.67(d, 1H), 7.53(d, 2H), 7.36(d, 2H), 6.95(d, 1H), 6.85(dd, 1H), 5.55(q, 1H), 4.93~4.86(m, 1H), 3.92(dd, 1H), 3.48(t, 1H), 3.39~3.35(m, 1H), 3.28~3.23(m, 1H)

Mass[M+H]: 458.07

EXAMPLE 30

Preparation of N-(4-(((2S,5S)-3-(4-cyano-3-(trifluoromethyl)phenyl)-2-(trifluoromethyl)oxazolidin-5-yl)methoxy)phenyl)acetamide

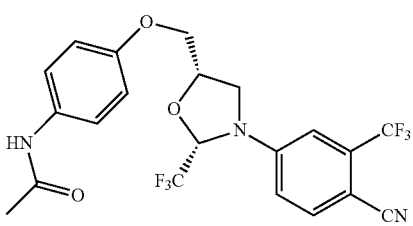 [SMILES: CC(=O)Nc1ccc(OC[C@@H]2CN(c3ccc(C#N)c(C(F)(F)F)c3)[C@H](C(F)(F)F)O2)cc1]

In a 25-ml flask, the compound ((2S,5S)-3-(4-cyano-3-(trifluoromethyl)phenyl)-2-(trifluoromethyl)oxazolidin-5-yl)methyl methanesulfonate obtained in Preparation Example 3 and 4-acetamidophenol were used to obtain 23 mg (40%) of a title compound in the same manner as in Example 6.

$^1$H NMR (CDCl$_3$, 400 MHz) δ 7.69(d, 1H), 7.40(d, 2H), 7.18(br, 1H), 6.92(dd, 1H), 6.86(d, 2H), 5.71~5.68(m, 1H), 4.68~4.61(m, 1H), 4.28~4.24(m, 1H), 4.12~4.07(m, 2H), 3.68~3.63(m, 1H), 2.14(s, 3H)

Mass[M+H]: 474.12

EXAMPLE 31

Preparation of 4-(2R,5S)-5-((3-fluoro-4-nitrophenoxy)methyl)-2-(trifluoromethyl)oxazolidin-3-yl)-2-(trifluoromethyl)benzonitrile

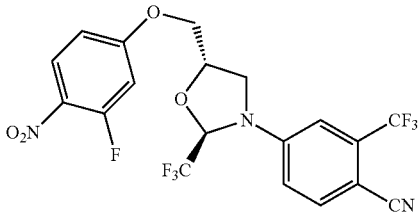 [SMILES: N#Cc1ccc(N2C[C@@H](COc3ccc([N+](=O)[O-])c(F)c3)O[C@@H]2C(F)(F)F)cc1C(F)(F)F]

The compound ((2R,5S)-3-(4-cyano-3-(trifluoromethyl)phenyl)-2-(trifluoromethyl)oxazolidin-5-yl)methyl methanesulfonate obtained in Step 1 of Example 7 and 3-fluoro-4-nitrophenol were used to obtain 28.5 mg (25%) of a title compound in the same manner as in Example 6.

$^1$H NMR (CDCl$_3$, 400 MHz) δ 8.07(t, 1H), 7.72(d, 1H), 7.02(d, 1H), 6.91(dd, 1H), 6.70(dd, 2H), 5.65~5.61(m, 1H), 5.07~5.01(m, 1H), 4.30~4.21(m, 2H), 4.00~3.96(m, 1H), 3.68~3.64(m, 1H)

Mass[M+H]: 480.07

EXAMPLE 32

Preparation of 4-(((2R,5S)-3-(4-cyano-3-(trifluoromethyl)phenyl)-2-(trifluoromethyl)oxazolidin-5-yl)methoxy)-N-methylbenzamide

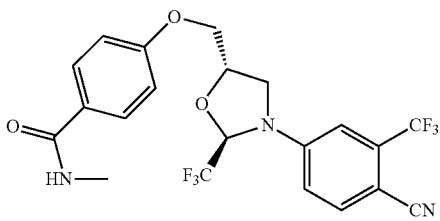 [SMILES: CNC(=O)c1ccc(OC[C@@H]2CN(c3ccc(C#N)c(C(F)(F)F)c3)[C@@H](C(F)(F)F)O2)cc1]

100 mg (0.217 mmol, 1.04 eq) of the compound 4-(((2R,5S)-3-(4-cyano-3-(trifluoromethyl)phenyl)-2-(trifluoromethyl)oxazolidin-5-yl)methoxy)benzoic acid obtained in Example 9 was added and stirred, together with 2 ml of N,N-dimethylformamide 17.7 mg (0.261 mmol, 1.25 eq) of methylamine hydrochloride was added thereto, and 0.16 ml (0.962 mmol, 4.6 eq) of N,N-diisopropylethylamine and 80 mg (0.209 mmol, 1.0 eq) of HATU were added, followed by stirring at room temperature for about 16 hours. After completion of the reaction, the reaction product was diluted with ethyl acetate (30 ml) and washed with water (70 ml). After separation of layers, an organic layer was washed with a saturated NH$_4$Cl aqueous solution, and then washed with water. The organic layer was separated and then washed with a NaCl aqueous solution, dehydrated and dried over MgSO$_4$, followed by concentration under reduced pressure. A concentrate was separated by a column to obtain 31 mg (30%) of a title compound.

$^1$H NMR (CDCl$_3$, 400 MHz) δ 7.72~7.64(m, 3H), 7.01(s, 1H), 6.89(dd, 1H), 6.81(d, 2H), 6.02(br, 1H), 5.64~5.61(m, 1H), 5.02~4.99(m, 1H), 4.24~4.16(m, 2H), 3.97~3.93(m, 1H), 3.73~3.69(m, 1H), 3.00(d, 3H)

Mass[M+H]: 474.12

EXAMPLE 33

Preparation of 4-((2R,5S)-5-((2-fluoro-4-nitrophenoxy)methyl)-2-(trifluoromethyl)oxazolidin-3-yl)-2-(trifluoromethyl)benzonitrile

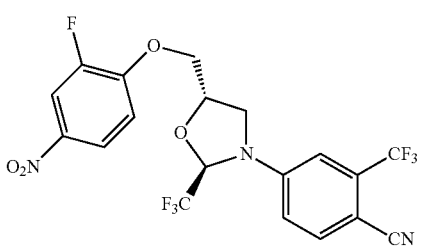 [SMILES: N#Cc1ccc(N2C[C@@H](COc3ccc([N+](=O)[O-])cc3F)O[C@@H]2C(F)(F)F)cc1C(F)(F)F]

The compound ((2R,5S)-3-(4-cyano-3-(trifluoromethyl)phenyl)-2-(trifluoromethyl)oxazolidin-5-yl)methyl methanesulfonate obtained in Step 1 of Example 7 and 2-fluoro-4-nitrophenol were used to obtain 37 mg (32%) of a title compound in the same manner as in Example 6.

$^1$H NMR (CDCl$_3$, 400 MHz) δ 8.04~7.94(m, 2H), 7.71(d, 1H), 7.10~6.99(m, 2H), 6.91(d, 1H), 5.64(q, 1H), 5.08~5.02(m, 1H), 4.38~4.30(m, 2H), 4.00(t, 1H), 3.76(t, 1H)

Mass[M+H]: 480.07

EXAMPLE 34

Preparation of 4-(((2R,5S)-3-(4-cyano-3-(trifluoromethyl)phenyl)-2-(trifluoromethyl)oxazolidin-5-yl)methoxy)-N,N-dimethylbenzamide

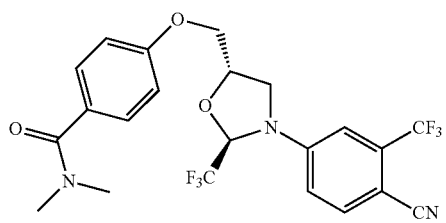 [SMILES: CN(C)C(=O)c1ccc(OC[C@@H]2CN(c3ccc(C#N)c(C(F)(F)F)c3)[C@@H](C(F)(F)F)O2)cc1]

100 mg (0.217 mmol, 1.04 eq) of the compound 4-(((2R,5S)-3-(4-cyano-3-(trifluoromethyl)phenyl)-2-(trifluoromethyl)oxazolidin-5-yl)methoxy)benzoic acid obtained in Example 9 and 2 M-dimethylamine were used to obtain 35 mg (33%) of a title compound in the same manner as in Example 32.

$^1$H NMR (CDCl$_3$, 400 MHz) δ 7.71(d, 1H), 3.36(d, 2H), 7.02(s, 1H), 6.91(dd, 1H), 6.79(d, 2H), 5.63(q, 1H), 5.02~4.99(m, 1H), 4.22~4.09(m, 2H), 3.94(t, 1H), 3.69(t, 1H), 3.05(br, 3H), 2.98(br, 3H)

Mass[M+H]: 488.13

EXAMPLE 35

Preparation of 4-((2S,5S)-5-((4-nitrophenoxy)methyl)-2-(trifluoromethyl)oxazolidin-3-yl)-2-(trifluoromethyl)benzonitrile

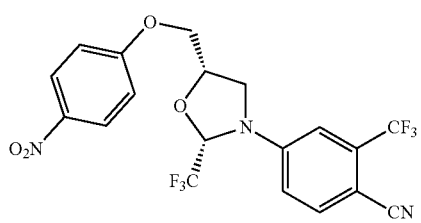 [SMILES: N#Cc1ccc(N2C[C@@H](COc3ccc([N+](=O)[O-])cc3)O[C@H]2C(F)(F)F)cc1C(F)(F)F]

In a 25-ml flask, the compound ((2S,5S)-3-(4-cyano-3-(trifluoromethyl)phenyl)-2-(trifluoromethyl)oxazolidin-5-yl)methyl methanesulfonate obtained in Preparation Example 3 and 4-nitrophenol were used to obtain 87 mg (40%) of a title compound in the same manner as in Example 6.

$^1$H NMR (CDCl$_3$, 400 MHz) δ 8.22(d, 2H), 7.71(d, 1H), 7.05(s, 1H), 7.00(d, 2H), 6.94(d, 1H), 5.72(q, 1H), 4.77~4.67(m, 1H), 4.39~4.35(m, 1H), 4.28~4.07(t, 1H), 3.74~3.69(t, 1H)

Mass[M+H]: 462.08

EXAMPLE 36

Preparation of methyl(4-(((2R,5S)-3-(4-cyano-3-(trifluoromethyl)phenyl)-2-(trifluoromethyl)oxazolidin-5-yl)methoxy)phenyl)carbamate

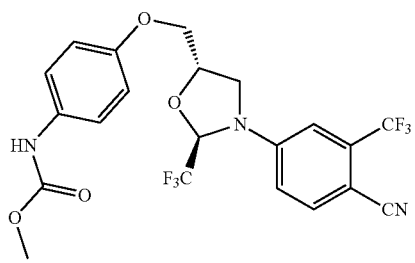 [SMILES: COC(=O)Nc1ccc(OC[C@@H]2CN(c3ccc(C#N)c(C(F)(F)F)c3)[C@@H](C(F)(F)F)O2)cc1]

4-((2R,5S)-5 aminophenoxy)methyl)-2-(trifluoromethyl)oxazolidin-3-yl)-2-(trifluoromethyl)benzonitrile obtained in Example 14 and methyl chloroformate were used to obtain 21 mg (88%) of a title compound in the same manner as in Step 1 of Example 17.

¹H NMR (CDCl₃, 400 MHz) δ 7.70(d, 1H), 7.25(d, 2H), 7.01(d, 1H), 6.90(dd, 1H), 6.74~6.71(m, 2H), 6.49(br, 1H), 5.61(q, 1H), 4.99~4.95(m, 1H), 4.16~4.07(m, 2H), 3.94~3.88(m, 1H), 3.75~3.68(m, 1H), 3.74(s, 3H)

Mass[M+H]: 490.11

EXAMPLE 37

Preparation of 2-(trifluoromethyl)-4-((2R,5S)-2-(trifluoromethyl)-5-((4-(trifluoromethyl)phenoxy)methyl)oxazolidin-3-yl)benzonitrile

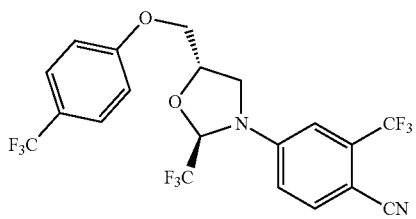 [SMILES: N#Cc1ccc(N2C[C@@H](COc3ccc(C(F)(F)F)cc3)O[C@@H]2C(F)(F)F)cc1C(F)(F)F]

The compound ((2R,5S)-3-(4-cyano-3-(trifluoromethyl)phenyl)-2-(trifluoromethyl)oxazolidin-5-yl)methyl methanesulfonate obtained in Step 1 of Example 7 and 4-(trifluoromethyl)phenol were used to obtain 65 mg (50%) of a title compound in the same manner as in Example 6.

¹H NMR (CDCl₃, 600 MHz) δ 7.71(d, 1H), 7.52(d, 2H), 7.02(d, 1H), 6.91(dd, 1H), 6.86(d, 2H), 5.63(q, 1H), 5.05~5.01(m, 1H), 4.24~4.18(m, 2H), 4.96(dd, 1H), 3.70(t, 1H)

Mass[M+H]: 485.08

EXAMPLE 38

Preparation of 4-((2R,5S)-5-((4-(2-oxooxazolidin-3-yl)phenoxy)methyl)-2-(trifluoromethyl)oxazolidin-3-yl)-2-(trifluoromethyl)benzonitrile

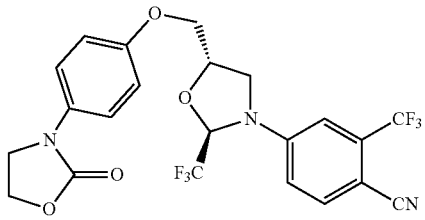 [SMILES: N#Cc1ccc(N2C[C@@H](COc3ccc(N4CCOC4=O)cc3)O[C@@H]2C(F)(F)F)cc1C(F)(F)F]

Step 1. Preparation of 4-((2R,5S)-5-((4-((2-hydroxyethyl)amino)phenoxy)methyl)-2-(trifluoromethyl)oxazolidin-3-yl)-2-(trifluoromethyl)benzonitrile

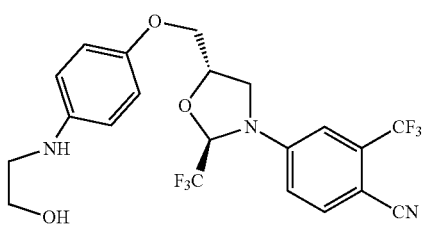 [SMILES: N#Cc1ccc(N2C[C@@H](COc3ccc(NCCO)cc3)O[C@@H]2C(F)(F)F)cc1C(F)(F)F]

To a 25-ml flask, 200 mg (0.464 mmol) of 4-((2R,5S)-5-((4-aminophenoxy)methyl)-2-(trifluoromethyl)oxazolidin-3-yl)-2-(trifluoromethyl)benzonitrile obtained in Example 14 was added and dissolved in 4 ml of toluene, followed by stirring. 0.26 ml (0.927 mmol, 4.0 eq) of triethylamine and 0.1 ml (1.4 mmol, 3.0 eq) of 2-bromoethanol were added thereto, followed by stirring at 100° C. for 7 hours. After completion of the reaction, the reaction product was diluted with ethyl acetate (30 ml) and washed with water (70 ml). After separation of layers, an organic layer was washed with a saturated NH₄Cl aqueous solution and then washed with water. The organic layer was separated and then washed with a NaCl aqueous solution, dehydrated and dried over MgSO₄, and concentrated under reduced pressure to obtain 45 mg (20%) of a title compound.

¹H NMR (CDCl₃, 600 MHz) δ 7.69(d, 1H), 7.00(d, 1H), 6.89(dd, 1H), 6.66~6.64(m, 2H), 6.58~6.56(m, 2H), 5.61(q, 1H), 4.95~4.93(m, 1H), 4.11~4.05(m, 2H), 3.90(dd, 1H), 3.81~3.79(m, 2H), 3.71~3.68(m, 1H), 3.23~3.22(m, 2H)

Mass[M+H]: 476.13

Step 2. Preparation of 4-((2R,5S)-5-((4-(2-oxooxazolidin-3-yl)phenoxy)methyl)-2-(trifluoromethyl)oxazolidin-3-yl)-2-(trifluoromethyl)benzonitrile To a 25-ml flask, 45 mg (0.173 mmol) of the compound 4-((2R,5S)-5-((4-((2-hydroxyethyl)amino)phenoxy)methyl)-2-(trifluoromethyl)oxazolidin-3-yl)-2-(trifluoromethyl)benzonitrile obtained in Step 1 of Example 38 was added, and dissolved in 4 ml of toluene, followed by stirring. 0.15 ml (0.12 mmol, 0.6 eq) of 0.5M-sodium methoxide and 0.1 ml (0.78 mmol, 4.5 eq) of diethyl carbonate were added thereto, followed by stirring at 105° C. for 7 hours. After completion of the reaction, the reaction product was diluted with ethyl acetate (30 ml) and washed with water (70 ml). After separation of layers, an organic layer was washed with a saturated NH₄Cl aqueous solution and then washed with water. The organic layer was separated and then washed with a NaCl aqueous solution, dehydrated and dried over MgSO₄, and concentrated under reduced pressure to obtain 34 mg (40%) of a title compound.

¹H NMR (CDCl₃, 600 MHz) δ 7.71(d, 1H), 4.41(d, 2H), 7.02(s, 1H), 6.90(d, 1H), 6.79(d, 2H), 5.62(q, 1H), 4.99~4.98(m, 1H), 4.46(t, 2H), 4.18~4.12(m, 2H), 4.00(t, 2H), 3.93(t, 1H), 3.71(t, 1H)

Mass[M+H]: 502.11

EXAMPLE 39

Preparation of N-(4-(((2R,5S)-3-(4-cyano-3-(trifluoromethyl)phenyl)-2-(trifluoromethyl)oxazolidin-5-yl)methoxy)phenyl)methanesulfonamide

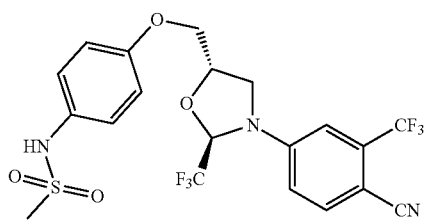 [SMILES: CS(=O)(=O)Nc1ccc(OC[C@@H]2CN(c3ccc(C#N)c(C(F)(F)F)c3)[C@@H](C(F)(F)F)O2)cc1]

4-((2R,5S)-5 aminophenoxy)methyl)-2-(trifluoromethyl)oxazolidin-3-yl)-2-(trifluoromethyl)benzonitrile obtained in Example 14 and methanesulfonic anhydride were used to obtain 98 mg (82%) of a title compound in the same manner as in Step 1 of Example 17.

¹H NMR (CDCl₃, 600 MHz) δ 7.71(t, 1H), 7.15(d, 1H), 7.01(dd, 1H), 6.90(td, 1H), 6.78(d, 1H), 6.63~6.58(m, 2H), 5.63~5.59(m, 1H), 5.02~4.94(m, 1H), 3.95~3.89(m, 1H), 3.70(t, 1H), 2.93(s, 3H)

Mass[M+H]: 510.08

EXAMPLE 40

Preparation of 3-(4-(((2R,5S)-3-(4-cyano-3-(trifluoromethyl)phenyl)-2-(trifluoromethyl)oxazolidin-5-yl)methoxy)phenyl)-1,1-dimethylurea

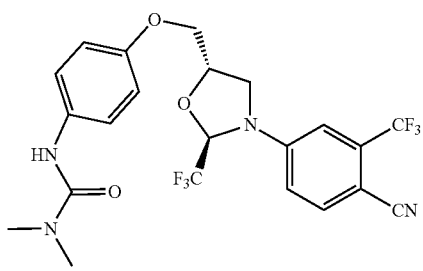 [SMILES: CN(C)C(=O)Nc1ccc(OC[C@@H]2CN(c3ccc(C#N)c(C(F)(F)F)c3)[C@@H](C(F)(F)F)O2)cc1]

4-((2R,5S)-5-((4-aminophenoxy)methyl)-2-(trifluoromethyl)oxazolidin-3-yl)-2-(trifluoromethyl)benzonitrile obtained in Example 14 and N,N-dimethylcarbamoyl chloride were used to obtain 52 mg (45%) of a title compound in the same manner as in Step 1 of Example 17.

¹H NMR (Acetond-d₆, 600 MHz) δ 7.87(d, 1H), 7.57(br, 1H), 7.35~7.33(m, 3H), 7.28(dd, 1H), 6.70~6.68(m, 2H), 6.23(q, 1H), 5.04~5.02(m, 1H), 4.22(dd, 1H), 4.14(dd, 1H), 3.90(dd, 1H), 2.97(s, 3H), 2.85(s, 3H)

Mass[M+H]: 503.14

EXAMPLE 41

Preparation of ethyl(4-(((2R,5S)-3-(4-cyano-3-(trifluoromethyl)phenyl)-2-(trifluoromethyl)oxazolidin-5-yl)methoxy)phenyl)carbamate

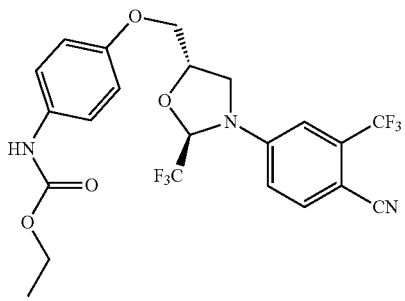 [SMILES: CCOC(=O)Nc1ccc(OC[C@@H]2CN(c3ccc(C#N)c(C(F)(F)F)c3)[C@@H](C(F)(F)F)O2)cc1]

4-((2R,5S)-5-((4-aminophenoxy)methyl)-2-(trifluoromethyl)oxazolidin-3-yl)-2-(trifluoromethyl)benzonitrile obtained in Example 14 and ethyl chloroformate were used to obtain 95 mg (82%) of a title compound in the same manner as in Step 1 of Example 17.

¹H NMR (CDCl₃, 600 MHz) δ 7.69(d, 1H), 7.26(br, 2H), 7.01(d, 1H), 6.89(dd, 1H), 6.90~6.71(m, 2H), 6.50(br, 1H), 6.20(q, 1H), 4.98~4.96(m, 1H), 4.20~4.10(m, 4H), 3.91(dd, 1H), 3.69(t, 1H)

Mass[M+H]: 504.13

EXAMPLE 42

Preparation of isopropyl (4-(((2R,5S)-3-(4-cyano-3-(trifluoromethyl)phenyl)-2-(trifluoromethyl)oxazolidin-5-yl)methoxy)phenyl)carbamate

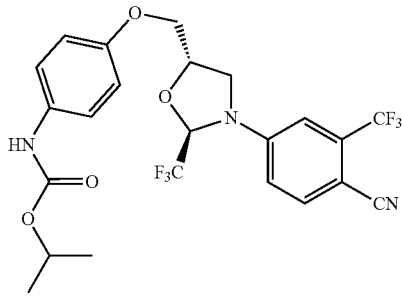 [SMILES: CC(C)OC(=O)Nc1ccc(OC[C@@H]2CN(c3ccc(C#N)c(C(F)(F)F)c3)[C@@H](C(F)(F)F)O2)cc1]

4-((2R,5S)-5-((4-aminophenoxy)methyl)-2-(trifluoromethyl)oxazolidin-3-yl)-2-(trifluoromethyl)benzonitrile obtained in Example 14 and isopropyl chloroformate were used to obtain 100 mg (83%) of a title compound in the same manner as in Step 1 of Example 17.

¹H NMR (CDCl₃, 600 MHz) δ 7.70(d, 1H), 7.26(br, 2H), 7.01(s, 1H), 6.90(dd, 1H), 6.73(d, 2H), 6.38(br, 1H), 5.62(q, 1H), 4.98~4.95(m, 2H), 4.16~4.10(m, 2H), 3.92(t, 1H), 3.70(t, 1H), 1.27(d, 6H)

Mass[M+H]: 518.14

EXAMPLE 43

Preparation of phenyl (4-(((2R,5S)-3-(4-cyano-3-(trifluoromethyl)phenyl)-2-(trifluoromethyl)oxazolidin-5-yl)methoxy)phenyl)carbamate

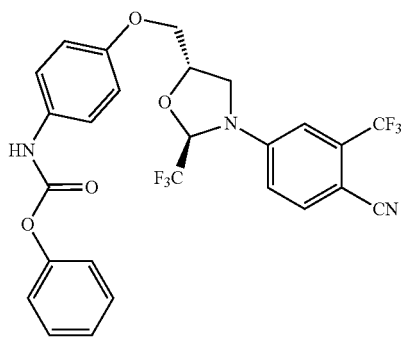 [SMILES: N#Cc1ccc(N2C[C@@H](COc3ccc(NC(=O)Oc4ccccc4)cc3)O[C@@H]2C(F)(F)F)cc1C(F)(F)F]

4-((2R,5S)-5-((4-aminophenoxy)methyl)-2-(trifluoromethyl)oxazolidin-3-yl)-2-(trifluoromethyl)benzonitrile obtained in Example 14 and phenyl chloroformate were used to obtain 114 mg (89%) of a title compound in the same manner as in Step 1 of Example 17.

¹H NMR (CDCl₃, 600 MHz) δ 7.69(d, 1H), 7.38~7.34(m, 3H), 7.32(br, 1H), 7.22(t, 1H), 7.15(d, 2H), 7.01(s, 1H), 6.89(d, 2H), 6.76(d, 2H), 5.62(q, 1H), 4.99~4.96(m, 1H), 4.17~4.10(m, 2H), 3.92(t, 1H), 3.69(t, 1H)

Mass[M+H]: 552.13

EXAMPLE 44

Preparation of 5-(((2R,5S)-3-(4-cyano-3-(trifluoromethyl)phenyl)-2-(trifluoromethyl)oxazolidin-5-yl)methoxy)picolinonitrile

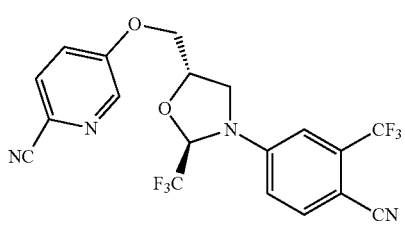 [SMILES: N#Cc1ccc(OC[C@@H]2CN(c3ccc(C#N)c(C(F)(F)F)c3)[C@@H](C(F)(F)F)O2)cn1]

The compound ((2R,5S)-3-(4-cyano-3-(trifluoromethyl)phenyl)-2-(trifluoromethyl)oxazolidin-5-yl)methyl methanesulfonate obtained in Step 1 of Example 7 and 5-hydroxypicolinonitrile were used to obtain 65 mg (50%) of a title compound in the same manner as in Example 6.

¹H NMR (CDCl₃, 600 MHz) δ 8.31(d, 1H), 7.71(d, 1H), 7.63(d, 1H), 7.22(dd, 1H), 7.02(d, 1H), 6.91(dd, 1H), 5.63(q, 1H), 5.08~5.04(m, 1H), 4.34~4.26(m, 2H), 3.98(dd, 1H), 3.68(t, 1H)

Mass[M+H]: 443.09

EXAMPLE 45

Preparation of 5-(((2S,5S)-3-(4-cyano-3-(trifluoromethyl)phenyl)-2-(trifluoromethyl)oxazolidin-5-yl)methoxy)picolinonitrile

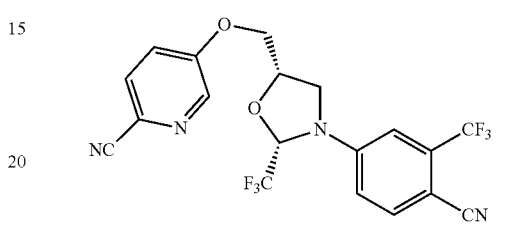

In a 25-ml flask, the compound ((2S,5S)-3-(4-cyano-3-(trifluoromethyl)phenyl)-2-(trifluoromethyl)oxazolidin-5-yl)methyl methanesulfonate obtained in Preparation Example 3 and 5-hydroxypicolinonitrile were used to obtain 75 mg (71%) of a title compound in the same manner as in Example 6.

¹H NMR (CDCl₃, 400 MHz) δ 8.41(d, 1H), 7.71(d, 1H), 7.64(d, 1H), 7.30(dd, 1H), 7.05(d, 1H), 6.93(dd, 1H), 5.72(q, 1H), 4.74~4.70(mm, 1H), 4.38(dd, 1H), 4.31(dd, 1H), 4.14 (t, 1H), 3.72(t, 1H)

Mass[M+H]: 443.09

EXAMPLE 46

Preparation of 4-((2R,5S)-5-((3-cyanophenoxy)methyl)-2-(trifluoromethyl)oxazolidin-3-yl)-2-(trifluoromethyl)benzonitrile

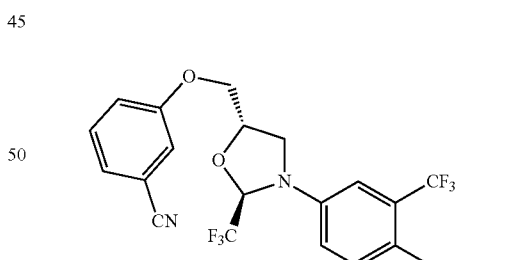

The compound ((2R,5S)-3-(4-cyano-3-(trifluoromethyl)phenyl)-2-(trifluoromethyl)oxazolidin-5-yl)methyl methanesulfonate obtained in Step 1 of Example 7 and 3-cyanophenol were used to obtain 69 mg (66%) of a title compound in the same manner as in Example 6.

¹H NMR (CDCl₃, 600 MHz) δ 7.71(d, 1H), 7.40(t, 1H), 7.27(dd, 1H), 7.09(dd, 1H), 7.04~7.02(m, 2H), 6.91(dd, 1H), 5.64(q, 1H), 5.03~5.01(m, 1H), 4.22~4.16(m, 2H), 3.96(dd, 1H), 3.68(t, 1H)

Mass[M+H]: 442.09

EXAMPLE 47

Preparation of 4-((2R,5S-5-((4-cyanophenoxy)methyl)-2-(hydroxymethyl)oxazolidin-3-yl)-2-(trifluoromethyl)benzonitrile

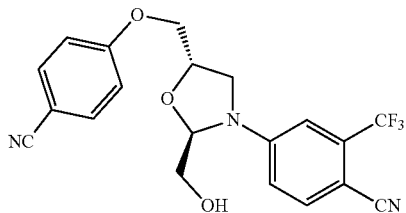 [SMILES: N#Cc1ccc(OC[C@@H]2CN(c3ccc(C#N)c(C(F)(F)F)c3)[C@@H](CO)O2)cc1]

Step 1. Preparation of 4-((2R,5S)-2-((benzyloxy)methyl)-5-(hydroxymethyl)oxazolidin-3-yl)-2-(trifluoromethyl)benzonitrile

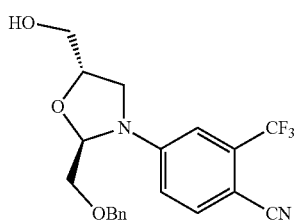 [SMILES: N#Cc1ccc(N2C[C@@H](CO)O[C@@H]2COCc2ccccc2)cc1C(F)(F)F]

2 g (7.69 mmol) of the compound (S)-4-((2,3-dihydroxypropyl)amino)-2-(trifluoromethyl)benzonitrile obtained in Preparation Example 1 was added and dissolved in 40 ml of dichloromethane, followed by stirring. 146 mg (0.769 mmol, 0.1 eq) of p-toluenesulfonic acid monohydrate and 1.08 ml (7.69 mmol, 1.0 eq) of benzyloxyacetaldehyde were added and stirred at room temperature for 1 hour. After completion of the reaction, the reaction product was concentrated under reduced pressure and diluted with ethyl acetate (30 ml) and washed with water (70 ml). After separation of layers, an organic layer was washed with a saturated NH$_4$Cl aqueous solution and then washed with water. The organic layer was separated and then washed with a NaCl aqueous solution, dehydrated and dried over MgSO$_4$, and concentrated under reduced pressure to obtain 3.01 g (>99%) of a title compound.

Mass[M+H]: 393.13

Step 2. Preparation of ((5S)-2-((benzyloxy)methyl)-3-(4-cyano-3-(trifluoromethyl)phenyl)oxazolidin-5-yl)methyl methanesulfonate

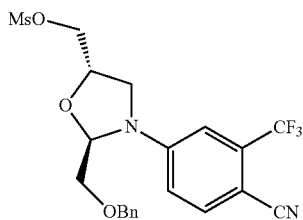 [SMILES: CS(=O)(=O)OC[C@@H]1CN(c2ccc(C#N)c(C(F)(F)F)c2)[C@@H](COCc2ccccc2)O1]

The compound 4-((2R,5S)-2-((benzyloxy)methyl)-5-(hydroxymethyl)oxazolidin-3-yl)-2-(trifluoromethyl)benzonitrile obtained in Step 1 of Example 47 was used to obtain 3.6 g (99%) of a title compound in the same manner as in Preparation Example 3.

Mass [M+H]: 471.11

Step 3. Preparation of 4-((2R,5S)-2-((benzyloxy)methyl)-5-((4-cyanophenoxy)methyl)oxazolidin-3-yl)-2-(trifluoromethyl)benzonitrile

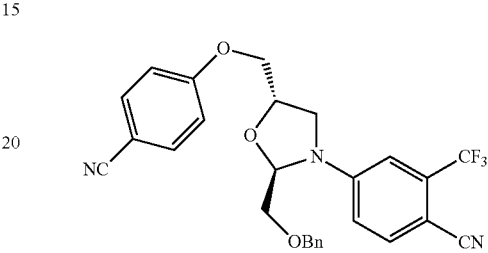

The compound ((5S)-2-((benzyloxy)methyl)-3-(4-cyano-3-(trifluoromethyl)phenyl)oxazolidin-5-yl)methyl methanesulfonate obtained in Step 2 of Example 47 and 4-cyanophenol were used to separate an (S)-isomer in the same manner as in Example 6, thereby obtaining 400 mg (11%) of a title compound.

$^1$H NMR (CDCl$_3$, 600 MHz) δ 7.58~7.56(m, 3H), 7.28~7.26(m, 3H), 7.17~7.16(m, 2H), 6.90~6.89(m, 3H), 6.67(dd, 1H), 5.51(t, 1H), 4.63~4.61(m, 1H), 4.50~4.45(m, 2H), 4.25(dd, 1H), 4.17(dd, 1H), 3.82(t, 1H), 3.67(ddd, 2H), 3.55(t, 1H)

Mass[M+H]: 494.16

Step 4. Preparation of 4-((2R,5S)-5-((4-cyanophenoxy)methyl)-2-(hydroxymethyl)oxazolidin-3-yl)-2-(trifluoromethyl)benzonitrile 400 mg (0.811 mmol) of the compound 4-((2R,5S)-2-((benzyloxy)methyl)-5-((4-cyanophenoxy)methyl)oxazolidin-3-yl)-2-(trifluoromethyl)benzonitrile obtained in Step 3 of Example 47 was dissolved in 20 ml of tetrahydrofuran, followed by stirring. 80 mg (20wt %) of Pd(OH)$_2$/C was added, and 5 drops of trifluoroacetic acid were added thereto. Then, the atmosphere was replaced with hydrogen gas, followed by stirring at room temperature for 16 hours. After completion of the reaction, filtration was performed using Celite, and a filtrate was concentrated under reduced pressure to obtain 200 mg (61%) of a title compound.

$^1$H NMR (CDCl$_3$, 600 MHz) δ 7.64(d, 1H), 7.63~7.60(m, 2H), 7.00~6.98(m, 2H), 6.88(d, 1H), 5.50(t, 1H), 4.67~4.63 (m, 1H), 4.36(dd, 1H), 4.26(dd, 1H), 3.86~3.83(m, 3H), 3.73(t, 1H)

Mass[M+H]: 404.11

EXAMPLE 48

Preparation of 4-((2R,5S)-5-((4-cyanophenoxy)methyl)-2-((R)-2,2,2-trifluoro-1-hydroxyethyl)oxazolidin-3-yl)-2-(trifluoromethyl)benzonitrile

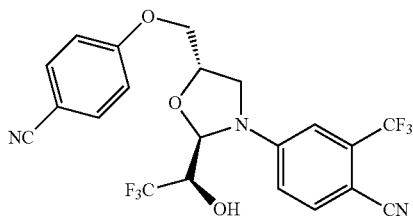 [SMILES: N#Cc1ccc(OC[C@@H]2CN(c3ccc(C#N)c(C(F)(F)F)c3)[C@@H]([C@@H](O)C(F)(F)F)O2)cc1]

Step 1. Preparation of 4-((2R,5S)-5-((4-cyanophenoxy)methyl)-2-formyloxazolidin-3-yl)-2-(trifluoromethyl)benzonitrile

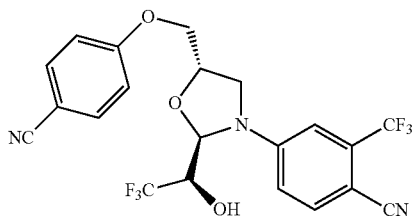 [SMILES: N#Cc1ccc(OC[C@@H]2CN(c3ccc(C#N)c(C(F)(F)F)c3)[C@@H]([C@@H](O)C(F)(F)F)O2)cc1]

200 mg (0.496 mmol) of the compound 4-((2R,5S)-5-((4-cyanophenoxy)methyl)-2-(hydroxymethyl)oxazolidin-3-yl)-2-(trifluoromethyl)benzonitrile obtained in Step 4 of Example 47 was used to obtain 58 mg (25%) of a title compound in the same manner as in Step 1 of Example 21.

$^1$H NMR (CDCl$_3$, 600 MHz) δ 9.37(d, 1H), 7.65~7.53(m, 3H), 7.00~6.91(m, 3H), 6.80(dd, 1H), 5.28(d, 1H), 4.92~4.86(m, 1H), 4.34(dd, 1H), 4.24(dd, 1H), 3.94(t, 1H), 3.80(dd, 1H)

Mass[M+H]: 402.10

Step 2. Preparation of 4-((2R,5S)-5-((4-cyanophenoxy)methyl)-2-((R)-2,2,2-trifluoro-1-hydroxyethyl)oxazolidin-3-yl)-2-(trifluoromethyl)benzonitrile 58 mg (0.145 mmol) of the compound 4-((2R,5S)-5-((4-cyanophenoxy)methyl)-2-formyloxazolidin-3-yl)-2-(trifluoromethyl)benzonitrile obtained in Step 1 of Example 48 and 2 ml of tetrahydrofuran were added, and the atmosphere was replaced with nitrogen under stirring, and 110 mg (0.723 mmol, 5.0 eq) of CsF was injected. This reaction solution was cooled to −78° C., and 32 ul (0.218 mmol, 1.5 eq) of (trifluoromethyl)trimethylsilane was added dropwise. The temperature of the reaction solution was slowly raised to room temperature and stirred for 16 hours. 16 ml of ethanol was added to this reaction solution, followed by stirring for 1 hour. 30 ml of ethyl acetate and 30 ml of 1 N-hydrochloric acid aqueous solution were added to this reaction solution, followed by stirring and separation of layers. An aqueous layer was removed, and an organic layer was separated, dehydrated and dried over MgSO$_4$, and then concentrated under reduced pressure. A concentrate was subjected to column chromatography to separate an (R)-isomer, thereby obtaining 5.8 mg (8.5%) of a title compound.

$^1$H NMR (CDCl$_3$, 600 MHz) δ 7.67(d, 1H), 7.60(dd, 2H), 6.99(dd, 2H), 6.94(d, 2H), 6.74(dd, 1H), 5.66(s, 1H), 4.68~4.64(m, 1H), 4.37(dd, 1H), 4.24~4.20(m, 2H), 3.93(dd, 1H), 3.51(t, 1H)

Mass[M+H]: 472.10

EXAMPLE 49

Preparation of 4-((2R,5S)-5-((4-cyanophenoxy)methyl)-2-((S)-2,2,2-trifluoro-1-hydroxyethyl)oxazolidin-3-yl)-2-(trifluoromethyl)benzonitrile

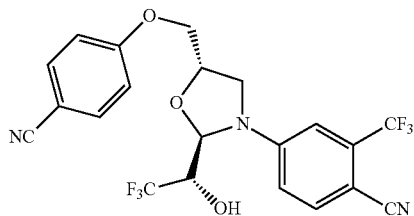 [SMILES: N#Cc1ccc(OC[C@@H]2CN(c3ccc(C#N)c(C(F)(F)F)c3)[C@@H]([C@H](O)C(F)(F)F)O2)cc1]

58 mg (0.145 mmol) of the compound 4-((2R,5S)-5-((4-cyanophenoxy)methyl)-2-formyloxazolidin-3-yl)-2-(trifluoromethyl)benzonitrile obtained in Step 1 of Example 48 and 2 ml of tetrahydrofuran were added, and the atmosphere was replaced with nitrogen under stirring, and 110 mg (0.723 mmol, 5.0 eq) of CsF was injected. This reaction solution was cooled to −78° C., and 32 ul (0.218 mmol, 1.5 eq) of (trifluoromethyl)trimethylsilane was added dropwise thereto. The temperature of the reaction solution was slowly raised to room temperature and stirred for 16 hours. 16 ml of ethanol was added to this reaction solution, followed by stirring for 1 hour. 30 ml of ethyl acetate and 30 ml of 1 N-hydrochloric acid aqueous solution were added to this reaction solution, followed by stirring and separation of layers. An aqueous layer was removed, and an organic layer was separated, dehydrated and dried over MgSO$_4$, and then concentrated under reduced pressure. A concentrate was subjected to column chromatography to separate an (S)-isomer, thereby obtaining 22.4 mg (33%) of a title compound.

$^1$H NMR (CDCl$_3$, 600 MHz) δ 7.63(d, 1H), 7.61(d, 2H), 7.10(d, 1H), 6.95(d, 2H), 6.94(dd, 1H), 5.64(d, 1H), 4.59~4.56(m, 1H), 4.27(dd, 1H), 4.21(dd, 1H), 4.03~3.98(m, 2H), 3.67(dd, 1H)

Mass[M+H]: 472.10

EXAMPLE 50

Preparation of 2-amino-N-(4-(((2R,5S)-3-(4-cyano-3-(trifluoromethyl)phenyl)-2-(trifluoromethyl)oxazolidin-5-yl)methoxy)phenyl)acetamide 2,2,2-trifluoroacetate

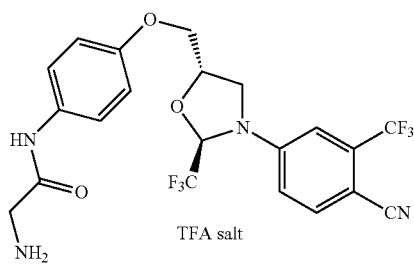 [SMILES: N#Cc1ccc(N2C[C@@H](COc3ccc(NC(=O)CN)cc3)O[C@@H]2C(F)(F)F)cc1C(F)(F)F]

Step 1. Preparation of t-butyl(2-((4-(((2R,5S)-3-(4-cyano-3-(trifluoromethyl)phenyl)-2-(trifluoromethyl)oxazolidin-5-yl)methoxy)phenyl)amino)-2-oxoethyl)carbamate

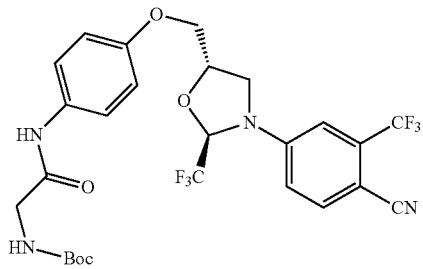 [SMILES: CC(C)(C)OC(=O)NCC(=O)Nc1ccc(OC[C@@H]2CN(c3ccc(C#N)c(C(F)(F)F)c3)[C@@H](C(F)(F)F)O2)cc1]

To a 25-ml flask, 200 mg (0.464 mmol) of 4-((2R,5S)-5-((4-aminophenoxy)methyl)-2-(trifluoromethyl)oxazolidin-3-yl)-2-(trifluoromethyl)benzonitrile obtained in Example 14 was added, and dissolved in 2 ml of dimethyl sulfoxide, followed by stirring. 162 mg (0.927 mmol, 2.0 eq) of N-(t-Boc) glycine, 0.13 ml (0.927 mmol, 2.0 eq) of triethylamine, and 176 mg (0.464 mmol, 1.0 eq) of HATU were added thereto, followed by stirring at room temperature for about 1 hour. After completion of the reaction, the reaction solution was diluted with ethyl acetate (50 ml) and washed with water (250 ml) three times. After separation of layers, an aqueous layer was removed and an organic layer was washed with a saturated NaCl aqueous solution, and then dehydrated and dried over $MgSO_4$, and concentrated under reduced pressure to obtain 201 mg (74%) of a title compound.

$^1$H NMR (CDCl$_3$, 400 MHz) δ 8.00(br, 1H), 7.70(d, 1H), 7.38(d, 2H), 7.01(d, 1H), 6.89(dd, 1H), 6.74(d, 2H), 5.62(q, 1H), 5.17(br, 1H), 4.18~4.10(m, 1H), 3.94~3.88(m, 2H), 3.70(t, 1H), 2.78(s, 2H), 1.44(d, 9H)

Mass[M+H]: 589.18

Step 2. Preparation of 2-amino-N-(4-(((2R,5S)-3-(4-cyano-3-(trifluoromethyl)phenyl)-2-(trifluoromethyl)oxazolidin-5-yl)methoxy)phenyl)acetamide 2,2,2-trifluoroacetate To a 25-ml flask, t-butyl (2-((4-(((2R,5S)-3-(4-cyano-3-(trifluoromethyl)phenyl)-2-(trifluoromethyl)oxazolidin-5-yl)methoxy)phenyl)amino)-2-oxoethyl)carbamate obtained in Step 1 of Example 50 was added, and dissolved in 3 ml of dichloromethane, followed by stirring. 3 ml of trifluoroacetic acid was added, followed by stirring at room temperature for about 20 minutes. After completion of the reaction, the reaction product was concentrated under reduced pressure to obtain 187 mg (91%) of a title compound.

$^1$H NMR (Acetone-d$_6$, 400 MHz) δ 7.90(d, 1H), 7.54~7.50(m, 2H), 7.37(d, 2H), 7.31(dd, 1H), 6.83~6.79(m, 2H), 6.29(q, 1H), 5.09~5.04(m, 1H), 4.79(s, 2H), 4.29(dd, 1H), 4.20(dd, 1H), 4.12(dd, 1H), 3.92(dd, 1H)

Mass[M+H]: 489.13

EXAMPLE 51

Preparation of (S)-N-(4-(((2R,5S)-3-(4-cyano-3-(trifluoromethyl)phenyl)-2-(trifluoromethyl)oxazolidin-5-yl)methoxy)phenyl)pyrrolidine-2-carboxamide 2,2,2-trifluoroacetate

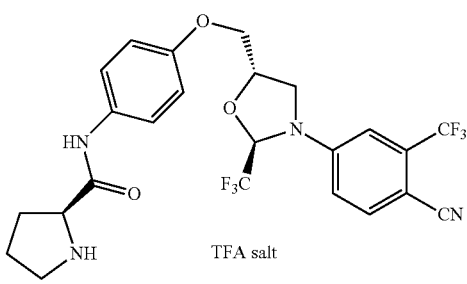 [SMILES: N#Cc1ccc(N2C[C@@H](COc3ccc(NC(=O)[C@@H]4CCCN4)cc3)O[C@@H]2C(F)(F)F)cc1C(F)(F)F]

Step 1. Preparation of t-butyl(S)-2-((4-(((2R,5S)-3-(4-cyano-3-(trifluoromethyl)phenyl)-2-(trifluoromethyl)oxazolidin-5-yl)methoxy)phenyl)carbamoyl)pyrrolidine-1-carboxylate

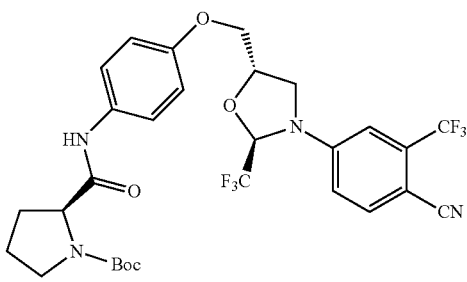 [SMILES: CC(C)(C)OC(=O)N1CCC[C@H]1C(=O)Nc1ccc(OC[C@@H]2CN(c3ccc(C#N)c(C(F)(F)F)c3)[C@@H](C(F)(F)F)O2)cc1]

In a 25-ml flask, 4-((2R,5S)-5-((4-aminophenoxy)methyl)-2-(trifluoromethyl)oxazolidin-3-yl)-2-(trifluoromethyl)benzonitrile obtained in Example 14 and N-(t-Boc)-L-proline were used to obtain 248 mg (85%) of a title compound in the same manner as in Step 1 of Example 49.

$^1$H NMR (CDCl$_3$, 400 MHz) δ 9.38(br, 1H), 7.70(d, 1H), 7.39(d, 2H), 7.01(d, 1H), 6.89(dd, 1H), 6.73(d, 2H), 5.61(q, 1H), 4.98~4.94(m, 1H), 4.4(br, 1H), 4.17~4.10(m, 3H), 3.92(t, 1H), 3.69(t, 1H), 3.42~3.35(m, 2H), 2.50(br, 1H), 1.96~1.86(m, 2H), 1.47(br, 9H)

Mass[M+H]: 629.21

Step 2. Preparation of (S)-N-(4-(((2R,5S)-3-(4-cyano-3-(trifluoromethyl)phenyl)-2-(trifluoromethyl)oxazolidin-5-yl)methoxy)phenyl)pyrrolidine-2-carboxamide 2,2,2-trifluoroacetate t-Butyl (S)-2-((4-(((2R,5S)-3-(4-cyano-3-(trifluoromethyl)phenyl)-2-(trifluoromethyl)oxazolidin-5-yl)methoxy)phenyl)carbamoyl)pyrrolidine-1-carboxylate obtained in Step 1 of Example 51 was used to obtain 237 mg (58%) of a title compound in the same manner as in Step 2 of Example 49.

$^1$H NMR (CDCl$_3$, 400 MHz) δ 9.12(s, 1H), 7.70(d, 1H), 7.36(d, 2H), 7.01(d, 1H), 6.99(dd, 1H), 6.72(d, 2H), 5.62(q, 1H), 5.02~4.95(m, 2H), 4.18~4.10(m, 2H), 3.92(t, 1H), 3.70(t, 1H), 3.51~3.45(m, 2H), 2.53~2.48(m, 1H), 2.17~2.05(m, 3H)

Mass[M+H]: 529.16

EXAMPLE 52

Preparation of 2-(4-(((2R,5S)-3-(4-cyano-3-(trifluoromethyl)phenyl)-2-(trifluoromethyl)oxazolidin-5-yl)methoxy)phenyl)acetic acid

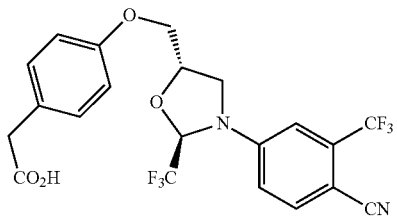 [SMILES: N#Cc1ccc(N2C[C@@H](COc3ccc(CC(=O)O)cc3)O[C@@H]2C(F)(F)F)cc1C(F)(F)F]

Step 1. Preparation of methyl 2-(4-(((2R,5S)-3-(4-cyano-3-(trifluoromethyl)phenyl)-2-(trifluoromethyl)oxazolidin-5-yl)methoxy)phenyl)acetate

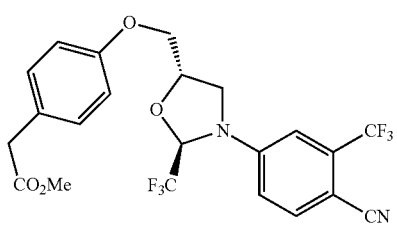 [SMILES: COC(=O)Cc1ccc(OC[C@@H]2CN(c3ccc(C#N)c(C(F)(F)F)c3)[C@@H](C(F)(F)F)O2)cc1]

The compound ((2R,5S)-3-(4-cyano-3-(trifluoromethyl)phenyl)-2-(trifluoromethyl)oxazolidin-5-yl)methyl methanesulfonate obtained in Step 1 of Example 7 and methyl 2-(4-hydroxyphenyl)acetate were used to obtain 200 mg (70%) of a title compound in the same manner as in Example 6.

$^1$H NMR (CDCl$_3$, 600 MHz) δ 7.69(d, 1H), 7.15(d, 2H), 7.01(d, 1H), 6.90(dd, 1H), 6.73(d, 2H), 5.62(q, 1H), 4.98~4.96(m, 1H), 4.16~4.11(m, 2H), 3.91(dd, 1H), 3.70(t, 1H), 3.66(s, 3H), 3.54(s, 2H)

Mass[M+H]: 489.12

Step 2. Preparation of 2-(4-(((2R,5S)-3-(4-cyano-3-(trifluoromethyl)phenyl)-2-(trifluoromethyl)oxazolidin-5-yl)methoxy)phenyl)acetic acid To a 100-ml flask, the compound methyl 2-(4-(((2R,5S)-3-(4-cyano-3-(trifluoromethyl)phenyl)-2-(trifluoromethyl)oxazolidin-5-yl)methoxy)phenyl)acetate obtained in Step 1 of Example 52 was added and 10 ml tetrahydrofuran was added, followed by stirring. To the reaction product, 10 ml of a supersaturated LiOH aqueous solution was added, followed by stirring for about 1 hour. After completion of the reaction, the reaction solution was diluted with ethyl acetate (50 ml) and neutralized with a 1 N hydrochloric acid aqueous solution, followed by washing with water (150 ml). After separation of layers, an aqueous layer was removed and an organic layer was washed with a saturated NaCl aqueous solution, and then dehydrated and dried over MgSO$_4$, and concentrated under reduced pressure to obtain 178 mg (91%) of a title compound.

$^1$H NMR (CDCl$_3$, 600 MHz) δ 7.69(d, 1H), 7.15(d, 2H), 7.01(s, 1H), 6.89(d, 1H), 6.73(d, 2H), 5.62(d, 1H), 4.97(br, 1H), 4.16~4.10(m, 2H), 3.92(t, 1H), 3.70(t, 1H), 3.56(s, 2H)

Mass[M+H]: 475.10

EXAMPLE 53

Preparation of 4-(((2R,5S)-3-(3-methyl-4-nitrophenyl)-2-(trifluoromethyl)oxazolidin-5-yl)methoxy)benzonitrile

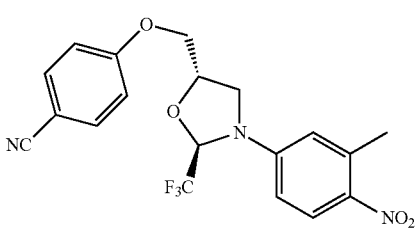 [SMILES: Cc1cc(N2C[C@@H](COc3ccc(C#N)cc3)O[C@@H]2C(F)(F)F)ccc1[N+](=O)[O-]]

The compound ((2R,5S)-3-(3-methyl-4-nitrophenyl)-2-(trifluoromethyl)oxazolidin-5-yl)methyl methanesulfonate obtained in Preparation Example 6 and 4-cyanophenol were used to obtain 139 mg (87%) of a title compound in the same manner as in Example 6.

$^1$H NMR (CDCl$_3$, 600 MHz) δ 8.10(d, 1H), 7.56(d, 2H), 6.87(d, 2H), 6.61(dd, 1H), 6.54(d, 1H), 5.61(q, 1H), 5.00~4.98(m, 1H), 4.22~4.17(m, 2H), 3.93(t, 1H), 3.68(t, 1H), 2.65(s, 3H)

Mass[M+H]: 408.11

EXAMPLE 54

Preparation of N-(4-(((2R,5S)-3-(3-methyl-4-nitrophenyl)-2-(trifluoromethyl)oxazolidin-5-yl)methoxy)phenyl)acetamide

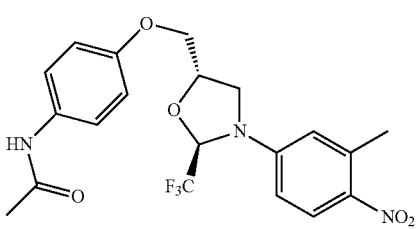 [SMILES: CC(=O)Nc1ccc(OC[C@@H]2CN(c3ccc([N+](=O)[O-])c(C)c3)[C@@H](C(F)(F)F)O2)cc1]

The compound ((2R,5S)-3-(3-methyl-4-nitrophenyl)-2-(trifluoromethyl)oxazolidin-5-yl)methyl methanesulfonate obtained in Preparation Example 6 and 4-acetamidophenol were used to obtain 42 mg (53%) of a title compound in the same manner as in Example 6.

$^1$H NMR (CDCl$_3$, 600 MHz) δ 8.10(d, 1H), 7.36(dd, 2H), 7.00(br, 1H), 6.76(dd, 2H), 6.61(dd, 1H), 6.54(d, 1H), 5.62(q, 1H), 4.96~4.93(m, 1H), 4.11(d, 2H), 3.89(dd, 1H), 3.69(t, 1H), 2.64(s, 3H), 2.14(s, 3H)

Mass[M+H]: 440.10

EXAMPLE 55

Preparation of 5-(((2R,5S)-3-(3-methyl-4-nitrophenyl)-2-(trifluoromethyl)oxazolidin-5-yl)methoxy)picolinonitrile

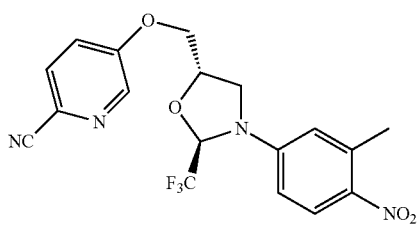 [SMILES: Cc1cc(N2C[C@@H](COc3ccc(C#N)nc3)O[C@@H]2C(F)(F)F)ccc1[N+](=O)[O-]]

The compound ((2R,5S)-3-(3-methyl-4-nitrophenyl)-2-(trifluoromethyl)oxazolidin-5-yl)methyl methanesulfonate obtained in Preparation Example 6 and 5-hydroxypicolinonitrile were used to obtain 38 mg (51%) of a title compound in the same manner as in Example 6.

$^1$H NMR (CDCl$_3$, 600 MHz) δ 8.31(d, 1H), 8.10(d, 1H), 7.62(d, 1H), 7.21(dd, 1H), 6.61(dd, 1H), 6.55(d, 1H), 5.62(q, 1H), 5.04~5.00(m, 1H), 4.30(dd, 1H), 4.25(dd, 1H), 3.95 (dd, 1H), 3.67(t, 1H), 2.65(s, 3H)

Mass[M+H]: 409.10

EXAMPLE 56

Preparation of 4-((2R,5S)-5-((4-chlorophenoxy)methyl)-2-(trifluoromethyl)oxazolidin-3-yl)-2-(trifluoromethyl)benzonitrile

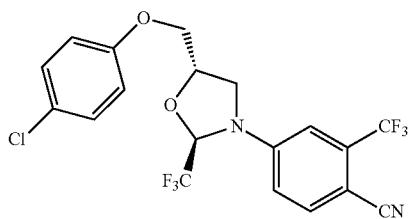 [SMILES: N#Cc1ccc(N2C[C@@H](COc3ccc(Cl)cc3)O[C@@H]2C(F)(F)F)cc1C(F)(F)F]

The compound ((2R,5S)-3-(4-cyano-3-(trifluoromethyl)phenyl)-2-(trifluoromethyl)oxazolidin-5-yl)methyl methanesulfonate obtained in Step 1 of Example 7 and 4-chlorophenol were used to obtain 86 mg (80%) of a title compound in the same manner as in Example 6.

$^1$H NMR (CDCl$_3$, 400 MHz) δ 7.71(d, 1H), 7.21(d, 2H), 7.01(d, 1H), 6.90(dd, 1H), 6.72(dd, 2H), 5.61(q, 1H), 4.99~4.97(m, 1H), 4.17~4.09(m, 2H), 3.93(t, 1H), 3.69(t, 1H)

Mass[M+H]: 451.06

EXAMPLE 57

Preparation of 4-((2R,5S)-5-((4-((E)-(hydroxyimino)methyl)phenoxy)methyl)-2-(trifluoromethyl)oxazolidin-3-yl)-2-(trifluoromethyl)benzonitrile

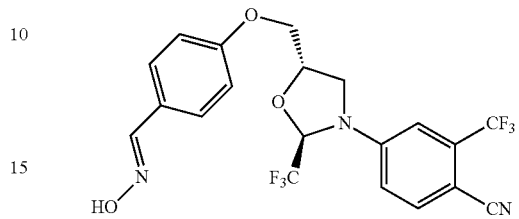

Step 1. Preparation of 4-hydroxybenzaldehyde oxime

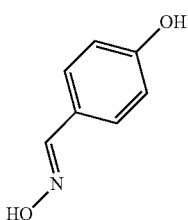

To a 100-ml flask, 500 mg (4.09 mmol) of 4-hydroxybenzaldehyde was added and dissolved in 10 ml of ethanol, followed by stirring. 1 ml (12.3 mmol, 3.0 eq) of pyridine and 427 mg (6.14 mmol, 1.5 eq) of hydroxylamine hydrochloride were added thereto, and refluxed at 80° C. under stirring for 1 hour. After completion of the reaction, the reaction product was concentrated under reduced pressure and diluted with ethyl acetate (30 ml) and washed with water (70 ml). After separation of layers, an organic layer was washed with a saturated NH$_4$Cl aqueous solution, and then washed with water. An organic layer was separated and washed with a NaCl aqueous solution, and then dehydrated and dried over MgSO$_4$, and concentrated under reduced pressure to obtain 550 mg (98%) of a title compound.

$^1$H NMR (dimethyl sulfoxide-d$_4$, 600 MHz) δ 10.83(s, 1H), 9.75(br, 1H), 7.99(s, 1H), 7.38(d, 2H), 6.75(d, 2H)

Mass[M+H]: 138.05

Step 2. Preparation of 4-((2R,5S)-5-((4-((E)-(hydroxyimino)methyl)phenoxy)methyl)-2-(trifluoromethyl)oxazolidin-3-yl)-2-(trifluoromethyl)benzonitrile The compound 4-hydroxybenzaldehyde oxime obtained in Step 1 of Example 57 was used to obtain 128 mg (78%) in the same manner as in Example 6.

$^1$H NMR (CDCl$_3$, 600 MHz) δ 8.05(s, 1H), 7.70(d, 1H), 7.47(d, 2H), 7.02(d, 1H), 6.90(dd, 1H), 6.78(d, 2H), 5.62(q, 1H), 5.01~4.99(m, 1H), 4.22~4.15(m, 2H), 3.94(t, 1H), 3.71(t, 1H)

Mass[M+H]: 460.10

EXAMPLE 58

Preparation of 4-((2R,5S)-5-(phenoxymethyl)-2-(trifluoromethyl)oxazolidin-3-yl)-2-(trifluoromethyl)benzonitrile

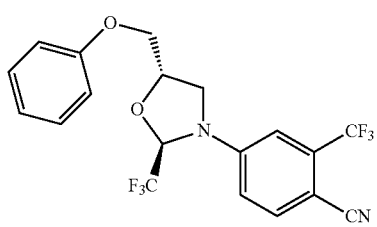 [SMILES: N#Cc1ccc(N2C[C@@H](COc3ccccc3)O[C@@H]2C(F)(F)F)cc1C(F)(F)F]

The compound ((2R,5S)-3-(4-cyano-3-(trifluoromethyl)phenyl)-2-(trifluoromethyl)oxazolidin-5-yl)methyl methanesulfonate obtained in Step 1 of Example 7 and phenol were used to obtain 38 g (49%) of a title compound in the same manner as in Example 6.

$^1$H NMR (CDCl$_3$, 600 MHz) δ 7.70(dd, 1H), 7.25(dd, 2H), 7.02(d, 1H), 6.97(t, 1H), 6.90(dd, 1H), 6.77(d, 2H), 5.62(q, 1H), 5.00~4.98(m, 1H), 4.19~4.13(m, 2H), 3.93(dd, 1H), 3.72(t, 1H)

Mass[M+H]: 417.10

EXAMPLE 59

Preparation of 4-((2R,5S)-5-((pyridin-4-yloxy)methyl)-2-(trifluoromethyl)oxazolidin-3-yl)-2-(trifluoromethyl)benzonitrile

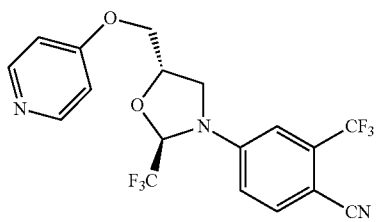 [SMILES: N#Cc1ccc(N2C[C@@H](COc3ccncc3)O[C@@H]2C(F)(F)F)cc1C(F)(F)F]

The compound ((2R,5S)-3-(4-cyano-3-(trifluoromethyl)phenyl)-2-(trifluoromethyl)oxazolidin-5-yl)methyl methanesulfonate obtained in Step 1 of Example 7 and 4-pyridinol were used to obtain 41 mg (52%) of a title compound in the same manner as in Example 6.

$^1$H NMR (CDCl$_3$, 600 MHz) δ 8.43(d, 2H), 7.71(d, 1H), 7.02(d, 1H), 6.90(dd, 1H), 6.72(dd, 2H), 5.62(q, 1H), 5.04~5.00(m, 1H), 4.24(dd, 1H), 4.19(dd, 1H), 3.95(dd, 1H), 3.68(t, 1H)

Mass[M+H]: 418.09

EXAMPLE 60

Preparation of 4-((2R,5S)-5-((pyridin-3-yloxy)methyl)-2-(trifluoromethyl)oxazolidin-3-yl)-2-(trifluoromethyl)benzonitrile

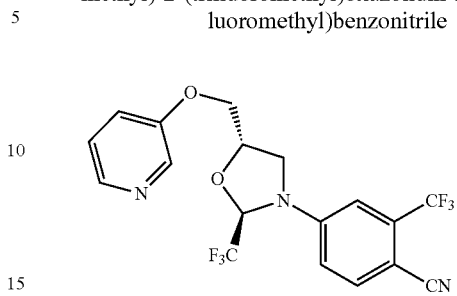

The compound ((2R,5S)-3-(4-cyano-3-(trifluoromethyl)phenyl)-2-(trifluoromethyl)oxazolidin-5-yl)methyl methanesulfonate obtained in Step 1 of Example 7 and 3-pyridinol were used to obtain 41 mg (47%) of a title compound in the same manner as in Example 6.

$^1$H NMR (CDCl$_3$, 600 MHz) δ 8.25(d, 2H), 7.71(d, 1H), 7.21(dd, 1H), 7.13(ddd, 1H), 7.02(d, 1H), 6.91(dd, 1H), 5.63(q, 1H), 5.04~5.00(m, 1H), 4.26~4.20(m, 2H), 3.96(dd, 1H), 3.70(t, 1H)

Mass[M+H]: 418.09

EXAMPLE 61

Preparation of (S)-4-(5-((4-cyanophenoxy)methyl)-2,2-dimethyloxazolidin-3-yl)-2-(trifluoromethyl)benzonitrile

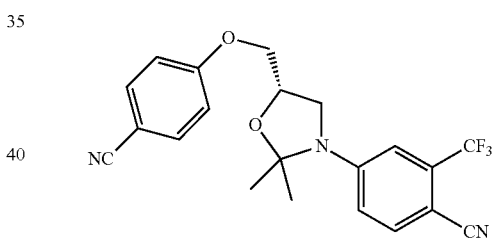

Step 1. Preparation of (S)-4-((3-((t-butyldimethylsilyl)oxy)-2-hydroxypropyl)amino)-2-(trifluoromethyl)benzonitrile

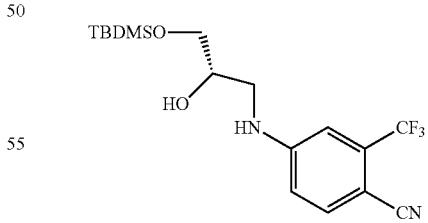

To a 100-ml flask, 1 g (3.84 mmol) of the compound (S)-3-((3-methyl-4-nitrophenyl)amino)propane-1,2-diol obtained in Preparation Example 4 was added, and dissolved in 10 ml of dichloromethane, followed by stirring. 0.6 ml (4.23 mmol, 1.1 eq) of triethylamine, 637 mg (4.23 mmol, 1.1 eq) of t-butyldimethylsilyl chloride, and 47 mg (0.384 mmol, 0.1 eq) of 4-(dimethylamino)pyridine were added thereto, followed by stirring at room temperature for 2 hours. After completion of the reaction, the reaction product was concentrated under reduced pressure, and diluted with ethyl acetate (30 ml), and washed with water (70 ml). After separation of layers, an organic layer was washed with a saturated NH₄Cl aqueous solution, and then washed with water. The organic layer was separated and washed with a NaCl aqueous solution, dehydrated and dried over MgSO₄, and concentrated under reduced pressure to obtain 1.41 g (98%) of a title compound.

¹H NMR (CDCl₃, 400 MHz) δ 7.53(d, 1H), 6.85(d, 1H), 6.68(dd, 1H), 4.95(br, 1H), 3.92~3.87(m, 1H), 3.71(dd, 1H), 3.72(dd, 1H), 3.35~3.29(m, 1H), 3.21~3.15(m, 1H), 2.49(d, 1H), 0.90(s, 9H), 0.08(s, 6H)

Mass[M+H]: 375.16

Step 2. Preparation of (S)-4-(5-(((t-butyldimethylsilyl)oxy)methyl)-2,2-dimethyloxazolidin-3-yl)-2-(trifluoromethyl)benzonitrile

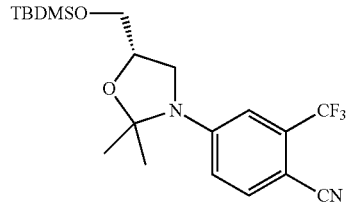 [SMILES: CC1(C)O[C@H](CO[Si](C)(C)C(C)(C)C)CN1c1ccc(C#N)c(C(F)(F)F)c1]

In a 100-ml flask, 700 mg (1.87 mmol) of the compound (S)-4-((3-((t-butyldimethylsilyl)oxy)-2-hydroxypropyl)amino)-2-(trifluoromethyl)benzonitrile obtained in Step 1 of Example 61 was dissolved in 10 ml of dichloromethane, and then cooled to 0° C. 3 ml (24.4 mmol, 13 eq) of 2,2-dimethoxypropane and 36 mg (0.187 mmol, 0.1 eq) of p-toluenesulfonic acid monohydrate were added thereto, followed by stirring at room temperature for 16 hours. After completion of the reaction, the reaction product was concentrated under reduced pressure, and diluted with ethyl acetate (30 ml) and washed with water (70 ml). After separation of layers, an organic layer was washed with a saturated NH₄Cl aqueous solution and then washed with water. The organic layer was separated and washed with a NaCl aqueous solution, and then dehydrated and dried over MgSO4, followed by concentration under reduced pressure. A concentrate was purified by column chromatography to obtain 160 mg (21%) of a title compound.

¹H NMR (CDCl₃, 400 MHz) δ 7.57(d, 1H, 6.89(d, 1H), 6.74(dd, 1H), 4.32~4.28(m, 1H), 3.86~3.75(m, 2H), 3.53 (dd, 1H), 3.42(t, 1H), 1.61(d, 6H), 0.88(s, 9H), 0.8(s, 6H)

Mass[M+H]: 415.20

Step 3. Preparation of (S)-4-(5-(hydroxymethyl)-2,2-dimethyloxazolidin-3-yl)-2-(trifluoromethyl)benzonitrile

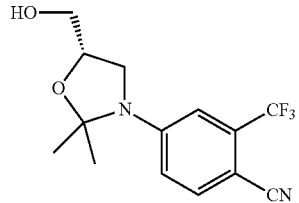 [SMILES: CC1(C)O[C@H](CO)CN1c1ccc(C#N)c(C(F)(F)F)c1]

To a 50-ml flask, 160 mg (0.386 mmol) of the compound (S)-4-(5-(((t-butyldimethylsilyl)oxy)methyl)-2,2-dimethyloxazolidin-3-yl)-2-(trifluoromethyl)benzonitrile obtained in Step 2 of Example 61 was added, and dissolved in 2 ml of tetrahydrofuran, followed by stirring. 2 ml of tetrabutylammonium fluoride (1.0 M) was added, followed by stirring at room temperature for 30 minutes. After completion of the reaction, the reaction product was concentrated under reduced pressure to obtain 116 mg (>99%) of a title compound.

¹H NMR (CDCl₃, 400 MHz) δ 7.58(d, 1H), 6.89(d, 1H), 6.75(dd, 1H), 4.41~4.36(m, 1H), 3.94(d, 1H), 3.74(d, 1H), 3.50(dd, 2H), 1.86(br, 1H), 1.64(d, 6H)

Mass[M+H]: 301.11

Step 4. Preparation of (S)-(3-(4-cyano-3-(trifluoromethyl)phenyl)-2,2-dimethyloxazolidin-5-yl) methyl methanesulfonate

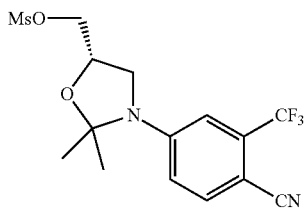 [SMILES: CC1(C)O[C@H](COS(C)(=O)=O)CN1c1ccc(C#N)c(C(F)(F)F)c1]

In a 25-ml flask, the compound (S)-4-(5-(hydroxymethyl)-2,2-dimethyloxazolidin-3-yl)-2-(trifluoromethyl)benzonitrile obtained in Step 3 of Example 61 was used to obtain 146 mg (>99%) of a title compound in the same manner as in Preparation Example 3.

¹H NMR (CDCl₃, 400 MHz) δ 7.60(d, 1H), 6.90(d, 1H), 6.77(dd, 1H), 4.59~4.50(m, 1H), 4.46~4.36(m, 2H), 3.62 (dd, 1H), 3.46(t, 1H), 3.08(s, 3H), 1.6(d, 6H)

Mass[M+H]: 379.09

Step 5. Preparation of (S)-4-(5-((4-cyanophenoxy)methyl)-2,2-dimethyloxazolidin-3-yl)-2-(trifluoromethyl)benzonitrile In a 25-ml flask, the compound (S)-(3-(4-cyano-3-(trifluoromethyl)phenyl)-2,2-dimethyloxazolidin-5-yl)methyl methanesulfonate obtained in Step 4 of Example 61 and 4-cyanophenol were used to obtain 71 mg (56%) of a title compound in the same manner as in Example 6.

¹H NMR (CDCl₃, 400 MHz) δ 7.57(d, 3H), 6.98(d, 2H), 6.91(d, 1H), 6.79(dd, 1H), 4.71~4.53(m, 1H), 4.26~4.19(m, 2H), 3.70(dd, 1H), 3.52(t, 1H), 1.65(d, 6H)

Mass[M+H]: 402.14

EXAMPLE 62

Preparation of 4-((2R,5S)-5-((4-(methylsulfonyl)phenoxy)methyl)-2-(trifluoromethyl)oxazolidin-3-yl)-2-(trifluoromethyl)benzonitrile

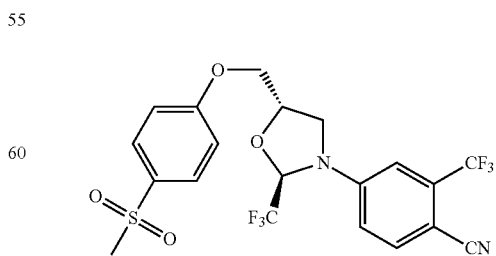

The compound ((2R,5S)-3-(4-cyano-3-(trifluoromethyl)phenyl)-2-(trifluoromethyl)oxazolidin-5-yl)methyl methanesulfonate obtained in Step 1 of Example 7 and 4-(methylsulfonyl)phenol were used to obtain 114 mg (70%) of a title compound in the same manner as in Example 6.

$^1$H NMR (CDCl$_3$, 400 MHz) δ 7.84(d, 2H), 7.72(d, 1H), 7.04(d, 1H), 6.97~6.92(m, 3H), 5.65(q, 1H), 5.07~5.64(m, 1H), 4.30~4.22(m, 2H), 3.98(t, 1H), 3.71(t, 1H), 3.01(s, 3H)

Mass[M+H]: 495.07

EXAMPLE 63

Preparation of 4-(((2R,5S)-3-(3,4-dichlorophenyl)-2-(trifluoromethyl)oxazolidin-5-yl)methoxy)benzonitrile

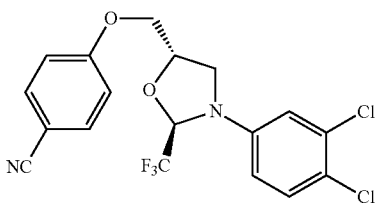 [SMILES: N#Cc1ccc(OC[C@@H]2CN(c3ccc(Cl)c(Cl)c3)[C@@H](C(F)(F)F)O2)cc1]

Step 1. Preparation of (S)-3-((3,4-dichlorophenyl)amino)propane-1,2-diol

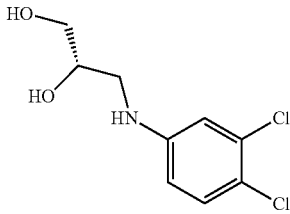 [SMILES: OC[C@@H](O)CNc1ccc(Cl)c(Cl)c1]

To a 100-ml flask, 1 g (6.17 mmol) of 3,4-dichloroanillin was added and dissolved in 20 ml of methanol, followed by stirring at room temperature. 0.7 ml (10.5 mmol, 1.7 eq) of (R)-glycidol was added thereto, and refluxed at 90° C. under stirring for 18 hours. 0.86 ml (6.17 mmol, 1.0 eq) of triethylamine was added thereto, followed by stirring for 6 hours. The reaction product was concentrated under reduced pressure, and diluted with ethyl acetate (70 ml) and washed with water (180 ml). After separation of layers, the layer was washed with a NaCl aqueous solution, dehydrated and dried over MgSO$_4$, concentrated under reduced pressure, and purified by column chromatography to obtain 520 mg (36%) of a title compound.

$^1$H NMR (CDCl$_3$, 600 MHz) δ 7.17(d, 1H), 6.69(d, 1H), 6.46(dd, 1H), 4.11(br, 1H), 3.94(m, 1H), 3.79~3.77(m, 1H), 3.65~3.62(m, 1H), 3.26~3.22(m, 1H), 3.16~3.11(m, 1H), 2.38(d, 1H), 1.83(br, 1H)

Mass[M+H]: 236.02

Step 2. Preparation of 4-(((2R,5S)-3-(3,4-dichlorophenyl)-2-(trifluoromethyl)oxazolidin-5-yl)methanol

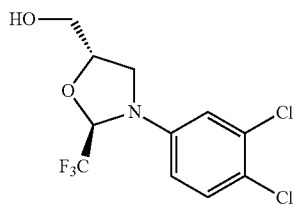 [SMILES: OC[C@@H]1CN(c2ccc(Cl)c(Cl)c2)[C@@H](C(F)(F)F)O1]

The compound (S)-3-((3,4-dichlorophenyl)amino)propane-1,2-diol obtained in Step 1 of Example 63 was used to obtain 20 mg (3%) of a title compound in the same manner as in Preparation Example 2.

$^1$H NMR (CDCl$_3$, 600 MHz) δ 7.29(d, 1H), 6.79(d, 1H), 6.55(dd, 1H), 5.40(q, 1H), 4.72~4.70(m, 1H), 3.95~3.92(m, 1H), 3.71~3.67(m, 2H), 3.42(t, 1H), 1.74(t, 1H)

Mass[M+H]: 316.00

Step 3. Preparation of ((2R,5S)-3-(3,4-dichlorophenyl)-2-(trifluoromethyl)oxazolidin-5-yl)methyl methanesulfonate

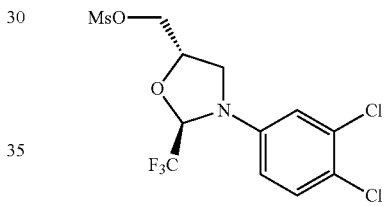

The compound 4-(((2R,5S)-3-(3,4-dichlorophenyl)-2-(trifluoromethyl)oxazolidin-5-yl)methanol obtained in Step 2 of Example 63 was used to obtain 25 mg (>99%) of a title compound in the same manner as in Preparation Example 3.

$^1$H NMR (CDCl$_3$, 400 MHz) δ 7.31(d, 1H), 6.79(d, 1H), 6.56(dd, 1H), 5.45(q, 1H), 3.86~4.82(m, 1H), 4.42~4.29(m, 2H), 3.79(t, 1H), 3.42(t, 1H), 3.00(s, 3H)

Mass[M+H]: 393.98

Step 4. Preparation of 4-(((2R,5S)-3-(3,4-dichlorophenyl)-2-(trifluoromethyl)oxazolidin-5-yl)methoxy)benzonitrile The compound ((2R,5S)-3-(3,4-dichlorophenyl)-2-(trifluoromethyl)oxazolidin-5-yl)methyl methanesulfonate obtained in Step 3 of Example 63 and 4-cyanophenol were used to obtain 16 mg (80%) of a title compound in the same manner as in Example 6.

$^1$H NMR (CDCl$_3$, 600 MHz) δ 7.56(d, 2H), 7.31(d, 1H), 6.87(d, 2H), 6.82(d, 1H), 6.58(dd, 1H), 5.46(q, 1H), 4.96~4.92(m, 1H), 4.20~4.10(m, 2H), 3.85(t, 1H), 3.54(t, 1H)

Mass[M+H]: 317.03

Each compound of Example 64~Example 79 of the following Table 1 was prepared from ((2R,5S)-3-(3-trifluoromethyl-4-nitrophenyl)-2-(trifluoromethyl)oxazolidin-5-yl)methyl methanesulfonate obtained in Preparation Example 9, ((2R,5S)-3-(3-methyl-4-nitrophenyl)-2-(trifluoromethyl)oxazolidin-5-yl)methyl methanesulfonate obtained in Preparation Example 6, ((2R,5S)-3-(3-chloro-4-cyanophenyl)-2-(trifluoromethyl)oxazolidin-5-yl)methyl methanesulfonate obtained in Preparation Example 39, ((2R,5S)-3-(3-chloro-4-cyano-2-methylphenyl)-2-(trifluoromethyl)oxazolidin-5-yl)methyl methanesulfonate obtained in Preparation Example 44, ((2R,5S)-3-(4-cyano-3-(trifluoromethyl)phenyl)-2-(trifluoromethyl)oxazolidin-5-yl)methylmethanesulfonate obtained in Step 1 of Example 7 in the same manner as in Example 6, respectively.

[General Formula of Table 1]

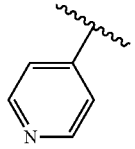

TABLE 1

| Example | R$^A$ | R$^B$ | R$^C$ | R$^D$ | M + H |
|---|---|---|---|---|---|
| 64 | H | CF$_3$ | NO$_2$ | 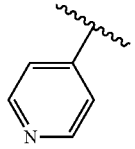 [SMILES: *c1ccncc1] | 462 |
| 65 | H | CF$_3$ | NO$_2$ | 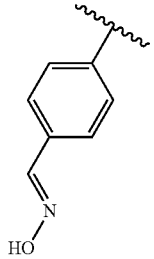 | 463 |
| 66 | H | CF$_3$ | NO$_2$ | 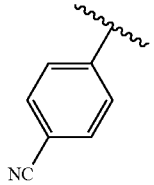 | 438 |
| 67 | H | CF$_3$ | CN | 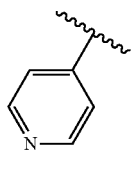 [SMILES: *c1ccncc1] | 447 |
| 68 | H | CF$_3$ | CN | 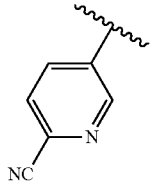 [SMILES: *c1ccc(C#N)nc1] | 452 |

TABLE 1-continued

| Example | R$^A$ | R$^B$ | R$^C$ | R$^D$ | M + H |
|---|---|---|---|---|---|
| 69 | H | CH$_3$ | NO$_2$ | 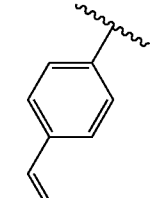 | 384 |
| 70 | H | CH$_3$ | NO$_2$ | 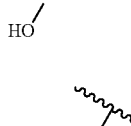 | 426 |
| 71 | H | Cl | CN | 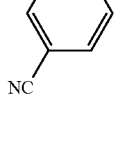 | 408 |
| 72 | H | Cl | CN |  | 384 |
| 73 | H | Cl | CN | 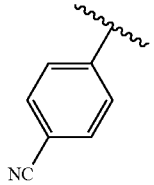 | 409 |
| 74 | H | Cl | CN | 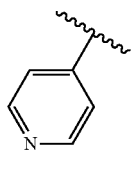 [SMILES: *c1ccncc1] | 426 |
| 75 | CH$_3$ | Cl | CN | 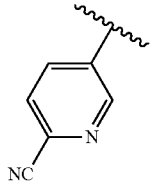 [SMILES: *c1ccc(C#N)nc1] | 422 |

TABLE 1-continued

| Example | $R^A$ | $R^B$ | $R^C$ | $R^D$ | M + H |
|---|---|---|---|---|---|
| 76 | CH₃ | Cl | CN | 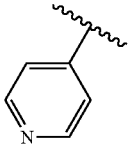 | 398 |
| 77 | CH₃ | Cl | CN | 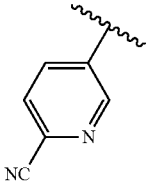 | 423 |
| 78 | CH₃ | Cl | CN | 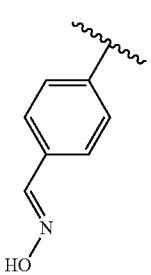 | 440 |
| 79 | H | CH₃ | NO₂ | 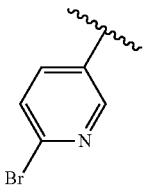 | 462 |

Structural name of the compound of each Example described in <Table 1> is as follows:

EXAMPLE 64

4-(((2R,5S)-3-(4-nitro-3-(trifluoromethyl)phenyl)-2-(trifluoromethyl)oxazolidin-5-yl)methoxy)benzonitrile

EXAMPLE 65

5-(((2R,5S)-3-(4-nitro-3-(trifluoromethyl)phenyl)-2-(trifluoromethyl)oxazolidin-5-yl)methoxy)picolinonitrile

EXAMPLE 66

(2R,5S)-3-(4-nitro-3-(trifluoromethyl)phenyl)-5-((pyridin-4-yloxy)methyl)-2-(trifluoromethyl)oxazolidine

EXAMPLE 67

4-((2R,5S)-5-((4-(hydroxymethyl)phenoxy)methyl)-2-(trifluoromethyl)oxazolidin-3-yl)-2-(trifluoromethyl)benzonitrile

EXAMPLE 68

4-((2R,5S)-5-(((2-chloropyridin-4-yl)oxy)methyl)-2-(trifluoromethyl)oxazolidin-3-yl)-2-(trifluoromethyl)benzonitrile

EXAMPLE 69

(2R,5S)-3-(3-methyl-4-nitrophenyl)-5-((pyridin-4-yloxy)methyl)-2-(trifluoromethyl)oxazolidine

EXAMPLE 70

(E)-4-(((2R,5S)-3-(3-methyl-4-nitrophenyl)-2-(trifluoromethyl)oxazolidin-5-yl)methoxy)benzaldehyde oxime

EXAMPLE 71

2-chloro-4-((2R,5S)-5-((4-cyanophenoxy)methyl)-2-(trifluoromethyl)oxazolidin-3-yl)benzonitrile

EXAMPLE 72

2-chloro-4-((2R,5S)-5-((pyridin-4-yloxy)methyl)-2-(trifluoromethyl)oxazolidin-3-yl)benzonitrile

EXAMPLE 73

5-(((2R,5S)-3-(3-chloro-4-cyanophenyl)-2-(trifluoromethyl)oxazolidin-5-yl)methoxy)picolinonitrile

EXAMPLE 74

2-chloro-4-((2R,5S)-5-((4-((E)-(hydroxyimino)methyl)phenoxy)methyl)-2-(trifluoromethyl)oxazolidin-3-yl)benzonitrile

EXAMPLE 75

2-chloro-4-((2R,5S)-5-((4-cyanophenoxy)methyl)-2-(trifluoromethyl)oxazolidin-3-yl)-3-methylbenzonitrile

EXAMPLE 76

2-chloro-3-methyl-4-((2R,5S)-5-((pyridin-4-yloxy)methyl)-2-(trifluoromethyl)oxazolidin-3-yl)benzonitrile

EXAMPLE 77

5-(((2R,5S)-3-(3-chloro-4-cyano-2-methylphenyl)-2-(trifluoromethyl)oxazolidin-5-yl)methoxy)picolinonitrile

EXAMPLE 78

2-chloro-4-((2R,5S)-5-((4-((E)-(hydroxyimino)methyl)phenoxy)methyl)-2-(trifluoromethyl)oxazolidin-3-yl)-3-methylbenzonitrile

EXAMPLE 79

(2R,5S)-5-(((6-bromopyridin-3-yl)oxy)methyl)-3-(3-methyl-4-nitrophenyl)-2-(trifluoromethyl)oxazolidine Further, each compound of Example 80~Example 84 of the following Table 2 was prepared from ((2R,5S)-3-(3-trifluoromethyl-4-nitrophenyl)-2-(trifluoromethyl)oxazolidin-5-yl)methyl methanesulfonate obtained in Preparation Example 3, ((2S,5S)-3-(3-trifluoromethyl-4-nitrophenyl)-2-(trifluoromethyl)oxazolidin-5-yl)methyl methanesulfonate obtained in Preparation Example 46, ((2S,5S)-3-(3-methyl-4-nitrophenyl)-2-(trifluoromethyl)oxazolidin-5-yl)methyl methanesulfonate obtained in Preparation Example 34, ((2S,5S)-3-(3-chloro-4-cyanophenyl)-2-(trifluoromethyl)oxazolidin-5-yl)methyl methanesulfonate obtained in Preparation Example 37, ((2S,5S)-3-(3-chloro-4-cyano-2-methylphenyl)-2-(trifluoromethyl)oxazolidin-5-yl)methyl methanesulfonate obtained in Preparation Example 42 in the same manner as in Example 6, respectively.

TABLE 2

| Example | $R^A$ | $R^B$ | $R^C$ | $R^D$ | M + H |
|---|---|---|---|---|---|
| 80 | H | $CF_3$ | CN | 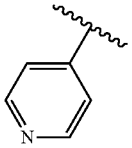 [SMILES: *c1ccncc1] | 418 |
| 81 | H | $CF_3$ | $NO_2$ | 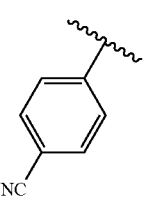 [SMILES: *c1ccc(C#N)cc1] | 462 |
| 82 | H | $CH_3$ | $NO_2$ | 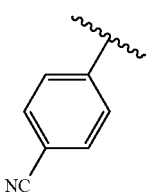 [SMILES: *c1ccc(C#N)cc1] | 408 |
| 83 | H | Cl | CN | 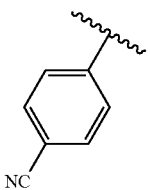 [SMILES: *c1ccc(C#N)cc1] | 408 |
| 84 | $CH_3$ | Cl | CN | 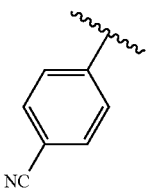 | 422 |

Structural name of the compound of each Example described in <Table 2> is as follows:

EXAMPLE 80

4-((2S,5S)-5-((pyridin-4-yloxy)methyl)-2-(trifluoromethyl)oxazolidin-3-yl)-2-(trifluoromethyl)benzonitrile

EXAMPLE 81

4-(((2S,5S)-3-(4-nitro-3-(trifluoromethyl)phenyl)-2-(trifluoromethyl)oxazolidin-5-yl)methoxy)benzonitrile

EXAMPLE 82

4-(((2S,5S)-3-(3-methyl-4-nitrophenyl)-2-(trifluoromethyl)oxazolidin-5-yl)methoxy)benzonitrile

EXAMPLE 83

2-chloro-4-((2S,5S)-5-((4-cyanophenoxy)methyl)-2-(trifluoromethyl)oxazolidin-3-yl)benzonitrile

EXAMPLE 84

2-chloro-4-((2S,5S)-5-((4-cyanophenoxy)methyl)-2-(trifluoromethyl)oxazolidin-3-yl)-3-methylbenzonitrile

EXAMPLE 85

Preparation of 4-((2R,5S)-5-((4-((E)-(methoxyimino)methyl)phenoxy)methyl)-2-(trifluoromethyl)oxazolidin-3-yl)-2-(trifluoromethyl)benzonitrile

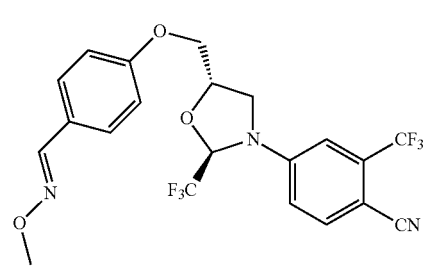 [SMILES: CO/N=C/c1ccc(OC[C@@H]2CN(c3ccc(C#N)c(C(F)(F)F)c3)[C@@H](C(F)(F)F)O2)cc1]

Step 1. Preparation of 4-hydroxybenzaldehyde O-methyl oxime

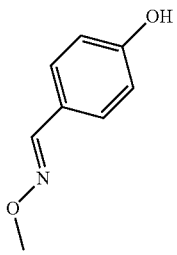

To a 100-ml flask, 500 mg (4.09 mmol) of 4-hydroxybenzaldehyde was added, and dissolved in 10 ml of methanol, followed by stirring. 1.34 g (16.4 mmol, 4.0 eq) of sodium acetate and 0.62 ml (8.19 mmol, 2.0 eq) of methoxyamine hydrochloride were added thereto, and refluxed at 80° C. under stirring for 1 hour. After completion of the reaction, the reaction product was concentrated under reduced pressure, and diluted with ethyl acetate (30 ml) and washed with water (70 ml). An organic layer was separated and then washed with a NaCl aqueous solution, dehydrated and dried over MgSO$_4$, and concentrated under reduced pressure to obtain 550 mg (98%) of a title compound.

Mass[M+H]: 152.06

Step 2. Preparation of 4-((2R,5S)-5-((4-((E)-(methoxyimino)methyl)phenoxy)methyl)-2-(trifluoromethyl)oxazolidin-3-yl)-2-(trifluoromethyl)benzonitrile The compound 4-hydroxybenzaldehyde O-methyl oxime obtained in Step 1 of Example 85 was used to obtain 50 mg (78%) of a title compound in the same manner as in Example 6.

Mass[M+H]: 474.12

EXAMPLE 86

Preparation of 4-((2R,5S)-5-((4-((E)-(hydroxyimino)methyl)phenoxy)methyl)-2-(trifluoromethyl)oxazolidin-3-yl)-2-(trifluoromethyl)benzonitrile

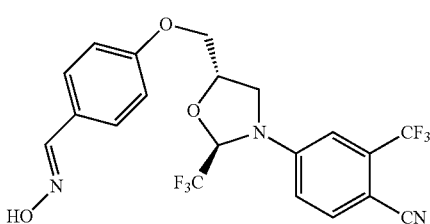 [SMILES: N#Cc1ccc(N2C[C@@H](COc3ccc(/C=N/O)cc3)O[C@@H]2C(F)(F)F)cc1C(F)(F)F]

4-Hydroxybenzaldehyde oxime obtained in Step 1 of Example 57 was used to obtain 60 mg (70%) of a title compound in the same manner as in Example 6.

Mass[M+H]: 460.10

EXAMPLE 87

Preparation of (E)-4-(((2R,5S)-3-(4-nitro-3-(trifluoromethyl)phenyl)-2-(trifluoromethyl)oxazolidin-5-yl)methoxy)benzaldehyde oxime

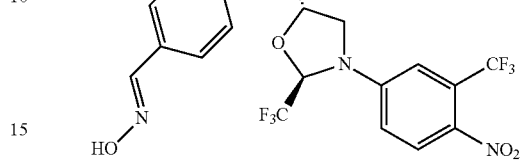

((2R,5S)-3-(3-trifluoromethyl-4-nitrophenyl)-2-(trifluoromethyl)oxazolidin-5-yl)methyl methanesulfonate obtained in Preparation Example 9 and 4-hydroxybenzaldehyde oxime obtained in Step 1 of Example 57 were used to obtain 60 mg (70%) of a title compound in the same manner as in Example 6.

Mass[M+H]: 480.09

EXAMPLE 88

Preparation of (t-butyl (4-(((2R,5S)-3-(4-cyano-3-(trifluoromethyl)phenyl)-2-(trifluoromethyl)oxazolidin-5-yl)methoxy)benzyl)carbamate

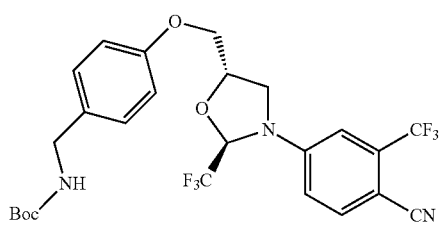 [SMILES: CC(C)(C)OC(=O)NCc1ccc(OC[C@@H]2CN(c3ccc(C#N)c(C(F)(F)F)c3)[C@@H](C(F)(F)F)O2)cc1]

The compound ((2R,5S)-3-(4-cyano-3-(trifluoromethyl)phenyl)-2-(trifluoromethyl)oxazolidin-5-yl)methyl methanesulfonate obtained in Step 1 of Example 7 and t-butyl (4-hydroxybenzyl)carbamate obtained in Preparation Example 10 were used to obtain 80 mg (70%) of a title compound in the same manner as in Example 6.

Mass[M+H]: 546.17

EXAMPLE 89

Preparation of 4-((2R,5S)-5-((4-(aminomethyl)phenoxy)methyl)-2-(trifluoromethyl)oxazolidin-3-yl)-2-(trifluoromethyl)benzonitrile hydrochloride

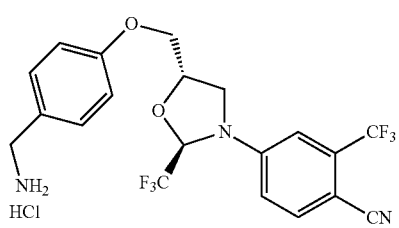 [SMILES: N#Cc1ccc(N2C[C@@H](COc3ccc(CN)cc3)O[C@@H]2C(F)(F)F)cc1C(F)(F)F ; Cl]

100 mg of the compound O-butyl(4-(((2R,5S)-3-(4-cyano-3-(trifluoromethyl)phenyl)-2-(trifluoromethyl)oxazolidin-5-yl)methoxy)benzyl)carbamate obtained in Example 88 was dissolved in a 4 N hydrochloric acid 1,4-dioxane solution, followed by stirring at room temperature for 2 hours. After completion of the reaction, the reaction solution was concentrated under reduced pressure to obtain 50 mg of a title compound.

Mass[M+H]: 446.12

EXAMPLE 90

Preparation of N-(4-(((2R,5S)-3-(4-cyano-3-(trifluoromethyl)phenyl)-2-(trifluoromethyl)oxazolidin-5-yl)methoxy)benzyl)acetamide

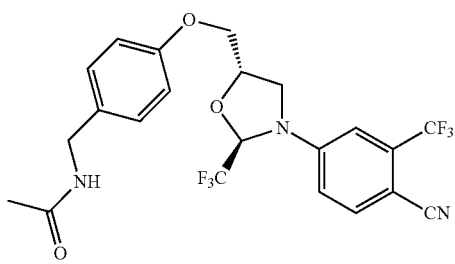 [SMILES: CC(=O)NCc1ccc(OC[C@@H]2CN(c3ccc(C#N)c(C(F)(F)F)c3)[C@@H](C(F)(F)F)O2)cc1]

To a 50-ml flask, 50 mg (0.104 mmol) of the compound 4-((2R,5S)-5-((4-(aminomethyl)phenoxy)methyl)-2-(trifluoromethyl)oxazolidin-3-yl)-2-(trifluoromethyl)benzonitrile hydrochloride obtained in Example 89 was added, and 3 ml of dichloromethane was added, followed by stirring. To this reaction solution, 67 ul (0.832 mmol, 8.0 eq) of pyridine and 39 ul (0.415 mmol, 4.0 eq) of anhydrous acetic acid were added, followed by stirring at room temperature for 16 hours. After completion of the reaction, the reaction product was concentrated under reduced pressure and diluted with ethyl acetate (10 ml) and washed with water (20 ml). An organic layer was separated and washed with a NaCl aqueous solution, dehydrated and dried over MgSO₄, and concentrated under reduced pressure to obtain 35 mg (76%) of a title compound.

Mass[M+H]: 488.13

EXAMPLE 91

Preparation of 1-(4-(((2R,5S)-3-(4-cyano-3-(trifluoromethyl)phenyl)-2-(trifluoromethyl)oxazolidin-5-yl)methoxy)benzyl)urea

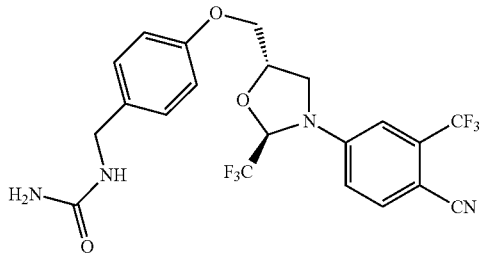 [SMILES: N#Cc1ccc(N2C[C@@H](COc3ccc(CNC(N)=O)cc3)O[C@@H]2C(F)(F)F)cc1C(F)(F)F]

The compound 4-((2R,5S)-5-((4-(aminomethyl)phenoxy)methyl)-2-(trifluoromethyl)oxazolidin-3-yl)-2-(trifluoromethyl)benzonitrile hydrochloride obtained in Example 89 was used to obtain 30 mg (50%) of a title compound in the same manner as in Example 15.

Mass[M+H]: 489.13

EXAMPLE 92

Preparation of 1-(4-(((2R,5S)-3-(4-cyano-3-(trifluoromethyl)phenyl)-2-(trifluoromethyl)oxazolidin-5-yl)methoxy)benzyl)-3-methylurea

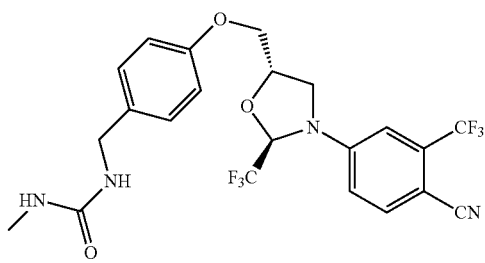 [SMILES: CNC(=O)NCc1ccc(OC[C@@H]2CN(c3ccc(C#N)c(C(F)(F)F)c3)[C@@H](C(F)(F)F)O2)cc1]

The compound 4-((2R,5S)-5-((4-(aminomethyl)phenoxy)methyl)-2-(trifluoromethyl)oxazolidin-3-yl)-2-(trifluoromethyl)benzonitrile hydrochloride obtained in Example 89 was used to obtain 30 mg (50%) of a title compound in the same manner as in Step 1 and 2 of Example 16.

Mass[M+H]: 503.14

EXAMPLE 93

Preparation of methyl(4-(((2R,5S)-3-(4-cyano-3-(trifluoromethyl)phenyl)-2-(trifluoromethyl)oxazolidin-5-yl)methoxy)benzyl)carbamate

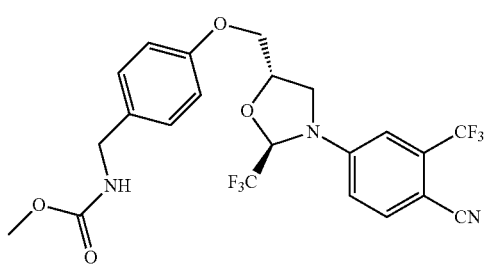 [SMILES: COC(=O)NCc1ccc(OC[C@@H]2CN(c3ccc(C#N)c(C(F)(F)F)c3)[C@@H](C(F)(F)F)O2)cc1]

The compound 4-((2R,5S)-5-((4-(aminomethyl)phenoxy)methyl)-2-(trifluoromethyl)oxazolidin-3-yl)-2-(trifluoromethyl)benzonitrile hydrochloride obtained in Example 89 was used to obtain 35 mg (65%) of a title compound in the same manner as in Step 1 of Example 17.

Mass[M+H]: 504.13

EXAMPLE 94

Preparation of N-(4-(((2R,5S)-3-(4-cyano-3-(trifluoromethyl)phenyl)-2-(trifluoromethyl)oxazolidin-5-yl)methoxy)phenyl)-2-hydroxyacetamide

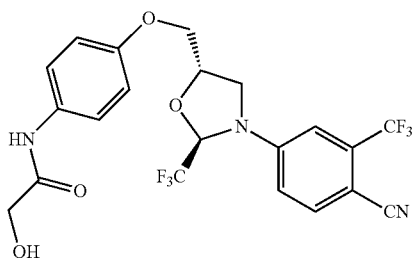 [SMILES: N#CCC(=O)Nc1ccc(OC[C@@H]2CN(c3ccc(C#N)c(C(F)(F)F)c3)[C@@H](C(F)(F)F)O2)cc1]

To a 25-ml flask, 100 mg (0.232 mmol) of 4-((2R,5S)-5-((4-aminophenoxy)methyl)-2-(trifluoromethyl)oxazolidin-3-yl)-2-(trifluoromethyl)benzonitrile obtained in Example 14 was added, and dissolved in 1 ml of dichloromethane, followed by stirring. 0.04 ml (0.278 mmol, 1.2 eq) of triethylamine and 0.03 ml (0.255 mmol, 1.1 eq) of acetoxyacetyl chloride were added thereto, followed by stirring at room temperature. After 1 hour, the reaction product was concentrated and dissolved in 1 ml of THF, and 20 mg of LiOH was added thereto, followed by stirring at room temperature for 30 minutes. After completion of the reaction, the reaction product was diluted with ethyl acetate (30 ml) and washed with water (70 ml). After separation of layers, an organic layer was washed with a saturated NH$_4$Cl aqueous solution, and then washed with water. The organic layer was separated and then washed with a NaCl aqueous solution, dehydrated and dried over MgSO$_4$, and concentrated under reduced pressure to obtain 98 mg (86%) of a title compound.

Mass[M+H]: 490.11

EXAMPLE 95

Preparation of 2-cyano-N-(4-(((2R,5S)-3-(4-cyano-3-(trifluoromethyl)phenyl)-2-(trifluoromethyl)oxazolidin-5-yl)methoxy)phenyl)acetamide

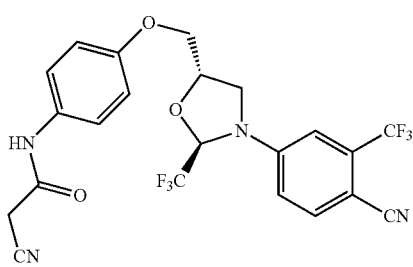

To a 25-ml flask, 20 mg (0.232 mmol, 1.0 eq) of cyanoacetic acid was added, and dissolved in 1 ml of N,N-dimethylacetamide, followed by stirring. 0.05 ml (0.696 mmol, 3.0 eq) of SOCl$_2$ was added thereto, followed by stirring at room temperature. After 1 hour, to the reaction product, 100 mg (0.464 mmol, 1.0 eq) of 4-((2R,5S)-5-((4-aminophenoxy)methyl)-2-(trifluoromethyl)oxazolidin-3-yl)-2-(trifluoromethyl)benzonitrile obtained in Example 14 was added, followed by stirring at room temperature for 2 hours. After completion of the reaction, the reaction product was diluted with ethyl acetate (30 ml), and washed with water (70 ml). After separation of layers, an organic layer was washed with a saturated NH$_4$Cl aqueous solution, and then washed with water. The organic layer was separated and then washed with a NaCl aqueous solution, dehydrated and dried over MgSO$_4$, and concentrated under reduced pressure to obtain 103 mg (89%) of a title compound.

Mass[M+H]: 499.11

EXAMPLE 96

Preparation of 2-(4-(((2R,5S)-3-(4-cyano-3-(trifluoromethyl)phenyl)-2-(trifluoromethyl)oxazolidin-5-yl)methoxy)phenyl)acetamide

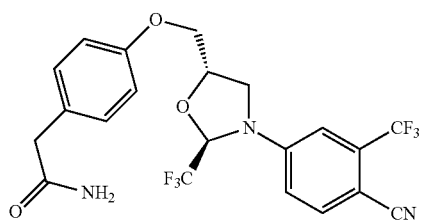 [SMILES: N#Cc1ccc(N2C[C@@H](COc3ccc(CC(N)=O)cc3)O[C@@H]2C(F)(F)F)cc1C(F)(F)F]

To a 25-ml flask, 73 mg (0.154 mmol) of 2-(4-(((2R,5S)-3-(4-cyano-3-(trifluoromethyl)phenyl)-2-(trifluoromethyl)oxazolidin-5-yl)methoxy)phenyl)acetic acid obtained in Example 52 was added, and dissolved in 2 ml of N,N-dimethylformamide, followed by stirring. 35.5 mg (0.185 mmol, 1.2 eq) of EDC-HCl, 25 mg (0.185 mmol, 1.2 eq) of HOBt, 0.055 ml (0.385 mmol, 2.5 eq) of triethylamine, and 9 mg (0.154 mmol, 1.0 eq) of ammonia (~28% aqueous solution) were added thereto, followed by stirring at room temperature for 18 hours. After completion of the reaction, the reaction product was diluted with ethyl acetate (30 ml), and washed with water (70 ml). After separation of layers, an organic layer was washed with a saturated NH$_4$Cl aqueous solution, and then washed with water. The organic layer was separated and then washed with a NaCl aqueous solution, dehydrated and dried over MgSO$_4$, and concentrated under reduced pressure to obtain 45 mg (62%) of a title compound.

Mass[M+H]: 474.12

EXAMPLE 97

Preparation of 4-(((2R,5S)-3-(4-cyano-3-(trifluoromethyl)phenyl)-2-(trifluoromethyl)oxazolidin-5-yl)methoxy)benzamide

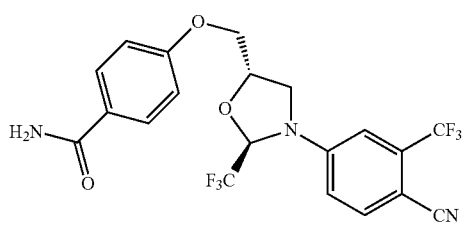 [SMILES: N#Cc1ccc(N2C[C@@H](COc3ccc(C(N)=O)cc3)O[C@@H]2C(F)(F)F)cc1C(F)(F)F]

In a 25-mg flask, 45 mg of 4-(((2R,5S)-3-(4-cyano-3-(trifluoromethyl)phenyl)-2-(trifluoromethyl)oxazolidin-5-yl)methoxy)benzoic acid obtained in Example 9 was used to obtain 21 mg (47%) of a title compound in the same manner as in Example 96.

Mass[M+H]: 460.10

EXAMPLE 98

Preparation of 4-((2R,5S)-5-((4-((E)-(hydroxyimino)methyl)-2-nitrophenoxy)methyl)-2-(trifluoromethyl)oxazolidin-3-yl)-2-(trifluoromethyl)benzonitrile

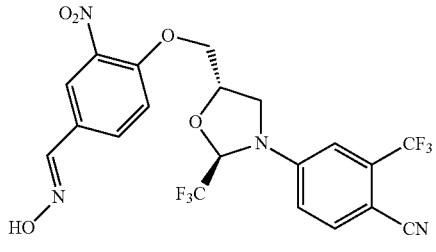 [SMILES: N#Cc1ccc(N2C[C@@H](COc3ccc(/C=N/O)cc3[N+](=O)[O-])O[C@@H]2C(F)(F)F)cc1C(F)(F)F]

Step 1. Preparation of 4-((2R,5S)-5-((4-formyl-2-nitrophenoxy)methyl)-2-(trifluoromethyl)oxazolidin-3-yl)-2-(trifluoromethyl)benzonitrile

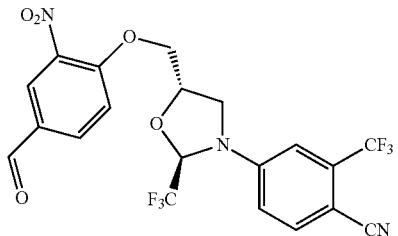 [SMILES: N#Cc1ccc(N2C[C@@H](COc3ccc(C=O)cc3[N+](=O)[O-])O[C@@H]2C(F)(F)F)cc1C(F)(F)F]

In a 25-mg flask, the compound ((2R,5S)-3-(4-cyano-3-(trifluoromethyl)phenyl)-2-(trifluoromethyl)oxazolidin-5-yl)methyl methanesulfonate obtained in Step 1 of Example 7 and 4-hydroxy-3-nitrobenzaldehyde were used to obtain 420 mg (73%) of a title compound in the same manner as in Example 6.

Mass[M+H]: 490.08

Step 2. Preparation of 4-((2R,5S)-5-((4-((E)-(hydroxyimino)methyl)-2-nitrophenoxy)methyl)-2-(trifluoromethyl)oxazolidin-3-yl)-2-(trifluoromethyl) benzonitrile To a 25-mg flask, 250 mg (0.511 mmol) of 4-((2R,5S)-5-((4-formyl-2-nitrophenoxy)methyl)-2-(trifluoromethyl)oxazolidin-3-yl)-2-(trifluoromethyl)benzonitrile obtained in Step 1 of Example 98 was added and dissolved in 4 ml of ethanol, followed by stirring. 53 mg (0.766 mmol, 1.5 eq) of hydroxylamine hydrochloride and 0.124 ml (1.53 mmol, 3.0 eq) of pyridine were added thereto, and refluxed at 90° C. under stirring for 1 hour. The reaction solution was cooled to room temperature and concentrated under reduced pressure, and 50 ml of ethyl acetate and 50 ml of a 2 N-hydrochloric acid aqueous solution were injected thereto, followed by stirring and separation of layers. An aqueous layer was removed and an organic layer was separated, dehydrated and dried over MgSO$_4$, and concentrated under reduced pressure. A concentrate was purified by column chromatography to obtain 164 mg (64%) of a title compound.

Mass[M+H]: 505.09

EXAMPLE 99

Preparation of 4-((2R,5S)-5-((4-cyano-2-nitrophenoxy)methyl)-2-(trifluoromethyl)oxazolidin-3-yl)-2-(trifluoromethyl)benzonitrile

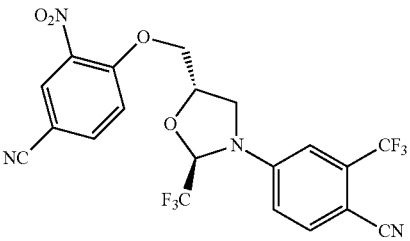 [SMILES: N#Cc1ccc(OC[C@@H]2CN(c3ccc(C#N)c(C(F)(F)F)c3)[C@@H](C(F)(F)F)O2)c([N+](=O)[O-])c1]

In a 25-ml flask, 150 mg (0.295 mmol) of 4-((2R,5S)-5-((4-((E)-(hydroxyimino)methyl)-2-nitrophenoxy)methyl)-2-(trifluoromethyl)oxazolidin-3-yl)-2-(trifluoromethyl)benzonitrile obtained in Example 98 was dissolved in 6 ml of dichloromethane, followed by stirring. 0.25 ml (1.77 mmol, 6.0 eq) of triethylamine and 0.25 ml (1.77 mmol, 6.0 eq) of trifluoroacetic anhydride were added thereto, and refluxed at 60° C. under stirring for 24 hours. After completion of the reaction, the reaction product was diluted with ethyl acetate (40 ml) and washed with water (70 ml). An organic layer was separated and then washed with a NaCl aqueous solution, and dehydrated and dried over MgSO$_4$, followed by concentration under reduced pressure. A concentrate was purified by column chromatography to obtain 125 mg (87%) of a title compound.

Mass[M+H]: 487.08

EXAMPLE 100

Preparation of 4-((2R,5S)-5-((2-amino-4-cyanophenoxy)methyl)-2-(trifluoromethyl)oxazolidin-3-yl)-2-(trifluoromethyl)benzonitrile

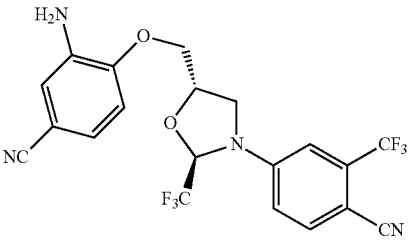

In a 25-ml flask, 110 mg (0.226 mmol) of 4-((2R,5S)-5-((4-cyano-2-nitrophenoxy)methyl)-2-(trifluoromethyl)oxazolidin-3-yl)-2-(trifluoromethyl)benzonitrile obtained in Example 99 was used to obtain 87 mg (85%) of a title compound in the same manner as in Example 14.
Mass[M+H]: 457.10

EXAMPLE 101

Preparation of N-(5-cyano-2-(((2R,5S)-3-(4-cyano-3-(trifluoromethyl)phenyl)-2-(trifluoromethyl)oxazolidin-5-yl)methoxy)phenyl)acetamide

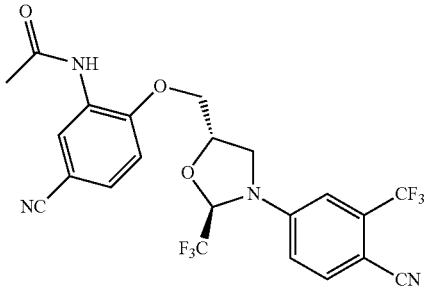 [SMILES: CC(=O)Nc1cc(C#N)ccc1OC[C@@H]1CN(c2ccc(C#N)c(C(F)(F)F)c2)[C@@H](C(F)(F)F)O1]

In a 25-ml flask, 22 mg (0.048 mmol) of 4-((2R,5S)-5-((2-amino-4-cyanophenoxy)methyl)-2-(trifluoromethyl)oxazolidin-3-yl)-2-(trifluoromethyl)benzonitrile obtained in Example 100 was used to obtain 18 mg (75%) of a title compound in the same manner as in Example S-44.
Mass[M+H]: 499.11

EXAMPLE 102

Preparation of methyl(5-cyano-2-(((2R,5S)-3-(4-cyano-3-(trifluoromethyl)phenyl)-2-(trifluoromethyl)oxazolidin-5-yl)methoxy)phenyl)carbamate

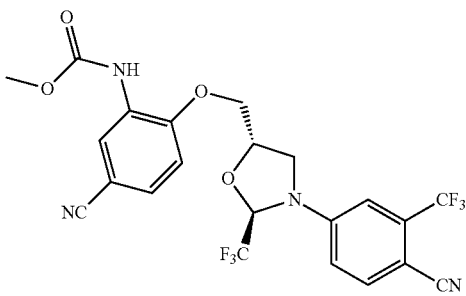 [SMILES: COC(=O)Nc1cc(C#N)ccc1OC[C@@H]1CN(c2ccc(C#N)c(C(F)(F)F)c2)[C@@H](C(F)(F)F)O1]

In a 25-ml flask, 22 mg (0.048 mmol) of 4-((2R,5S)-5-((2-amino-4-cyanophenoxy)methyl)-2-(trifluoromethyl)oxazolidin-3-yl)-2-(trifluoromethyl)benzonitrile obtained in Example 100 was dissolved in 1 ml of dichloromethane, followed by stirring. 5.8 ul (0.072 mmol, 1.5 eq) of pyridine and 3.7 ul (0.048 mmol, 1.0 eq) of methyl chloroformate were added thereto, followed by stirring at room temperature for 1 hour. The reaction product was cooled to room temperature and concentrated under reduced pressure, and then 50 ml of ethyl acetate and 50 ml of a 2 N-hydrochloric acid aqueous solution were injected thereto, followed by stirring and separation of layers. An aqueous layer was removed and an organic layer was separated, and dehydrated and dried over MgSO$_4$, followed by concentration under reduced pressure. A concentrate was purified by column chromatography to obtain 19 mg (77%) of a title compound.
Mass [M+H]: 515.11

EXAMPLE 103

Preparation of 4-((2R,5R)-5-(((4-cyanophenyl)amino)methyl)-2-(trifluoromethyl)oxazolidin-3-yl)-2-(trifluoromethyl)benzonitrile

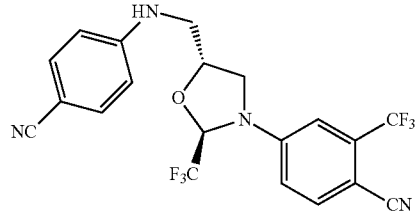 [SMILES: N#Cc1ccc(NC[C@@H]2CN(c3ccc(C#N)c(C(F)(F)F)c3)[C@@H](C(F)(F)F)O2)cc1]

To a 50-ml flask, 100 mg (0.295 mmol) of the compound 4-((2R,5R)-5-(aminomethyl)-2-(trifluoromethyl)oxazolidin-3-yl)-2-(trifluoromethyl)benzonitrile obtained in Preparation Example 12 was added and 3 ml of toluene was added, followed by stirring. To this reaction solution, 54 mg (0.295 mmol, 1.0 eq) of 4-bromobenzonitrile was added and 288 mg (0.885 mmol, 3.0 eq) of Cs$_2$CO$_3$, 8.1 mg (0.0088 mmol, 0.03 eq) of Pd$_2$(dba)$_3$, and 16.4 mg (0.026 mmol, 0.09 eq) of rac-BINAP were injected thereto. The reaction solution was refluxed at 140° C. for 16 hours. After completion of the reaction, the reaction product was concentrated under reduced pressure and diluted with ethyl acetate (10 ml) and washed with water (20 ml). An organic layer was separated and then washed with a NaCl aqueous solution, dehydrated and dried over MgSO$_4$, and concentrated under reduced pressure to obtain 70 mg (57%) of a title compound.
Mass[M+H]: 441.11

EXAMPLE 104

Preparation of 4-((2R,5R)-5-(((4-cyanophenyl)amino)methyl)-2-(trifluoromethyl)oxazolidin-3-yl)-2-(trifluoromethyl)benzonitrile

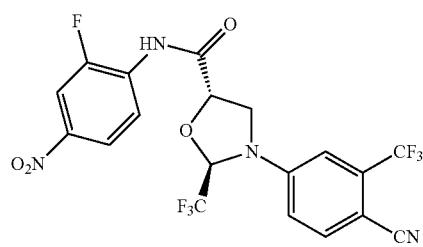

To a 50-ml flask, 100 mg (0.14 mmol) of the compound (2R,5S)-3-(4-cyano-3-(trifluoromethyl)phenyl)-2-(trifluoromethyl)oxazolidine-5-carboxylic acid obtained in Preparation Example 16 was added and 2 ml of N,N-dimethylacetamide was added, followed by stirring. To this reaction solution, 100 ul (1.41 mmol, 10.0 eq) of SOCl$_2$ was added, followed by stirring at room temperature for 1 hour. To this reaction solution, 22 mg (0.14 mmol, 1.0 eq) of 2-fluoro-4-nitroaniline was added, followed by stirring at room temperature for 1 hour. After completion of the reaction, the reaction product was diluted with ethyl acetate (10 ml) and washed with water (20 ml). After separation of layers, an organic layer was washed with a saturated $NH_4Cl$ aqueous solution and then washed with water. The organic layer was separated and then washed with a NaCl aqueous solution, dehydrated and dried over $MgSO_4$, and concentrated under reduced pressure to obtain 90 mg (80%) of a title compound.

$^1$H NMR ($CDCl_3$, 600 MHz) δ 8.64(s, 1H), 8.58(t, 1H), 8.08(d, 1H), 8.28(dd, 1H), 7.73(d, 1H), 7.04(d, 1H), 6.92(dd, 1H), 5.86(q, 1H), 5.24(t, 1H), 4.21(t, 1H), 4.00 (t, 1H)

Mass[M+H]: 493.07

EXAMPLE 105

Preparation of (2R,5S)-N-(4-amino-2-fluorophenyl)-3-(4-cyano-3-(trifluoromethyl)phenyl)-2-(trifluoromethyl)oxazolidine-5-carboxamide

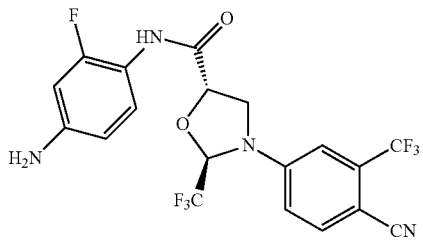 [SMILES: N#Cc1ccc(N2C[C@@H](C(=O)Nc3ccc([N+](=O)[O-])cc3F)O[C@@H]2C(F)(F)F)cc1C(F)(F)F]

In a 50-ml flask, 50 mg (0.14 mmol) of the compound 4-((2R,5R)-5-(((4-cyanophenyl)amino)methyl)-2-(trifluoromethyl)oxazolidin-3-yl)-2-(trifluoromethyl)benzonitrile obtained in Example 104 was used to obtain 35 mg (80%) of a title compound in the same manner as in Example 14.

Mass[M+H]: 463.09

EXAMPLE 106

Preparation of (2R,5S)-N-(4-acetamido-2-fluorophenyl)-3-(4-cyano-3-(trifluoromethyl)phenyl)-2-(trifluoromethyl)oxazolidine-5-carboxamide

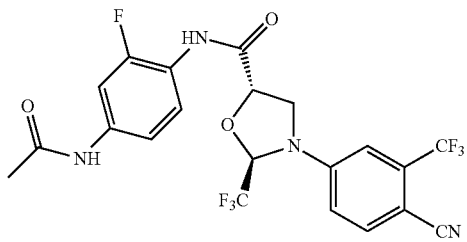 [SMILES: CC(=O)Nc1ccc(NC(=O)[C@@H]2CN(c3ccc(C#N)c(C(F)(F)F)c3)[C@@H](C(F)(F)F)O2)c(F)c1]

In a 50-ml flask, 50 mg (0.16 mmol) of the compound (2R,5S)-N-(4-amino-2-fluorophenyl)-3-(4-cyano-3-(trifluoromethyl)phenyl)-2-(trifluoromethyl)oxazolidine-5-carboxamide obtained in Example 105 was used to obtain 45 mg (83%) of a title compound in the same manner as in Example 90.

Mass[M+H]: 505.10

Further, each compound of Example 107~Example 150 of the following Table 3 was prepared from (2R,5S)-3-(4-cyano-3-(trifluoromethyl)phenyl)-2-(trifluoromethyl)oxazolidine-5-carboxylic acid obtained in Preparation Example 16, (2R,5S)-3-(3-chloro-4-nitrophenyl)-2-(trifluoromethyl)oxazolidine-5-carboxylic acid obtained in Preparation Example 28, (2R,5S)-3-(4-nitro-3-(trifluoromethyl)phenyl)-2-(trifluoromethyl)oxazolidine-5-carboxylic acid obtained in Preparation Example 32, (2R,5S)-3-(3-methyl-4-nitrophenyl)-2-(trifluoromethyl)oxazolidine-5-carboxylic acid obtained in Preparation Example 24, (2R,5S)-3-(3-chloro-4-cyanophenyl)-2-(trifluoromethyl)oxazolidine-5-carboxylic acid obtained in Preparation Example 20 in the same manner as in Example 104, respectively.

[Chemical Formula of Table 3]

TABLE 3

| Example | $R^A$ | $R^B$ | $R^C$ | $R^D$ | M + H |
|---|---|---|---|---|---|
| 107 | H | $CF_3$ | CN | 4-pyridyl | 431 |
| 108 | H | $CF_3$ | CN | 6-cyano-3-pyridyl | 456 |
| 109 | H | $CF_3$ | CN | 4-acetamidophenyl | 487 |
| 110 | H | $CF_3$ | CN | 3-pyridyl | 431 |
| 111 | H | $CF_3$ | CN | 2-chloro-4-cyanophenyl | 489 |

TABLE 3-continued
| Example | R^A | R^B | R^C | R^D | M + H |
|---|---|---|---|---|---|
| 112 | H | CF$_3$ | CN | 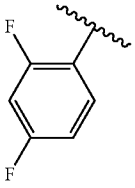 | 366 |
| 113 | H | CF$_3$ | CN | 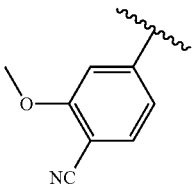 [SMILES: *c1ccc(C#N)c(OC)c1] | 485 |
| 114 | H | CF$_3$ | CN | 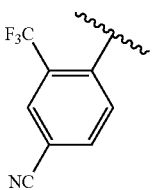 | 523 |
| 115 | H | CF$_3$ | CN | 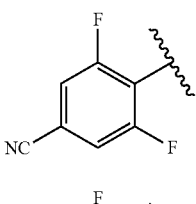 | 491 |
| 116 | H | CF$_3$ | CN | 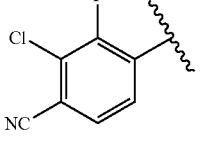 | 507 |
| 117 | H | CF$_3$ | CN | 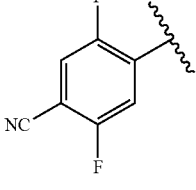 | 491 |
| 118 | H | CF$_3$ | CN | 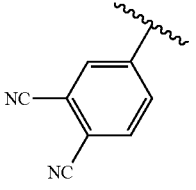 | 480 |
| 119 | H | CF$_3$ | CN | 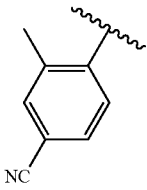 | 469 |
| 120 | H | CF$_3$ | CN | 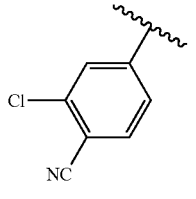 [SMILES: *c1ccc(C#N)c(Cl)c1] | 489 |
| 121 | H | CF$_3$ | CN | 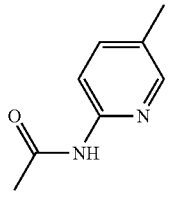 | 488 |
| 122 | H | CH$_3$ | NO$_2$ |  | 421 |
| 123 | H | CH$_3$ | NO$_2$ | 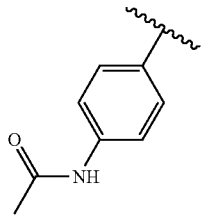 [SMILES: *c1ccc(NC(C)=O)cc1] | 453 |
| 124 | H | CH$_3$ | NO$_2$ | 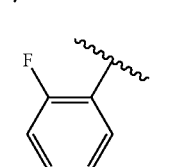 | 439 |
| 125 | H | CH$_3$ | NO$_2$ | 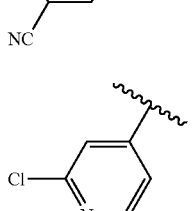 | 422 |
| 126 | H | CH$_3$ | NO$_2$ | 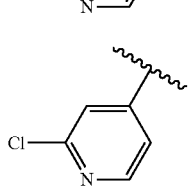 | 431 |
| 127 | H | Cl | CN | 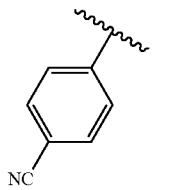 [SMILES: *c1ccc(C#N)cc1] | 421 |

TABLE 3-continued

| Example | $R^A$ | $R^B$ | $R^C$ | $R^D$ | M + H |
|---|---|---|---|---|---|
| 128 | H | Cl | CN | 4-(acetamido)phenyl | 453 |
| 129 | H | Cl | CN | 4-cyano-2-fluorophenyl | 439 |
| 130 | H | Cl | CN | 6-cyanopyridin-3-yl | 422 |
| 131 | H | Cl | CN | pyridin-4-yl | 397 |
| 132 | H | Cl | CN | 2-chloropyridin-4-yl | 431 |
| 133 | H | Cl | NO$_2$ | 4-cyanophenyl | 441 |
| 134 | H | Cl | NO$_2$ | 4-(acetamido)phenyl | 473 |
| 135 | H | Cl | NO$_2$ | 4-cyano-2-fluorophenyl | 459 |
| 136 | H | Cl | NO$_2$ | 6-cyanopyridin-3-yl | 442 |
| 137 | H | Cl | NO$_2$ | pyridin-4-yl | 417 |
| 138 | H | CF$_3$ | CN | 4-cyanophenyl | 455 |
| 139 | H | CF$_3$ | CN | 4-cyano-2-fluorophenyl | 473 |
| 140 | H | CF$_3$ | CN | 3,4-difluorophenyl | 466 |
| 141 | H | CF$_3$ | CN | 3-cyanophenyl | 455 |
| 142 | H | CF$_3$ | CN | 2-chloropyridin-4-yl | 465 |
| 143 | H | CF$_3$ | CN | 4-cyano-2,3,5,6-tetrafluorophenyl | 527 |

TABLE 3-continued

| Example | $R^A$ | $R^B$ | $R^C$ | $R^D$ | M + H |
|---|---|---|---|---|---|
| 144 | H | CF$_3$ | CN | 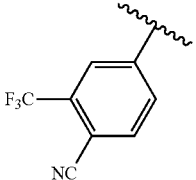 [SMILES: *c1ccc(C#N)c(C(F)(F)F)c1] | 523 |
| 145 | H | CF$_3$ | CN | 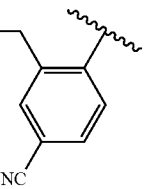 | 483 |
| 146 | H | CF$_3$ | CN | 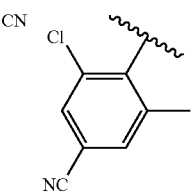 | 503 |
| 147 | H | CF$_3$ | CN | 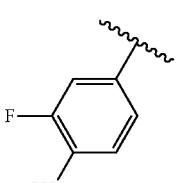 | 473 |
| 148 | H | CF$_3$ | CN | 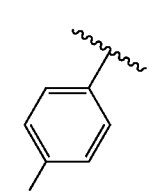 | 446 |
| 149 | H | Cl | NO$_2$ | 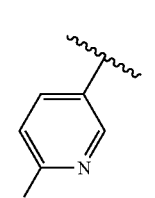 | 451 |
| 150 | H | CF$_3$ | NO$_2$ | 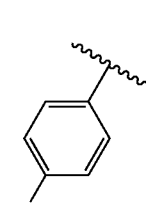 | 507 |

Structural name of the compound of each Example described in <Table 3> is as follows:

EXAMPLE 107

(2R,5S)-3-(4-cyano-3-(trifluoromethyl)phenyl)-N-(pyridin-4-yl)-2-(trifluoromethyl)oxazolidine-5-carboxamide

EXAMPLE 108

(2R,5S)-3-(4-cyano-3-(trifluoromethyl)phenyl)-N-(6-cyanopyridin-3-yl)-2-(trifluoromethyl)oxazolidine-5-carboxamide

EXAMPLE 109

(2R,5S)-N-(4-acetamidophenyl)-3-(4-cyano-3-(trifluoromethyl)phenyl)-2-(trifluoromethyl)oxazolidine-5-carboxamide

EXAMPLE 110

(2R,5S)-3-(4-cyano-3-(trifluoromethyl)phenyl)-N-(pyridin-3-yl)-2-(trifluoromethyl)oxazolidine-5-carboxamide

EXAMPLE 111

(2R,5S)-N-(4-cyanophenyl)-3-(3-methyl-4-nitrophenyl)-2-(trifluoromethyl)oxazolidine-5-carboxamide

EXAMPLE 112

(2R,5S)-N-(4-acetamidophenyl)-3-(3-methyl-4-nitrophenyl)-2-(trifluoromethyl)oxazolidine-5-carboxamide

EXAMPLE 113

(2R,5S)-N-(4-cyano-2-fluorophenyl)-3-(3-methyl-4-nitrophenyl)-2-(trifluoromethyl)oxazolidine-5-carboxamide

EXAMPLE 114

(2R,5S)-N-(2-chloro-4-cyanophenyl)-3-(4-cyano-3-(trifluoromethyl)phenyl)-2-(trifluoromethyl)oxazolidine-5-carboxamide

EXAMPLE 115

(2R,5S)-3-(4-cyano-3-(trifluoromethyl)phenyl)-N-(2,4-difluorophenyl)-2-(trifluoromethyl)oxazolidine-5-carboxamide

EXAMPLE 116

(2R,5S)-N-(6-cyanopyridin-3-yl)-3-(3-methyl-4-nitrophenyl)-2-(trifluoromethyl)oxazolidine-5-carboxamide

EXAMPLE 117

(2R,5S)-3-(3-chloro-4-cyanophenyl)-N-(4-cyanophenyl)-2-(trifluoromethyl)oxazolidine-5-carboxamide

EXAMPLE 118

(2R,5S)-N-(4-acetamidophenyl)-3-(3-chloro-4-cyanophenyl)-2-(trifluoromethyl)oxazolidine-5-carboxamide

EXAMPLE 119

(2R,5S)-3-(3-chloro-4-cyanophenyl)-N-(4-cyano-2-fluorophenyl)-2-(trifluoromethyl)oxazolidine-5-carboxamide

EXAMPLE 120

(2R,5S)-3-(3-chloro-4-cyanophenyl)-N-(6-cyanopyridin-3-yl)-2-(trifluoromethyl)oxazolidine-5-carboxamide

EXAMPLE 121

(2R,5S)-3-(3-chloro-4-cyanophenyl)-N-(pyridin-4-yl)-2-(trifluoromethyl)oxazolidine-5-carboxamide

EXAMPLE 122

(2R,5S)-3-(3-chloro-4-nitrophenyl)-N-(4-cyanophenyl)-2-(trifluoromethyl)oxazolidine-5-carboxamide

EXAMPLE 123

(2R,5S)-N-(4-acetamidophenyl)-3-(3-chloro-4-nitrophenyl)-2-(trifluoromethyl)oxazolidine-5-carboxamide

EXAMPLE 124

(2R,5S)-3-(3-chloro-4-nitrophenyl)-N-(4-cyano-2-fluorophenyl)-2-(trifluoromethyl)oxazolidine-5-carboxamide

EXAMPLE 125

(2R,5S)-3-(3-chloro-4-nitrophenyl)-N-(6-cyanopyridin-3-yl)-2-(trifluoromethyl)oxazolidine-5-carboxamide

EXAMPLE 126

(2R,5S)-3-(3-chloro-4-nitrophenyl)-N-(pyridin-4-yl)-2-(trifluoromethyl)oxazolidine-5-carboxamide

EXAMPLE 127

(2R,5S)-3-(4-cyano-3-(trifluoromethyl)phenyl)-N-(4-cyano-3-methoxyphenyl)-2-(trifluoromethyl)oxazolidine-5-carboxamide

EXAMPLE 128

(2R,5S)-N-(4-cyano-2-(trifluoromethyl)phenyl)-3-(4-cyano-3-(trifluoromethyl)phenyl)-2-(trifluoromethyl)oxazolidine-5-carboxamide

EXAMPLE 129

(2R,5S)-N-(4-cyano-2,6-difluorophenyl)-3-(4-cyano-3-(trifluoromethyl)phenyl)-2-(trifluoromethyl)oxazolidine-5-carboxamide

EXAMPLE 130

(2R,5S)-N-(3-chloro-4-cyano-2-fluorophenyl)-3-(4-cyano-3-(trifluoromethyl)phenyl)-2-(trifluoromethyl)oxazolidine-5-carboxamide

EXAMPLE 131

(2R,5S)-N-(4-cyano-2,5-difluorophenyl)-3-(4-cyano-3-(trifluoromethyl)phenyl)-2-(trifluoromethyl)oxazolidine-5-carboxamide

EXAMPLE 132

(2R,5S)-3-(4-cyano-3-(trifluoromethyl)phenyl)-N-(3,4-dicyanophenyl)-2-(trifluoromethyl)oxazolidine-5-carboxamide

EXAMPLE 133

(2R,5S)-N-(4-cyano-2-methylphenyl)-3-(4-cyano-3-(trifluoromethyl)phenyl)-2-(trifluoromethyl)oxazolidine-5-carboxamide

EXAMPLE 134

(2R,5S)-N-(3-chloro-4-cyanophenyl)-3-(4-cyano-3-(trifluoromethyl)phenyl)-2-(trifluoromethyl)oxazolidine-5-carboxamide

EXAMPLE 135

(2R,5S)-N-(6-acetamidopyridin-3-yl)-3-(4-cyano-3-(trifluoromethyl)phenyl)-2-(trifluoromethyl)oxazolidine-5-carboxamide

EXAMPLE 136

(2R,5S)-3-(3-chloro-4-cyanophenyl)-N-(2-chloropyridin-4-yl)-2-(trifluoromethyl)oxazolidine-5-carboxamide

EXAMPLE 137

(2R,5S)-N-(2-chloropyridin-4-yl)-3-(3-methyl-4-nitrophenyl)-2-(trifluoromethyl)oxazolidine-5-carboxamide

EXAMPLE 138

(2R,5S)-3-(4-cyano-3-(trifluoromethyl)phenyl)-N-(4-cyanophenyl)-2-(trifluoromethyl)oxazolidine-5-carboxamide

EXAMPLE 139

(2R,5S)-N-(4-cyano-2-fluorophenyl)-3-(4-cyano-3-(trifluoromethyl)phenyl)-2-(trifluoromethyl)oxazolidine-5-carboxamide

EXAMPLE 140

(2R,5S)-3-(4-cyano-3-(trifluoromethyl)phenyl)-N-(3,4-difluorophenyl)-2-(trifluoromethyl)oxazolidine-5-carboxamide

EXAMPLE 141

(2R,5S)-3-(4-cyano-3-(trifluoromethyl)phenyl)-N-(3-cyanophenyl)-2-(trifluoromethyl)oxazolidine-5-carboxamide

EXAMPLE 142

(2R,5S)-N-(2-chloropyridin-4-yl)-3-(4-cyano-3-(trifluoromethyl)phenyl)-2-(trifluoromethyl)oxazolidine-5-carboxamide

EXAMPLE 143

(2R,5S)-N-(4-cyano-2,3,5,6-tetrafluorophenyl)-3-(4-cyano-3-(trifluoromethyl)phenyl)-2-(trifluoromethyl)oxazolidine-5-carboxamide

EXAMPLE 144

(2R,5S)-N,3-bis(4-cyano-3-(trifluoromethyl)phenyl)-2-(trifluoromethyl)oxazolidine-5-carboxamide

EXAMPLE 145

(2R,5S)-N-(4-cyano-2-ethylphenyl)-3-(4-cyano-3-(trifluoromethyl)phenyl)-2-(trifluoromethyl)oxazolidine-5-carboxamide

EXAMPLE 146

(2R,5S)-N-(2-chloro-4-cyano-6-methylphenyl)-3-(4-cyano-3-(trifluoromethyl)phenyl)-2-(trifluoromethyl)oxazolidine-5-carboxamide

EXAMPLE 147

(2R,5S)-3-(4-cyano-3-(trifluoromethyl)phenyl)-N-(4-cyano-3-fluorophenyl)-2-(trifluoromethyl)oxazolidine-5-carboxamide

EXAMPLE 148

(2R,5S)-3-(4-cyano-3-(trifluoromethyl)phenyl)-N-(4-hydroxyphenyl)-2-(trifluoromethyl)oxazolidine-5-carboxamide

EXAMPLE 149

(2R,5S)-3-(3-chloro-4-nitrophenyl)-N-(6-chloropyridin-3-yl)-2-(trifluoromethyl)oxazolidine-5-carboxamide

EXAMPLE 150

(2R,5S)-N-(4-acetamidophenyl)-3-(4-nitro-3-(trifluoromethyl)phenyl)-2-(trifluoromethyl)oxazolidine-5-carboxamide

EXAMPLE 151

Preparation of (2R,5S)-N-(2-chloro-4-nitrophenyl)-3-(4-cyano-3-(trifluoromethyl)phenyl)-2-(trifluoromethyl)oxazolidine-5-carboxamide

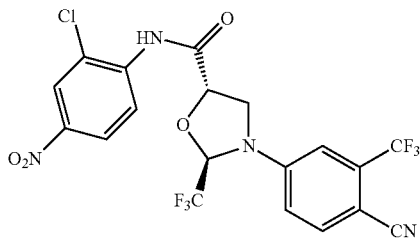 [SMILES: N#Cc1ccc(N2C[C@@H](C(=O)Nc3ccc([N+](=O)[O-])cc3Cl)O[C@@H]2C(F)(F)F)cc1C(F)(F)F]

In a 100-ml flask, 500 mg (1.41 mmol) of (2R,5S)-3-(4-cyano-3-(trifluoromethyl)phenyl)-2-(trifluoromethyl)oxazolidine-5-carboxylic acid obtained in Preparation Example 16 and 243 mg (1.41 mmol, 1.0 eq) of 2-chloro-4-nitroaniline were used to obtain 300 mg (42%) of a title compound in the same manner as in Example 104.
Mass[M+H]: 509.04

EXAMPLE 152

Preparation of (2R,5S)-N-(4-amino-2-chlorophenyl)-3-(4-cyano-3-(trifluoromethyl)phenyl)-2-(trifluoromethyl)oxazolidine-5-carboxamide

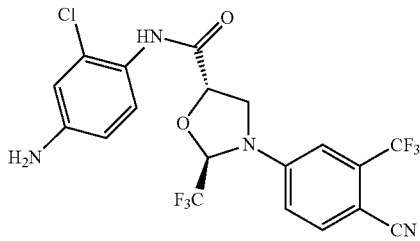

In a 500-ml flask, 300 mg (0.59 mmol) of (2R,5S)-N-(2-chloro-4-nitrophenyl)-3-(4-cyano-3-(trifluoromethyl)phenyl)-2-(trifluoromethyl)oxazolidine-5-carboxamide obtained in Example 151 was used to obtain 100 mg (36%) of a title compound in the same manner as in Example 14.
Mass[M+H]: 479.06

EXAMPLE 153

Preparation of (2R,5S)-N-(4-acetamido-2-chlorophenyl)-3-(4-cyano-3-(trifluoromethyl)phenyl)-2-(trifluoromethyl)oxazolidine-5-carboxamide

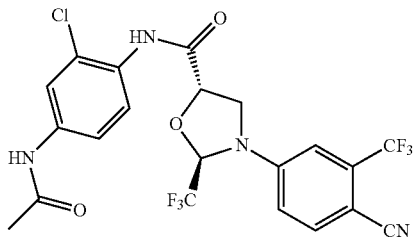 [SMILES: CC(=O)Nc1ccc(NC(=O)[C@@H]2CN(c3ccc(C#N)c(C(F)(F)F)c3)[C@@H](C(F)(F)F)O2)c(Cl)c1]

In a 25-ml flask, 21 mg (0.044 mmol) of (2R,5S)-N-(4-amino-2-chlorophenyl)-3-(4-cyano-3-(trifluoromethyl)phenyl)-2-(trifluoromethyl)oxazolidine-5-carboxamide obtained in Example 152 and 3 ul (0.44 mmol, 1.0 eq) of acetyl chloride were used to obtain 17 mg (77%) of a title compound in the same manner as in Example 102.

Mass[M+H]: 521.07

EXAMPLE 154

Preparation of methyl(3-chloro-4-((2R,5S)-3-(4-cyano-3-(trifluoromethyl)phenyl)-2-(trifluoromethyl)oxazolidine-5-carboxamido)phenyl)carbamate

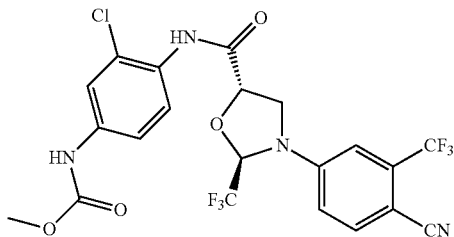 [SMILES: COC(=O)Nc1ccc(NC(=O)[C@@H]2CN(c3ccc(C#N)c(C(F)(F)F)c3)[C@@H](C(F)(F)F)O2)c(Cl)c1]

In a 25-ml flask, 21 mg (0.044 mmol) of (2R,5S)-N-(4-amino-2-chlorophenyl)-3-(4-cyano-3-(trifluoromethyl)phenyl)-2-(trifluoromethyl)oxazolidine-5-carboxamide obtained in Example 152 and 3.4 ul (0.44 mmol, 1.0 eq) of methyl chloroformate were used to obtain 19 mg (79%) of a title compound in the same manner as in Example 102.

Mass[M+H]: 537.07

EXAMPLE 155

Preparation of (2R,5S)-3-(4-cyano-3-(trifluoromethyl)phenyl)-N-(4-nitrophenyl)-2-(trifluoromethyl)oxazolidine-5-carboxamide

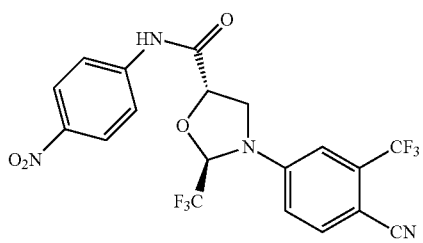 [SMILES: N#Cc1ccc(N2C[C@@H](C(=O)Nc3ccc([N+](=O)[O-])cc3)O[C@@H]2C(F)(F)F)cc1C(F)(F)F]

In a 100-ml flask, 550 mg (1.55 mmol) of (2R,5S)-3-(4-cyano-3-(trifluoromethyl)phenyl)-2-(trifluoromethyl)oxazolidine-5-carboxylic acid obtained in Preparation Example 16 and 214 mg (1.55 mmol, 1.0 eq) of 4-nitroaniline were used to obtain 615 mg (84%) of a title compound in the same manner as in Example 104.

Mass[M+H]: 475.08

EXAMPLE 156

Preparation of (2R,5S)-N-(4-aminophenyl)-3-(4-cyano-3-(trifluoromethyl)phenyl)-2-(trifluoromethyl)oxazolidine-5-carboxamide

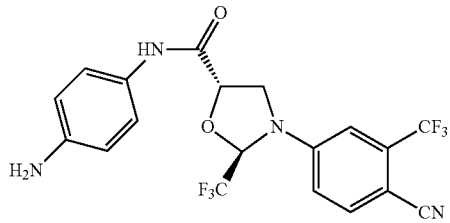 [SMILES: N#Cc1ccc(N2C[C@@H](C(=O)Nc3ccc(N)cc3)O[C@@H]2C(F)(F)F)cc1C(F)(F)F]

In a 100-ml flask, 615 mg (1.3 mmol) of (2R,5S)-3-(4-cyano-3-(trifluoromethyl)phenyl)-N-(4-nitrophenyl)-2-(trifluoromethyl)oxazolidine-5-carboxamide obtained in Example 155 was used to obtain 511 mg (88%) of a title compound in the same manner as in Example 14.

Mass[M+H]: 445.10

EXAMPLE 157

Preparation of methyl(4-((2R,5S)-3-(4-cyano-3-(trifluoromethyl)phenyl)-2-(trifluoromethyl)oxazolidine-5-carboxamido)phenyl)carbamate

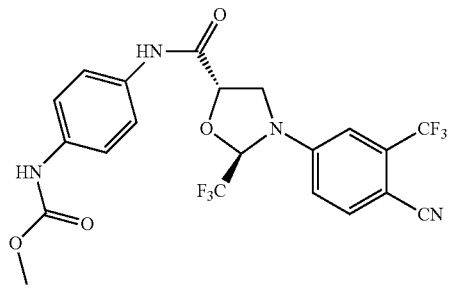 [SMILES: COC(=O)Nc1ccc(NC(=O)[C@@H]2CN(c3ccc(C#N)c(C(F)(F)F)c3)[C@@H](C(F)(F)F)O2)cc1]

In a 25-ml flask, 50 mg (0.113 mmol) of (2R,5S)-N-(4-aminophenyl)-3-(4-cyano-3-(trifluoromethyl)phenyl)-2-(trifluoromethyl)oxazolidine-5-carboxamide obtained in Example 156 and methyl chloroformate were used to obtain 37 mg (65%) of a title compound in the same manner as in Example 102.

Mass[M+H]: 503.11

EXAMPLE 158

Preparation of (2R,5S)-3-(4-cyano-3-(trifluoromethyl)phenyl)-N-(4-propionamidophenyl)-2-(trifluoromethyl)oxazolidine-5-carboxamide

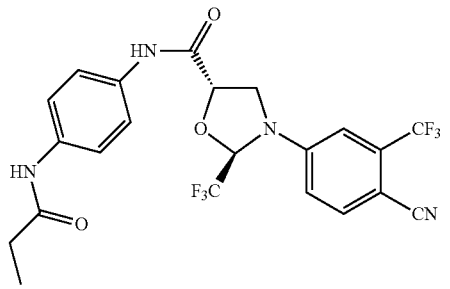 [SMILES: CCC(=O)Nc1ccc(NC(=O)[C@@H]2CN(c3ccc(C#N)c(C(F)(F)F)c3)[C@@H](C(F)(F)F)O2)cc1]

In a 25-ml flask, 50 mg (0.113 mmol) of (2R,5S)-N-(4-aminophenyl)-3-(4-cyano-3-(trifluoromethyl)phenyl)-2-(trifluoromethyl)oxazolidine-5-carboxamide obtained in Example 156 and propionyl chloride were used to obtain 35 mg (61%) of a title compound in the same manner as in Example 102.

Mass[M+H]: 501.13

EXAMPLE 159

Preparation of (2R,5S)-3-(4-cyano-3-(trifluoromethyl)phenyl)-N-(4-isobutylamidophenyl)-2-(trifluoromethyl)oxazolidine-5-carboxamide

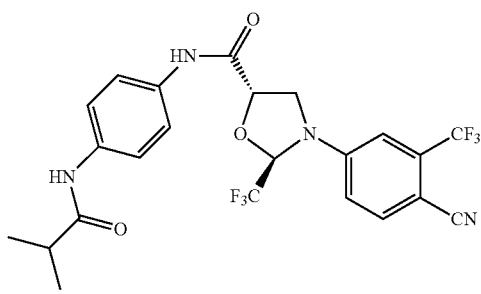 [SMILES: CC(C)C(=O)Nc1ccc(NC(=O)[C@@H]2CN(c3ccc(C#N)c(C(F)(F)F)c3)[C@@H](C(F)(F)F)O2)cc1]

In a 25-ml flask, 50 mg (0.113 mmol) of (2R,5S)-N-(4-aminophenyl)-3-(4-cyano-3-(trifluoromethyl)phenyl)-2-(trifluoromethyl)oxazolidine-5-carboxamide obtained in Example 156 and isobutyryl chloride were used to obtain 42 mg (72%) of a title compound in the same manner as in Example 102.

Mass[M+H]: 515.14

EXAMPLE 160

Preparation of (2R,5S)-3-(4-cyano-3-(trifluoromethyl)phenyl)-N-(4-(2-hydroxyacetamido)phenyl)-2-(trifluoromethyl)oxazolidine-5-carboxamide

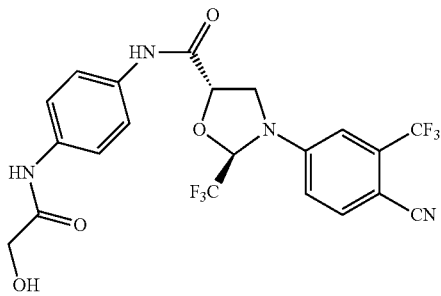 [SMILES: N#Cc1ccc(N2C[C@@H](C(=O)Nc3ccc(NC(=O)CO)cc3)O[C@@H]2C(F)(F)F)cc1C(F)(F)F]

In a 25-ml flask, 70 mg (0.158 mmol) of (2R,5S)-N-(4-aminophenyl)-3-(4-cyano-3-(trifluoromethyl)phenyl)-2-(trifluoromethyl)oxazolidine-5-carboxamide obtained in Example 156 was used to obtain 68 mg (87%) of a title compound in the same manner as in Example 94.

Mass[M+H]: 503.11

EXAMPLE 161

Preparation of (2R,5S)-3-(4-cyano-3-(trifluoromethyl)phenyl)-2-(trifluoromethyl)-N-(4-ureidophenyl)oxazolidine-5-carboxamide

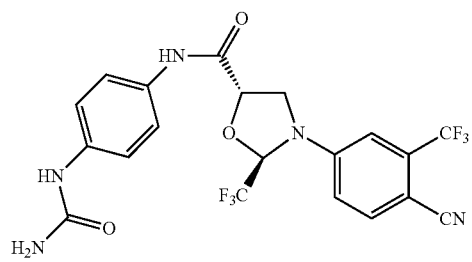 [SMILES: N#Cc1ccc(N2C[C@@H](C(=O)Nc3ccc(NC(N)=O)cc3)O[C@@H]2C(F)(F)F)cc1C(F)(F)F]

In a 25-ml flask, 50 mg (0.113 mmol) of (2R,5S)-N-(4-aminophenyl)-3-(4-cyano-3-(trifluoromethyl)phenyl)-2-(trifluoromethyl)oxazolidine-5-carboxamide obtained in Example 156 was used to obtain 32 mg (58%) of a title compound in the same manner as in Example 15.

Mass[M+H]: 488.11

EXAMPLE 162

Preparation of (2R,5S)-3-(4-cyano-3-(trifluoromethyl)phenyl)-N-(4-(2-cyanoacetamido)phenyl)-2-(trifluoromethyl)oxazolidine-5-carboxamide

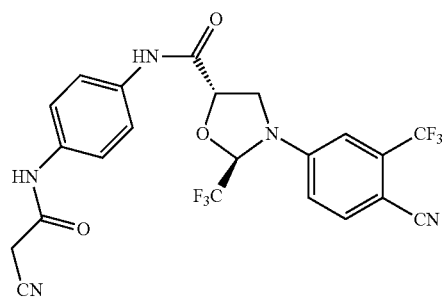 [SMILES: N#CCC(=O)Nc1ccc(NC(=O)[C@@H]2CN(c3ccc(C#N)c(C(F)(F)F)c3)[C@@H](C(F)(F)F)O2)cc1]

In a 25-ml flask, 25 mg (0.056 mmol) of (2R,5S)-N-(4-aminophenyl)-3-(4-cyano-3-(trifluoromethyl)phenyl)-2-(trifluoromethyl)oxazolidine-5-carboxamide obtained in Example 156 and cyanoacetic acid were used to obtain 17 mg (59%) of a title compound in the same manner as in Example 32.

Mass [M+H]: 512.11

EXAMPLE 163

Preparation of (2R,5S)-N-(4-(2-aminoacetamido)phenyl)-3-(4-cyano-3-(trifluoromethyl)phenyl)-2-(trifluoromethyl)oxazolidine-5-carboxamide hydrochloride

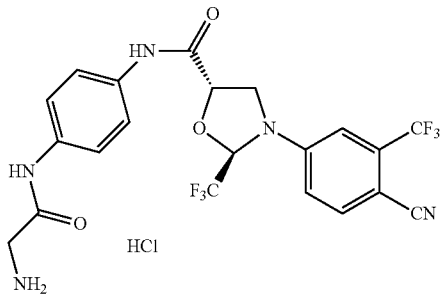 [SMILES: N#Cc1ccc(N2C[C@@H](C(=O)Nc3ccc(NC(=O)CN)cc3)O[C@@H]2C(F)(F)F)cc1C(F)(F)F ; Cl]

In a 25-ml flask, 25 mg (0.056 mmol) of (2R,5S)-N-(4-aminophenyl)-3-(4-cyano-3-(trifluoromethyl)phenyl)-2-(trifluoromethyl)oxazolidine-5-carboxamide obtained in Example 156 and glycine were used to obtain 13 mg (43%) of a title compound in the same manner as in Example 50.
Mass[M+H]: 502.12

EXAMPLE 164

Preparation of (2S,5S)-3-(4-cyano-3-(trifluoromethyl)phenyl)-N-(4-cyanophenyl)-2-(trifluoromethyl)oxazolidine-5-carboxamide

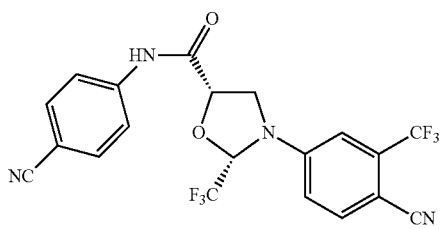 [SMILES: N#Cc1ccc(NC(=O)[C@@H]2CN(c3ccc(C#N)c(C(F)(F)F)c3)[C@H](C(F)(F)F)O2)cc1]

In a 25-ml flask, 11 mg (0.031 mmol) of (2S,5S)-3-(4-cyano-3-(trifluoromethyl)phenyl)-2-(trifluoromethyl)oxazolidine-5-carboxylic acid obtained in Preparation Example 48 and 4 mg (0.031 mmol, 1.0 eq) of 4-cyanoaniline were used to obtain 9 mg (64%) of a title compound in the same manner as in Example 104.
$^1$H NMR (CDCl$_3$, 600 MHz) δ 8.29(s, 1H), 7.74(d, 1H), 7.69~7.65(m, 4H), 7.07(d, 1H), 6.95(dd, 1H), 5.86(q, 1H), 4.96(t, 1H), 4.34(t, 1H), 3.96(dd, 1H)
Mass[M+H]: 455.09

EXAMPLE 165

Preparation of 4-((2R,5S)-5-(((4-cyanophenyl)sulfonyl)methyl)-2-(trifluoromethyl)oxazolidin-3-yl)-2-(trifluoromethyl)benzonitrile

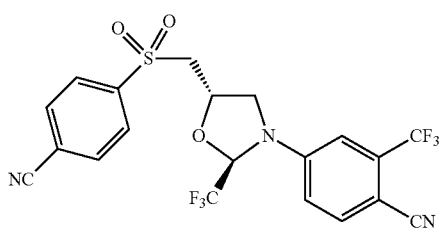 [SMILES: N#Cc1ccc(S(=O)(=O)C[C@@H]2CN(c3ccc(C#N)c(C(F)(F)F)c3)[C@@H](C(F)(F)F)O2)cc1]

To a 25-ml flask, 70 mg (0.15 mmol) of 4-((2R,5S)-5-(((4-cyanophenyl)thio)methyl)-2-(trifluoromethyl)oxazolidin-3-yl)-2-(trifluoromethyl)benzonitrile obtained in Example 29 was added, and dissolved in 2 ml of dichloromethane, and then cooled to 0° C. 84 mg (0.37 mmol, 2.5 eq) of 3-chloroperbenzoic acid was added thereto, followed by stirring at room temperature. 2 hours later, the resulting product was diluted with 30 ml of dichloromethane and washed with a saturated sodium hydrogen carbonate aqueous solution. An organic layer was separated and then washed with a NaCl aqueous solution, dehydrated and dried over MgSO$_4$, followed by concentration under reduced pressure. A concentrate was purified by column chromatography to obtain 61 mg (84%) of a title compound.
$^1$H NMR (CDCl$_3$, 400 MHz) δ 8.04(d, 2H), 7.88(d, 2H), 7.67(d, 1H), 6.95(d, 1H), 6.85(dd, 1H), 5.38(q, 1H), 5.12~5.05(m, 1H), 4.12~4.04(m, 1H), 3.61~3.56(m, 1H), 3.49~3.43(m, 2H)
Mass[M+H]: 490.06

EXAMPLE 166

Preparation of 4-((2R,5S)-5-(1-hydroxy-2-phenylethyl)-2-(trifluoromethyl)oxazolidin-3-yl)-2-(trifluoromethyl)benzonitrile

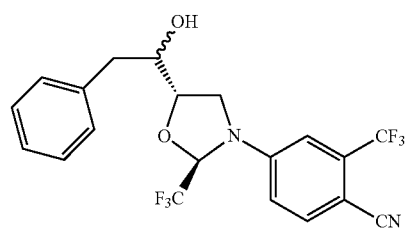 [SMILES: N#Cc1ccc(N2C[C@@H](C(O)Cc3ccccc3)O[C@@H]2C(F)(F)F)cc1C(F)(F)F]

Step 1. Preparation of (2R,5S)-3-(4-cyano-3-(trifluoromethyl)phenyl)-N-methoxy-N-methyl-2-(trifluoromethyl)oxazolidine-5-carboxamide

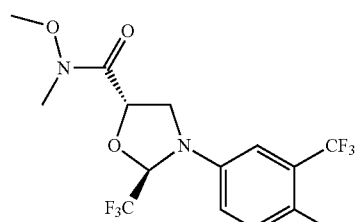

In a 100-ml flask, 1 g (2.82 mmol) of (2R,5S)-3-(4-cyano-3-(trifluoromethyl)phenyl)-2-(trifluoromethyl)oxazolidine-5-carboxylic acid obtained in Preparation Example 16 and 275 mg (2.82 mmol, 1.0 eq) of N,O-dimethylhydroxylaminehydrochloride were used to obtain 688 mg (61%) of a title compound in the same manner as in Example 104.
$^1$H NMR (CDCl$_3$, 600 MHz) δ 7.67(d, 1H), 6.99(d, 1H), 6.89(dd, 1H), 5.78(q, 1H), 5.33(t, 1H), 3.67(t, 1H), 3.88~3.86(m, 1H), 3.78(s, 3H), 3.20(s, 3H)
Mass[M+H]: 398.09

Step 2. Preparation of 4-((2R,5S)-5-(2-phenylacetyl)-2-(trifluoromethyl)oxazolidin-3-yl)-2-(trifluoromethyl)benzonitrile

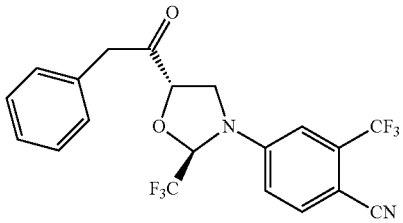 [SMILES: N#Cc1ccc(N2C[C@@H](C(=O)Cc3ccccc3)O[C@@H]2C(F)(F)F)cc1C(F)(F)F]

To a 50-ml flask, 200 mg (0.503 mmol) of (2R,5S)-3-(4-cyano-3-(trifluoromethyl)phenyl)-N-methoxy-N-methyl-2-(trifluoromethyl)oxazolidine-5-carboxamide obtained in Step 1 of Example 166 was added, and dissolved in 2 ml of tetrahydrofuran, and then cooled to 0° C. To this reaction solution, 1.7 ml (1.51 mmol, 3.0 eq) of 0.9 M benzylmagnesium bromide solution was injected, followed by stirring at room temperature for 2 hours. After completion of the reaction, the reaction product was diluted with ethyl acetate (30 ml) and washed with water (70 ml). After separation of layers, an organic layer was washed with a saturated NH$_4$Cl aqueous solution, and then washed with water. The organic layer was separated and washed with a NaCl aqueous solution, dehydrated and dried over MgSO$_4$, followed by concentration under reduced pressure. A concentrate was purified by column chromatography to obtain 112 mg (52%) of a title compound.

$^1$H NMR (CDCl$_3$, 400 MHz) δ 7.63(d, 1H), 7.35(d, 1H), 7.21~7.11(m, 4H), 6.76(d, 1H), 6.70(dd, 1H), 5.40(q, 1H), 4.67(dd, 1H), 3.98(d, 1H), 3.86(d, 1H), 3.81(d, 1H), 3.72(dd, 1H)

Mass[M+H]: 429.10

Step 3. Preparation of 4-((2R,5S)-5-(1-hydroxy-2-phenylethyl)-2-(trifluoromethyl)oxazolidin-3-yl)-2-(trifluoromethyl)benzonitrile In a 25-ml flask, 110 mg (0.257 mmol) of 4-((2R,5S)-5-(2-phenylacetyl)-2-(trifluoromethyl)oxazolidin-3-yl)-2-(trifluoromethyl)benzonitrile obtained in Step 2 of Example 166 was dissolved in 2 ml of ethanol, followed by stirring. To this reaction solution, 10 mg (0.257 mmol, 1.0 eq) of NaBH$_4$ was added, followed by stirring at room temperature for 1 hour. After completion of the reaction, the reaction product was concentrated and diluted with ethyl acetate (30 ml) and washed with water (70 ml). After separation of layers, an organic layer was washed with a saturated NH$_4$Cl aqueous solution, and then washed with water. The organic layer was separated and washed with a NaCl aqueous solution, dehydrated and dried over MgSO$_4$, followed by concentration under reduced pressure. A concentrate was purified by column chromatography to obtain 41 mg (37%) of a title compound.

$^1$H NMR (CDCl$_3$, 400 MHz) δ 7.67(dd, 1H), 7.35~7.22(m, 4H), 6.96(dd, 1H), 6.84(ddd, 1H), 5.60~5.55(m, 1H), 4.63~4.55(m, 1H), 4.10~4.07(m, 0.5H), 3.90~3.87(m, 0.5H), 3.73(t, 0.5H), 3.69~3.61(m, 1H), 3.53(t, 0.5H), 3.01~2.88(m, 1.5H), 2.76(dd, 0.5H)1.94(d, 1H)

Mass[M+H]: 431.11

EXAMPLE 167

Preparation of 4-((2R,5S)-5-(4-isocyanopiperidine-1-carbonyl)-2-(trifluoromethyl)oxazolidin-3-yl)-2-(trifluoromethyl)benzonitrile

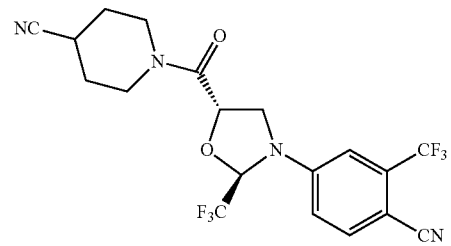 [SMILES: N#Cc1ccc(N2C[C@@H](C(=O)N3CCC(C#N)CC3)O[C@@H]2C(F)(F)F)cc1C(F)(F)F]

50 mg (0.14 mmol) of the compound (2R,5S)-3-(4-cyano-3-(trifluoromethyl)phenyl)-2-(trifluoromethyl)oxazolidine-5-carboxylic acid obtained in Preparation Example 16 and 4-cyanopiperidine were used to obtain 42 mg (83%) of a title compound in the same manner as in Example 104.

Mass[M+H]: 447.12

EXAMPLE 168

Preparation of t-butyl 4-((2R,5S)-3-(4-cyano-3-(trifluoromethyl)phenyl)-2-(trifluoromethyl)oxazolidine-5-carboxamido)piperidine-1-carboxylate

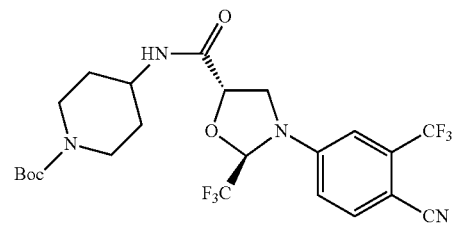 [SMILES: CC(C)(C)OC(=O)N1CCC(NC(=O)[C@@H]2CN(c3ccc(C#N)c(C(F)(F)F)c3)[C@@H](C(F)(F)F)O2)CC1]

194 mg (0.55 mmol) of the compound (2R,5S)-3-(4-cyano-3-(trifluoromethyl)phenyl)-2-(trifluoromethyl)oxazolidine-5-carboxylic acid obtained in Preparation Example 16 and 4-amino-1-boc-piperidine were used to obtain 122 mg (65%) of a title compound in the same manner as in Example 104.

Mass[M+H]: 537.19

EXAMPLE 169

Preparation of (2R,5S)-3-(4-cyano-3-(trifluoromethyl)phenyl)-N-(piperidin-4-yl)-2-(trifluoromethyl)oxazolidine-5-carboxamide

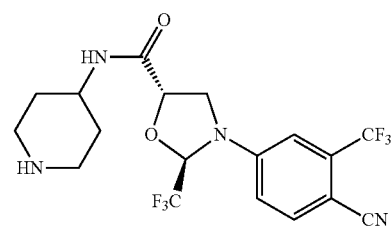 [SMILES: N#Cc1ccc(N2C[C@@H](C(=O)NC3CCNCC3)O[C@@H]2C(F)(F)F)cc1C(F)(F)F]

118 mg (0.22 mmol) of the compound t-butyl 4-((2R,5S)-3-(4-cyano-3-(trifluoromethyl)phenyl)-2-(trifluoromethyl)oxazolidine-5-carboxamido)piperidine-1-carboxylate obtained in Example 168 was used to obtain 92 mg (95%) of a title compound in the same manner as in Example 89.

Mass[M+H]: 437.13

EXAMPLE 170

Preparation of (2R,5S)-N-(1-acetylpiperidin-4-yl)-3-(4-cyano-3-(trifluoromethyl)phenyl)-2-(trifluoromethyl)oxazolidine-5-carboxamide

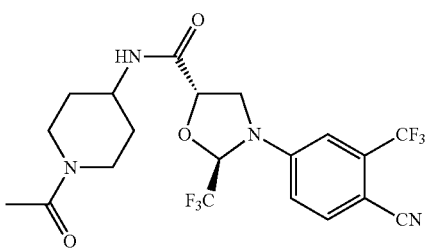 [SMILES: CC(=O)N1CCC(NC(=O)[C@@H]2CN(c3ccc(C#N)c(C(F)(F)F)c3)[C@@H](C(F)(F)F)O2)CC1]

88 mg (0.20 mmol) of the compound (2R,5S)-3-(4-cyano-3-(trifluoromethyl)phenyl)-N-(piperidin-4-yl)-2-(trifluoromethyl)oxazolidine-5-carboxamide obtained in Example 169 was used to obtain 48 mg (50%) of a title compound in the same manner as in Example 90.

¹H NMR (CDCl₃, 600 MHz) δ 7.63(d, 1H), 6.98(d, 1H), 6.87(t, 1H), 6.68(t, 1H), 5.77(s, 1H), 4.98(q, 1H), 4.49(dd, 1H), 4.09~4.05(m, 1H), 3.95(br, 1H), 3.81~3.71(m, 2H), 3.10(td, 1H), 2.63(q, 1H), 2.04(s, 3H), 1.86(t, 1H), 1.36~1.20(m, 3H)

Mass[M+H]: 479.14

EXAMPLE 171

Preparation of 4-((2R,5S)-5-(piperazine-1-carbonyl)-2-(trifluoromethyl)oxazolidin-3-yl)-2-(trifluoromethyl)benzonitrile hydrochloride

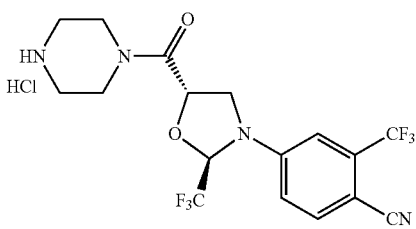 [SMILES: Cl ; N#Cc1ccc(N2C[C@@H](C(=O)N3CCNCC3)O[C@@H]2C(F)(F)F)cc1C(F)(F)F]

Step 1. Preparation of t-butyl 4-((2R,5S)-3-(4-cyano-3-(trifluoromethyl)phenyl)-2-(trifluoromethyl)oxazolidine-5-carbonyl)piperazine-1-carboxylate

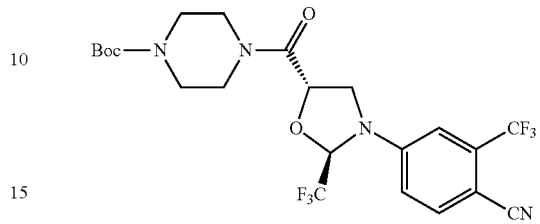

499 mg (1.41 mmol) of the compound (2R,5S)-3-(4-cyano-3-(trifluoromethyl)phenyl)-2-(trifluoromethyl)oxazolidine-5-carboxylic acid obtained in Preparation Example 16 and N-boc-piperazine were used to obtain 270 mg (37%) of a title compound in the same manner as in Example 104.

Mass[M+H]: 523.17

Step 2. Preparation of 4-((2R,5S)-5-(piperazine-1-carbonyl)-2-(trifluoromethyl)oxazolidin-3-yl)-2-(trifluoromethyl)benzonitrile hydrochloride 270 mg (0.52 mmol) of the compound t-butyl 4-((2R,5S)-3-(4-cyano-3-(trifluoromethyl)phenyl)-2-(trifluoromethyl)oxazolidine-5-carbonyl)piperazine-1-carboxylate obtained in Example 171 was used to obtain 250 mg (99%) of a title compound in the same manner as in Example 89.

Mass[M+H]: 423.12

EXAMPLE 172

Preparation of 4-((2R,5S)-5-(4-acetylpiperazine-1-carbonyl)-2-(trifluoromethyl)oxazolidin-3-yl)-2-(trifluoromethyl)benzonitrile

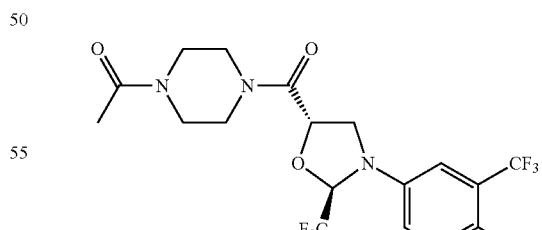

50 mg (0.11 mmol) of the compound 4-((2R,5S)-5-(piperazine-1-carbonyl)-2-(trifluoromethyl)oxazolidin-3-yl)-2-(trifluoromethyl)benzonitrile hydrochloride obtained in Example 171 was used to obtain 43 mg (84%) of a title compound in the same manner as in Example 90.

Mass[M+H]: 465.13

EXAMPLE 173

Preparation of methyl 4-((2R,5S)-3-(4-cyano-3-(trifluoromethyl)phenyl)-2-(trifluoromethyl)oxazolidine-5-carbonyl)piperazine-1-carboxylate

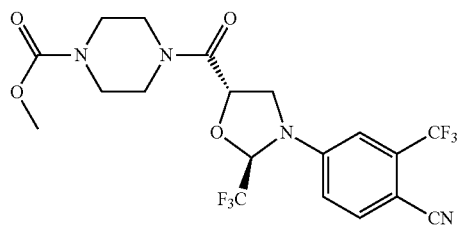 [SMILES: COC(=O)N1CCN(C(=O)[C@@H]2CN(c3ccc(C#N)c(C(F)(F)F)c3)[C@@H](C(F)(F)F)O2)CC1]

50 mg (0.11 mmol) of the compound 4-((2R,5S)-5-(piperazine-1-carbonyl)-2-(trifluoromethyl)oxazolidin-3-yl)-2-(trifluoromethyl)benzonitrile hydrochloride obtained in Example 171 was used to obtain 30 mg (57%) of a title compound in the same manner as in Step 1 of Example 17.

$^1$H NMR (CDCl$_3$, 600 MHz) δ 7.70(d, 1H), 7.41(d, 1H), 6.92(dd, 1H), 5.63(q, 1H), 5.23(t, 1H), 4.37(q, 1H), 3.85(q, 1H), 3.80~3.60(m, 7H), 3.52~3.30(m, 4H)

Mass[M+H]: 481.12

EXAMPLE 174

Preparation of 4-((2R,5S)-3-(4-cyano-3-(trifluoromethyl)phenyl)-2-(trifluoromethyl)oxazolidine-5-carbonyl)piperazine-1-carbonitrile

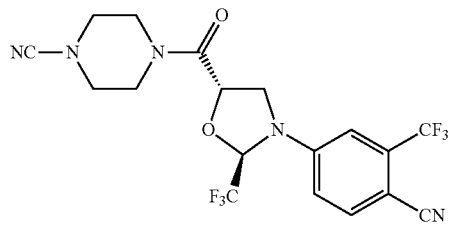 [SMILES: N#Cc1ccc(N2C[C@@H](C(=O)N3CCN(C#N)CC3)O[C@@H]2C(F)(F)F)cc1C(F)(F)F]

To a 50-ml flask, 50 mg (0.11 mmol) of the compound 4-((2R,5S)-5-(piperazine-1-carbonyl)-2-(trifluoromethyl)oxazolidin-3-yl)-2-(trifluoromethyl)benzonitrile hydrochloride obtained in Example 171 was added, and 3 ml of dichloromethane was added, followed by stirring. To this reaction product, 17.3 mg (0.163 mmol, 1.5 eq) of cyanogen bromide and 57 ul (0.327 mmol, 3.0 eq) of N,N-diisopropylethylamine were added, followed by stirring at room temperature for 2 hours. After completion of the reaction, the reaction product was concentrated under reduced pressure, and diluted with ethyl acetate (10 ml) and washed with water (20 ml). An organic layer was separated and washed with a NaCl aqueous solution, and then dehydrated and dried over MgSO$_4$, followed by concentration under reduced pressure. A concentrate was separated by a column to obtain 2.7 mg (5%) of a title compound.

Mass[M+H]: 448.11

EXAMPLE 175

Preparation of 4-((2R,5S)-5-(4-aminopiperidine-1-carbonyl)-2-(trifluoromethyl)oxazolidin-3-yl)-2-(trifluoromethyl)benzonitrile hydrochloride

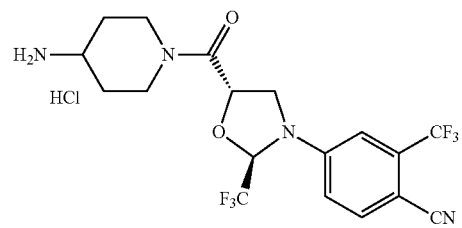 [SMILES: N#Cc1ccc(N2C[C@@H](C(=O)N3CCC(N)CC3)O[C@@H]2C(F)(F)F)cc1C(F)(F)F ; Cl]

Step 1. Preparation of t-butyl(1-((2R,5S)-3-(4-cyano-3-(trifluoromethyl)phenyl)-2-(trifluoromethyl)oxazolidine-5-carbonyl)piperidin-4-yl)carbamate

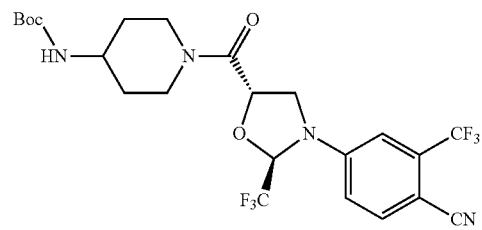 [SMILES: CC(C)(C)OC(=O)NC1CCN(C(=O)[C@@H]2CN(c3ccc(C#N)c(C(F)(F)F)c3)[C@@H](C(F)(F)F)O2)CC1]

306 mg (0.86 mmol) of the compound (2R,5S)-3-(4-cyano-3-(trifluoromethyl)phenyl)-2-(trifluoromethyl)oxazolidine-5-carboxylic acid obtained in Preparation Example 16 and 4-(N-boc-amino)piperidine were used to obtain 113 mg (24%) of a title compound in the same manner as in Example 104.

Mass[M+H]: 537.19

Step 2. Preparation of 4-((2R,5S)-5-(4-aminopiperidine-1-carbonyl)-2-(trifluoromethyl)oxazolidin-3-yl)-2-(trifluoromethyl)benzonitrile hydrochloride 113 mg (0.21 mmol) of the compound t-butyl (1-((2R,5S)-3-(4-cyano-3-(trifluoromethyl)phenyl)-2-(trifluoromethyl)oxazolidine-5-carbonyl)piperidin-4-yl)carbamate obtained in Step 1 of Example 175 was used to obtain 103 mg (99%) of a title compound in the same manner as in Example 89.

Mass[M+H]: 437.13

EXAMPLE 176

Preparation of 4-((2R,5S)-5-(4-acetylpiperazine-1-carbonyl)-2-(trifluoromethyl)oxazolidin-3-yl)-2-(trifluoromethyl)benzonitrile

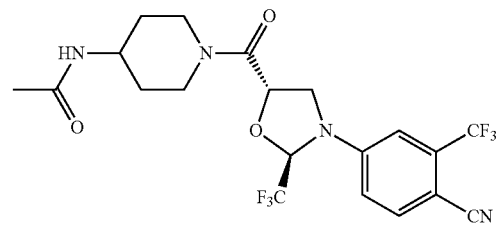 [SMILES: CC(=O)NC1CCN(C(=O)[C@@H]2CN(c3ccc(C#N)c(C(F)(F)F)c3)[C@@H](C(F)(F)F)O2)CC1]

83 mg (0.18 mmol) of the compound 4-((2R,5S)-5-(4-aminopiperidine-1-carbonyl)-2-(trifluoromethyl)oxazolidin-3-yl)-2-(trifluoromethyl)benzonitrile hydrochloride obtained in Example 175 was used to obtain 60 mg (71%) of a title compound in the same manner as in Example 90.
Mass[M+H]: 479.14

EXAMPLE 177

Preparation of t-butyl 4-((2R,5S)-3-(4-cyano-3-(trifluoromethyl)phenyl)-2-(trifluoromethyl)oxazolidine-5-carboxamido)piperidine-1-carboxylate

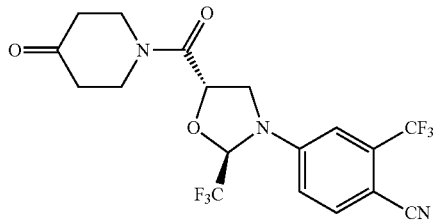 [SMILES: N#Cc1ccc(N2C[C@@H](C(=O)N3CCC(=O)CC3)O[C@@H]2C(F)(F)F)cc1C(F)(F)F]

To a 50-ml flask, 85.3 mg (0.024 mmol) of the compound (2R,5S)-3-(4-cyano-3-(trifluoromethyl)phenyl)-2-(trifluoromethyl)oxazolidine-5-carboxylic acid obtained in Preparation Example 16 was added, and 3 ml of N,N-dimethylacetamide was added. Then, 176 ul (2.41 mmol, 10.0 eq) of SOCl₂ was added thereto, followed by stirring for 1 hour (1). To another 50-ml flask, 31 mg (0.229 mmol, 0.95 eq) of 4-piperidone hydrochloride and 2 ml of N,N-dimethylacetamide were added, and then 38 ul (0.265 mmol, 1.1 eq) of triethylamine was added thereto, followed by stirring for 5 minutes. This solution was added dropwise to the flask (1) and stirred at room temperature for 1 hour. After completion of the reaction, the reaction product was diluted with ethyl acetate (10 ml) and washed with water (20 ml). After separation of layers, an organic layer was washed with a saturated NH₄Cl aqueous solution, and then washed with water. The organic layer was separated and washed with a NaCl aqueous solution, and dehydrated and dried over MgSO4, and concentrated under reduced pressure to obtain 40 mg (38%) of a title compound.
Mass[M+H]: 436.10

EXAMPLE 178

Preparation of methyl 4-((2R,5S)-3-(3-chloro-4-cyanophenyl)-2-(trifluoromethyl)oxazolidine-5-carbonyl)piperazine-1-carboxylate

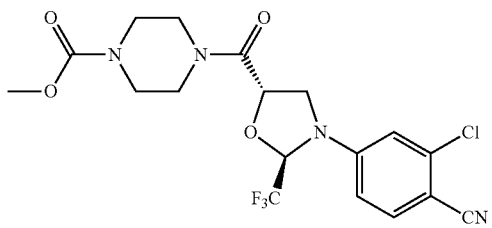 [SMILES: COC(=O)N1CCN(C(=O)[C@@H]2CN(c3ccc(C#N)c(Cl)c3)[C@@H](C(F)(F)F)O2)CC1]

98 mg (0.31 mmol) of the compound (2R,5S)-3-(3-chloro-4-cyanophenyl)-2-(trifluoromethyl)oxazolidine-5-carboxylic acid obtained in Preparation Example 20 and methyl piperazine-1-carboxylate hydrochloride were used to obtain 50 mg (43%) of a title compound in the same manner as in Example 104.
Mass[M+H]: 447.10

EXAMPLE 179

Preparation of methyl 4-((2R,5S)-3-(3-methyl-4-nitrophenyl)-2-(trifluoromethyl)oxazolidine-5-carbonyl)piperazine-1-carboxylate

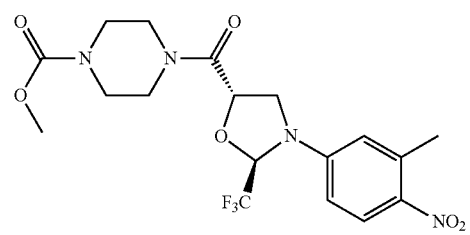 [SMILES: COC(=O)N1CCN(C(=O)[C@@H]2CN(c3ccc([N+](=O)[O-])c(C)c3)[C@@H](C(F)(F)F)O2)CC1]

100 mg (0.31 mmol) of the compound (2R,5S)-3-(3-methyl-4-nitrophenyl)-2-(trifluoromethyl)oxazolidine-5-carboxylic acid obtained in Preparation Example 24 and methyl piperazine-1-carboxylate hydrochloride were used to obtain 70 mg (50%) of a title compound in the same manner as in Example 104.
Mass[M+H]: 447.14

EXAMPLE 180

Preparation of methyl(2-((2R,5S)-3-(4-cyano-3-(trifluoromethyl)phenyl)-2-(trifluoromethyl)oxazolidine-5-carboxamido)ethyl)carbamate

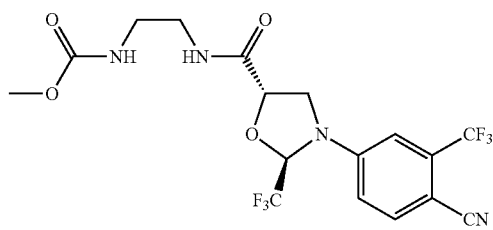 [SMILES: COC(=O)NCCNC(=O)[C@@H]1CN(c2ccc(C#N)c(C(F)(F)F)c2)[C@@H](C(F)(F)F)O1]

Step 1. Preparation of t-butyl(2-((2R,5S)-3-(4-cyano-3-(trifluoromethyl)phenyl)-2-(trifluoromethyl)oxazolidine-5-carboxamido)ethyl)carbamate

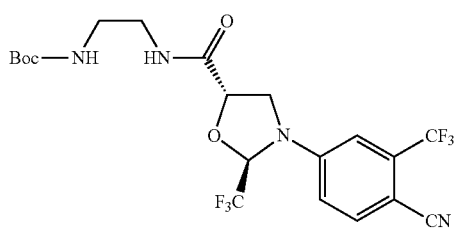 [SMILES: CC(C)(C)OC(=O)NCCNC(=O)[C@@H]1CN(c2ccc(C#N)c(C(F)(F)F)c2)[C@@H](C(F)(F)F)O1]

To a 100-ml flask, 1.46 g (4.12 mmol) of the compound (2R,5S)-3-(4-cyano-3-(trifluoromethyl)phenyl)-2-(trifluoromethyl)oxazolidine-5-carboxylic acid obtained in Preparation Example 16 was added and 21 ml of tetrahydrofuran was added, followed by stirring. To this reaction solution, 460 ul (4.938 mmol, 1.2 eq) of N,N-dimethylacetamide was added, and the solution was cooled to 0° C. 360 ul (4.938 mmol, 1.eq) of SOCl₂ was added, followed by stirring for 1 hour. To this reaction solution, 649 ul (4.115 mmol, 1.0 eq) of N-boc-ethylenediamine was added, followed by stirring at room temperature for 1 hour. After completion of the reaction, the solution was concentrated under reduced pressure and diluted with ethyl acetate (10 ml) and washed with water (20 ml). An organic layer was separated and then washed with a NaCl aqueous solution, dehydrated and dried over MgSO₄, and then concentrated under reduced pressure to obtain 1.94 g (95%) of a title compound.

Mass[M+H]: 467.15

Step 2. Preparation of (2R,5S)-N-(2-aminoethyl)-3-(4-cyano-3-(trifluoromethyl)phenyl)-2-(trifluoromethyl)oxazolidine-5-carboxamide hydrochloride

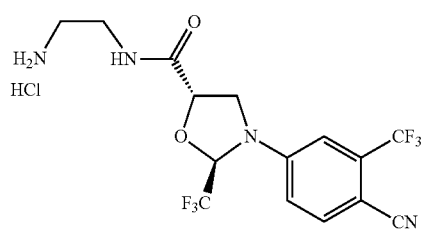 [SMILES: Cl ; N#Cc1ccc(N2C[C@@H](C(=O)NCCN)O[C@@H]2C(F)(F)F)cc1C(F)(F)F]

The compound t-butyl (2-((2R,5S)-3-(4-cyano-3-(trifluoromethyl)phenyl)-2-(trifluoromethyl)oxazolidine-5-carboxamido)ethyl)carbamate obtained in Step 1 of Example 180 was used to obtain 1.7 g (99%) of a title compound in the same manner as in Example 89.

Mass[M+H]: 397.50

Step 3. Preparation of methyl(2-((2R,5S)-3-(4-cyano-3-(trifluoromethyl)phenyl)-2-(trifluoromethyl)oxazolidine-5-carboxamido)ethyl)carbamate 300 mg (0.69 mmol) of the compound (2R,5S)-N-(2-aminoethyl)-3-(4-cyano-3-(trifluoromethyl)phenyl)-2-(trifluoromethyl)oxazolidine-5-carboxamide hydrochloride obtained in Step 2 of Example 180 and methylchloroformate were used to obtain 137 mg (44%) of a title compound in the same manner as in Step 1 of Example 17.

¹H NMR (CDCl₃, 600 MHz) δ 7.70(d, 1H), 7.16(s, 1H), 7.02(d, 1H), 6.90(dd, 1H), 5.79(d, 1H), 4.99(t, 1H), 4.93(s, 1H), 4.05(t, 1H), 3.89(t, 1H), 3.57(s, 3H), 3.44(br, 1H), 3.33~3.27(m, 3H)

Mass[M+H]: 456.11

EXAMPLE 181

Preparation of 4-((2R,5S)-5-(4-(methylsulfonyl)piperazine-1-carbonyl)-2-(trifluoromethyl)oxazolidin-3-yl)-2-(trifluoromethyl)benzonitrile

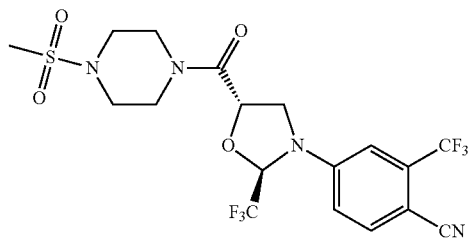 [SMILES: CS(=O)(=O)N1CCN(C(=O)[C@@H]2CN(c3ccc(C#N)c(C(F)(F)F)c3)[C@@H](C(F)(F)F)O2)CC1]

To a 50-ml flask, 300 mg (0.65 mmol) of the compound (2R,5S)-3-(4-cyano-3-(trifluoromethyl)phenyl)-2-(trifluoromethyl)oxazolidine-5-carboxylic acid obtained in Preparation Example 16 was added, and 10 ml of dichloromethane was added, followed by stirring. To this reaction solution, 275 ul (1.962 mmol, 3.0 eq) of triethylamine was added, and 50 ul (0.65 mmol, 1.0 eq) of methanesulfonyl chloride was added, followed by stirring at room temperature for 1 hour. After completion of the reaction, the resulting product was concentrated under reduced pressure, and diluted with ethyl acetate (10 ml) and washed with water (20 ml). An organic layer was separated and then washed with a NaCl aqueous solution, dehydrated and dried over MgSO₄, and concentrated under reduced pressure to obtain 261 mg (80%) of a title compound.

Mass[M+H]: 501.10

EXAMPLE 182

Preparation of 4-((2R,5S)-5-(4-isopropylpiperazine-1-carbonyl)-2-(trifluoromethyl)oxazolidin-3-yl)-2-(trifluoromethyl)benzonitrile

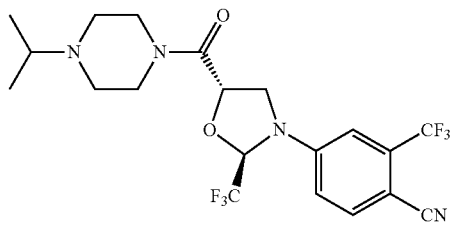 [SMILES: CC(C)N1CCN(C(=O)[C@@H]2CN(c3ccc(C#N)c(C(F)(F)F)c3)[C@@H](C(F)(F)F)O2)CC1]

To a 50-ml flask, 300 mg (0.65 mmol) of the compound (2R,5S)-3-(4-cyano-3-(trifluoromethyl)phenyl)-2-(trifluoromethyl)oxazolidine-5-carboxylic acid obtained in Preparation Example 16 was added and 10 ml of ethanol was added, followed by stirring. To this reaction solution, 208 mg (1.962 mmol, 3.0 eq) of Na₂CO₃ was added, and 62 ul (0.65 mmol, 1.0 eq) of 2-bromopropane was added dropwise, and refluxed at 100° C. for 16 hours. After completion of the reaction, the reaction product was concentrated under reduced pressure and diluted with ethyl acetate (10 ml) and washed with water (20 ml). An organic layer was separated and then washed with a NaCl aqueous solution, dehydrated and dried over MgSO₄, and then concentrated under reduced pressure to obtain 43 mg (10%) of a title compound.

Mass[M+H]: 465.16

EXAMPLE 183

Preparation of 4-((2R,5S)-5-(4-(2-cyanoethyl)piperazine-1-carbonyl)-2-(trifluoromethyl)oxazolidin-3-yl)-2-(trifluoromethyl)benzonitrile

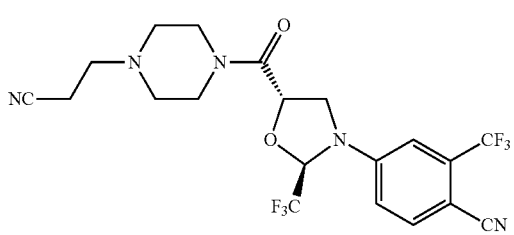 [SMILES: N#CCCN1CCN(C(=O)[C@@H]2CN(c3ccc(C#N)c(C(F)(F)F)c3)[C@@H](C(F)(F)F)O2)CC1]

To a 50-ml flask, 300 mg (0.65 mmol) of the compound (2R,5S)-3-(4-cyano-3-(trifluoromethyl)phenyl)-2-(trifluoromethyl)oxazolidine-5-carboxylic acid obtained in Preparation Example 16 was added and 10 ml of N,N-dimethylformamide was added, followed by stirring. To this reaction solution, 346 ul (1.962 mmol, 3.0 eq) of N,N-diisopropylethylamine was added, and 54 ul (0.65 mmol, 1.0 eq) of 3-bromopropionitrile was added dropwise, and refluxed at 100° C. for 16 hours. After completion of the reaction, the reaction product was concentrated under reduced pressure and diluted with ethyl acetate (10 ml) and washed with water (20 ml). After separation of layers, an organic layer was washed with a saturated NH$_4$Cl aqueous solution and then washed with water. The organic layer was separated and washed with a NaCl aqueous solution, dehydrated and dried over MgSO$_4$, and then concentrated under reduced pressure to obtain 100 mg (36%) of a title compound.

Mass[M+H]: 476.14

EXAMPLE 184

Preparation of 4-((2R,5S)-5-(4-(2-hydroxyethyl)piperazine-1-carbonyl)-2-(trifluoromethyl)oxazolidin-3-yl)-2-trifluoromethyl)benzonitrile

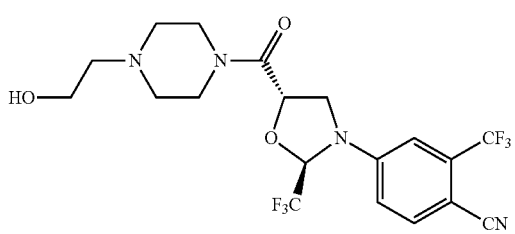

300 mg (0.65 mmol) of the compound (2R,5S)-3-(4-cyano-3-(trifluoromethyl)phenyl)-2-(trifluoromethyl)oxazolidine-5-carboxylic acid obtained in Preparation Example 16 and 2-bromoethanol were used to obtain 150 mg (34%) of a title compound in the same manner as in Example 181.

Mass[M+H]: 467.14
Mass[M+H]: 490.06

EXAMPLE 185

Preparation of 1-(((2R,5R)-3-(4-cyano-3-(trifluoromethyl)phenyl)-2-(trifluoromethyl)oxazolidin-5-yl)methyl)piperidine-4-carbonitrile

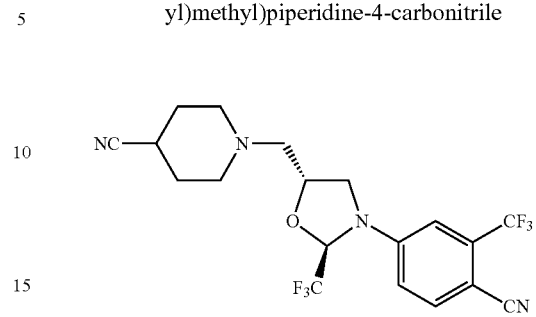

In a 25-ml flask, the compound ((2R,5S)-3-(4-cyano-3-(trifluoromethyl)phenyl)-2-(trifluoromethyl)oxazolidin-5-yl)methyl methanesulfonate obtained in Step 1 of Example 7 and 4-cyanopiperidine were used to obtain 133 mg (93%) of a title compound in the same manner as in Example 6.

Mass[M+H]: 433.14

EXAMPLE 186

Preparation of 1-((2R,5S)-3-(4-cyano-3-(trifluoromethyl)phenyl)-2-(trifluoromethyl)oxazolidine-5-carbonyl)piperidine-4-carboxamide

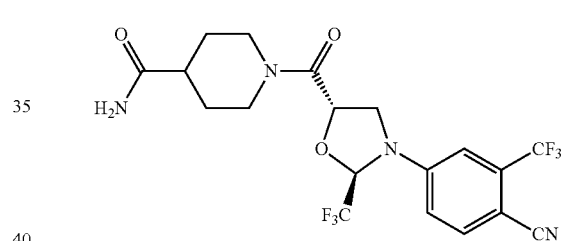

In a 25-ml flask, 100 mg (0.282 mmol) of the compound (2R,5S)-3-(4-cyano-3-(trifluoromethyl)phenyl)-2-(trifluoromethyl)oxazolidine-5-carboxylic acid obtained in Preparation Example 16 and 109 mg (0.847 mmol, 3.0 eq) of isonipecotamide were used to obtain 114 mg (84%) of a title compound in the same manner as in Example 32.

Mass[M+H]: 481.12

EXAMPLE 187

Preparation of ethyl 4-((2R,5S)-3-(4-cyano-3-(trifluoromethyl)phenyl)-2-(trifluoromethyl)oxazolidine-5-carbonyl)piperazine-1-carboxylate

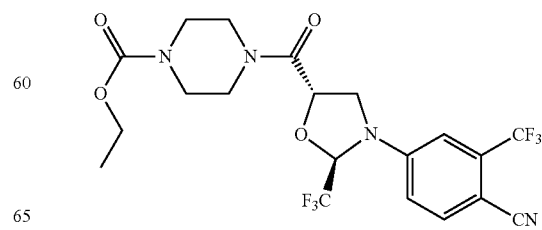

Step 1. Preparation of 1-(t-butyl) 4-ethyl piperazine-1,4-dicarboxylate

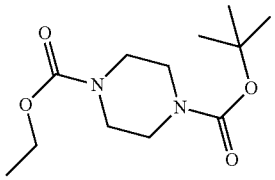 [SMILES: CCOC(=O)N1CCN(C(=O)OC(C)(C)C)CC1]

In a 50-ml flask, 300 mg (1.61 mmol) of t-butyl piperazine-1-carboxylate and 0.18 ml (1.93 mmol, 1.2 eq) of ethyl chloroformate were used to obtain 415 mg (99%) of a title compound in the same manner as in Example 102.
Mass[M+H]: 259.16 step 2. Preparation of ethyl piperazine-1-carboxylate hydrochloride

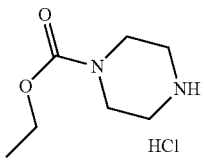

In a 50-ml flask, 415 mg (1.6 mmol) of 1-(t-butyl) 4-ethyl piperazine-1,4-dicarboxylate obtained in Step 1 of Example 187 was used to obtain 302 mg (97%) of a title compound in the same manner as in Step 2 of Example 50.
Mass[M+H]: 159.11

Step 3. Preparation of ethyl 4-((2R,5S)-3-(4-cyano-3-(trifluoromethyl)phenyl)-2-(trifluoromethyl)oxazolidine-5-carbonyl)piperazine-1-carboxylate In a 25-ml flask, 100 mg (0.282 mmol) of (2R,5S)-3-(4-cyano-3-(trifluoromethyl)phenyl)-2-(trifluoromethyl)oxazolidine-5-carboxylic acid obtained in Preparation Example 16 and 55 mg (0.282 mmol, 1.0 eq) of ethyl piperazine-1-carboxylate hydrochloride obtained in Step 2 of Example 187 were used to obtain 118 mg (85%) of a title compound in the same manner as in Example 104.
Mass[M+H]: 495.14

EXAMPLE 188

Preparation of 4-((2R,5S)-3-(4-cyano-3-(trifluoromethyl)phenyl)-2-(trifluoromethyl)oxazolidine-5-carbonyl)piperazine-1-carboxamide

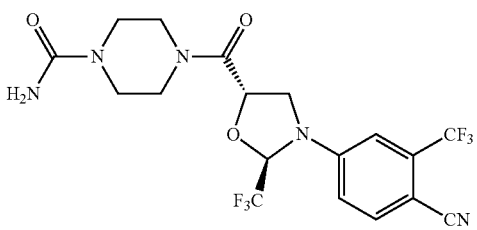 [SMILES: N#Cc1ccc(N2C[C@@H](C(=O)N3CCN(C(N)=O)CC3)O[C@@H]2C(F)(F)F)cc1C(F)(F)F]

Step 1. Preparation of t-butyl 4-carbamoylpiperazine-1-carboxylate

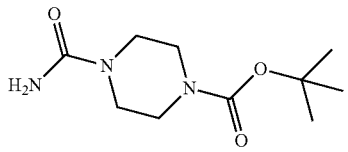 [SMILES: CC(C)(C)OC(=O)N1CCN(C(N)=O)CC1]

In a 100-ml flask, 500 mg (2.68 mmol) of t-butyl piperazine-1-carboxylate was dissolved in 5 ml of water, followed by stirring. 1.6 ml of acetic acid and 1.09 g (13.4 mmol, 5.0 eq) of potassium cyanate dissolved in water were added, followed by stirring at room temperature for 4 hours. After completion of the reaction, a solid was obtained by filtration while washing with water. The solid thus obtained was dissolved in dichloromethane, and then washed with water. An organic layer was separated and washed with a NaCl aqueous solution, dehydrated and dried over MgSO$_4$, and concentrated under reduced pressure to obtain 282 mg (46%) of a title compound.
Mass[M+H]: 230.14 step 2. Preparation of piperazine-1-carboxamide

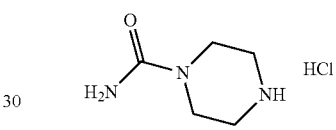

In a 50-ml flask, 280 mg (1.22 mmol) of t-butyl 4-carbamoylpiperazine-1-carboxylate obtained in Step 1 of Example 188 was used to obtain 183 mg (91%) of a title compound in the same manner as in Step 2 of Example 50.
Mass[M+H]: 166.07

Step 3. Preparation of 4-((2R,5S)-3-(4-cyano-3-(trifluoromethyl)phenyl)-2-(trifluoromethyl)oxazolidine-5-carbonyl)piperazine-1-carboxamide In a 25-ml flask, 100 mg (0.282 mmol) of (2R,5S)-3-(4-cyano-3-(trifluoromethyl)phenyl)-2-(trifluoromethyl)oxazolidine-5-carboxylic acid obtained in Preparation Example 16 and 47 mg (0.282 mmol, 1.0 eq) of piperazine-1-carboxamide obtained in Step 2 of Example 188 were used to obtain 87 mg (66%) of a title compound in the same manner as in Example 104.
Mass[M+H]: 466.12

EXAMPLE 189

Preparation of methyl 4-((2R,5S)-3-(3-chloro-4-nitrophenyl)-2-(trifluoromethyl)oxazolidine-5-carbonyl)piperazine-1-carboxylate

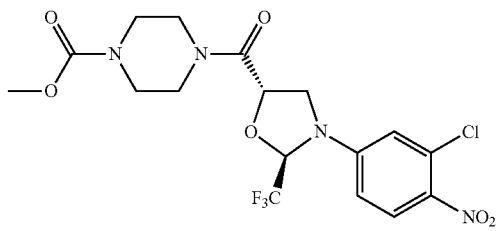 [SMILES: COC(=O)N1CCN(C(=O)[C@@H]2CN(c3ccc([N+](=O)[O-])c(Cl)c3)[C@@H](C(F)(F)F)O2)CC1]

In a 25-ml flask, 100 mg (0.294 mmol) of (2R,5S)-3-(3-chloro-4-nitrophenyl)-2-(trifluoromethyl)oxazolidine-5-carboxylic acid obtained in Preparation Example 28 and 53 mg (0.294 mmol) of methyl piperazine-1-carboxylate hydrochloride were used to obtain 119 mg (87%) of a title compound in the same manner as in Example 104.
Mass[M+H]: 467.09

EXAMPLE 190

Preparation of methyl 4-((2R,5S)-3-(4-nitro-3-(trifluoromethyl)phenyl)-2-(trifluoromethyl)oxazolidine-5-carbonyl)piperazine-1-carboxylate

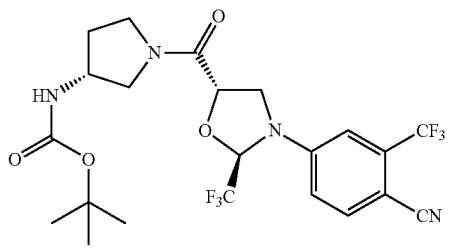 [SMILES: CC(C)(C)OC(=O)N[C@@H]1CCN(C(=O)[C@@H]2CN(c3ccc(C#N)c(C(F)(F)F)c3)[C@@H](C(F)(F)F)O2)C1]

In a 25-ml flask, 100 mg (0.267 mmol) of ((2R,5S)-3-(4-nitro-3-(trifluoromethyl)phenyl)-2-(trifluoromethyl)oxazolidine-5-carboxylic acid obtained in Preparation Example 32 and 48 mg (0.267 mmol) of methyl piperazine-1-carboxylate hydrochloride were used to obtain 109 mg (82%) of a title compound in the same manner as in Example 104.
Mass[M+H]: 501.11

EXAMPLE 191

Preparation of methyl 4-((2R,5S)-3-(4-cyano-3-(trifluoromethyl)phenyl)-2-(trifluoromethyl)oxazolidine-5-carbonyl)-1,4-diazepane-1-carboxylate

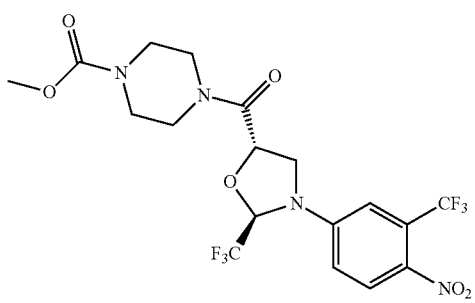 [SMILES: COC(=O)N1CCN(C(=O)[C@@H]2CN(c3ccc([N+](=O)[O-])c(C(F)(F)F)c3)[C@@H](C(F)(F)F)O2)CC1]

Step 1. Preparation of t-butyl 4-((2R,5S)-3-(4-cyano-3-(trifluoromethyl)phenyl)-2-(trifluoromethyl)oxazolidine-5-carbonyl)-1,4-diazepane-1-carboxylate

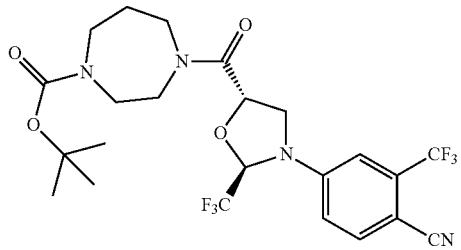 [SMILES: CC(C)(C)OC(=O)N1CCCN(C(=O)[C@@H]2CN(c3ccc(C#N)c(C(F)(F)F)c3)[C@@H](C(F)(F)F)O2)CC1]

In a 25-ml flask, 500 mg (1.41 mmol) of (2R,5S)-3-(4-cyano-3-(trifluoromethyl)phenyl)-2-(trifluoromethyl)oxazolidine-5-carboxylic acid obtained in Preparation Example 16 and 0.28 ml (1.41 mmol, 1.0 eq) of 1-Boc-hexahydro-1,4-diazepine were used to obtain 755 mg (99%) of a title compound in the same manner as in Example 104.
Mass[M+H]: 537.19

Step 2. Preparation of 4-((2R,5S)-5-(1,4-diazepane-1-carbonyl)-2-(trifluoromethyl)oxazolidin-3-yl)-2-(trifluoromethyl)benzonitrile hydrochloride

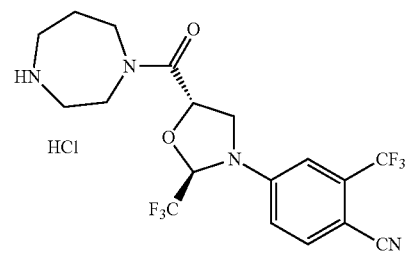 [SMILES: N#Cc1ccc(N2C[C@@H](C(=O)N3CCCNCC3)O[C@@H]2C(F)(F)F)cc1C(F)(F)F ; Cl]

In a 50-ml flask, 755 mg (1.41 mmol) of t-butyl 4-((2R,5S)-3-(4-cyano-3-(trifluoromethyl)phenyl)-2-(trifluoromethyl)oxazolidine-5-carbonyl)-1,4-diazepane-1-carboxylate obtained in Step 1 of Preparation Example 191 was used to obtain 652 mg (98%) of a title compound in the same manner as in Step 2 of Example 50.
Mass[M+H]: 437.13

Step 3. Preparation of methyl 4-((2R,5S)-3-(4-cyano-3-(trifluoromethyl)phenyl)-2-(trifluoromethyl)oxazolidine-5-carbonyl)-1,4-diazepane-1-carboxylate In a 25-ml flask, 100 mg (0.211 mmol) of 4-((2R,5S)-5-(1,4-diazepane-1-carbonyl)-2-(trifluoromethyl)oxazolidin-3-yl)-2-(trifluoromethyl)benzonitrile hydrochloride obtained in Step 2 of Example 191 and 33 ul (0.423 mmol, 2.0 eq) of methyl chloroformate were used to obtain 98 mg (94%) of a title compound in the same manner as in Example 102.
$^1$H NMR (CDCl$_3$, 400 MHz) δ 7.70~7.66(m, 1H), 7.03(s, 1H), 6.91(dd, 1H), 5.68~5.62(m, 1H), 5.26~5.19(m, 1H), 4.30~4.21(m, 1H), 3.94~3.10(m, 11), 1.99~1.78(m, 2H)
Mass[M+H]: 495.14

EXAMPLE 192

Preparation of methyl((R)-1-((2R,5S)-3-(4-cyano-3-(trifluoromethyl)phenyl)-2-(trifluoromethyl)oxazolidine-5-carbonyl)pyrrolidin-3-yl)carbamate

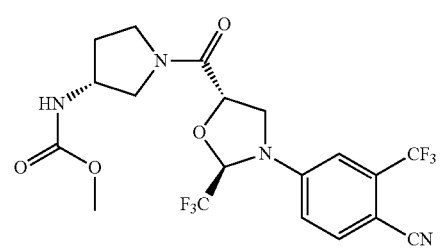 [SMILES: COC(=O)N[C@@H]1CCN(C(=O)[C@@H]2CN(c3ccc(C#N)c(C(F)(F)F)c3)[C@@H](C(F)(F)F)O2)C1]

Step 1. Preparation of t-butyl((R)-1-((2R,5S)-3-(4-cyano-3-(trifluoromethyl)phenyl)-2-(trifluoromethyl)oxazolidine-5-carbonyl)pyrrolidin-3-yl)carbamate

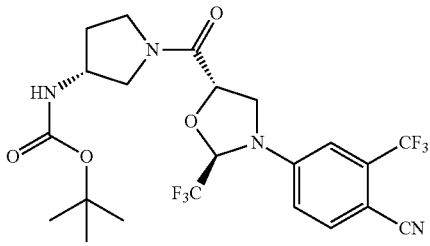 [SMILES: CC(C)(C)OC(=O)N[C@@H]1CCN(C(=O)[C@@H]2CN(c3ccc(C#N)c(C(F)(F)F)c3)[C@@H](C(F)(F)F)O2)C1]

In a 25-ml flask, 500 mg (1.41 mmol) of (2R,5S)-3-(4-cyano-3-(trifluoromethyl)phenyl)-2-(trifluoromethyl)oxazolidine-5-carboxylic acid obtained in Preparation Example 16 and 263 mg (1.41 mmol, 1.0 eq) of (R)-3-(Boc-amino)pyrrolidine were used to obtain 530 mg (72%) of a title compound in the same manner as in Example 104.
Mass[M+H]: 523.17

Step 2. Preparation of 4-((2R,5S)-5-((R)-3-aminopyrrolidine-1-carbonyl)-2-(trifluoromethyl)oxazolidin-3-yl)-2-(trifluoromethyl)benzonitrile hydrochloride

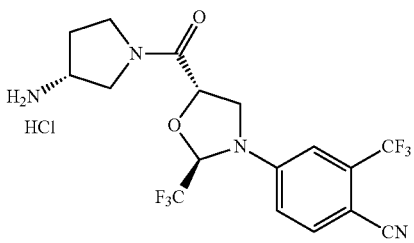 [SMILES: Cl ; N#Cc1ccc(N2C[C@@H](C(=O)N3CC[C@@H](N)C3)O[C@@H]2C(F)(F)F)cc1C(F)(F)F]

In a 50-ml flask, 530 mg (1.02 mmol) of t-butyl ((R)-1-((2R,5S)-3-(4-cyano-3-(trifluoromethyl)phenyl)-2-(trifluoromethyl)oxazolidine-5-carbonyl)pyrrolidin-3-yl)carbamate obtained in Step 1 of Example 192 was used to obtain 378 mg (81%) of a title compound in the same manner as in Step 2 of Example 50.
Mass[M+H]: 423.12

Step 3. Preparation of methyl((R)-1-((2R,5S)-3-(4-cyano-3-(trifluoromethyl)phenyl)-2-(trifluoromethyl)oxazolidine-5-carbonyl)pyrrolidin-3-yl)carbamate In a 25-ml flask, 100 mg (0.218 mmol) of 4-((2R,5S)-5-((R)-3-aminopyrrolidine-1-carbonyl)-2-(trifluoromethyl)oxazolidin-3-yl)-2-(trifluoromethyl)benzonitrile hydrochloride obtained in Step 2 of Example 192 and 34 ul (0.436 mmol, 2.0 eq) of methyl chloroformate were used to obtain 90 mg (86%) of a title compound in the same manner as in Example 102.
$^1$H NMR (CDCl$_3$, 400 MHz) δ 7.68(d, 1H), 6.93(s, 1H), 6.90(dd, 1H), 5.65(q, 1H), 5.16~5.08(m, 1H), 4.82~4.74(m, 1H), 4.32~4.21(m, 2H), 3.88~3.80(m, 2H), 3.71~3.36(m, 6H), 2.32~2.15(m, 1H), 1.86~1.81(m, 1H)
Mass[M+H]: 481.12

EXPERIMENTAL EXAMPLE 1

Test of Binding Ability to Androgen Receptor

In order to examine binding ability of the agonists of the present invention to androgen receptors, the following in-vitro experiment was performed. African green monkey kidney fibroblast-like cell line, COS-7 (ATCC, #CRL-1651) was seeded in a 48-well plate at a density of 2.5×10$^4$ cells/well, and cultured for 24 hours. Then, a plasmid hAR-mixed medium was added thereto. The transfected cell line was treated with 1 nM of [3H]MIB and 0.1~10,000 nM of SARM derivatives, and then allowed to react for 2 hours. Thereafter, the cells were lysed and the amount of [3H]MIB bound to the intracellular androgen receptors was measured using a radiation dosimeter. The results were shown in Table 4 as 50% inhibition concentration (IC$_{50}$) relative to that of an untreated control group.

TABLE 4

| Compounds | IC$_{50}$ [nM] (mean ± SE) |
|---|---|
| Example 1 | 64.4 |
| Example 2 | 23.9 |
| Example 3 | 1091.9 |
| Example 4 | 657.3 |
| Example 5 | 91.6 |
| Example 6 | 11.0 |
| Example 7 | 15.7 |
| Example 8 | 13.7 |
| Example 9 | 366.9 |
| Example 10 | 6.3 |
| Example 11 | 10.5 |
| Example 12 | 145.0 |
| Example 13 | 14.5 |
| Example 19 | 7.6 |
| Example 20 | 1079.2 |
| Example 21 | 1057.9 |
| Example 22 | 1869.8 |
| Example 23 | 44.3 |
| Example 24 | 141.4 |
| Example 25 | 8.5 |
| Example 56 | 75.1 |
| Example 26 | 43.6 |
| Example 27 | 22.4 |
| Example 28 | 77.2 |
| Example 29 | 14.1 |
| Example 30 | 142.2 |
| Example 31 | 14.1 |
| Example 32 | 32.7 |
| Example 33 | 10.4 |
| Example 34 | 24.1 |
| Example 35 | 184.7 |

The experimental results confirmed that novel agonists bound to androgen receptors, indicating that the agonists of the present invention bind to androgen receptors to affect the actions of androgen receptors.

EXPERIMENTAL EXAMPLE 2

Test of Transcriptional Activity

In order to examine the transcriptional activity of the agonists of the present invention, the following in-vitro experiment was performed. CHO (Chinese hamster ovary) cell line (ATCC, #CCL-61) was seeded in a 96-well plate at a density of 1.5×10$^4$ cells/well, and cultured for 24 hours. Then, a plasmid hAR and plasmid ARE-Luc-mixed medium was added thereto. The transfected cell line was treated with 0.1~10,000 nM of SARM derivatives, and then allowed to react for 24 hours. Thereafter, a dual-luciferase assay was performed and luminescence in the medium was measured using a SpectraMAX L. The results are shown in Table 5 as a concentration of 50% transcription activity ($EC_{50}$) when the activity of an untreated control group is regarded as 0% and that activity of a 10 nM DHT-treated positive control group is regarded as 100%.

TABLE 5

| Compounds | $EC_{50}$ [nM] (mean ± SE) |
|---|---|
| Example 2 | 132.8 |
| Example 6 | 4.1 |
| Example 7 | 13.1 |
| Example 8 | 20.0 |
| Example 10 | 11.1 |
| Example 11 | 4.5 |
| Example 13 | 9.9 |
| Example 14 | 111.0 |
| Example 15 | 15.7 |
| Example 16 | 21.3 |
| Example 17 | 24.0 |
| Example 18 | 18.6 |
| Example 19 | 1.0 |
| Example 25 | 0.7 |
| Example 26 | 8.6 |
| Example 29 | 7.5 |
| Example 31 | 17.7 |
| Example 33 | 10.7 |
| Example 34 | 110.6 |
| Example 36 | 8.1 ± 1.9 |
| Example 37 | 31.6 |
| Example 38 | 165.1 |
| Example 39 | 42.6 |
| Example 40 | 437.7 |
| Example 41 | 16.2 |
| Example 42 | 514.5 |
| Example 43 | 21.3 |
| Example 44 | 2.6 ± 0.4 |
| Example 45 | 44.1 |
| Example 46 | 31.5 |
| Example 48 | 1518.7 |
| Example 49 | 1702.9 |
| Example 50 | 15.6 |
| Example 51 | 165.3 |
| Example 52 | 758.7 |
| Example 53 | 2.5 ± 0.7 |
| Example 54 | 0.86 |
| Example 55 | 4.49 |
| Example 56 | 75.1 |
| Example 57 | 2.41 |
| Example 58 | 107 |
| Example 59 | 3.25 |
| Example 60 | 10.45 |
| Example 63 | 36.28 |
| Example 64 | 34.03 |
| Example 65 | 59.5 |
| Example 66 | 19.87 |
| Example 67 | 3.93 |
| Example 68 | 6.06 |
| Example 69 | 1.54 |
| Example 70 | 0.62 |
| Example 71 | 1.57 |
| Example 72 | 1.03 |
| Example 73 | 0.991 |
| Example 74 | 0.658 |
| Example 75 | 37.01 |
| Example 76 | 21.8 |
| Example 77 | 10.6 |
| Example 78 | 4.91 |
| Example 80 | 34.03 |
| Example 81 | 59.5 |
| Example 82 | 21.15 |
| Example 83 | 29.58 |
| Example 84 | 1144 |
| Example 85 | 9.84 |
| Example 86 | 48.82 |
| Example 87 | 9.22 |
| Example 88 | 925.54 |
| Example 89 | 34.25 |
| Example 94 | 4.12 |
| Example 95 | 2.81 |
| Example 98 | 2.91 |
| Example 99 | 97.26 |
| Example 104 | 24.92 |
| Example 105 | 49.94 |
| Example 106 | 153.96 |
| Example 107 | 7.18 |
| Example 108 | 17.0 |
| Example 109 | 5.09 |
| Example 110 | 80.04 |
| Example 111 | 4.46 |
| Example 112 | 10.09 |
| Example 113 | 80.5 |
| Example 114 | 201.1 |
| Example 116 | 4.32 |
| Example 117 | 2.0 |
| Example 118 | 30.4 |
| Example 119 | 226.81 |
| Example 120 | 11.13 |
| Example 121 | 615.95 |
| Example 122 | 67.37 |
| Example 123 | 7.34 |
| Example 124 | 3.15 |
| Example 125 | 11.24 |
| Example 126 | 1.21 |
| Example 127 | 183.36 |
| Example 128 | 11.11 |
| Example 129 | 4.68 |
| Example 130 | 10.17 |
| Example 131 | 2.35 |
| Example 132 | 3.44 |
| Example 133 | 43.95 |
| Example 134 | 4.96 |
| Example 135 | 4.95 |
| Example 136 | 5.07 |
| Example 137 | 1.77 |
| Example 138 | 17.28 |
| Example 139 | 2.74 |
| Example 140 | 14.7 |
| Example 141 | 44.22 |
| Example 142 | 0.79 |
| Example 143 | 199..5 |
| Example 144 | 11.06 |
| Example 145 | 304.76 |
| Example 147 | 768.29 |
| Example 148 | 13.46 |
| Example 151 | 43.66 |
| Example 152 | 521.4 |
| Example 154 | 27.79 |
| Example 155 | 823.02 |
| Example 156 | 323.48 |
| Example 157 | 231.35 |
| Example 158 | 12.52 |
| Example 159 | 288 |
| Example 160 | 105.04 |
| Example 161 | 240.15 |
| Example 162 | 148.65 |
| Example 163 | 214.39 |
| Example 167 | 43.98 |
| Example 170 | 3562 |
| Example 172 | 699 |
| Example 173 | 5.34 |
| Example 174 | 139.37 |
| Example 175 | 85.2 |
| Example 176 | 197.95 |
| Example 178 | 21.23 |
| Example 179 | 42.05 |

The experimental results confirmed that the agonists acted on androgen receptors to increase activity of androgen.

EXPERIMENTAL EXAMPLE 3

Efficacy Test in Castrated Male Rat

SD (Sprague-Dawley) male rats (7-week-old) were castrated under ketamine/xylazine anesthesia, and 5 rats were randomly assigned to one group. From the next day, the agonists were dissolved in a vehicle solution and orally administered at a dose of 5 ml per kg once a day for 14 days. As the vehicle, DMSO, Co-solvent, and DW were prepared at a ratio of 4:80:16 (v/v/v), and Co-solvent was prepared by mixing PEG400, Ethanol, and Tween 80 at a ratio of 85:10:5 (v/v/v). 24 hours after last administration of the drug, their body weight was measured and killed. Thereafter, levator ani muscle, ventral prostate, and seminal vesicles were removed and weighed (Hershberger assay). As a result, their weight % relative to the organ weight of the intact control group is given in the following Table 6. The following Table 6 represents the result of the efficacy test in castrated male rats.

TABLE 6

| Compounds | dosage (mg/kg) | levator ani muscle | ventral prostate | seminal vesicles |
|---|---|---|---|---|
| Intact control group | | 100.0 ± 9.8 | 100.0 ± 11.8 | 100.0 ± 13.3 |
| Example 19 | 0.3 | 7.2 ± 4.3 | 1.7 ± 0.6 | 4.8 ± 1.3 |
| | 1 | 45.9 ± 5.8 | 10.2 ± 3.9 | 78.2 ± .1 |
| | 3 | 70.6 ± 6.6 | 11.4 ± 3.0 | 17.3 ± 5.6 |
| | 10 | 63.9 ± 4.8 | 14.4 ± 2.7 | 22.9 ± 4.3 |
| | 30 | 78.4 ± 11.0 | 18.3 ± 4.5 | 33.4 ± 2.0 |
| | 100 | 68.3 ± 7.3 | 18.0 ± 5.2 | 36.4 ± 9.2 |
| Example 25 | 0.01 | 6.7 ± 1.6 | 1.8 ± 0.3 | 0.9 ± 0.2 |
| | 0.03 | 8.4 ± 1.5 | 1.0 ± 0.4 | 0.7 ± 0.2 |
| | 0.1 | 26.5 ± 5.8 | 3.2 ± 0.9 | 0.9 ± 0.2 |
| | 0.3 | 38.5 ± 4.8 | 4.8 ± 1.6 | 3.4 ± 0.4 |
| | 1 | 61.1 ± 6.3 | 10.9 ± 3.4 | 4.7 ± 1.2 |
| | 3 | 79.8 ± 6.7 | 12.7 ± 2.5 | 8.7 ± 1.6 |
| Example 36 | 0.1 | 18.6 ± 2.2 | 1.0 ± 0.1 | 2.4 ± 0.6 |
| | 0.3 | 18.8 ± 2.7 | 0.6 ± 0.1 | -0.2 ± 0.0 |
| | 1 | 53.9 ± 6.5 | 8.0 ± 1.6 | 4.7 ± 1.0 |
| | 3 | 47.0 ± 2.6 | 4.7 ± 1.9 | 3.0 ± 0.7 |
| | 10 | 55.2 ± 10.3 | 5.8 ± 0.8 | 4.7 ± 0.7 |
| | 30 | 58.2 ± 5.8 | 10.8 ± 3.1 | 10.4 ± 3.1 |
| | 100 | 65.3 ± 7.9 | 12.6 ± 3.1 | 16.1 ± 4.0 |
| Example 44 | 0.1 | 43.3 ± 8.1 | 7.0 ± 3.2 | 6.7 ± 1.5 |
| | 0.3 | 66.6 ± 8.7 | 13.6 ± 5.0 | 16.9 ± 6.7 |
| | 1 | 82.4 ± 10.2 | 26.1 ± 5.2 | 37.9 ± 4.3 |
| | 3 | 92.1 ± 6.5 | 38.7 ± 8.3 | 54.5 ± 11.9 |
| | 10 | 87.0 ± 7.5 | 28.2 ± 5.5 | 46.1 ± 10.8 |
| | 30 | 74.2 ± 2.8 | 34.7 ± 4.1 | 49.6 ± 6.0 |
| | 100 | 90.5 ± 6.5 | 39.9 ± 4.7 | 72.4 ± 14.6 |
| Example 123 | 0.03 | 3.5 ± 0.5 | 0.5 ± 0.1 | 0.3 ± 0.0 |
| | 0.1 | 7.00 ± 0.7 | 0.1 ± 0..1 | 0.2 ± 0.0 |
| | 0.3 | 14.7 ± 1.5 | 1.6 ± 0.2 | 0.1 ± 0.0 |
| | 1 | 23.0 ± 1.1 | 0.7 ± 0.2 | 0.5 ± 0.1 |
| | 3 | 40.2 ± 4.2 | 5.6 ± 1.9 | 2.8 ± 1.2 |
| | 10 | 58.7 ± 4.1 | 7.9 ± 2.2 | 11.0 ± 2.3 |
| | 30 | 78.9 ± 4.0 | 23.0 ± 2.9 | 30.5 ± 5.7 |
| | 100 | 88.5 ± 4.7 | 39.0 ± 9.8 | 58.7 ± 10.8 |
| Example 136 | 0.03 | 3.7 ± 0.8 | 1.7 ± 0.5 | -0.1 ± 0.0 |
| | 0.1 | 4.5 ± 0.9 | -0.6 ± 0.3 | -0.4 ± 0.1 |
| | 0.3 | 10.0 ± 0.8 | 1.2 ± 0.3 | 0.8 ± 0.1 |
| | 1 | 29.1 ± 3.3 | 2.6 ± 0.4 | 0.9 ± 0.2 |
| | 3 | 36.6 ± 3.4 | 4.1 ± 0.9 | 2.4 ± 0.7 |
| | 10 | 61.8 ± 3.1 | 10.5 ± 3.7 | 11.0 ± 3.6 |
| | 30 | 81.4 ± 10.9 | 25.4 ± 7.8 | 35.8 ± 14.4 |
| | 100 | 98.5 ± 7.7 | 42.1 ± 7.5 | 57.8 ± 17.9 |
| Example 173 | 0.03 | 9.8 ± 0.6 | 0.6 ± 0.1 | 1.3 ± 0.4 |
| | 0.1 | 15.0 ± 1.2 | 3.2 ± 0.6 | 1.3 ± 0.3 |
| | 0.3 | 37.5 ± 2.3 | 3.5 ± 0.5 | 2.9 ± 0.3 |

TABLE 6-continued

| Compounds | dosage (mg/kg) | levator ani muscle | ventral prostate | seminal vesicles |
|---|---|---|---|---|
| | 1 | 61.1 ± 9.9 | 9.1 ± 2.1 | 5.9 ± 2.1 |
| | 3 | 69.9 ± 3.6 | 12.4 ± 3.5 | 20.3 ± 4.8 |
| | 10 | 93.0 ± 11.0 | 24.4 ± 2.0 | 34.5 ± 4.0 |
| | 30 | 91.4 ± 8.2 | 33.2 ± 3.3 | 45.5 ± 8.6 |
| | 100 | 99.5 ± 13.0 | 48.6 ± 9.3 | 52.8 ± 10.6 |

The experimental results showed that as shown in Table 6, the castrated rats showed reduction in the weights of levator ani muscle, ventral prostate, and seminal vesicles, compared to the intact rat. However, the rats orally administered with SARM agonists for 14 days showed a significant increase in the weight of levator ani muscle, compared to the castrated group. Further, the weight of levator ani muscle was remarkably increased, compared to the weight of ventral prostate or seminal vesicles, indicating that the SARM derivative compounds of the present invention act on androgen receptors to increase androgen activity and also have excellent tissue-selective pharmacologic al effects.

The invention claimed is:

1. A compound represented by the following Chemical Formula 1, an isomer thereof, or a pharmaceutically acceptable salt thereof:

[Chemical Formula 1]

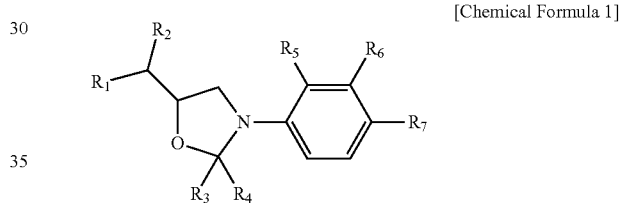

in Chemical Formula 1, $R_1$ is a substituent represented by the following Chemical Formula 2 or Chemical Formula 3, $R_2$ is hydrogen, oxo, or $C_1$-$C_6$ alkyl, $R_3$ and $R_4$ each independently is a substituent selected from the group consisting of hydrogen and $C_1$-$C_6$ alkyl, $R_5$ and $R_6$ each independently is a substituent selected from the group consisting of hydrogen, halogen, and $C_1$-$C_6$ alkyl, $R_7$ is halogen, cyano or nitro, the $C_1$-$C_6$ alkyl is substituted with one or more substituents selected from the group consisting of hydrogen, hydroxy, and halogen;

—X(CH$_2$)nR$_8$     [Chemical Formula 2]

in Chemical Formula 2, X is O, N(R), S or S(O)$_2$,

R is hydrogen, $R_8$ is hydrogen, $C_3$-$C_7$ heterocycle having a nitrogen atom, aryl, or heteroaryl having a nitrogen atom which has one or two rings, the heterocycle, aryl or heteroaryl each independently is substituted with one or more substituents selected from the group consisting of hydrogen, hydroxy, halogen, $C_1$-$C_6$ alkyl, $C_1$-$C_6$ alkoxy, a cyano group, a nitro group, a hydroxyimino group, a $C_1$-$C_6$ alkoxyimino group, $(CH_2)_p NR_{10}R_{11}$, $(CH_2)_p NC(O)R_{10}$, $(CH_2)_p NC(O)OR_{10}$, $(CH_2)_p NC(O)NR_{10}R_{11}$, $(CH_2)_p C(O)NR_{10}R_{11}$, $(CH_2)_p NS(O)_2 R_{10}$, $(CH_2)_p S(O)_2 R_{10} (CH_2)_p C(O)OR_{10}$,

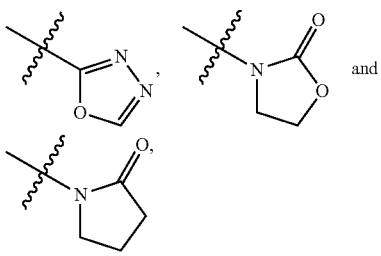 and p is an integer of 0 or 1,
R$_{10}$ and R$_{11}$ each independently is a substituent selected from the group consisting of hydrogen, C$_1$-C$_6$ alkyl, pyrrolidinyl, and phenyl,
the C$_1$-C$_6$ alkyl is substituted with one or more substituents selected from the group consisting of hydrogen, hydroxy, amino, cyano and halogen,
n is 0 or 1;

[Chemical Formula 3]

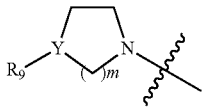

in Chemical Formula 3, Y is C or N,
m is an integer of 0, 1 or 2,
R$_9$ is a substituent selected from the group consisting of hydrogen, oxo, hydroxy, C$_1$-C$_6$ alkyl, cyano, C(O)R$_{12}$, C(O)OR$_{12}$, C(O)NR$_{12}$R$_{13}$, S(O)$_2$R$_{12}$, NC(O)R$_{13}$, NR$_{12}$R$_{13}$, and NC(O)OR$_{12}$,
R$_{12}$ and R$_{13}$ each independently is a substituent selected from the group consisting of hydrogen, hydroxy and C$_1$-C$_6$ alkyl, and
the C$_1$-C$_6$ alkyl is substituted with one or more substituents selected from the group consisting of hydrogen, hydroxy, halogen and cyano.

2. The compound, an isomer thereof, or a pharmaceutically acceptable salt thereof according to claim 1, wherein C$_3$-C$_7$ heterocycle is piperidine, aryl is phenyl and heteroary is pyridine in R$_8$ of Chemical Formula 2.

3. The compound, an isomer thereof, or a pharmaceutically acceptable salt thereof according to claim 1, wherein R$_3$ and R$_4$ of Chemical Formula 1 each independently is a substituent selected from the group consisting of hydrogen and C$_1$-C$_6$ alkyl,
the C$_1$-C$_6$ alkyl is substituted with one or more substituents selected from the group consisting of hydrogen, and halogen, and
R$_7$ is halogen, cyano, or nitro.

4. The compound, an isomer thereof, or a pharmaceutically acceptable salt thereof according to claim 1, wherein the isomer is in the form of a racemic mixture, an enantiomer, a diastereomer, a mixture of enantiomers, or a mixture of diastereomers.

5. The compound, an isomer thereof, or a pharmaceutically acceptable salt thereof according to claim 1, wherein the R$_1$ of Chemical Formula 1 is a substituent represented by the Chemical Formula 2, and is a compound selected from the group consisting of the following compounds, an isomer thereof, or a pharmaceutically acceptable salt thereof:
4-(5-(hydroxymethyl)-2-(trifluoromethyl)oxazolidin-3-yl)-2-(trifluoromethyl)benzonitrile,
4-(5-(((4-cyanobenzyl)oxy)methyl)-2-(trifluoromethyl)oxazolidin-3-yl)-2-(trifluoromethyl)benzonitrile,
4-(5-((4-cyanophenoxy)methyl)-2-(trifluoromethyl)oxazolidin-3-yl)-2-(trifluoromethyl)benzonitrile,
methyl 4-((3-(4-cyano-3-(trifluoromethyl)phenyl)-2-(trifluoromethyl)oxazolidin-5-yl)methoxy)benzoate,
4-(5-((4-nitrophenoxy)methyl)-2-(trifluoromethyl)oxazolidin-3-yl)-2-(trifluoromethyl)benzonitrile,
4-(3-(4-cyano-3-(trifluoromethyl)phenyl)-2-(trifluoromethyl)oxazolidin-5-yl)methoxy)benzoic acid,
4-(5-((3,4-difluorophenoxy)methyl)-2-(trifluoromethyl)oxazolidin-3-yl)-2-(trifluoromethyl)benzonitrile,
4-(5-((4-cyano-2-fluorophenoxy)methyl)-2-(trifluoromethyl)oxazolidin-3-yl)-2-(trifluoromethyl)benzonitrile,
4-(5-((2-chloro-4-nitrophenoxy)methyl)-2-(trifluoromethyl)oxazolidin-3- yl)-2-(trifluoromethyl)benzonitrile,
2-(trifluoromethyl)-4-(2-(trifluoromethyl)-5-((2,4,5-trifluorophenoxy)methyl)oxazolidin-3-yl)benzonitrile,
4-(5-((4-aminophenoxy)methyl)-2-(trifluoromethyl)oxazolidin-3-yl)-2-(trifluoromethyl)benzonitrile,
1-(4-((3-(4-cyano-3-(trifluoromethyl)phenyl)-2-(trifluoromethyl)oxazolidin-5-yl)methoxy)phenyl)urea,
1-(4-((3-(4-cyano-3-(trifluoromethyl)phenyl)-2-(trifluoromethyl)oxazolidin-5-yl)methoxy)phenyl)-3-methylurea,
4-(5-((4-(2-oxopyrrolidin-1-yl)phenoxy)methyl)-2-(trifluoromethyl)oxazolidin-3-yl)-2-(trifluoromethyl)benzonitrile,
4-(5-((4-(1,3,4-oxadiazol-2-yl)phenoxy)methyl)-2-(trifluoromethyl)oxazolidin-3-yl)-2-(trifluoromethyl)benzonitrile,
4-(5-((4-cyanophenoxy)methyl)-2-(trifluoromethyl)oxazolidin-3-yl)-2-(trifluoromethyl)benzonitrile,
4-(5-((4-cyanophenoxy)methyl)-2-(trifluoromethyl)oxazolidin-3-yl)-2-(trifluoromethyl)benzonitrile,
4-(5-(2,2,2-trifluoro-1-hydroxyethyl)-2-(trifluoromethyl)oxazolidin-3-yl)-2-(trifluoromethyl)benzonitrile,
4-(5-(2,2,2-trifluoro-1-hydroxyethyl)-2-(trifluoromethyl)oxazolidin-3-yl)-2-(trifluoromethyl)benzonitrile,
4-(5-(2,2,2-trifluoro-1-hydroxyethyl)-2-(trifluoromethyl)oxazolidin-3-yl)-2-(trifluoromethyl)benzonitrile,
4-(5-(2,2,2-trifluoro-1-hydroxyethyl)-2-(trifluoromethyl)oxazolidin-3-yl)-2-(trifluoromethyl)benzonitrile,
N-(4-((3-(4-cyano-3-(trifluoromethyl)phenyl)-2-(trifluoromethyl)oxazolidin-5-yl)methoxy)phenyl)acetamide,
4-(5-(((4-chlorophenyl)thio)methyl)-2-(trifluoromethyl)oxazolidin-3-yl)-2-(trifluoromethyl)benzonitrile,
4-(5-((4-methoxyphenoxy)methyl)-2-(trifluoromethyl)oxazolidin-3-yl)-2-(trifluoromethyl)benzonitrile,
4-(5-((3-methoxyphenoxy)methyl)-2-(trifluoromethyl)oxazolidin-3-yl)-2-(trifluoromethyl)benzonitrile,
4-(5-(((4-cyanophenyl)thio)methyl)-2-(trifluoromethyl)oxazolidin-3-yl)-2-(trifluoromethyl)benzonitrile,
N-(4-((3-(4-cyano-3-(trifluoromethyl)phenyl)-2-(trifluoromethyl)oxazolidin-5-yl)methoxy)phenyl)acetamide,
4-(5-((3-fluoro-4-nitrophenoxy)methyl)-2-(trifluoromethyl)oxazolidin-3-yl)-2-(trifluoromethyl)benzonitrile,
4-((3-(4-cyano-3-(trifluoromethyl)phenyl)-2-(trifluoromethyl)oxazolidin-5-yl)methoxy)-N-methylbenzamide,
4-(5-((2-fluoro-4-nitrophenoxy)methyl)-2-(trifluoromethyl)oxazolidin-3-yl)-2-(trifluoromethyl)benzonitrile,
4-(3-(4-cyano-3-(trifluoromethyl)phenyl)-2-(trifluoromethyl)oxazolidin-5-yl)methoxy)-N,N-dimethylbenzamide,
methyl (4-((3-(4-cyano-3-(trifluoromethyl)phenyl)-2-(trifluoromethyl)oxazolidin-5-yl)methoxy)phenyl)carbamate, 2-(trifluoromethyl)-4-(2-(trifluoromethyl)-5-((4-(trifluoromethyl)phenoxy)methyl)oxazolidin-3-yl)benzonitrile,
4-(5-((4-(2-oxooxazolidin-3-yl)phenoxy)methyl)-2-(trifluoromethyl)oxazolidin-3-yl)-2-(trifluoromethyl)benzonitrile,
N-(4-((3-(4-cyano-3-(trifluoromethyl)phenyl)-2-(trifluoromethyl)oxazolidin-5-yl)methoxy)phenyl)methanesulfonamide,
3-(4-((3-(4-cyano-3-(trifluoromethyl)phenyl)-2-(trifluoromethyl)oxazolidin-5-yl)methoxy)phenyl)-1,1-dimethylurea,
ethyl (4-((3-(4-cyano-3-(trifluoromethyl)phenyl)-2-(trifluoromethyl)oxazolidin-5-yl)methoxy)phenyl)carbamate,
isopropyl (4-((3-(4-cyano-3-(trifluoromethyl)phenyl)-2-(trifluoromethyl)oxazolidin-5-yl)methoxy)phenyl)carbamate,
phenyl(4-((3-(4-cyano-3-(trifluoromethyl)phenyl)-2-(trifluoromethyl)oxazolidin-5-yl)methoxy)phenyl)carbamate,
5-((3-(4-cyano-3-(trifluoromethyl)phenyl)-2-(trifluoromethyl)oxazolidin-5-yl)methoxy)picolinonitrile,
5-((3-(4-cyano-3-(trifluoromethyl)phenyl)-2-(trifluoromethyl)oxazolidin-5-yl)methoxy)picolinonitrile,
4-(5-((3-cyanophenoxy)methyl)-2-(trifluoromethyl)oxazolidin-3-yl)-2-(trifluoromethyl)benzonitrile,
4-(5-((4-cyanophenoxy)methyl)-2-(hydroxymethyl)oxazolidin-3-yl)-2-(trifluoromethyl)benzonitrile,
4-(5-((4-cyanophenoxy)methyl)-2-((R)-2,2,2-trifluoro-1-hydroxyethyl)oxazolidin-3-yl)-2-(trifluoromethyl)benzonitrile,
4-(5-((4-cyanophenoxy)methyl)-2-((S)-2,2,2-trifluoro-1-hydroxyethyl)oxazolidin-3-yl)-2-(trifluoromethyl)benzonitrile,
2-amino-N-(4-((3-(4-cyano-3-(trifluoromethyl)phenyl)-2-(trifluoromethyl)oxazolidin-5-yl)methoxy)phenyl)acetamide,
N-(4-((3-(4-cyano-3-(trifluoromethyl)phenyl)-2-(trifluoromethyl)oxazolidin-5-yl)methoxy)phenyl)pyrrolidine-2-carboxamide,
2-(4-((3-(4-cyano-3-(trifluoromethyl)phenyl)-2-(trifluoromethyl)oxazolidin-5-yl)methoxy)phenyl)acetic acid,
4-((3-(3-methyl-4-nitrophenyl)-2-(trifluoromethyl)oxazolidin-5-yl)methoxy)benzonitrile,
N-(4-((3-(3-methyl-4-nitrophenyl)-2-(trifluoromethyl)oxazolidin-5-yl)methoxy)phenyl)acetamide,
5-((3-(3-methyl-4-nitrophenyl)-2-(trifluoromethyl)oxazolidin-5-yl)methoxy)picolinonitrile,
4-(5-((4-chlorophenoxy)methyl)-2-(trifluoromethyl)oxazolidin-3-yl)-2-(trifluoromethyl)benzonitrile,
4-(5-((4-((E)-(hydroxyimino)methyl)phenoxy)methyl)-2-(trifluoromethyl)oxazolidin-3-yl)-2-(trifluoromethyl)benzonitrile,
4-(5-(phenoxymethyl)-2-(trifluoromethyl)oxazolidin-3-yl)-2-(trifluoromethyl)benzonitrile,
4-(5-((pyridin-4-yloxy)methyl)-2-(trifluoromethyl)oxazolidin-3-yl)-2-(trifluoromethyl)benzonitrile,
4-(5-((pyridin-3-yloxy)methyl)-2-(trifluoromethyl)oxazolidin-3-yl)-2-(trifluoromethyl)benzonitrile,
4-(5-((4-cyanophenoxy)methyl)-2,2-dimethyloxazolidin-3-yl)-2-(trifluoromethyl)benzonitrile,
4-(5-((4-(methylsulfonyl)phenoxy)methyl)-2-(trifluoromethyl)oxazolidin-3-yl)-2-(trifluoromethyl)benzonitrile,
4-((3-(3,4-dichlorophenyl)-2-(trifluoromethyl)oxazolidin-5-yl)methoxy)benzonitrile,
4-((3-(4-nitro-3-(trifluoromethyl)phenyl)-2-(trifluoromethyl)oxazolidin-5-yl)methoxy)benzonitrile,
5-((3-(4-nitro-3-(trifluoromethyl)phenyl)-2-(trifluoromethyl)oxazolidin-5-yl)methoxy)picolinonitrile,
3-(4-nitro-3-(trifluoromethyl)phenyl)-5-((pyridin-4-yloxy)methyl)-2-(trifluoromethyl)oxazolidine,
4-(5-((4-(hydroxymethyl)phenoxy)methyl)-2-(trifluoromethyl)oxazolidin-3-yl)-2-(trifluoromethyl)benzonitrile,
4-(5-(((2-chloropyridin-4-yl)oxy)methyl)-2-(trifluoromethyl)oxazolidin-3-yl)-2-(trifluoromethyl)benzonitrile,
3-(3-methyl-4-nitrophenyl)-5-((pyridin-4-yloxy)methyl)-2-(trifluoromethyl)oxazolidine,
(E)-4-((3-(3-methyl-4-nitrophenyl)-2-(trifluoromethyl)oxazolidin-5-yl)methoxy)benzaldehydeoxime,
2-chloro-4-(5-((4-cyanophenoxy)methyl)-2-(trifluoromethyl)oxazolidin-3-yl)benzonitrile,
2-chloro-4-(5-((pyridin-4-yloxy)methyl)-2-(trifluoromethyl)oxazolidin-3-yl)benzonitrile,
5-((3-(3-chloro-4-cyanophenyl)-2-(trifluoromethyl)oxazolidin-5-yl)methoxy)picolinonitrile,
2-chloro-4-(5-((4-((E)-(hydroxyimino)methyl)phenoxy)methyl)-2-(trifluoromethyl)oxazolidin-3-yl)benzonitrile,
2-chloro-4-(5-((4-cyanophenoxy)methyl)-2-(trifluoromethyl)oxazolidin-3-yl)-3-methylbenzonitrile,
2-chloro-3-methyl-4-(5-((pyridin-4-yloxy)methyl)-2-(trifluoromethyl)oxazolidin-3-yl)benzonitrile,
5-((3-(3-chloro-4-cyano-2-methylphenyl)-2-(trifluoromethyl)oxazolidin-5-yl)methoxy)picolinonitrile,
2-chloro-4-(5-((4-((E)-(hydroxyimino)methyl)phenoxy)methyl)-2-(trifluoromethyl)oxazolidin-3-yl)-3-methylbenzonitrile,
5-(((6-bromopyridin-3-yl)oxy)methyl)-3-(3-methyl-4-nitrophenyl)-2-(trifluoromethyl)oxazolidine,
4-(((pyridin-4-yloxy)methyl)-2-(trifluoromethyl)oxazolidin-3-yl)-2-(trifluoromethyl)benzonitrile,
4-((3-(4-nitro-3-(trifluoromethyl)phenyl)-2-(trifluoromethyl)oxazolidin-5-yl)methoxy)benzonitrile,
4-((3-(3-methyl-4-nitrophenyl)-2-(trifluoromethyl)oxazolidin-5-yl)methoxy)benzonitrile,
2-chloro-4-(5-((4-cyanophenoxy)methyl)-2-(trifluoromethyl)oxazolidin-3-yl)benzonitrile,
2-chloro-4-(5-((4-cyanophenoxy)methyl)-2-(trifluoromethyl)oxazolidin-3-yl)-3-methylbenzonitrile,
4-(5-((4-((E)-(methoxyimino)methyl)phenoxy)methyl)-2-(trifluoromethyl)oxazolidin-3-yl)-2-(trifluoromethyl)benzonitrile,
4-(5-((4-((E)-(hydroxyimino)methyl)phenoxy)methyl)-2-(trifluoromethyl)oxazolidin-3-yl)-2-(trifluoromethyl)benzonitrile,
(E)-4-((3-(4-nitro-3-(trifluoromethyl)phenyl)-2-(trifluoromethyl)oxazolidin-5-yl)methoxy)benzaldehyde oxime,
(t-butyl(4-((3-(4-cyano-3-(trifluoromethyl)phenyl)-2-(trifluoromethyl)oxazolidin-5-yl)methoxy)benzyl)carbamate,
4-(5-((4-(aminomethyl)phenoxy)methyl)-2-(trifluoromethyl)oxazolidin-3-yl)-2-(trifluoromethyl)benzonitrile,
N-(4-((3-(4-cyano-3-(trifluoromethyl)phenyl)-2-(trifluoromethyl)oxazolidin-5-yl)methoxy)benzyl)acetamide,
1-(4-((3-(4-cyano-3-(trifluoromethyl)phenyl)-2-(trifluoromethyl)oxazolidin-5-yl)methoxy)benzyl)urea,
1-(4-((3-(4-cyano-3-(trifluoromethyl)phenyl)-2-(trifluoromethyl)oxazolidin-5-yl)methoxy)benzyl)-3-methylurea, methyl(4-((3-(4-cyano-3-(trifluoromethyl)phenyl)-2-(trifluoromethyl)oxazolidin-5-yl)methoxy)benzyl)carbamate,
N-(4-((3-(4-cyano-3-(trifluoromethyl)phenyl)-2-(trifluoromethyl)oxazolidin-5-yl)methoxy)phenyl)-2-hydroxyacetamide,
2-cyano-N-(4-((3-(4-cyano-3-(trifluoromethyl)phenyl)-2-(trifluoromethyl)oxazolidin-5-yl)methoxy)phenyl)acetamide,
2-(4-((3-(4-cyano-3-(trifluoromethyl)phenyl)-2-(trifluoromethyl)oxazolidin-5-yl)methoxy)phenyl)acetamide,
4-(3-(4-cyano-3-(trifluoromethyl)phenyl)-2-(trifluoromethyl)oxazolidin-5-yl)methoxy)benzamide,
4-(5-((4-((E)-(hydroxyimino)methyl)-2-nitrophenoxy)methyl)-2-(trifluoromethyl)oxazolidin-3-yl)-2-(trifluoromethyl)benzonitrile,
4-(5-((4-cyano-2-nitrophenoxy)methyl)-2-(trifluoromethyl)oxazolidin-3-yl)-2-(trifluoromethyl)benzonitrile,
4-(5-((2-amino-4-cyanophenoxy)methyl)-2-(trifluoromethyl)oxazolidin-3-yl)-2-(trifluoromethyl)benzonitrile,
methyl(5-cyano-2-((3-(4-cyano-3-(trifluoromethyl)phenyl)-2-(trifluoromethyl)oxazolidin-5-yl)methoxy)phenyl)carbamate,
4-(5-(((4-cyanophenyl)amino)methyl)-2-(trifluoromethyl)oxazolidin-3-yl)-2-(trifluoromethyl)benzonitrile,
4-(5-(((4-cyanophenyl)amino)methyl)-2-(trifluoromethyl)oxazolidin-3-yl)-2-(trifluoromethyl)benzonitrile,
N-(4-amino-2-fluorophenyl)-3-(4-cyano-3-(trifluoromethyl)phenyl)-2-(trifluoromethyl)oxazolidine-5-carboxamide,
N-(4-acetamido-2-fluorophenyl)-3-(4-cyano-3-(trifluoromethyl)phenyl)-2-(trifluoromethyl)oxazolidine-5-carboxamide,
3-(4-cyano-3-(trifluoromethyl)phenyl)-N-(pyridin-4-yl)-2-(trifluoromethyl)oxazolidine-5-carboxamide,
3-(4-cyano-3-(trifluoromethyl)phenyl)-N-(6-cyanopyridin-3-yl)-2-(trifluoromethyl)oxazolidine-5-carboxamide,
N-(4-acetamidophenyl)-3-(4-cyano-3-(trifluoromethyl)phenyl)-2-(trifluoromethyl)oxazolidine-5-carboxamide,
3-(4-cyano-3-(trifluoromethyl)phenyl)-N-(pyridin-3-yl)-2-(trifluoromethyl)oxazolidine-5-carboxamide,
N-(4-cyanophenyl)-3-(3-methyl-4-nitrophenyl)-2-(trifluoromethyl)oxazolidine-5-carboxamide,
N-(4-acetamidophenyl)-3-(3-methyl-4-nitrophenyl)-2-(trifluoromethyl)oxazolidine-5-carboxamide,
N-(4-cyano-2-fluorophenyl)-3-(3-methyl-4-nitrophenyl)-2-(trifluoromethyl)oxazolidine-5-carboxamide,
N-(2-chloro-4-cyanophenyl)-3-(4-cyano-3-(trifluoromethyl)phenyl)-2-(trifluoromethyl)oxazolidine-5-carboxamide,
3-(4-cyano-3-(trifluoromethyl)phenyl)-N-(2,4-difluorophenyl)-2-(trifluoromethyl)oxazolidine-5-carboxamide,
N-(6-cyanopyridin-3-yl)-3-(3-methyl-4-nitrophenyl)-2-(trifluoromethyl)oxazolidine-5-carboxamide,
3-(3-chloro-4-cyanophenyl)-N-(4-cyanophenyl)-2-(trifluoromethyl)oxazolidine-5-carboxamide,
N-(4-acetamidophenyl)-3-(3-chloro-4-cyanophenyl)-2-(trifluoromethyl)oxazolidine-5-carboxamide,
3-(3-chloro-4-cyanophenyl)-N-(4-cyano-2-fluorophenyl)-2-(trifluoromethyl)oxazolidine-5-carboxamide,
3-(3-chloro-4-cyanophenyl)-N-(6-cyanopyridin-3-yl)-2-(trifluoromethyl)oxazolidine-5-carboxamide,
3-(3-chloro-4-cyanophenyl)-N-(pyridin-4-yl)-2-(trifluoromethyl)oxazolidine-5-carboxamide,
3-(3-chloro-4-nitrophenyl)-N-(4-cyanophenyl)-2-(trifluoromethyl)oxazolidine-5-carboxamide,
N-(4-acetamidophenyl)-3-(3-chloro-4-nitrophenyl)-2-(trifluoromethyl)oxazolidine-5-carboxamide,
3-(3-chloro-4-nitrophenyl)-N-(4-cyano-2-fluorophenyl)-2-(trifluoromethyl)oxazolidine-5-carboxamide,
3-(3-chloro-4-nitrophenyl)-N-(6-cyanopyridin-3-yl)-2-(trifluoromethyl)oxazolidine-5-carboxamide,
3-(3-chloro-4-nitrophenyl)-N-(pyridin-4-yl)-2-(trifluoromethyl)oxazolidine-5-carboxamide,
3-(4-cyano-3-(trifluoromethyl)phenyl)-N-(4-cyano-3-methoxyphenyl)-2-(trifluoromethyl)oxazolidine-5-carboxamide,
N-(4-cyano-2-(trifluoromethyl)phenyl)-3-(4-cyano-3-(trifluoromethyl)phenyl)-2-(trifluoromethyl)oxazolidine-5-carboxamide,
N-(4-cyano-2,6-difluorophenyl)-3-(4-cyano-3-(trifluoromethyl)phenyl)-2-(trifluoromethyl)oxazolidine-5-carboxamide,
N-(3-chloro-4-cyano-2-fluorophenyl)-3-(4-cyano-3-(trifluoromethyl)phenyl)-2-(trifluoromethyl)oxazolidine-5-carboxamide,
N-(4-cyano-2,5-difluorophenyl)-3-(4-cyano-3-(trifluoromethyl)phenyl)-2-(trifluoromethyl)oxazolidine-5-carboxamide,
3-(4-cyano-3-(trifluoromethyl)phenyl)-N-(3,4-dicyanophenyl)-2-(trifluoromethyl)oxazolidine-5-carboxamide,
N-(4-cyano-2-methylphenyl)-3-(4-cyano-3-(trifluoromethyl)phenyl)-2-(trifluoromethyl)oxazolidine-5-carboxamide,
N-(3-chloro-4-cyanophenyl)-3-(4-cyano-3-(trifluoromethyl)phenyl)-2-(trifluoromethyl)oxazolidine-5-carboxamide,
N-(6-acetamidopyridin-3-yl)-3-(4-cyano-3-(trifluoromethyl)phenyl)-2-(trifluoromethyl)oxazolidine-5-carboxamide,
3-(3-chloro-4-cyanophenyl)-N-(2-chloropyridin-4-yl)-2-(trifluoromethyl)oxazolidine-5-carboxamide,
N-(2-chloropyridin-4-yl)-3-(3-methyl-4-nitrophenyl)-2-(trifluoromethyl)oxazolidine-5-carboxamide,
3-(4-cyano-3-(trifluoromethyl)phenyl)-N-(4-cyanophenyl)-2-(trifluoromethyl)oxazolidine-5-carboxamide,
N-(4-cyano-2-fluorophenyl)-3-(4-cyano-3-(trifluoromethyl)phenyl)-2-(trifluoromethyl)oxazolidine-5-carboxamide,
3-(4-cyano-3-(trifluoromethyl)phenyl)-N-(3,4-difluorophenyl)-2-(trifluoromethyl)oxazolidine-5-carboxamide,
3-(4-cyano-3-(trifluoromethyl)phenyl)-N-(3-cyanophenyl)-2-(trifluoromethyl)oxazolidine-5-carboxamide,
N-(2-chloropyridin-4-yl)-3-(4-cyano-3-(trifluoromethyl)phenyl)-2-(trifluoromethyl)oxazolidine-5-carboxamide,
N-(4-cyano-2,3,5,6-tetrafluorophenyl)-3-(4-cyano-3-(trifluoromethyl)phenyl)-2-(trifluoromethyl)oxazolidine-5-carboxamide,
N,3-bis(4-cyano-3-(trifluoromethyl)phenyl)-2-(trifluoromethyl)oxazolidine-5-carboxamide,
N-(4-cyano-2-ethylphenyl)-3-(4-cyano-3-(trifluoromethyl)phenyl)-2-(trifluoromethyl)oxazolidine-5-carboxamide,
N-(2-chloro-4-cyano-6-methylphenyl)-3-(4-cyano-3-(trifluoromethyl)phenyl)-2-(trifluoromethyl)oxazolidine-5-carboxamide, 3-(4-cyano-3-(trifluoromethyl)phenyl)-N-(4-cyano-3-fluorophenyl)-2-(trifluoromethyl)oxazolidine-5-carboxamide, 3-(4-cyano-3-(trifluoromethyl)phenyl)-N-(4-hydroxyphenyl)-2-(trifluoromethyl)oxazolidine-5-carboxamide, 3-(3-chloro-4-nitrophenyl)-N-(6-chloropyridin-3-yl)-2-(trifluoromethyl)oxazolidine-5-carboxamide, N-(4-acetamidophenyl)-3-(4-nitro-3-(trifluoromethyl)phenyl)-2-(trifluoromethyl)oxazolidine-5-carboxamide, N-(2-chloro-4-nitrophenyl)-3-(4-cyano-3-(trifluoromethyl)phenyl)-2-(trifluoromethyl)oxazolidine-5-carboxamide, N-(4-amino-2-chlorophenyl)-3-(4-cyano-3-(trifluoromethyl)phenyl)-2-(trifluoromethyl)oxazolidine-5-carboxamide, N-(4-acetamido-2-chlorophenyl)-3-(4-cyano-3-(trifluoromethyl)phenyl)-2-(trifluoromethyl)oxazolidine-5-carboxamide, methyl(3-chloro-4-(3-(4-cyano-3-(trifluoromethyl)phenyl)-2-(trifluoromethyl)oxazolidine-5-carboxamido)phenyl)carbamate, 3-(4-cyano-3-(trifluoromethyl)phenyl)-N-(4-nitrophenyl)-2-(trifluoromethyl)oxazolidine-5-carboxamide, N-(4-aminophenyl)-3-(4-cyano-3-(trifluoromethyl)phenyl)-2-(trifluoromethyl)oxazolidine-5-carboxamide, methyl(4-(3-(4-cyano-3-(trifluoromethyl)phenyl)-2-(trifluoromethyl)oxazolidine-5-carboxamido)phenyl)carbamate, 3-(4-cyano-3-(trifluoromethyl)phenyl)-N-(4-propionamidophenyl)-2-(trifluoromethyl)oxazolidine-5-carboxamide, 3-(4-cyano-3-(trifluoromethyl)phenyl)-N-(4-isobutylamidophenyl)-2-(trifluoromethyl)oxazolidine-5-carboxamide, 3-(4-cyano-3-(trifluoromethyl)phenyl)-N-(4-(2-hydroxyacetamido)phenyl)-2-(trifluoromethyl)oxazolidine-5-carboxamide, 3-(4-cyano-3-(trifluoromethyl)phenyl)-2-(trifluoromethyl)-N-(4-ureidophenyl)oxazolidine-5-carboxamide, 3-(4-cyano-3-(trifluoromethyl)phenyl)-N-(4-(2-cyanoacetamido)phenyl)-2-(trifluoromethyl)oxazolidine-5-carboxamide, N-(4-(2-aminoacetamido)phenyl)-3-(4-cyano-3-(trifluoromethyl)phenyl)-2-(trifluoromethyl)oxazolidine-5-carboxamide, 3-(4-cyano-3-(trifluoromethyl)phenyl)-N-(4-cyanophenyl)-2-(trifluoromethyl)oxazolidine-5-carboxamide, 4-(5-(((4-cyanophenyl)sulfonyl)methyl)-2-(trifluoromethyl)oxazolidin-3-yl)-2-(trifluoromethyl)benzonitrile, t-butyl4-(3-(4-cyano-3-(trifluoromethyl)phenyl)-2-(trifluoromethyl)oxazolidine-5-carboxamido)piperidine-1-carboxylate, 3-(4-cyano-3-(trifluoromethyl)phenyl)-N-(piperidin-4-yl)-2-(trifluoromethyl)oxazolidine-5-carboxamide, and N-(1-acetylpiperidin-4-yl)-3-(4-cyano-3-(trifluoromethyl)phenyl)-2-(trifluoromethyl)oxazolidine-5-carboxamide.

6. The compound, an isomer thereof, or a pharmaceutically acceptable salt thereof according to claim 1, wherein the $R_1$ of Chemical Formula 1 is a substituent represented by the Chemical Formula 3, and is a compound selected from the group consisting of the following compounds, an isomer thereof, or a pharmaceutically acceptable salt thereof:

4-(5-(4-isocyanopiperidine-1-carbonyl)-2-(trifluoromethyl)oxazolidin-3-yl)-2-(trifluoromethyl)benzonitrile, 4-(5-(piperazine-1-carbonyl)-2-(trifluoromethyl)oxazolidin-3-yl)-2-(trifluoromethyl)benzonitrile, 4-(5-(4-acetylpiperazine-1-carbonyl)-2-(trifluoromethyl)oxazolidin-3-yl)-2-(trifluoromethyl)benzonitrile, methyl4-(3-(4-cyano-3-(trifluoromethyl)phenyl)-2-(trifluoromethyl)oxazolidine-5-carbonyl)piperazine-1-carboxylate, 4-(3-(4-cyano-3-(trifluoromethyl)phenyl)-2-(trifluoromethyl)oxazolidine-5-carbonyl)piperazine-1-carbonitrile, 4-(5-(4-aminopiperidine-1-carbonyl)-2-(trifluoromethyl)oxazolidin-3-yl)-2-(trifluoromethyl)benzonitrile, 4-(5-(4-acetylpiperazine-1-carbonyl)-2-(trifluoromethyl)oxazolidin-3-yl)-2-(trifluoromethyl)benzonitrile, t-butyl-4-(3-(4-cyano-3-(trifluoromethyl)phenyl)-2-(trifluoromethyl)oxazolidine-5-carboxamido)piperidine-1-carboxylate, methyl4-(3-(3-chloro-4-cyanophenyl)-2-(trifluoromethyl)oxazolidine-5-carbonyl)piperazine-1-carboxylate methyl4-(3-(3-methyl-4-nitrophenyl)-2-(trifluoromethyl)oxazolidine-5-carbonyl)piperazine-1-carboxylate, methyl(2-(3-(4-cyano-3-(trifluoromethyl)phenyl)-2-(trifluoromethyl)oxazolidine-5-carboxamido)ethyl)carbamate, 4-(5-(4-(methylsulfonyl)piperazine-1-carbonyl)-2-(trifluoromethyl)oxazolidin-3-yl)-2-(trifluoromethyl)benzonitrile, 4-(5-(4-isopropylpiperazine-1-carbonyl)-2-(trifluoromethyl)oxazolidin-3-yl)-2-(trifluoromethyl)benzonitrile, 4-(5-(4-(2-cyanoethyl)piperazine-1-carbonyl)-2-(trifluoromethyl)oxazolidin-3-yl)-2-(trifluoromethyl)benzonitrile, 4-(5-(4-(2-hydroxyethyl)piperazine-1-carbonyl)-2-(trifluoromethyl)oxazolidin-3-yl)-2-trifluoromethyl)benzonitrile, 1-((3-(4-cyano-3-(trifluoromethyl)phenyl)-2-(trifluoromethyl)oxazolidin-5-yl)methyl)piperidine-4-carbonitrile, 1-(3-(4-cyano-3-(trifluoromethyl)phenyl)-2-(trifluoromethyl)oxazolidine-5-carbonyl)piperidine-4-carboxamide, ethyl4-(3-(4-cyano-3-(trifluoromethyl)phenyl)-2-(trifluoromethyl)oxazolidine-5-carbonyl)piperazine-1-carboxylate, 4-(3-(4-cyano-3-(trifluoromethyl)phenyl)-2-(trifluoromethyl)oxazolidine-5-carbonyl)piperazine-1-carboxamide, methyl4-(3-(3-chloro-4-nitrophenyl)-2-(trifluoromethyl)oxazolidine-5-carbonyl)piperazine-1-carboxylate, methyl4-(3-(4-nitro-3-(trifluoromethyl)phenyl)-2-(trifluoromethyl)oxazolidine-5-carbonyl)piperazine-1-carboxylate, methyl4-(3-(4-cyano-3-(trifluoromethyl)phenyl)-2-(trifluoromethyl)oxazolidine-5-carbonyl)-1,4-diazepane-1-carboxylate, and methyl((R)-1-(3-(4-cyano-3-(trifluoromethyl)phenyl)-2-(trifluoromethyl)oxazolidine-5-carbonyl)pyrrolidin-3-yl)carbamate.

7. The compound, an isomer thereof, or a pharmaceutically acceptable salt thereof according to claim 5, wherein the $R_1$ of Chemical Formula 1 is a substituent represented by the Chemical Formula 2, and is a compound selected from the group consisting of the following compounds, an isomer thereof, or a pharmaceutically acceptable salt thereof:

4-((2R,5S)-5-(hydroxymethyl)-2-(trifluoromethyl)oxazolidin-3-yl)-2-(trifluoromethyl)benzonitrile, 4-((2R,5S)-5-(((4-cyanobenzyl)oxy)methyl)-2-(trifluoromethyl)oxazolidin-3-yl)-2-(trifluoromethyl)benzonitrile,
4-((2S,5R)-5-(hydroxymethyl)-2-(trifluoromethyl)oxazolidin-3-yl)-2-(trifluoromethyl)benzonitrile,
4-((2S,5R)-5-(((4-cyanobenzyl)oxy)methyl)-2-(trifluoromethyl)oxazolidin-3-yl)-2-(trifluoromethyl)benzonitrile,
4-((2R,5R)-5-((4-cyanophenoxy)methyl)-2-(trifluoromethyl)oxazolidin-3-yl)-2-(trifluoromethyl)benzonitrile,
4-((2S,5S)-5-((4-cyanophenoxy)methyl)-2-(trifluoromethyl)oxazolidin-3-yl)-2-(trifluoromethyl)benzonitrile,
methyl4-(((2R,5S)-3-(4-cyano-3-(trifluoromethyl)phenyl)-2-(trifluoromethyl)oxazolidin-5-yl)methoxy)benzoate,
4-((2R,5S)-5-((4-nitrophenoxy)methyl)-2-(trifluoromethyl)oxazolidin-3-yl)-2-(trifluoromethyl)benzonitrile,
4-(((2R,5S)-3-(4-cyano-3-(trifluoromethyl)phenyl)-2-(trifluoromethyl)oxazolidin-5-yl)methoxy)benzoic acid,
4-((2R,5S)-5-((3,4-difluorophenoxy)methyl)-2-(trifluoromethyl)oxazolidin-3-yl)-2-(trifluoromethyl)benzonitrile,
4-((2R,5S)-5-((4-cyano-2-fluorophenoxy)methyl)-2-(trifluoromethyl)oxazolidin-3-yl)-2-(trifluoromethyl)benzonitrile,
4-((2R,5S)-5-((2-chloro-4-nitrophenoxy)methyl)-2-(trifluoromethyl)oxazolidin-3-yl)-2-(trifluoromethyl)benzonitrile,
2-(trifluoromethyl)-4-((2R,5S)-2-(trifluoromethyl)-5-((2,4,5-trifluorophenoxy)methyl)oxazolidin-3-yl)benzonitrile,
4-((2R,5S)-5-((4-aminophenoxy)methyl)-2-(trifluoromethyl)oxazolidin-3-yl)-2-(trifluoromethyl)benzonitrile,
1-(4-(((2R,5S)-3-(4-cyano-3-(trifluoromethyl)phenyl)-2-(trifluoromethyl)oxazolidin-5-yl)methoxy)phenyl)urea,
1-(4-(((2R,5S)-3-(4-cyano-3-(trifluoromethyl)phenyl)-2-(trifluoromethyl)oxazolidin-5-yl)methoxy)phenyl)-3-methylurea,
4-((2R,5S)-5-((4-(2-oxopyrrolidin-1-yl)phenoxy)methyl)-2-(trifluoromethyl)oxazolidin-3-yl)-2-(trifluoromethyl)benzonitrile,
4-((2R,5S)-5-((4-(1,3,4-oxadiazol-2-yl)phenoxy)methyl)-2-(trifluoromethyl)oxazolidin-3-yl)-2-(trifluoromethyl)benzonitrile,
4-((2R,5S)-5-((4-cyanophenoxy)methyl)-2-(trifluoromethyl)oxazolidin-3-yl)-2-(trifluoromethyl)benzonitrile,
4-((2S,5R)-5-((4-cyanophenoxy)methyl)-2-(trifluoromethyl)oxazolidin-3-yl)-2-(trifluoromethyl)benzonitrile,
4-((2S,5R)-5-((R)-2,2,2-trifluoro-1-hydroxyethyl)-2-(trifluoromethyl)oxazolidin-3-yl)-2-(trifluoromethyl)benzonitrile,
4-((2S,5R)-5-((S)-2,2,2-trifluoro-1-hydroxyethyl)-2-(trifluoromethyl)oxazolidin-3-yl)-2-(trifluoromethyl)benzonitrile,
4-((2R,5S)-5-((R)-2,2,2-trifluoro-1-hydroxyethyl)-2-(trifluoromethyl)oxazolidin-3-yl)-2-(trifluoromethyl)benzonitrile,
4-((2R,5S)-5-((S)-2,2,2-trifluoro-1-hydroxyethyl)-2-(trifluoromethyl)oxazolidin-3-yl)-2-(trifluoromethyl)benzonitrile,
N-(4-(((2R,5S)-3-(4-cyano-3-(trifluoromethyl)phenyl)-2-(trifluoromethyl)oxazolidin-5-yl)methoxy)phenyl)acetamide,
4-((2R,5S)-5-(((4-chlorophenyl)thio)methyl)-2-(trifluoromethyl)oxazolidin-3-yl)-2-(trifluoromethyl)benzonitrile,
4-((2R,5S)-5-((4-methoxyphenoxy)methyl)-2-(trifluoromethyl)oxazolidin-3-yl)-2-(trifluoromethyl)benzonitrile,
4-((2R,5S)-5-((3-methoxyphenoxy)methyl)-2-(trifluoromethyl)oxazolidin-3-yl)-2-(trifluoromethyl)benzonitrile,
4-((2R,5S)-5-(((4-cyanophenyl)thio)methyl)-2-(trifluoromethyl)oxazolidin-3-yl)-2-(trifluoromethyl)benzonitrile,
N-(4-(((2S,5S)-3-(4-cyano-3-(trifluoromethyl)phenyl)-2-(trifluoromethyl)oxazolidin-5-yl)methoxy)phenyl)acetamide,
4-(2R,5S)-5-((3-fluoro-4-nitrophenoxy)methyl)-2-(trifluoromethyl)oxazolidin-3-yl)-2-(trifluoromethyl)benzonitrile,
4-(((2R,5S)-3-(4-cyano-3-(trifluoromethyl)phenyl)-2-(trifluoromethyl)oxazolidin-5-yl)methoxy)-N-methylbenzamide,
4-((2R,5S)-5-((2-fluoro-4-nitrophenoxy)methyl)-2-(trifluoromethyl)oxazolidin-3-yl)-2-(trifluoromethyl)benzonitrile,
4-(((2R,5S)-3-(4-cyano-3-(trifluoromethyl)phenyl)-2-(trifluoromethyl)oxazolidin-5-yl)methoxy)-N,N-dimethylbenzamide,
4-((2S,5S)-5-((4-nitrophenoxy)methyl)-2-(trifluoromethyl)oxazolidin-3-yl)-2-(trifluoromethyl)benzonitrile,
methyl(4-(((2R,5S)-3-(4-cyano-3-(trifluoromethyl)phenyl)-2-(trifluoromethyl)oxazolidin-5-yl)methoxy)phenyl)carbamate,
2-(trifluoromethyl)-4-((2R,5S)-2-(trifluoromethyl)-5-((4-(trifluoromethyl)phenoxy)methyl)oxazolidin-3-yl)benzonitrile,
4-((2R,5S)-5-((4-(2-oxooxazolidin-3-yl)phenoxy)methyl)-2-(trifluoromethyl)oxazolidin-3-yl)-2-(trifluoromethyl)benzonitrile,
N-(4-(((2R,5S)-3-(4-cyano-3-(trifluoromethyl)phenyl)-2-(trifluoromethyl)oxazolidin-5-yl)methoxy)phenyl)methanesulfonamide,
3-(4-(((2R,5S)-3-(4-cyano-3-(trifluoromethyl)phenyl)-2-(trifluoromethyl)oxazolidin-5-yl)methoxy)phenyl)-1,1-dimethylurea,
ethyl(4-(((2R,5S)-3-(4-cyano-3-(trifluoromethyl)phenyl)-2-(trifluoromethyl)oxazolidin-5-yl)methoxy)phenyl)carbamate,
isopropyl(4-(((2R,5S)-3-(4-cyano-3-(trifluoromethyl)phenyl)-2-(trifluoromethyl)oxazolidin-5-yl)methoxy)phenyl)carbamate,
phenyl(4-(((2R,5S)-3-(4-cyano-3-(trifluoromethyl)phenyl)-2-(trifluoromethyl)oxazolidin-5-yl)methoxy)phenyl)carbamate,
5-(((2R,5S)-3-(4-cyano-3-(trifluoromethyl)phenyl)-2-(trifluoromethyl)oxazolidin-5-yl)methoxy)picolinonitrile,
5-(((2S,5S)-3-(4-cyano-3-(trifluoromethyl)phenyl)-2-(trifluoromethyl)oxazolidin-5-yl)methoxy)picolinonitrile,
4-((2R,5S)-5-((3-cyanophenoxy)methyl)-2-(trifluoromethyl)oxazolidin-3-yl)-2-(trifluoromethyl)benzonitrile,
4-((2R,5S)-5-((4-cyanophenoxy)methyl)-2-(hydroxymethyl)oxazolidin-3-yl)-2-(trifluoromethyl)benzonitrile,
4-((2R,5S)-5-((4-cyanophenoxy)methyl)-2-((R)-2,2,2-trifluoro-1-hydroxyethyl)oxazolidin-3-yl)-2-(trifluoromethyl)benzonitrile, 4-((2R,5S)-5-((4-cyanophenoxy)methyl)-2-((S)-2,2,2-trifluoro-1-hydroxyethyl)oxazolidin-3-yl)-2-(trifluoromethyl)benzonitrile,
2-amino-N-(4-(((2R,5S)-3-(4-cyano-3-(trifluoromethyl)phenyl)-2-(trifluoromethyl)oxazolidin-5-yl)methoxy)phenyl)acetamide,
(S)-N-(4-(((2R,5S)-3-(4-cyano-3-(trifluoromethyl)phenyl)-2-(trifluoromethyl)oxazolidin-5-yl)methoxyphenyl)pyrrolidine-2-carboxamide,
2-(4-(((2R,5S)-3-(4-cyano-3-(trifluoromethyl)phenyl)-2-(trifluoromethyl)oxazolidin-5-yl)methoxy)phenyl)acetic acid,
4-(((2R,5S)-3-(3-methyl-4-nitrophenyl)-2-(trifluoromethyl)oxazolidin-5-yl)methoxy)benzonitrile,
N-(4-(((2R,5S)-3-(3-methyl-4-nitrophenyl)-2-(trifluoromethyl)oxazolidin-5-yl)methoxy)phenyl)acetamide,
5-(((2R,5S)-3-(3-methyl-4-nitrophenyl)-2-(trifluoromethyl)oxazolidin-5-yl)methoxy)picolinonitrile,
4-((2R,5S)-5-((4-chlorophenoxy)methyl)-2-(trifluoromethyl)oxazolidin-3-yl)-2-(trifluoromethyl)benzonitrile,
4-((2R,5S)-5-((4-((E)-(hydroxyimino)methyl)phenoxy)methyl)-2-(trifluoromethyl)oxazolidin-3-yl)-2-(trifluoromethyl)benzonitrile,
4-((2R,5S)-5-(phenoxymethyl)-2-(trifluoromethyl)oxazolidin-3-yl)-2-(trifluoromethyl)benzonitrile,
4-((2R,5S)-5-((pyridin-4-yloxy)methyl)-2-(trifluoromethyl)oxazolidin-3-yl)-2-(trifluoromethyl)benzonitrile,
4-((2R,5S)-5-((pyridin-3-yloxy)methyl)-2-(trifluoromethyl)oxazolidin-3-yl)-2-(trifluoromethyl)benzonitrile,
(S)-4-(5-((4-cyanophenoxy)methyl)-2,2-dimethyloxazolidin-3-yl)-2-(trifluoromethyl)benzonitrile,
4-((2R,5S)-5-((4-(methylsulfonyl)phenoxy)methyl)-2-(trifluoromethyl)oxazolidin-3-yl)-2-(trifluoromethyl)benzonitrile,
4-(((2R,5S)-3-(3,4-dichlorophenyl)-2-(trifluoromethyl)oxazolidin-5-yl)methoxy)benzonitrile,
4-(((2R,5S)-3-(4-nitro-3-(trifluoromethyl)phenyl)-2-(trifluoromethyl)oxazolidin-5-yl)methoxy)benzonitrile,
5-(((2R,5S)-3-(4-nitro-3-(trifluoromethyl)phenyl)-2-(trifluoromethyl)oxazolidin-5-yl)methoxy)picolinonitrile,
(2R,5S)-3-(4-nitro-3-(trifluoromethyl)phenyl)-5-((pyridin-4-yloxy)methyl)-2-(trifluoromethyl)oxazolidine,
4-((2R,5S)-5-((4-(hydroxymethyl)phenoxy)methyl)-2-(trifluoromethyl)oxazolidin-3-yl)-2-(trifluoromethyl)benzonitrile,
4-((2R,5S)-5-(((2-chloropyridin-4-yl)oxy)methyl)-2-(trifluoromethyl)oxazolidin-3-yl)-2-(trifluoromethyl)benzonitrile,
(2R,5S)-3-(3-methyl-4-nitrophenyl)-5-((pyridin-4-yloxy)methyl)-2-(trifluoromethyl)oxazolidine,
(E)-4-(((2R,5S)-3-(3-methyl-4-nitrophenyl)-2-(trifluoromethyl)oxazolidin-5-yl)methoxy)benzaldehyde oxime,
2-chloro-4-((2R,5S)-5-((4-cyanophenoxy)methyl)-2-(trifluoromethyl)oxazolidin-3-yl)benzonitrile,
2-chloro-4-((2R,5S)-5-((pyridin-4-yloxy)methyl)-2-(trifluoromethyl)oxazolidin-3-yl)benzonitrile,
5-(((2R,5S)-3-(3-chloro-4-cyanophenyl)-2-(trifluoromethyl)oxazolidin-5-yl)methoxy)picolinonitrile,
2-chloro-4-((2R,5S)-5-((4-((E)-(hydroxyimino)methyl)phenoxy)methyl)-2-(trifluoromethyl)oxazolidin-3-yl)benzonitrile,
2-chloro-4-((2R,5S)-5-((4-cyanophenoxy)methyl)-2-(trifluoromethyl)oxazolidin-3-yl)-3-methylbenzonitrile,
2-chloro-3-methyl-4-((2R,5S)-5-((pyridin-4-yloxy)methyl)-2-(trifluoromethyl)oxazolidin-3-yl)benzonitrile, 5-(((2R,5S)-3-(3-chloro-4-cyano-2-methylphenyl)-2-(trifluoromethyl)oxazolidin-5-yl)methoxy)picolinonitrile,
2-chloro-4-((2R,5S)-5-((4-((E)-(hydroxyimino)methyl)phenoxy)methyl)-2-(trifluoromethyl)oxazolidin-3-yl)-3-methylbenzonitrile,
(2R,5S)-5-((((6-bromopyridin-3-yl)oxy)methyl)-3-(3-methyl-4-nitronyl)-2-(trifluoromethyl)oxazolidine,
4-((2S,5S)-5-((pyridin-4-yloxy)methyl)-2-(trifluoromethyl)oxazolidin-3-yl)-2-(trifluoromethyl)benzonitrile,
4-(((2S,5S)-3-(4-nitro-3-(trifluoromethyl)phenyl)-2-(trifluoromethyl)oxazolidin-5-yl)methoxy)benzonitrile,
4-(((2S,5S)-3-(3-methyl-4-nitrophenyl)-2-(trifluoromethyl)oxazolidin-5-yl)methoxy)benzonitrile,
2-chloro-4-((2S,5S)-5-((4-cyanophenoxy)methyl)-2-(trifluoromethyl)oxazolidin-3-yl)benzonitrile,
2-chloro-4-((2S,5S)-5-((4-cyanophenoxy)methyl)-2-(trifluoromethyl)oxazolidin-3-yl)-3-methylbenzonitrile,
4-((2R,5S)-5-((4-((E)-(methoxyimino)methyl)phenoxy)methyl)-2-(trifluoromethyl)oxazolidin-3-yl)-2-(trifluoromethyl)benzonitrile,
4-((2R,5S)-5-((4-((E)-(hydroxyimino)methyl)phenoxy)methyl)-2-(trifluoromethyl)oxazolidin-3-yl)-2-(trifluoromethyl)benzonitrile,
(E)-4-(((2R,5S)-3-(4-nitro-3-(trifluoromethyl)phenyl)-2-(trifluoromethyl)oxazolidin-5-yl)methoxy)benzaldehyde oxime,
(t-butyl(4-(((2R,5S)-3-(4-cyano-3-(trifluoromethyl)phenyl)-2-(trifluoromethyl)oxazolidin-5-yl)methoxy)benzyl)carbamate,
4-((2R,5S)-5-((4-(aminomethyl)phenoxy)methyl)-2-(trifluoromethyl)oxazolidin-3-yl)-2-(trifluoromethyl)benzonitrile,
N-(4-(((2R,5S)-3-(4-cyano-3-(trifluoromethyl)phenyl)-2-(trifluoromethyl)oxazolidin-5-yl)methoxy)benzyl)acetamide,
1-(4-(((2R,5S)-3-(4-cyano-3-(trifluoromethyl)phenyl)-2-(trifluoromethyl)oxazolidin-5-yl)methoxy)benzyl)urea,
1-(4-(((2R,5S)-3-(4-cyano-3-(trifluoromethyl)phenyl)-2-(trifluoromethyl)oxazolidin-5-yl)methoxy)benzyl)-3-methylurea,
methyl(4-(((2R,5S)-3-(4-cyano-3-(trifluoromethyl)phenyl)-2-(trifluoromethyl)oxazolidin-5-yl)methoxy)benzyl)carbamate,
N-(4-(((2R,5S)-3-(4-cyano-3-(trifluoromethyl)phenyl)-2-(trifluoromethyl)oxazolidin-5-yl)methoxy)phenyl)-2-hydroxyacetamide,
2-cyano-N-(4-(((2R,5S)-3-(4-cyano-3-(trifluoromethyl)phenyl)-2-(trifluoromethyl)oxazolidin-5-yl)methoxy)phenyl)acetamide,
2-(4-(((2R,5S)-3-(4-cyano-3-(trifluoromethyl)phenyl)-2-(trifluoromethyl)oxazolidin-5-yl)methoxy)phenyl)acetamide,
4-(((2R,5S)-3-(4-cyano-3-(trifluoromethyl)phenyl)-2-(trifluoromethyl)oxazolidin-5-yl)methoxy)benzamide,
4-((2R,5S)-5-((4-((E)-(hydroxyimino)methyl)-2-nitrophenoxy)methyl)-2-(trifluoromethyl)oxazolidin-3-yl)-2-(trifluoromethyl)benzonitrile,
4-((2R,5S)-5-((4-cyano-2-nitrophenoxy)methyl)-2-(trifluoromethyl)oxazolidin-3-yl)-2-(trifluoromethyl)benzonitrile,
4-((2R,5S)-5-((2-amino-4-cyanophenoxy)methyl)-2-(trifluoromethyl)oxazolidin-3-yl)-2-(trifluoromethyl)benzonitrile,
methyl(5-cyano-2-(((2R,5S)-3-(4-cyano-3-(trifluoromethyl)phenyl)-2-(trifluoromethyl)oxazolidin-5-yl)methoxy)phenyl)carbamate, 4-((2R,5R)-5-(((4-cyanophenyl)amino)methyl)-2-(trifluoromethyl)oxazolidin-3-yl)-2-(trifluoromethyl)benzonitrile, 4-((2R,5R)-5-(((4-cyanophenyl)amino)methyl)-2-(trifluoromethyl)oxazolidin-3-yl)-2-(trifluoromethyl)benzonitrile, (2R,5S)-N-(4-amino-2-fluorophenyl)-3-(4-cyano-3-(trifluoromethyl)phenyl)-2-(trifluoromethyl)oxazolidine-5-carboxamide, (2R,5S)-N-(4-acetamido-2-fluorophenyl)-3-(4-cyano-3-(trifluoromethyl)phenyl)-2-(trifluoromethyl)oxazolidine-5-carboxamide, (2R,5S)-3-(4-cyano-3-(trifluoromethyl)phenyl)-N-(pyridin-4-yl)-2-(trifluoromethyl)oxazolidine-5-carboxamide, (2R,5S)-3-(4-cyano-3-(trifluoromethyl)phenyl)-N-(6-cyanopyridin-3-yl)-2-(trifluoromethyl)oxazolidine-5-carboxamide, (2R,5S)-N-(4-acetamidophenyl)-3-(4-cyano-3-(trifluoromethyl)phenyl)-2-(trifluoromethyl)oxazolidine-5-carboxamide, (2R,5S)-3-(4-cyano-3-(trifluoromethyl)phenyl)-N-(pyridin-3-yl)-2-(trifluoromethyl)oxazolidine-5-carboxamide, (2R,5S)-N-(4-cyanophenyl)-3-(3-methyl-4-nitrophenyl)-2-(trifluoromethyl)oxazolidine-5-carboxamide, (2R,5S)-N-(4-acetamidophenyl)-3-(3-methyl-4-nitrophenyl)-2-(trifluoromethyl)oxazolidine-5-carboxamide, (2R,5S)-N-(4-cyano-2-fluorophenyl)-3-(3-methyl-4-nitrophenyl)-2-(trifluoromethyl)oxazolidine-5-carboxamide, (2R,5S)-N-(2-chloro-4-cyanophenyl)-3-(4-cyano-3-(trifluoromethyl)phenyl)-2-(trifluoromethyl)oxazolidine-5-carboxamide, (2R,5S)-3-(4-cyano-3-(trifluoromethyl)phenyl)-N-(2,4-difluorophenyl)-2-(trifluoromethyl)oxazolidine-5-carboxamide, (2R,5S)-N-(6-cyanopyridin-3-yl)-3-(3-methyl-4-nitrophenyl)-2-(trifluoromethyl)oxazolidine-5-carboxamide, (2R,5S)-3-(3-chloro-4-cyanophenyl)-N-(4-cyanophenyl)-2-(trifluoromethyl)oxazolidine-5-carboxamide, (2R,5S)-N-(4-acetamidophenyl)-3-(3-chloro-4-cyanophenyl)-2-(trifluoromethyl)oxazolidine-5-carboxamide, (2R,5S)-3-(3-chloro-4-cyanophenyl)-N-(4-cyano-2-fluorophenyl)-2-(trifluoromethyl)oxazolidine-5-carboxamide, (2R,5S)-3-(3-chloro-4-cyanophenyl)-N-(6-cyanopyridin-3-yl)-2-(trifluoromethyl)oxazolidine-5-carboxamide, (2R,5S)-3-(3-chloro-4-cyanophenyl)-N-(pyridin-4-yl)-2-(trifluoromethyl)oxazolidine-5-carboxamide, (2R,5S)-3-(3-chloro-4-nitrophenyl)-N-(4-cyanophenyl)-2-(trifluoromethyl)oxazolidine-5-carboxamide, (2R,5S)-N-(4-acetamidophenyl)-3-(3-chloro-4-nitrophenyl)-2-(trifluoromethyl)oxazolidine-5-carboxamide, (2R,5S)-3-(3-chloro-4-nitrophenyl)-N-(4-cyano-2-fluorophenyl)-2-(trifluoromethyl)oxazolidine-5-carboxamide, (2R,5S)-3-(3-chloro-4-nitrophenyl)-N-(6-cyanopyridin-3-yl)-2-(trifluoromethyl)oxazolidine-5-carboxamide, (2R,5S)-3-(3-chloro-4-nitrophenyl)-N-(pyridin-4-yl)-2-(trifluoromethyl)oxazolidine-5-carboxamide, (2R,5S)-3-(4-cyano-3-(trifluoromethyl)phenyl)-N-(4-cyano-3-methoxyphenyl)-2-(trifluoromethyl)oxazolidine-5-carboxamide, (2R,5S)-N-(4-cyano-2-(trifluoromethyl)phenyl)-3-(4-cyano-3-(trifluoromethyl)phenyl)-2-(trifluoromethyl)oxazolidine-5-carboxamide, (2R,5S)-N-(4-cyano-2,6-difluorophenyl)-3-(4-cyano-3-(trifluoromethyl)phenyl)-2-(trifluoromethyl)oxazolidine-5-carboxamide, (2R,5S)-N-(3-chloro-4-cyano-2-fluorophenyl)-3-(4-cyano-3-(trifluoromethyl)phenyl)-2-(trifluoromethyl)oxazolidine-5-carboxamide, (2R,5S)-N-(4-cyano-2,5-difluorophenyl)-3-(4-cyano-3-(trifluoromethyl)phenyl)-2-(trifluoromethyl)oxazolidine-5-carboxamide, (2R,5S)-3-(4-cyano-3-(trifluoromethyl)phenyl)-N-(3,4-dicyanophenyl)-2-(trifluoromethyl)oxazolidine-5-carboxamide, (2R,5S)-N-(4-cyano-2-methylphenyl)-3-(4-cyano-3-(trifluoromethyl)phenyl)-2-(trifluoromethyl)oxazolidine-5-carboxamide, (2R,5S)-N-(3-chloro-4-cyanophenyl)-3-(4-cyano-3-(trifluoromethyl)phenyl)-2-(trifluoromethyl)oxazolidine-5-carboxamide, (2R,5S)-N-(6-acetamidopyridin-3-yl)-3-(4-cyano-3-(trifluoromethyl)phenyl)-2-(trifluoromethyl)oxazolidine-5-carboxamide, (2R,5S)-3-(3-chloro-4-cyanophenyl)-N-(2-chloropyridin-4-yl)-2-(trifluoromethyl)oxazolidine-5-carboxamide, (2R,5S)-N-(2-chloropyridin-4-yl)-3-(3-methyl-4-nitrophenyl)-2-(trifluoromethyl)oxazolidine-5-carboxamide, (2R,5S)-3-(4-cyano-3-(trifluoromethyl)phenyl)-N-(4-cyanophenyl)-2-(trifluoromethyl)oxazolidine-5-carboxamide, (2R,5S)-N-(4-cyano-2-fluorophenyl)-3-(4-cyano-3-(trifluoromethyl)phenyl)-2-(trifluoromethyl)oxazolidine-5-carboxamide, (2R,5S)-3-(4-cyano-3-(trifluoromethyl)phenyl)-N-(3,4-difluorophenyl)-2-(trifluoromethyl)oxazolidine-5-carboxamide, (2R,5S)-3-(4-cyano-3-(trifluoromethyl)phenyl)-N-(3-cyanophenyl)-2-(trifluoromethyl)oxazolidine-5-carboxamide, (2R,5S)-N-(2-chloropyridin-4-yl)-3-(4-cyano-3-(trifluoromethyl)phenyl)-2-(trifluoromethyl)oxazolidine-5-carboxamide, (2R,5S)-N-(4-cyano-2,3,5,6-tetrafluorophenyl)-3-(4-cyano-3-(trifluoromethyl)phenyl)-2-(trifluoromethyl)oxazolidine-5-carboxamide, (2R,5S)-N,3-bis(4-cyano-3-(trifluoromethyl)phenyl)-2-(trifluoromethyl)oxazolidine-5-carboxamide, (2R,5S)-N-(4-cyano-2-ethylphenyl)-3-(4-cyano-3-(trifluoromethyl)phenyl)-2-(trifluoromethyl)oxazolidine-5-carboxamide, (2R,5S)-N-(2-chloro-4-cyano-6-methylphenyl)-3-(4-cyano-3-(trifluoromethyl)phenyl)-2-(trifluoromethyl)oxazolidine-5-carboxamide, (2R,5S)-3-(4-cyano-3-(trifluoromethyl)phenyl)-N-(4-cyano-3-fluorophenyl)-2-(trifluoromethyl)oxazolidine-5-carboxamide, (2R,5S)-3-(4-cyano-3-(trifluoromethyl)phenyl)-N-(4-hydroxyphenyl)-2-(trifluoromethyl)oxazolidine-5-carboxamide, (2R,5S)-3-(3-chloro-4-nitrophenyl)-N-(6-chloropyridin-3-yl)-2-(trifluoromethyl)oxazolidine-5-carboxamide, (2R,5S)-N-(4-acetamidophenyl)-3-(4-nitro-3-(trifluoromethyl)phenyl)-2-(trifluoromethyl)oxazolidine-5-carboxamide, (2R,5S)-N-(2-chloro-4-nitrophenyl)-3-(4-cyano-3-(trifluoromethyl)phenyl)-2-(trifluoromethyl)oxazolidine-5-carboxamide,
(2R,5S)-N-(4-amino-2-chlorophenyl)-3-(4-cyano-3-(trifluoromethyl)phenyl)-2-(trifluoromethyl)oxazolidine-5-carboxamide,
(2R,5S)-N-(4-acetamido-2-chlorophenyl)-3-(4-cyano-3-(trifluoromethyl)phenyl)-2-(trifluoromethyl)oxazolidine-5-carboxamide,
methyl(3-chloro-4-((2R,5S)-3-(4-cyano-3-(trifluoromethyl)phenyl)-2-(trifluoromethyl)oxazolidine-5-carboxamido)phenyl)carbamate,
(2R,5S)-3-(4-cyano-3-(trifluoromethyl)phenyl)-N-(4-nitrophenyl)-2-(trifluoromethyl)oxazolidine-5-carboxamide,
(2R,5S)-N-(4-aminophenyl)-3-(4-cyano-3-(trifluoromethyl)phenyl)-2-(trifluoromethyl)oxazolidine-5-carboxamide,
methyl(4-((2R,5S)-3-(4-cyano-3-(trifluoromethyl)phenyl)-2-(trifluoromethyl)oxazolidine-5-carboxamido)phenyl)carbamate,
(2R,5S)-3-(4-cyano-3-(trifluoromethyl)phenyl)-N-(4-propionamidophenyl)-2-(trifluoromethyl)oxazolidine-5-carboxamide,
(2R,5S)-3-(4-cyano-3-(trifluoromethyl)phenyl)-N-(4-isobutylamidophenyl)-2-(trifluoromethyl)oxazolidine-5-carboxamide,
(2R,5S)-3-(4-cyano-3-(trifluoromethyl)phenyl)-N-(4-(2-hydroxyacetamido)phenyl)-2-(trifluoromethyl)oxazolidine-5-carboxamide,
(2R,5S)-3-(4-cyano-3-(trifluoromethyl)phenyl)-2-(trifluoromethyl)-N-(4-ureidophenyl)oxazolidine-5-carboxamide,
(2R,5S)-3-(4-cyano-3-(trifluoromethyl)phenyl)-N-(4-(2-cyanoacetamido)phenyl)-2-(trifluoromethyl)oxazolidine-5-carboxamide,
(2R,5S)-N-(4-(2-aminoacetamido)phenyl)-3-(4-cyano-3-(trifluoromethyl)phenyl)-2-(trifluoromethyl)oxazolidine-5-carboxamide,
(2S,5S)-3-(4-cyano-3-(trifluoromethyl)phenyl)-N-(4-cyanophenyl)-2-(trifluoromethyl)oxazolidine-5-carboxamide,
4-((2R,5S)-5-(((4-cyanophenyl)sulfonyl)methyl)-2-(trifluoromethyl)oxazolidin-3-yl)-2-(trifluoromethyl)benzonitrile,
t-butyl4-((2R,5S)-3-(4-cyano-3-(trifluoromethyl)phenyl)-2-(trifluoromethyl)oxazolidine-5-carboxamido)piperidine-1-carboxylate,
(2R,5S)-3-(4-cyano-3-(trifluoromethyl)phenyl)-N-(piperidin-4-yl)-2-(trifluoromethyl)oxazolidine-5-carboxamide, and (2R,5S)-N-(1-acetylpiperidin-4-yl)-3-(4-cyano-3-(trifluoromethyl)phenyl)-2-(trifluoromethyl)oxazolidine-5-carboxamide.

8. The compound, an isomer thereof, or a pharmaceutically acceptable salt thereof according to claim 6, wherein the $R_1$ of Chemical Formula 1 is a substituent represented by the Chemical Formula 3, and is a compound selected from the group consisting of the following compounds, an isomer thereof, or a pharmaceutically acceptable salt thereof:
4-((2R,5S)-5-(4-isocyanopiperidine-1-carbonyl)-2-(trifluoromethyl)oxazolidin-3-yl)-2-(trifluoromethyl)benzonitrile,
4-((2R,5S)-5-(piperazine-1-carbonyl)-2-(trifluoromethyl)oxazolidin-3-yl)-2-(trifluoromethyl)benzonitrile,
4-((2R,5S)-5-(4-acetylpiperazine-1-carbonyl)-2-(trifluoromethyl)oxazolidin-3-yl)-2-(trifluoromethyl)benzonitrile,
methyl4-((2R,5S)-3-(4-cyano-3-(trifluoromethyl)phenyl)-2-(trifluoromethyl)oxazolidine-5-carbonyl)piperazine-1-carboxylate,
4-((2R,5S)-3-(4-cyano-3-(trifluoromethyl)phenyl)-2-(trifluoromethyl)oxazolidine-5-carbonyl)piperazine-1-carbonitrile,
4-((2R,5S)-5-(4-aminopiperidine-1-carbonyl)-2-(trifluoromethyl)oxazolidin-3-yl)-2-(trifluoromethyl)benzonitrile,
4-((2R,5S)-5-(4-acetylpiperazine-1-carbonyl)-2-(trifluoromethyl)oxazolidin-3-yl)-2-(trifluoromethyl)benzonitrile,
t-butyl 4-((2R,5S)-3-(4-cyano-3-(trifluoromethyl)phenyl)-2-(trifluoromethyl)oxazolidine-5-carboxamido)piperidine-1-carboxylate,
methyl4-((2R,5S)-3-(3-chloro-4-cyanophenyl)-2-(trifluoromethyl)oxazolidine-5-carbonyl)piperazine-1-carboxylate
methyl4-((2R,5S)-3-(3-methyl-4-nitrophenyl)-2-(trifluoromethyl)oxazolidine-5-carbonyl)piperazine-1-carboxylate,
methyl(2-((2R,5S)-3-(4-cyano-3-(trifluoromethyl)phenyl)-2-(trifluoromethyl)oxazolidine-5-carboxamido)ethyl)carbamate,
4-((2R,5S)-5-(4-(methylsulfonyl)piperazine-1-carbonyl)-2-(trifluoromethyl)oxazolidin-3-yl)-2-(trifluoromethyl)benzonitrile,
4-((2R,5S)-5-(4-isopropylpiperazine-1-carbonyl)-2-(trifluoromethyl)oxazolidin-3-yl)-2-(trifluoromethyl)benzonitrile,
4-((2R,5S)-5-(4-(2-cyanoethyl)piperazine-1-carbonyl)-2-(trifluoromethyl)oxazolidin-3-yl) -2-(trifluoromethyl)benzonitrile,
4-((2R,5S)-5-(4-(2-hydroxyethyl)piperazine-1-carbonyl)-2-(trifluoromethyl)oxazolidin-3-yl)-2-trifluoromethyl)benzonitrile,
1-(((2R,5R)-3-(4-cyano-3-(trifluoromethyl)phenyl)-2-(trifluoromethyl)oxazolidin-5-yl)methyl)piperidine-4-carbonitrile,
1-((2R,5S)-3-(4-cyano-3-(trifluoromethyl)phenyl)-2-(trifluoromethyl)oxazolidine-5-carbonyl)piperidine-4-carboxamide,
ethyl4-((2R,5S)-3-(4-cyano-3-(trifluoromethyl)phenyl)-2-(trifluoromethyl)oxazolidine-5-carbonyl)piperazine-1-carboxylate,
4-((2R,5S)-3-(4-cyano-3-(trifluoromethyl)phenyl)-2-(trifluoromethyl)oxazolidine-5-carbonyl)piperazine-1-carboxamide,
methyl4-((2R,5S)-3-(3-chloro-4-nitrophenyl)-2-(trifluoromethyl)oxazolidine-5-carbonyl)piperazine-1-carboxylate,
methyl4-((2R,5S)-3-(4-nitro-3-(trifluoromethyl)phenyl)-2-(trifluoromethyl)oxazolidine-5-carbonyl)piperazine-1-carboxylate,
methyl4-((2R,5S)-3-(4-cyano-3-(trifluoromethyl)phenyl)-2-(trifluoromethyl)oxazolidine-5-carbonyl)-1,4-diazepane-1-carboxylate, and
methyl((R)-1-((2R,5S)-3-(4-cyano-3-(trifluoromethyl)phenyl)-2-(trifluoromethyl)oxazolidine-5-carbonyl)pyrrolidin-3-yl)carbamate.

9. A method of preparing a compound of Chemical Formula 1a comprising the steps of:
preparing a compound of Chemical Formula 5 from a fluorobenzene compound of Chemical Formula 4 by substitution reaction, and preparing the compound of Chemical Formula 1a from the compound of Chemical Formula 5 by cyclodehydration reaction with aldehyde, ketone, or a precursor thereof:

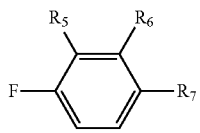
[Chemical Formula 4]

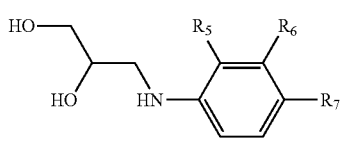
[Chemical Formula 5]

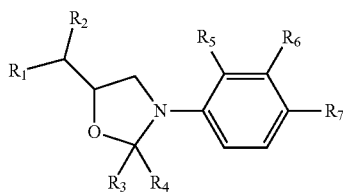
[Chemical Formula 1a]

in Chemical Formula 1a, $R_1$ is a substituent represented by the following Chemical Formula 2, $R_2$ is hydrogen,

—X(CH$_2$)nR$_8$          [Chemical Formula 2]

in Chemical Formula 2, X is O, n is 0, $R_8$ is hydrogen, $R_3$ and $R_4$ each independently is a substituent selected from the group consisting of hydrogen and $C_1$-$C_6$ alkyl, $R_5$ and $R_6$ each independently is a substituent selected from the group consisting of hydrogen, halogen and $C_1$-$C_6$ alkyl, $R_7$ is halogen, cyano, or nitro, and the $C_1$-$C_6$ alkyl is substituted with one or more substituents selected from the group consisting of hydrogen, hydroxy, and halogen.

10. The method according to claim 9, wherein the method comprises the steps of:

preparing the compound of Chemical Formula 5 from the fluorobenzene compound of Chemical Formula 4 by substitution reaction, preparing the compound of Chemical Formula 1a from the compound of Chemical Formula 5 by cyclodehydration reaction with aldehyde, ketone, or a precursor thereof, and preparing the compound of Chemical Formula 1b from the compound of Chemical Formula 1a via mesylate with phenol or thiophenol,

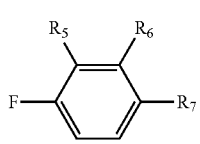
[Chemical Formula 4]

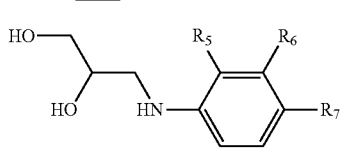
[Chemical Formula 5]

-continued

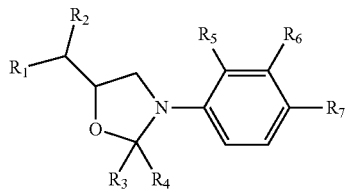
[Chemical Formula 1a]

in Chemical Formula 1a, $R_1$ is a substituent represented the following Chemical Formula 2, $R_2$ is hydrogen,

—X(CH$_2$)nR$_8$          [Chemical Formula 2]

in Chemical Formula 2, X is O, n is 0, $R_8$ is hydrogen, $R_3$ and $R_4$ each independently is a substituent selected from the group consisting of hydrogen and $C_1$-$C_6$ alkyl, $R_5$ and $R_6$ each independently is a substituent selected from the group consisting of hydrogen, halogen, and $C_1$-$C_6$ alkyl, $R_7$ is halogen, cyano, or nitro, the $C_1$-$C_6$ alkyl is substituted with one or more substituents selected from the group consisting of hydrogen, hydroxy, and halogen,

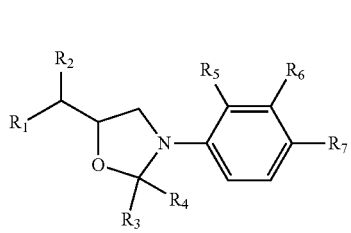
[Chemical Formula 1b]

in Chemical Formula 1b, $R_1$ is a substituent represented by the following Chemical Formula 2, $R_2$ is hydrogen, $R_3$ and $R_4$ each independently is a substituent selected from the group consisting of hydrogen and $C_1$-$C_6$ alkyl, $R_5$ and $R_6$ each independently is a substituent selected from the group consisting of hydrogen, halogen, and $C_1$-$C_6$ alkyl, $R_7$ is halogen, cyano, or nitro, the $C_1$-$C_6$ alkyl is substituted with one or more substituents selected from the group consisting of hydrogen, hydroxy, and halogen;

—X(CH$_2$)nR$_8$          [Chemical Formula 2]

in Chemical Formula 2, X is O or S, n is an integer of 0 or 1, $R_8$ is hydrogen, $C_3$-$C_7$ heterocycle having a nitrogen atom, aryl, or heteroaryl having a nitrogen atom, the heterocycle, aryl or heteroaryl each independently is substituted with one or more substituents selected from the group consisting of hydrogen, hydroxy, halogen, $C_1$-$C_6$ alkyl, $C_1$-$C_6$ alkoxy, a cyano group, a nitro group, a hydroxyimino group, a $C_1$-$C_6$ alkoxyimino group, $(CH_2)_pNR_{10}R_{11}$, $(CH_2)_pNC(O)OR_{10}$, $(CH_2)_pNC(O)NR_{10}R_{11}$, $(CH_2)_pC(O)NR_{10}R_{11}$, $(CH_2)_pNS(O)_2R_{10}$, $(CH_2)_pS(O)_2R_{10}$ $(CH_2)_pC(O)OR_{10}$,

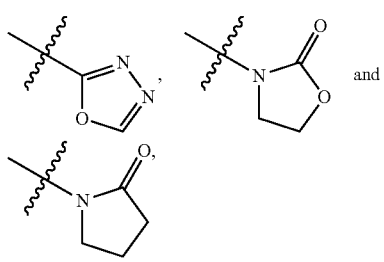

p is an integer of 0 or 1,
$R_{10}$ and $R_{11}$ each independently is a substituent selected from the group consisting of hydrogen, $C_1$-$C_6$ alkyl, pyrrolidinyl, and phenyl,
the $C_1$-$C_6$ alkyl is substituted with one or more substituents selected from the group consisting of hydrogen, hydroxy, amino, cyano and halogen, and
n is 0 or 1.

11. The method according to claim 9, wherein the method comprises the steps of:
preparing the compound of Chemical Formula 5 from the fluorobenzene compound of Chemical Formula 4 by substitution reaction,
preparing the compound of Chemical Formula 1a from the compound of Chemical Formula 5 by cyclodehydration reaction with aldehyde, ketone, or a precursor thereof,
preparing the compound of Chemical Formula 6 from the compound of Chemical Formula 1a by oxidation reaction, and
preparing the compound of Chemical Formula 1c by reacting the compound of Chemical Formula 6 with a silane compound, followed by acid treatment,

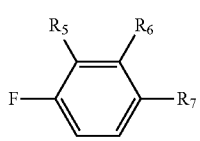

[Chemical Formula 4]

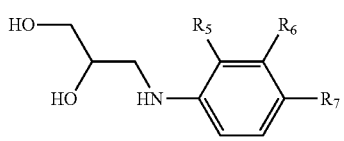

[Chemical Formula 5]

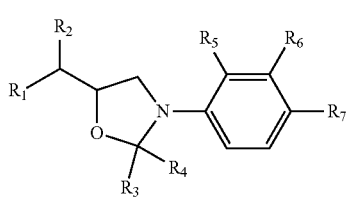

[Chemical Formula 1a]

in Chemical Formula 1a, $R_1$ is a substituent represented by the following Chemical Formula 2,
$R_2$ is hydrogen,

[Chemical Formula 2]

in Chemical Formula 2, X is O, n is 0, $R_8$ is hydrogen,
$R_3$ and $R_4$ each independently is a substituent selected from the group consisting of hydrogen and $C_1$-$C_6$ alkyl, $R_5$ and $R_6$ each independently is a substituent selected from the group consisting of hydrogen, halogen and $C_1$-$C_6$ alkyl,
$R_7$ is halogen, cyano or nitro,
the $C_1$-$C_6$ alkyl is substituted with one or more substituents selected from the group consisting of hydrogen, hydroxy, and halogen,

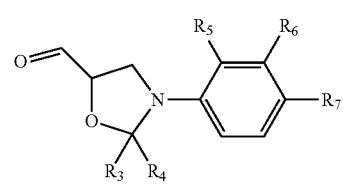

[Chemical Formula 6]

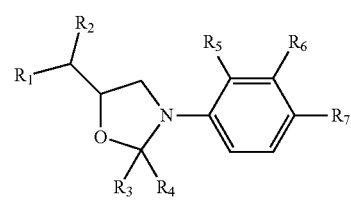

[Chemical Formula 1c]

in Chemical Formula 1c, $R_1$ is a substituent represented by the following Chemical Formula 2,
$R_2$ is $C_1$-$C_6$ alkyl, and the $C_1$-$C_6$ alkyl is substituted with one or more substituents selected from the group consisting of hydrogen, hydroxy and halogen,

[Chemical Formula 2]

in Chemical Formula 2, X is O, n is 0, $R_8$ is hydrogen,
$R_3$ and $R_4$ each independently is a substituent selected from the group consisting of hydrogen and $C_1$-$C_6$ alkyl,
$R_5$ and $R_6$ each independently is a substituent selected from the group consisting of hydrogen, halogen and $C_1$-$C_6$ alkyl,
$R_7$ is halogen, cyano, or nitro, and
the $C_1$-$C_6$ alkyl is substituted with one or more substituents selected from the group consisting of hydrogen, hydroxy and halogen.

12. A method of preparing a compound of Chemical Formula 1d comprising the steps of:
preparing a compound of Chemical Formula 7 from the fluorobenzene compound of Chemical Formula 4 by substitution reaction,
preparing a compound of Chemical Formula 8 from the compound of Chemical Formula 7 by cyclodehydration reaction with aldehyde, ketone, or a precursor thereof, and
preparing a compound of Chemical Formula 1d from the compound of Chemical Formula 8 by amide formation reaction with amine,

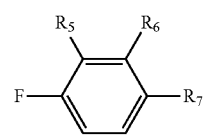

[Chemical Formula 4]

-continued

[Chemical Formula 7]

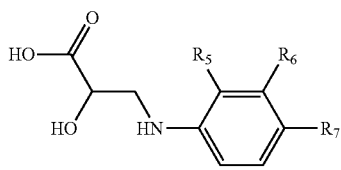

[Chemical Formula 8]

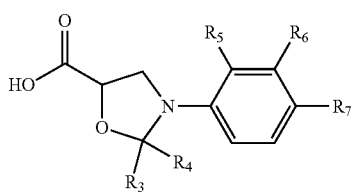

[Chemical Formula 1d]

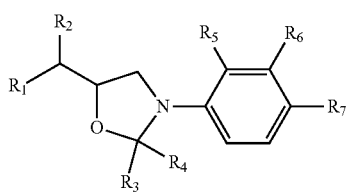

in Chemical Formula 1d, $R_1$ is a substituent represented by the following Chemical Formula 2 or Chemical Formula 3, $R_2$ is an oxo group, $R_3$ and $R_4$ each independently is a substituent selected from the group consisting of hydrogen and $C_1$-$C_6$ alkyl, $R_5$ and $R_6$ each independently is a substituent selected from the group consisting of hydrogen, halogen, and $C_1$-$C_6$ alkyl, $R_7$ is halogen, cyano, or nitro, and the $C_1$-$C_6$ alkyl is substituted with one or more substituents selected from the group consisting of hydrogen, hydroxy, and halogen;

 —X(CH$_2$)nR$_8$ [Chemical Formula 2]

in Chemical Formula 2, X is N(R), n is an integer of 0 or 1,

R is hydrogen, $R_8$ is hydrogen, $C_3$-$C_7$ heterocycle having a nitrogen atom, aryl, or heteroaryl having a nitrogen atom which has one or more rings, the heterocycle, aryl, or heteroaryl each independently is substituted with one or more substituents selected from the group consisting of hydrogen, hydroxy, halogen, $C_1$-$C_6$ alkyl, $C_1$-$C_6$ alkoxy, a cyano group, a nitro group, a hydroxyimino group, a $C_1$-$C_6$ alkoxyimino group, $(CH_2)_pNR_{10}R_{11}$, $(CH_2)_pNC(O)R_{10}$, $(CH_2)_pNC(O)OR_{10}$, $(CH_2)_pNC(O)NR_{10}R_{11}$, $(CH_2)_pNS(O)_2R_{10}$, $(CH_2)S(O)_2R_{10}(CH_2)_pC(O)OR_{10}$,

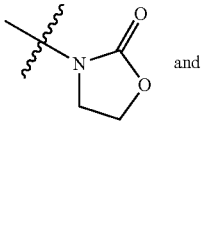

and p is an integer of 0 or 1, $R_{10}$ and $R_{11}$ each independently is a substituent selected from the group consisting of hydrogen, $C_1$-$C_6$ alkyl, pyrrolidinyl, and phenyl, and the $C_1$-$C_6$ alkyl is substituted with one or more substituents selected from the group consisting of hydrogen, hydroxy, amino, cyano and halogen,

[Chemical Formula 3]

in Chemical Formula 3, Y is C or N, m is an integer of 0, 1 or 2, $R_9$ is a substituent selected from the group consisting of hydrogen, oxo, hydroxy, $C_1$-$C_6$ alkyl, cyano, $C(O)R_{12}$, $C(O)OR_{12}$, $C(O)NR_{12}R_{13}$, $S(O)_2R_{12}$, $NC(O)R_{13}$, and $NC(O)OR_{12}$, $R_{12}$ and $R_{13}$ each independently is a substituent selected from the group consisting of hydrogen, hydroxy, and $C_1$-$C_6$ alkyl, and the $C_1$-$C_6$ alkyl is substituted with one or more substituents selected from the group consisting of hydrogen, hydroxy, halogen and cyano.

13. A pharmaceutical composition for the treatment of diseases or conditions, of which symptoms may be improved or may respond to treatment by increased activity of androgen receptor, comprising a compound, an isomer thereof, or a pharmaceutically acceptable salt thereof according to claim 1, as an active ingredient.

14. The pharmaceutical composition according to claim 13, wherein the diseases, of which symptoms may be improved or may respond to treatment by increased activity of androgen receptor, are selected from the group consisting of sexual dysfunction, decreased sexual libido, male erectile dysfunction, hypogonadism, sarcopenia, muscle dystrophy caused by reduction in the number or mass of muscle cells, cachexia, muscular dystrophy, post-operative muscle loss, neuromuscular disease caused by neurotransmitter system disorder, rheumatic disease, sarcopenic obesity, alterations in cognition and mood, depression, anemia, hair loss, obesity, endometriosis, breast cancer, uterine cancer, ovarian cancer, muscle wasting disorder, osteopenia, and osteoporosis.

* * * * *